(12) United States Patent
Kranzusch et al.

(10) Patent No.: US 12,146,168 B2
(45) Date of Patent: Nov. 19, 2024

(54) HUMAN CGAS-DNA COMPLEX AND ENCODED PROTEIN

(71) Applicants: President and Fellows of Harvard College, Cambridge, MA (US); Dana-Farber Cancer Institute, Inc., Boston, MA (US)

(72) Inventors: Philip J. Kranzusch, Brighton, MA (US); John J. Mekalanos, Newton, MA (US); Aaron T. Whiteley, Brookline, MA (US); Wen Zhou, Boston, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 149 days.

(21) Appl. No.: 17/252,454

(22) PCT Filed: Jun. 26, 2019

(86) PCT No.: PCT/US2019/039171
§ 371 (c)(1),
(2) Date: Dec. 15, 2020

(87) PCT Pub. No.: WO2020/006038
PCT Pub. Date: Jan. 2, 2020

(65) Prior Publication Data
US 2021/0324351 A1    Oct. 21, 2021

Related U.S. Application Data

(60) Provisional application No. 62/692,347, filed on Jun. 29, 2018.

(51) Int. Cl.
C12N 9/12        (2006.01)
A01K 67/0278     (2024.01)
A61P 35/00       (2006.01)
A61K 38/00       (2006.01)

(52) U.S. Cl.
CPC ........ *C12N 9/1241* (2013.01); *A01K 67/0278* (2013.01); *A61P 35/00* (2018.01); *A61K 38/00* (2013.01); *C07B 2200/13* (2013.01); *C07K 2299/00* (2013.01)

(58) Field of Classification Search
None
See application file for complete search history.

(56) References Cited

U.S. PATENT DOCUMENTS

| | | | |
|---|---|---|---|
| 10,010,607 B2 * | 7/2018 | Manel | C12N 7/00 |
| 10,501,733 B2 * | 12/2019 | King | C07K 14/435 |
| 2014/0329889 A1 | 11/2014 | Vance et al. | |
| 2017/0296655 A1 | 10/2017 | Chen et al. | |
| 2018/0118777 A1 | 5/2018 | Patel et al. | |
| 2021/0324351 A1 * | 10/2021 | Kranzusch | A01K 67/0278 |

FOREIGN PATENT DOCUMENTS

| WO | WO-2017/075477 A1 | 5/2017 |
|---|---|---|
| WO | WO-2020/006038 A1 | 1/2020 |

OTHER PUBLICATIONS

Decout et al., "Human cGas Has a Slighty Different Taste for dsDNA," Immunity, 49(2): 206-208 (2018).
International Search Report and Written Opinion for International Application No. PCT/US2019/039171 dated Oct. 4, 2019.
Zhou et al., "Structure of the Human cGAS-DNA Complex Reveals Enhanced Control of Immune Surveillance," Cell, 174:300-311 (24 pages)(2018).
Extended European Search Report for EP Application No. 19824484.0 dated Mar. 23, 2022.
Wang et al., "Molecular cloning and functional characterization of porcine cyclic GMP-AMP synthase," Molecular Immunology, 65(2): 436-445 (2015).

* cited by examiner

*Primary Examiner* — Hope A Robinson
(74) *Attorney, Agent, or Firm* — Foley Hoag LLP

(57) ABSTRACT

The present invention is based, in part, on the discovery of the human-specific regulatory control of cGAS and the structure of the active human cGAS-DNA complex, as well as compositions comprising the modified hcGAS polypeptide, hcGAS-DNA complex, hcGAS-DNA-ATP complex, and methods of screening for modulators of the structure, expression, and/or activity of such polypeptides and complexes.

20 Claims, 32 Drawing Sheets
Specification includes a Sequence Listing.

hcGAS-DNA contacts hcGAS K187N/L195R - DNA complex

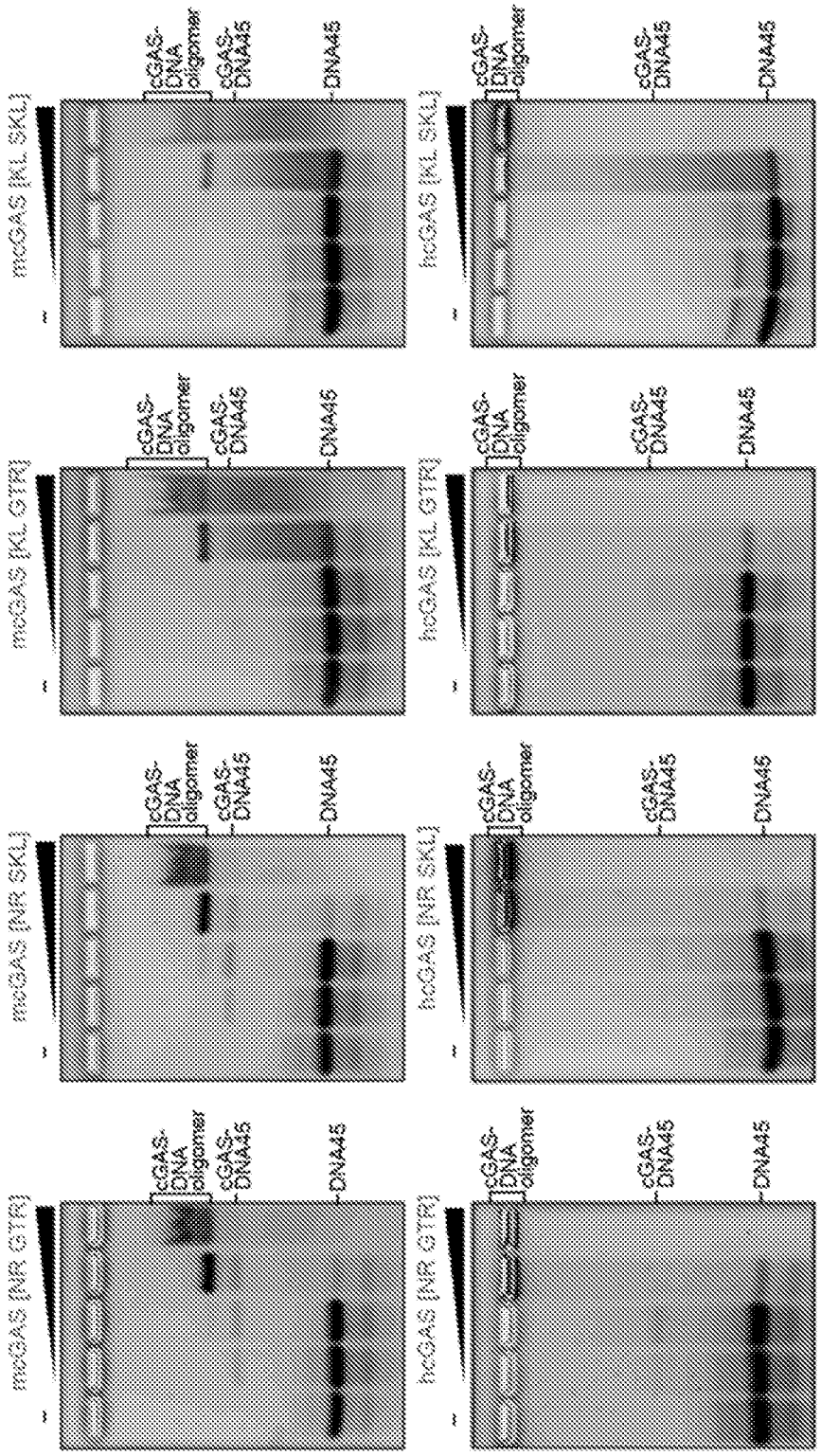

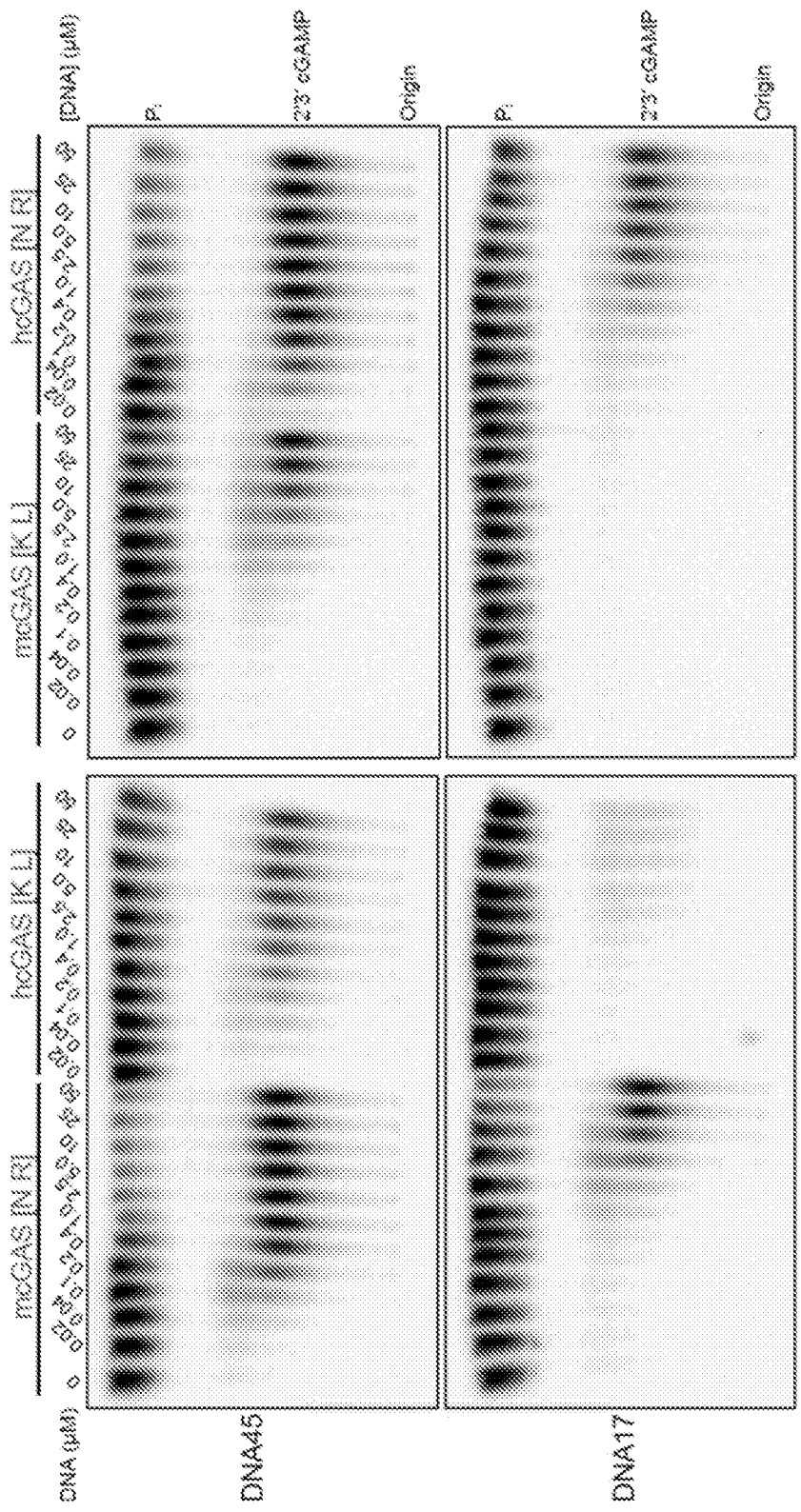

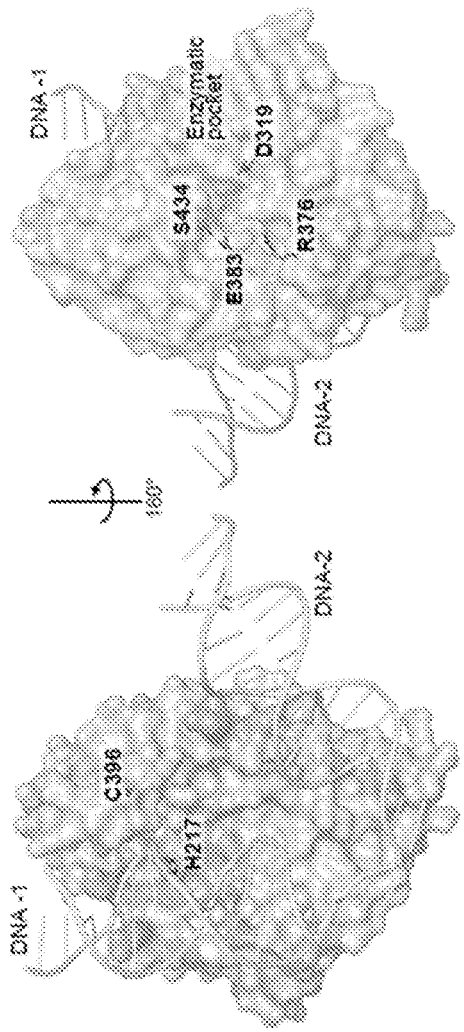
FIG. 10A
FIG. 10B
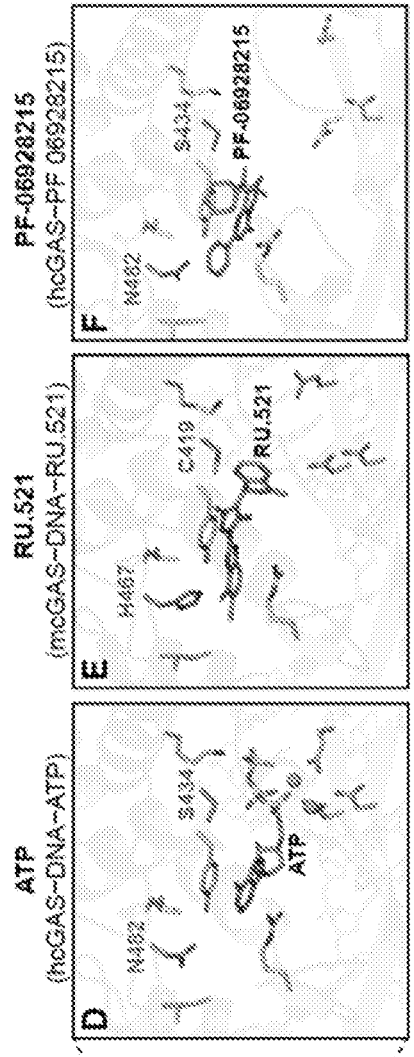
FIG. 10C
FIG. 10D
FIG. 10E
FIG. 10F

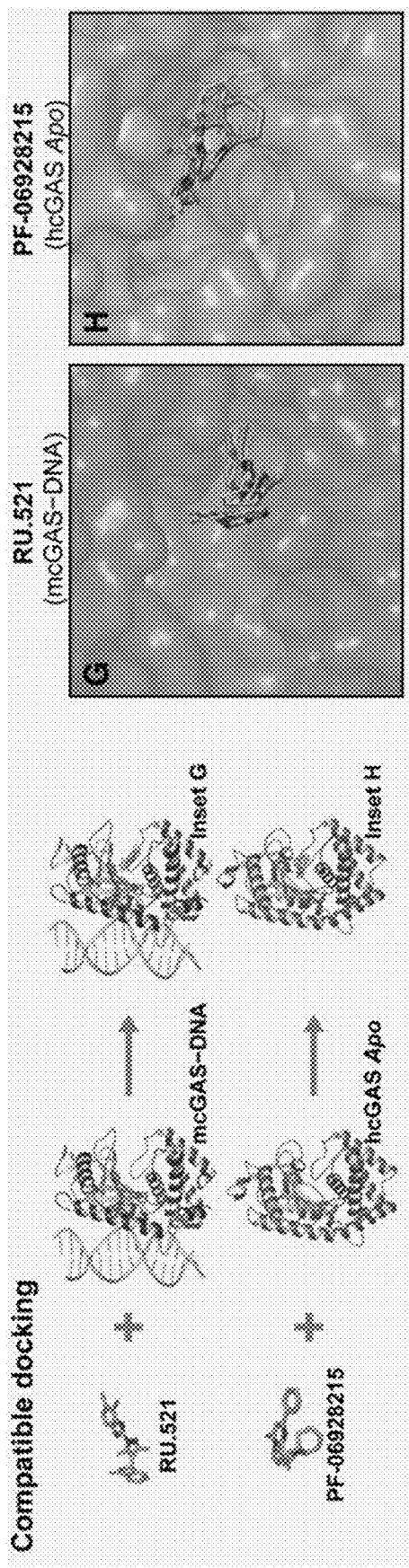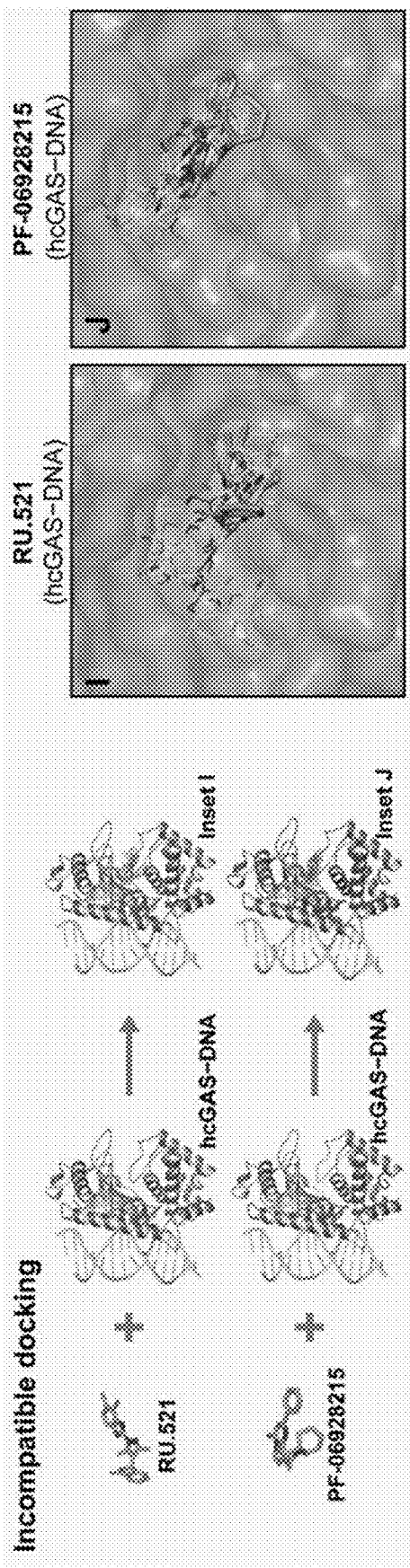
FIG. 10G  FIG. 10H  FIG. 10I  FIG. 10J

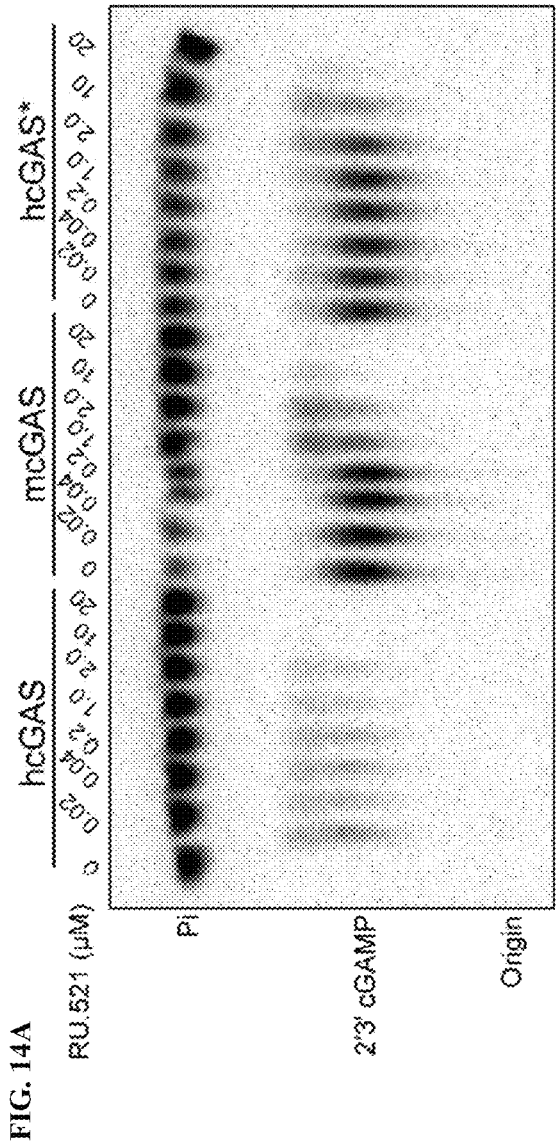
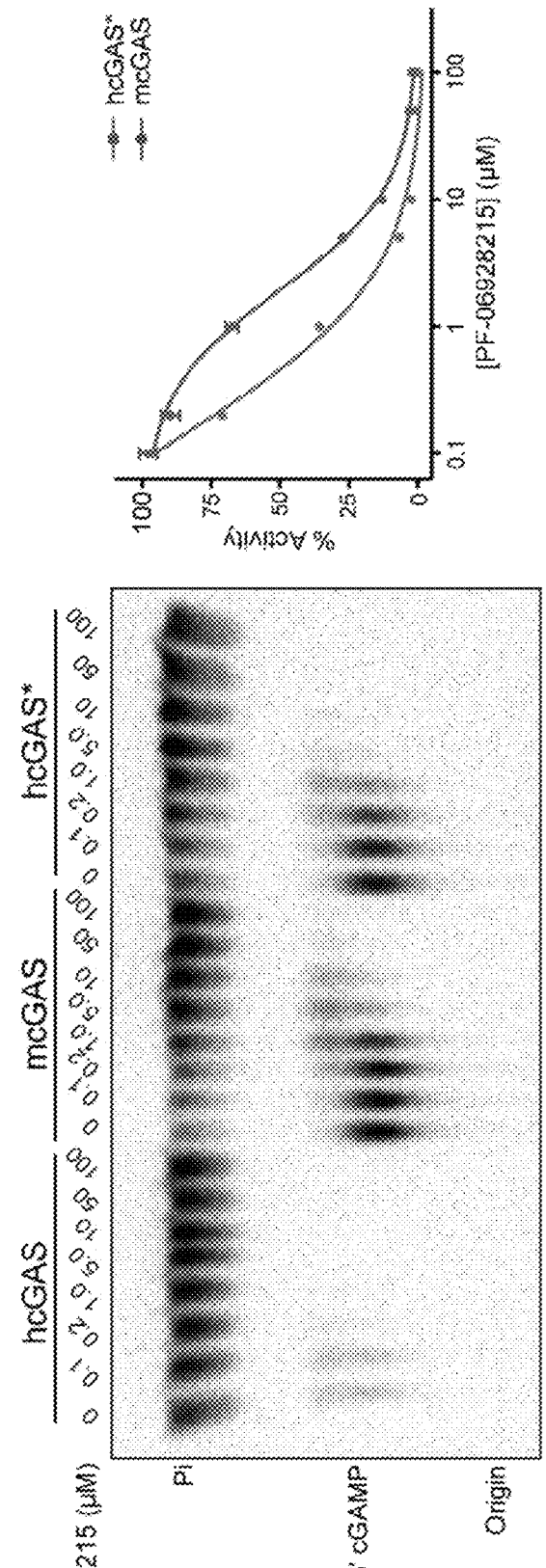
FIG. 14A
FIG. 14B

HUMAN CGAS-DNA COMPLEX AND ENCODED PROTEIN

CROSS-REFERENCE TO RELATED APPLICATIONS

This application is the U.S. national phase of International Patent Application No. PCT/US2019/039171, filed on Jun. 26, 2019, which claims the benefit of priority to U.S. Provisional Application Ser. No. 62/692,347, filed on Jun. 29, 2018; the entire contents of each of said applications are incorporated herein in their entirety by this reference.

STATEMENT OF RIGHTS

This invention was made with government support under grant numbers AI-018045, AI-026289, P41 GM103403, and S10 RR029205 awarded by The National Institutes of Health; and under grant number DE-AC02-06CH11357 awarded by The Department of Energy. The government has certain rights in the present invention.

SEQUENCE LISTING

The instant application contains a Sequence Listing which has been submitted electronically in ASCII format and is hereby incorporated by reference in its entirety. Said ASCII copy, created on Jul. 29, 2019, is named DFS-25501_Sequence_Listing.txt and is 116,336 bytes in size.

BACKGROUND OF THE INVENTION

Aberrant localization of DNA into the cytosol of human cells induces activation of a potent immune response. In addition to DNA released during pathogen replication, accurate detection of cytosolic self-DNA is critical for the cellular responses to mitochondrial stress, abnormal chromosomal segregation, and cancer (Bakhoum et al. (2018) *Nature* 553:467-472; Deng et al. (2014) *Immunity* 41:843-852; Dou et al. (2017) *Nature* 550:402-406; Gluck et al. (2017) *Nat Cell Biol* 19:1061-1070; Harding et al. (2017) *Nature* 548:466-470; Mackenzie et al. (2017) *Nature* 548: 461-465; Woo et al. (2014) *Immunity* 41:830-842; Yang et al. (2017) *Proc Natl Acad Sci USA* 114:E4612-E4620). A major component of DNA sensing is controlled by the cytosolic enzyme cyclic GMP-AMP synthase (cGAS) (Sun et al. (2013) *Science* 339:786-791). cGAS is a direct innate immune sensor that binds double-stranded DNA and catalyzes production of the second messenger 2'-5'/3'-5' cyclic GMP-AMP (2'3' cGAMP) (Ablasser et al. (2013) *Nature* 498:380-384; Civril et al. (2013) *Nature* 498, 332-337; Diner et al. (2013) *Cell Rep* 3:1355-1361; Gao et al. (2013) *Cell* 153:1094-1107; Kranzusch et al. (2013) *Cell Rep* 3:1362-1368; Li et al. (2013) *Immunity* 39:1019-1031; Sun et al. (2013) *Science* 339:786-791; Zhang et al. (2014) *Cell Rep* 6:421-430). 2'3' cGAMP then activates the receptor Stimulator of Interferon Genes (STING) to initiate a downstream transcription cascade and type I interferon signaling (Burdette et al. (2011) *Nature* 478:515-518; Gao et al. (2013) *Cell* 154:748-762; Ishikawa and Barber (2008) *Nature* 455:674-678; Jin et al. (2008) *Mol Cell Biol* 28:5014-5026; Sun et al. (2013) *Science* 339:786-791; Sun et al. (2009) *Proc Natl Acad Sci USA* 106:8653-8658; Zhang et al. (2013) *Mol Cell* 51:226-235; Zhong et al. (2008) *Immunity* 29:538-550). The ability of cGAS to catalyze multi-turnover production of 2'3' cGAMP enables dramatic signal amplification, allowing cells to sensitively detect and respond to small amounts of DNA. However, the enzymatic potential of cGAS necessitates strict regulatory control, and human mutations that disrupt normal tolerance to self-DNA result in severe autoimmunity (Lee-Kirsch et al. (2006) *Am J Hum Genet* 79:731-737; Liu et al. (2014) *N Engl J Med* 371:507-518; Rice et al. (2007) *Am J Hum Genet* 80:811-815; Stetson et al. (2008) *Cell* 134:587-598). Recent experiments have highlighted a role for post-translational modification (Chen et al. (2016) *Mol Cell* 64:105-119; Xia et al. (2016) *Nat Immunol* 17:369-378) and auxiliary binding partners (Liang et al. (2014) *Cell Host Microbe* 15:228-238; Yoh et al. (2015) *Cell* 161:1293-1305) in regulating cGAS activation. However, the ability of human cGAS to synthesize 2'3' cGAMP is severely reduced compared to other mammalian homologs, indicating the existence of additional unknown layers of regulation controlling primary enzymatic function.

A major limitation in the understanding of cGAS function is that no structural information exists for activated human cGAS (hcGAS) bound to DNA. All structural understanding of DNA recognition is instead derived from structures of the inactive human enzyme (Kato et al. (2013) *PLoS One* 8:e76983; Li et al. (2013) *Immunity* 39:1019-1031; Zhang et al. (2014) *Cell Rep* 6:421-430) and studies of mouse cGAS (mcGAS) and mammalian homologs (Andreeva et al. (2017) *Nature* 549:394-398; Civril et al. (2013) *Nature* 498, 332-337; Gao et al. (2013) *Cell* 153:1094-1107; Li et al. (2013) *Immunity* 39:1019-1031; Zhang et al. (2014) *Cell Rep* 6:421-430). cGAS is one of the most rapidly diverging genes in the human genome (George et al. (2011) *Genome Res* 21:1686-1694; Hancks et al. (2015) *PLoS Genet* 11:e1005203; Mozzi et al. (2015) *Genome Biol Evol* 7:1016-1032), and the human and mouse enzymes share <60% amino acid identity. The high variability in cGAS primary sequence limits the ability of existing homolog cGAS-DNA structures to enable structure-guided design of small molecules targeting the active human enzyme. While structures of mammalian homolog cGAS-DNA complexes provide a critically important model for DNA recognition and enzyme activation, they cannot explain the importance or function of human-specific cGAS variations.

Accordingly, there remains a great need in the art to elucidate the structure of human cGAS in an active conformation bound to DNA and to understand the human-specific regulatory control of cGAS DNA-recognition and enzyme activation in order to design better cGAS-based therapeutics.

SUMMARY OF THE INVENTION

The present invention is based, at least in part, on the elucidation of the structure of hcGAS in an active conformation bound to DNA, and the identification of a functional role of human-specific divergence in cGAS sequence in balancing DNA-sensing specificity and sensitivity.

For example, in one aspect, an isolated polypeptide that binds double-stranded DNA and catalyzes production of 2'-5'/3'-5' cyclic GMP-AMP (2'3' cGAMP), wherein said polypeptide comprises an amino acid sequence having at least 70% identity to the human cGAS (hcGAS) amino acid sequence of any one of SEQ ID NOs: 1-2 and further comprises amino acid substitutions at positions corresponding to K187 and L195 of SEQ ID NO: 1, is provided.

Numerous embodiments are further provided that can be applied to any aspect of the present invention and/or combined with any other embodiment described herein. For example, in one embodiment, the isolated polypeptide comprises an amino acid sequence having at least 90% identity to the human cGAS (hcGAS) amino acid sequence of any one of SEQ ID NOs: 1-2 and further comprises amino acid substitutions at positions corresponding to K187 and L195 of SEQ ID NO: 1. In another embodiment, the isolated polypeptide comprises an amino acid sequence having the amino acid sequence of any one of SEQ ID NOs: 1-2 and further comprises amino acid substitutions at positions corresponding to K187 and L195 of SEQ ID NO: 1. In still another embodiment, the isolated polypeptide comprises an amino acid sequence of SEQ ID NO: 2 and further comprises amino acid substitutions at positions corresponding to K187 and L195 of SEQ ID NO: 1. In yet another embodiment, the residue corresponding to K187 is substituted with a residue that is capable of making direct contact with the DNA phosphate backbone. In another embodiment, the residue corresponding to K187 is substituted with a polar residue selected from the group consisting of tyrosine, serine, threonine, asparagine, glutamine and cysteine. In still another embodiment, the residue corresponding to K187 is substituted with an asparagine residue. In yet another embodiment, the residue corresponding to L195 is substituted with a residue that increases the overall positive charge of the A-site DNA-binding surface. In another embodiment, the residue corresponding to L195 is substituted with a basic residue selected from the group consisting of lysine, arginine and histidine. In still another embodiment, the residue corresponding to L195 is substituted with an arginine residue. In yet another embodiment, the isolated polypeptide further comprises amino acid substitutions at positions corresponding to S328, K350 and/or L354 of SEQ ID NO: 1. In another embodiment, the isolated polypeptide has one or more biological properties selected from the group consisting of: a) increased 2'3' cGAMP synthesis compared to hcGAS having the amino acid sequence of SEQ ID NO: 1; b) increased repression of V. cholera chemotaxis compared to hcGAS having the amino acid sequence of SEQ ID NO: 1; c) similar enzyme kinetics to mouse cGAS having the amino acid sequence of SEQ ID NO: 5; d) recognizing DNA shorter than 45 bp; e) stabilized active enzyme conformation; f) stabilized interactions with DNA; and g) increased minimal cGAS-DNA complex formation compared to hcGAS having the amino acid sequence of SEQ ID NO: 1. In still another embodiment, the 2'3' cGAMP synthesis mediated by the isolated polypeptide described herein is increased by at least 5-fold. In yet another embodiment, the isolated polypeptide further comprises a heterologous polypeptide. In another embodiment, the heterologous polypeptide is selected from the group consisting of a signal peptide, a peptide tag, a dimerization domain, an oligomerization domain, an antibody, or an antibody fragment. In still another embodiment, the peptide tag is a thioredoxin, Maltose-binding protein (MBP), SUMO2, Glutathione-S-Transferase (GST), calmodulin binding protein (CBP), protein C tag, Myc tag, HaloTag®, HA tag, FLAG® tag, His tag, biotin tag, V5 tag, or OmpA signal sequence tag. In yet another embodiment, the antibody fragment is an Fc domain. In another embodiment, the isolated polypeptide is immobilized on an object selected from the group consisting of a cell, a metal, a resin, a polymer, a ceramic, a glass, a microelectrode, a graphitic particle, a bead, a gel, a plate, an array, and a capillary tube.

In another aspect, a composition comprising the isolated polypeptide described herein and a pharmaceutically acceptable agent selected from the group consisting of excipients, diluents, and carriers, is provided.

In still another aspect, an isolated nucleic acid molecule encoding the polypeptide described herein is provided.

In yet another aspect, an isolated nucleic acid molecule comprising a nucleotide sequence, which is complementary to the nucleic acid sequence of the isolated nucleic acid molecule encoding the polypeptide described herein, is provided.

In another aspect, a vector comprising the nucleic acid molecule encoding the polypeptide described herein or the nucleic acid molecule comprising a nucleotide sequence that is complementary to the nucleic acid sequence of the nucleic acid molecule encoding the polypeptide described herein, is provided. In one embodiment, the vector is an expression vector.

In still another aspect, a host cell transfected with the expression vector described herein, is provided.

In yet another aspect, a method of producing a polypeptide comprising culturing the host cell in an appropriate culture medium to, thereby, produce the polypeptide, is provided.

As described above, numerous embodiments are further provided that can be applied to any aspect of the present invention and/or combined with any other embodiment described herein. For example, in one embodiment, the host cell is a bacterial cell or a eukaryotic cell. In another embodiment, the host cell is genetically engineered to express a selectable marker. In still another embodiment, the method further comprises the step of isolating the polypeptide from the medium or host cell.

In another aspect, a method for detecting the presence of a polypeptide described herein in a sample comprising: a) contacting the sample with a compound which selectively binds to the polypeptide; and b) determining whether the compound binds to the polypeptide in the sample to thereby detect the presence of the polypeptide in the sample.

In one embodiment, the compound which binds to the polypeptide is an antibody, is provided.

In still another aspect, a non-human animal model engineered to express a polypeptide described herein, is provided. As described above, numerous embodiments are further provided that can be applied to any aspect of the present invention and/or combined with any other embodiment described herein. For example, in one embodiment, the polypeptide is overexpressed. In another embodiment, the animal is a knock-in or a transgenic animal. In still another embodiment, the animal is a rodent.

In yet another aspect, a method for identifying an agent that modulates the expression and/or activity of a polypeptide described herein or biologically active fragment thereof comprising: a) contacting the polypeptide or biologically active fragment thereof, or a cell expressing the polypeptide or biologically active fragment thereof, with a test agent; and b) determining the effect of the test agent on the expression and/or activity of the polypeptide or biologically active fragment thereof to thereby identify an agent which modulates the expression and/or activity of the polypeptide or biologically active fragment thereof, is provided.

As described above, numerous embodiments are further provided that can be applied to any aspect of the present invention and/or combined with any other embodiment described herein. For example, in one embodiment, the activity is selected from the group consisting of: a) 2'3' cGAMP synthesis; b) repression of V. cholera chemotaxis; c) enzyme kinetics; d) nucleotide coordination; e) protein stability; f) interactions with DNA; g) DNA-length specificity; h) enzyme conformation; and i) STING pathway activation. In another embodiment, the step of contacting occurs in vivo, ex vivo, or in vitro. In still another embodiment, the agent increases the expression and/or activity of the polypeptide described herein, or biologically active fragment thereof. In yet another embodiment, the agent is selected from the group consisting of a nucleic acid molecule described herein, a polypeptide described herein, and a small molecule that binds to a polypeptide described herein. In another embodiment, the agent is used to treat cancer. In still another embodiment, the agent decreases the expression and/or activity of the polypeptide described herein or biologically active fragment thereof. In yet another embodiment, the agent is a small molecule inhibitor, CRISPR guide RNA (gRNA), RNA interfering agent, oligonucleotide, peptide or peptidomimetic inhibitor, aptamer, antibody, or intrabody. The RNA interfering agent may comprise or be, e.g., a small interfering RNA (siRNA), CRISPR RNA (crRNA), CRISPR guide RNA (gRNA), a small hairpin RNA (shRNA), a microRNA (miRNA), or a piwi-interacting RNA (piRNA). In another embodiment, the agent comprises an antibody and/or intrabody, or an antigen binding fragment thereof, which specifically binds to the polypeptide described herein or biologically active fragment thereof. In still another embodiment, the antibody and/or intrabody, or antigen binding fragment thereof, is chimeric, humanized, composite, or human. In yet another embodiment, the antibody and/or intrabody, or antigen binding fragment thereof, comprises an effector domain, comprises an Fc domain, and/or is selected from the group consisting of Fv, Fav, F(ab')2, Fab', dsFv, scFv, sc(Fv)2, and diabodies fragments. In another embodiment, the agent is used to treat autoimmune diseases.

In another aspect, a modified hcGAS-DNA complex, wherein the complex comprises at least one double-stranded DNA and at least one human cGAS polypeptide having an amino acid sequence of a polypeptide described herein, is provided.

As described above, numerous embodiments are further provided that can be applied to any aspect of the present invention and/or combined with any other embodiment described herein. For example, in one embodiment, the DNA is an activating DNA. In another embodiment, the DNA is 45 bp or longer. In still another embodiment, the DNA is a genomic DNA. In yet another embodiment, the human cGAS oligomerizes on the DNA. In another embodiment, the DNA is shorter than 45 bp. For example, the DNA may be 17 bp. In still another embodiment, the modified hcGAS-DNA complex comprises two molecules of human cGAS and two molecules of double-stranded DNA. In yet another embodiment, the human cGAS is in an active enzyme conformation. In another embodiment, the complex has the set of structural coordinates according to Table 3+/−the root mean square deviation from the backbone atoms of the hcGAS-DNA complex of less than 2 Angstroms. In still another embodiment, the conformation of the complex is the conformation shown in FIGS. 5B, 6A, 6C, 6D, 7D and/or 7E. In yet another embodiment, the complex has hcGAS and DNA contacts as those shown in FIGS. 6B and/or 7C.

In still another aspect, a modified hcGAS-DNA-ATP complex, wherein the complex comprises at least one double-stranded DNA, at least one human cGAS polypeptide having an amino acid sequence of a polypeptide described herein, and at least one ATP molecule, is provided.

As described above, numerous embodiments are further provided that can be applied to any aspect of the present invention and/or combined with any other embodiment described herein. For example, in one embodiment, the DNA is an activating DNA. In another embodiment, the DNA is 45 bp or longer. In still another embodiment, the DNA is a genomic DNA. In yet another embodiment, the human cGAS oligomerizes on the DNA. In another embodiment, the DNA is shorter than 45 bp. For example, the DNA may be 17 bp. In still another embodiment, the modified hcGAS-DNA complex comprises two molecules of human cGAS and two molecules of double-stranded DNA. In yet another embodiment, the human cGAS is in an active enzyme conformation. In another embodiment, the complex has the set of structural coordinates according to Table 3+/−the root mean square deviation from the backbone atoms of the hcGAS-DNA-ATP complex of less than 2 Angstroms. In still another embodiment, the conformation of the complex is the conformation shown in FIGS. 5C, 6D, 10A, and/or 10B.

In yet another aspect, a crystal of an hcGAS-DNA complex comprising an hcGAS polypeptide having an amino acid sequence of a polypeptide described herein and a double-stranded DNA, wherein the crystal effectively diffracts X-rays for the determination of the atomic coordinates of the hcGAS-DNA complex to a resolution of greater than 5.0 Angstroms, is provided.

As described above, numerous embodiments are further provided that can be applied to any aspect of the present invention and/or combined with any other embodiment described herein. For example, in one embodiment, the crystal has a hexagonal space group P $6_1$ 2 2. In another embodiment, the crystal has a unit cell of dimensions of a=b=101.17 Å, and c=241.06 Å. In still another embodiment, the crystal has the set of structural coordinates as given in Table 3+/−the root mean square deviation from the backbone atoms of the hcGAS-DNA complex of less than 2 Angstroms. In another embodiment, the crystal is obtained by hanging drop vapor diffusion. In still another embodiment, the crystal is obtained using a reservoir containing 0.1 M HEPES-NaOH pH 7.0 and 1.4 M sodium citrate. In another embodiment, the crystal has one copy of the hcGAS-DNA complex in the asymmetric unit. In still another embodiment, each hcGAS comprises two separate DNA-binding surfaces. In yet another embodiment, the DNA is a 17 bp activating DNA. In another embodiment, the DNA comprises a sense stand of SEQ ID NO: 8 and an antisense strand of SEQ ID NO: 9. In still another embodiment, the conformation of the complex is the conformation shown in FIGS. 5B, 6A, 6C, 6D, 7D and/or 7E. In yet another embodiment, the complex has hcGAS and DNA contacts as those shown in FIGS. 6B and/or 7C.

In another aspect, a crystal of an hcGAS-DNA-ATP complex comprising an hcGAS polypeptide having an amino acid sequence of a polypeptide described herein, an ATP, and a double-stranded DNA, wherein the crystal effectively diffracts X-rays for the determination of the atomic coordinates of the hcGAS-DNA-ATP complex to a resolution of greater than 5.0 Angstroms, is provided.

As described above, numerous embodiments are further provided that can be applied to any aspect of the present invention and/or combined with any other embodiment described herein. For example, in one embodiment, the crystal has a hexagonal space group P $6_1$ 2 2. In another embodiment, the crystal has a unit cell of dimensions of a=b=100.49 Å, and c=236.75 Å.

In still another embodiment, the crystal has the set of structural coordinates as given in Table 3+/−the root mean square deviation from the backbone atoms of the hcGAS-DNA-ATP complex of less than 2 Angstroms. In yet another embodiment, the crystal is obtained by hanging drop vapor diffusion. In another embodiment, the crystal is obtained using a reservoir containing 0.1 M HEPES-NaOH pH 7.0 and 1.4 M sodium citrate, and transferred to a solution without citrate. In still another embodiment, the crystal has one copy of the hcGAS-DNA-ATP complex in the asymmetric unit. In another embodiment, each hcGAS comprises two separate DNA-binding surfaces. In yet another embodiment, the DNA is a 17 bp activating DNA. In another embodiment, the DNA comprises a sense stand of SEQ ID NO: 8 and an antisense strand of SEQ ID NO: 9. In still another embodiment, the conformation of the complex is the conformation shown in FIGS. 5C, 6D, 10A, and/or 10B.

In still another aspect, a method for identifying an agent which modulates activity of hcGAS comprising the steps of: a) using a three-dimensional structure of a hcGAS-DNA complex as defined by atomic coordinates according to Table 3, or a three-dimensional structure of a hcGAS-DNA-ATP complex as defined by atomic coordinates according to Table 3; b) employing the three-dimensional structure to design or select an agent; c) synthesizing the agent; and d) contacting the agent with the hcGAS or a polypeptide described herein, or biologically active fragment thereof, to determine the ability of the agent to modulate activity of hcGAS, is provided.

As described above, numerous embodiments are further provided that can be applied to any aspect of the present invention and/or combined with any other embodiment described herein. For example, in one embodiment, the step of employing the three-dimensional structure to design or select an agent comprises the steps of: a) identify chemical entities or fragments capable of associating with the hcGAS; and b) assembling the identified chemical entities or fragments into a single molecule to provide the structure of the agent. In another embodiment, the agent is designed de novo. In still another embodiment, the agent is designed from a known agonist or antagonist of hcGAS. In yet another embodiment, the activity of hcGAS is selected from the group consisting of: a) 2'3' cGAMP synthesis; b) repression of V. cholera chemotaxis; c) enzyme kinetics; d) nucleotide coordination; e) protein stability; f) interactions with DNA; g) DNA-length specificity; h) enzyme conformation; and i) STING pathway activation.

In yet another aspect, a method of using an hcGAS polypeptide described herein to produce a crystal of an hcGAS-DNA complex comprising: a) contacting an hcGAS polypeptide described herein with a double-stranded DNA fragment, wherein the hcGAS polypeptide described herein forms a hcGAS-DNA complex with the DNA; and b) growing the crystal of the hcGAS-DNA complex; wherein the crystal effectively diffracts X-rays for the determination of the atomic coordinates of the hcGAS-DNA complex to a resolution of greater than 5.0 Angstroms, is provided.

As described above, numerous embodiments are further provided that can be applied to any aspect of the present invention and/or combined with any other embodiment described herein. For example, in one embodiment, said growing is performed by hanging drop vapor diffusion. In another embodiment, the crystal is grown using a reservoir containing 0.1 M HEPES-NaOH pH 7.0 and 1.4 M sodium citrate.

In another aspect, a method of using the three-dimensional structure coordinates of Table 3 comprising: a) determining structure factors from the coordinates; b) applying said structure factor information to a set of X-ray diffraction data obtained from a crystal of an hcGAS-DNA complex; and c) solving the three-dimensional structure of the hcGAS-DNA complex, is provided.

BRIEF DESCRIPTION OF THE DRAWINGS

FIG. 1A shows the cGAS production of 2'3' cGAMP in vitro with purified components. A concentration gradient of recombinant hcGAS and mcGAS was activated with 45 bp double-stranded DNA and 2'3' cGAMP formation was monitored by incorporation of [α-32P] ATP. Reactions were visualized by treating with alkaline phosphatase and separating by thin-layer chromatography. FIG. 1B shows a schematic of a rapid, genetic cGAS activity assay. V. cholerae harboring an overexpression plasmid encoding an MBP fusion protein were inoculated onto chemotaxis agar. As bacteria grow and consume nutrients, they swim outward towards fresh media (chemotaxis). cGAMP inhibits chemotaxis, which is visualized and quantified as the area of motile bacterial. FIG. 1C shows chemotaxis of V. cholerae strains overexpressing indicated cGAMP synthases. Genes were codon optimized and expressed as N-terminal MBP fusion proteins. Expression of each fusion protein 1 hour post induction at log phase was visualized by Western blot. Images are representative of at least three independent experiments. FIG. 1D and FIG. 1E shows quantification of V. cholerae chemotaxis repression for strains overexpressing the synthases indicated (SEQ ID NOs: 51-52, respectively, in order of appearance). Dotted line represents mcGAS level of repression for reference. Data are the mean+/−standard error of the mean (SEM) for ≥3 independent experiments. Schematic of hcGAS Chimera 4.3 and alignment of the mcGAS N172-R181 region replacing hcGAS K187-R196 was shown below. FIG. 1F shows analysis of hcGAS, mcGAS and hcGAS K187N/L195R enzyme kinetics. cGAS enzyme activity was measured as a function of varying ATP concentration, and 2'3' cGAMP product formation was quantified and fit according to Michaelis-Menten kinetics accounting for substrate inhibition. Data are the mean+/−SD of three independent experiments.

FIG. 3A shows in vitro analysis of hcGAS and mcGAS activation in response to bacterial genomic DNA. 2'3' cGAMP synthesis in the presence of purified V. cholerae genomic DNA was visualized by with thin-layer chromatography as in FIG. 1A and quantified relative to maximal activity observed with mcGAS. Data are represented as mean±SD of three independent experiments. FIG. 3B shows quantification of V. cholerae chemotaxis repression for strains overexpressing the synthases indicated. Schematic representation of chimeric and mutant cGAS constructs is shown left. Metal coordinating residues in the active site are represented as asterisks, the Zn-ribbon is represented in orange, amino acid numbers are colored magenta for hcGAS and blue for mcGAS. Schematic is not to scale. Reference dotted lines represent mcGAS (in blue) or hcGAS (in magenta) levels of repression. Data are the mean+/−SEM for ≥3 independent experiments. FIG. 3C shows in vitro analysis of hcGAS and mcGAS activation in response to bacterial genomic DNA. 2'3' cGAMP synthesis in the presence of purified *V. cholerae* genomic DNA was visualized by thin-layer chromatography as in FIG. 1A and quantified relative to maximal activity observed with mcGAS. Data are represented as mean±SD of three independent experiments.

FIG. 4A shows the purified hcGAS and mcGAS enzymes used in this study. Purified recombinant cGAS (~1 pg each) was resolved on a denaturing SDS-PAGE gel and visualized with coomassie G-250 stain. Initial chimera screening was conducted with 6×His-SUMO2-tagged ("6×His" disclosed as SEQ ID NO: 50) cGAS variants purified with Ni-NTA affinity. All subsequent biochemistry was performed with 1 untagged cGAS variants purified with Ni-NTA, Heparin ion-exchange, and SUPERDEX® S75 size-exclusion chromatography. FIG. 4B shows in vitro analysis of hcGAS chimera 2'3' cGAMP synthesis. The relative 2'3' cGAMP synthesis levels of key active hcGAS chimeras were visualized by thin-layer chromatography as in FIG. 1A, and compared to relative levels of wildtype hcGAS and mcGAS activity. The minimal element required for human-like cGAS regulation maps to chimera 4.3 (Chi 4.3). Data are representative of at least two individual experiments.

FIG. 5A shows in vitro analysis of the role of hcGAS K187 and L195 variation 1 in 2'3' cGAMP synthesis regulation. Human and mouse amino acid sequences at 187 (human K187 and mouse-equivalent N187, denoted K or N) and 195 (denoted L or R) were analyzed in both hcGAS and mcGAS backgrounds. Enzymes were stimulated with 45 bp DNA, and 2'3' cGAMP synthesis was measured as in FIG. 1A and quantified relative to maximal activity observed with mcGAS. Data are the mean+/−SD of three independent experiments. FIG. 5B shows the schematic and overview of the hcGAS-DNA complex. hcGAS forms a 2:2 complex with DNA where each cGAS monomer has two distinct DNA-binding surfaces (DNA A-Site and DNA B Site). Stars in the schematic denote the enzyme metal-coordinating active site residues, schematic not to scale. FIG. 5C shows the overview of a single 1:1 cGAS-DNA unit in the hcGAS-DNA-ATP complex. Zoom-in cutaways of the locations of K187 and L195 human-specific cGAS substitutions in the DNA A site. The water molecule coordinated by the K187N mutation and Y215 is depicted as a grey sphere.

FIG. 6A shows 2Fo-Fc electron density map of the 2.3 A hcGAS-DNA complex (contoured at 1.0 6). hcGAS protein is shown as a ribbon (magenta) and the double-stranded DNA is shown as sticks (yellow). FIG. 6B shows the schematic map of protein-DNA contacts in the hcGAS-DNA and mcGAS-DNA complexes. Human-specific contacts are highlighted in magenta, and mouse-specific contacts are highlighted in blue. Black dots denote interactions bridged by water molecules. Black labels indicate contacts directly observed in the hcGAS-DNA complex, grey labels indicate water-mediated contacts potentially conserved with mcGAS but not observed in the hcGAS-DNA complex. FIG. 6C shows superposition of apo hcGAS (PDB 4KM5, grey) and the hcGAS-DNA complex (magenta). FIG. 6D shows the superposition of the hcGAS-DNA complex (grey) and hcGAS-DNA-ATP ternary complex (magenta). The mechanism of hcGAS structural activation upon DNA-binding is conserved with mammalian cGAS homologs (Civril et al. (2013) *Nature* 498, 332-337; Gao et al. (2013) *Cell* 153:1094-1107; Li et al. (2013) *Immunity* 39:1019-1031; Zhang et al. (2014) *Cell Rep* 6:421-430). Double-stranded DNA recognition causes a conformational change in cGAS resulting in remodeling of the N-terminal "spine helix" (shown in inset of C) and repositioning of an active site loop that allows metal coordination and nucleotide binding (depicted in inset of D).

FIG. 7A shows a cladogram depicting evolution of hcGAS DNA A-site K187 and L195 positions in primates and relevant vertebrates. Human-specific substitutions are denoted in magenta, and the mouse cGAS sequence is denoted in blue as reference. FIG. 7B shows the electrophoretic mobility shift assay measurement of in vitro cGAS-DNA complex formation. hcGAS and mcGAS variants were incubated with 45 bp DNA and the resulting stable complexes were resolved on a 2% agarose gel. FIG. 7C shows a schematic map of protein-DNA contacts in the hcGAS-DNA complex. Human-specific contacts are highlighted in magenta, and black dots denote interactions bridged by water molecules. Black labels indicate contacts directly observed in the hcGAS-DNA complex, grey labels indicate water-mediated contacts potentially conserved with mcGAS but not observed in the hcGAS-DNA complex. FIG. 7D shows an overview of the hcGAS-DNA complex highlighting the location of human-specific DNA A-site and B-site substitutions. A-site substitutions have a major role in enzyme regulation, and B-site substitutions play an additional minor role. Human-specific substitutions are shown as sticks in magenta, and the mouse-like K187N and L195R DNA A-site mutations are denoted in blue. One cGAS protein monomer from the 2:2 complex is omitted for clarity. FIG. 7E shows a cartoon model of the hcGAS bound to short DNA (yellow) overlaid with the path of long DNA (orange) derived from the mcGAS-39 bp DNA structure (PDB 5N6I). Human-specific cGAS substitutions (magenta) weaken DNA-interactions in a portion of the DNA-binding surface that is not required for recognition of long DNA. Short and long DNA share identical interactions in the top conserved portion of the cGAS DNA A-site (blue), but assembly of an oligomerized cGAS-DNA complex causes long DNA to curve away and no longer make contacts with the bottom portion of the cGAS DNA A-site where the human-specific substitutions K187 and L195 are located.

FIG. 8A-FIG. 8E shows that human-specific cGAS substitutions in the DNA B site refine control DNA recognition and enzyme regulation. FIG. 8A shows a cladogram depicting evolution of hcGAS DNA A-site and B-site substitutions in primates. Human-specific substitutions are denoted in magenta, and the mouse cGAS sequence is denoted in blue for reference. FIG. 8B shows an in vitro analysis of the role of hcGAS DNA B-site variation in 2'3' cGAMP synthesis regulation. Human and mouse amino acid sequences at S328, K350, and L354 (human S328/K350/L354 and mouse-equivalent G/T/R positions are denoted SKL or GTR respectively) were analyzed in both hcGAS and mcGAS backgrounds. Enzymes were stimulated with 45 bp DNA, and 2'3' cGAMP synthesis was measured as in FIG. 1A and quantified relative to maximal activity observed with mcGAS. Data are the mean+/−SD of at least two independent experiments. FIG. 8C shows the in vitro electrophoretic mobility shift assay measurement of cGAS-DNA complex formation. hcGAS and mcGAS variants were incubated with 45 bp DNA and the resulting stable complexes were resolved on a 2% agarose gel. FIG. 8D shows in vitro electrophoretic mobility shift assay measurement of WT mcGAS-DNA and hcGAS K187N/L195R (NR)-DNA complex formation. Complexes were assembled directly in low salt (75 mM KCl) and visualized on a 2% agarose gel. Alternatively, cGAS-DNA complexes were assembled during gradient dialysis (400 to 50 mM KCl, over 48 h) to specifically monitor stable complex formation. FIG. 8E shows in vitro analysis of hcGAS, mcGAS, and hcGAS K187N/L195R (NR) 2'3' cGAMP synthesis, confirming that the elevated protein concentration conditions used for the electrophoretic mobility shift assay analysis support functional enzyme activation. The relative 2'3' cGAMP synthesis levels were visualized by thin-layer chromatography as in FIG. 1A, and compared to relative levels of WT mcGAS activity. Data are representative of at least two individual experiments.

FIG. 9A-FIG. 9C show that human cGAS adaptations re-shape DNA length specificity. FIG. 9A shows an in vitro analysis of cGAS DNA length-specificity. Purified hcGAS and mcGAS enzymes were stimulated with increasing concentration of 45 bp (top) or 17 bp (bottom) DNA. Enzyme activation was analyzed as in FIG. 1A. Unlike mcGAS, hcGAS is only able to activate 2'3' cGAMP synthesis in the presence of long 45 bp DNA. FIG. 9B shows an identical experiment as in FIG. 9A, using mcGAS with human-like K187 and L195 substitutions or hcGAS with mouse-like N187 and R195 substitutions. Human-specific K187 and L195 substitutions are necessary and sufficient for cGAS length-dependent DNA discrimination. FIG. 9C shows the quantification of cGAS DNA length-dependent activation experiments in FIGS. 9A and 9B. 2'3' cGAMP synthesis was quantified as in FIG. 1A and graphed as total conversion of ATP to 2'3' cGAMP. Data are the mean+/−SD of three independent experiments.

FIG. 10A-FIG. 10J shows that the hcGAS-DNA structure provides insight into small molecule inhibitor design and tumor-associated mutations. FIG. 10A shows tumor-associated mutations in cGAS (Konno et al. (2018) *Oncogene* 37:2037-2051) and the proposed structural role of each mutated residue in the hcGAS-DNA-ATP ternary complex.

FIG. 10B shows the highlights of the tumor-associated mutations in hcGAS on the hcGAS-DNA-ATP ternary complex. FIG. 10C-FIG. 10F show an overview of a single 1:1 cGAS-unit in the hcGAS-DNA-ATP ternary complex with (FIGS. 10D, 10E, and 10F) zoom-in cutaways of the cGAS active-site showing protein residues in contact with ATP and small molecule inhibitors. Nucleotide substrate and inhibiting compounds are shown in green, human specific cGAS substitutions are in magenta, corresponding mcGAS residues are in blue, and conserved active-site amino acids are in grey. FIG. 10E shows the mcGAS RU.521 image derived from the mcGAS-DNA-RU.521 structure (PDB 5XZG) (Vincent et al. (2017) *Nat Commun* 8:750). FIG. 10F shows the hcGAS inhibitor PF-06928215 is modeled into the hcGAS-DNA-ATP ternary complex structure based on superposition with the apo hcGAS structure (PDB 5V8N) (Hall et al. (2017) *PLoS One* 12: e0184843). FIG. 10G-FIG. 10J shows molecular docking analysis of the compatibility of existing cGAS inhibitors with the active hcGAS-DNA complex. All top docked inhibitor poses of the mcGAS inhibitor RU.521 (PDB: 5XZG) and hcGAS inhibitor PF-06928215 (PDB: 5V8N) shown in orange lines are compatible with the mcGAS-DNA complex and apo hcGAS structure, respectively, and agree with the experimentally derived crystallographic binding poses shown in green sticks for reference. In contrast, the docked inhibitor poses with the active hcGAS-DNA complex structure are distinct, further confirming that the hcGAS active site differs from previously observed structures.

FIG. 11A shows that human-specific substitutions modify cGAS to have increased DNA length specificity. Control of DNA sensing must be balanced to maintain sensitivity to pathogen-or stress-derived DNA, and allow accurate tolerance of non-immunostimulatory self-DNA. Human substitutions in cGAS reshape this balance, and reduce 2'3' cGAMP synthesis in order to favor enhanced DNA selectivity. FIG. 11B shows that binding of DNA to cGAS induces a large conformational change, resulting in an "open" active site conformation that is competent to associate with nucleotides for 2'3' cGAMP synthesis. Structures of active human cGAS is critical to guide drug development and analysis of human disease-related cGAS polymorphisms.

FIG. 12A shows the purified full-length hcGAS enzymes used in this study. Full-length variants were expressed as 6 3 His-SUMO2-tagged fusions and purified with Ni-NTA, Heparin ion-exchange, and SUPERDEX® S200 size-exclusion chromatography. Each protein (rv1 mg each) was resolved on a denaturing SDS-PAGE gel and visualized with Coomassie G-250 stain. FIG. 12B shows the in vitro analysis of full-length hcGAS and hcGAS K187N/L195R (NR) 2'3' cGAMP synthesis and DNA-length specificity. Purified full-length hcGAS variants were stimulated with increasing concentration of 45 bp (top) or 17 bp (bottom) DNA, and enzyme activation was visualized as in FIG. 1A and analyzed as in FIG. 9. Human-specific K187 and L195 cGAS substitutions prevent activation of 2'3' cGAMP synthesis in the presence of short 17 bp DNA. FIG. 12C shows quantification of cGAS DNA length-dependent activation experiments in FIG. 12B. 2'3' cGAMP synthesis was quantified as in FIG. 1A and graphed as total conversion of ATP to 2'3' cGAMP. Data are represented as mean±SD of three independent experiments.

FIG. 13A shows the in vitro analysis of mcGAS and hcGAS K187N/L195R (hcGAS*) 2'3' cGAMP synthesis with increasing concentration of the mcGAS inhibitor RU.521. Enzyme activation was analyzed as in FIG. 1A. FIG. 13B shows an identical experiment as in FIG. 13A, using mcGAS with humanizing C419S/H467N mutations or hcGAS* with mouse-like S434C/N482H mutations in the inhibitor binding pocket. Mouse-specific C419 and H467 substitutions are necessary and sufficient for susceptibility to RU.521. FIG. 13C shows quantification of cGAS inhibition by RU.521. 2'3' cGAMP synthesis was quantified as in FIG. 1A and was normalized to the DMSO control (set as 100%). Data are represented as mean±SD of two independent experiments.

FIG. 14A-FIG. 14D show that human-specific substitutions impact the potency of cGAS small-molecule inhibition. FIG. 14A-FIG. 14B show the in vitro analysis of hcGAS, mcGAS, and hcGAS K187N/L195R (hcGAS*) 2'3' cGAMP synthesis with increasing concentration of cGAS inhibitor RU.521 (FIG. 14A) or PF-06928215 (FIG. 14B). Enzyme activation was analyzed as in FIG. 1A, and inhibition was quantified and normalized to the DMSO control (set as 100%). Data are represented as mean±SD of two independent experiments. RU.521 more potently blocks mcGAS and the PF-06928215 compound more potently blocks hcGAS. hcGAS* exhibits similar inhibitor sensitivities as WT hcGAS, and was selected for further inhibition analysis due to elevated levels of 2'3' cGAMP synthesis. FIG. 14C shows a cladogram depicting evolution of hcGAS S434/N482 in primates. Human-like substitutions are denoted in magenta, and the mcGAS sequence is denoted in blue for reference. FIG. 14D shows the SDS-PAGE and Coomassie G-250 analysis of purified mcGAS and hcGAS* inhibitor binding site variants used in this study (~1 mg each).

Figure 1A:
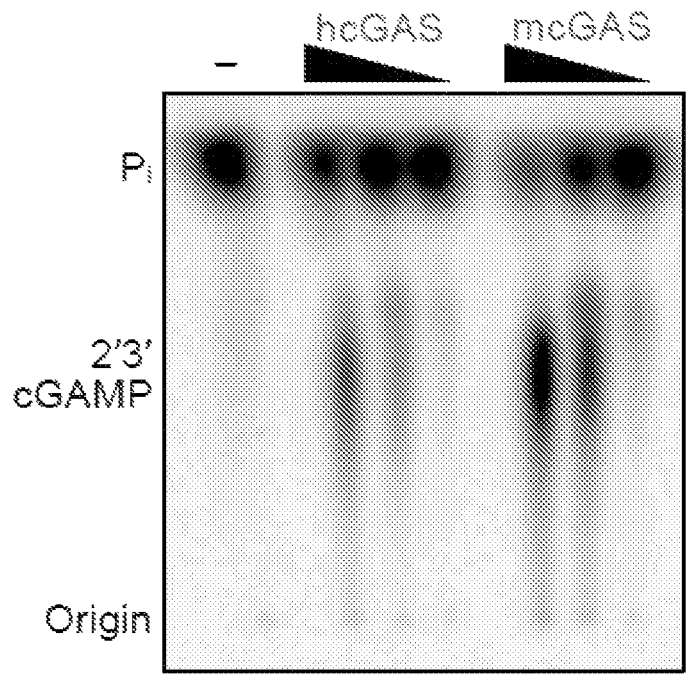
FIG. 1A-FIG. 1F show that a rapid cGAS activity assay in bacteria reveals the molecular determinants of human-specific cGAS regulation.

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the elucidation of the structure of hcGAS in an active conformation bound to DNA, and the identification of a functional role of human-specific divergence in cGAS sequence in balancing DNA-sensing specificity and sensitivity. Using reconstitution of cGAMP signaling in bacteria, the molecular determinant of human cGAS regulation was mapped to two amino acid substitutions in the DNA-binding surface, hcGAS K187 and L195. Human-specific substitutions were necessary and sufficient to dramatically enhance the ability of cGAS to discriminate short and long DNAs. High-resolution crystal structures of the active hcGAS-DNA complex revealed why human K187 and L195 substitutions are necessary for stringent DNA-length specificity, and explained how human-specific substitutions remodel DNA interactions to favor higher-order cGAS-DNA oligomerization. The study defined how human DNA-sensing adapted for enhanced specificity, and provide a model of the active human cGAS-DNA complex to enable structure-guided design of cGAS therapeutics. Accordingly, compositions based on the modified hcGAS polypeptide, the modified hcGAS-DNA complex, the modified hcGAS-DNA-ATP complex, and methods of use thereof, such as methods of screening for modulators of hcGAS, are provided.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes.

The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

Unless otherwise specified here within, the terms "antibody" and "antibodies" broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site.

Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a modified hcGAS polypeptide of the present invention, or a complex thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, protein subunit peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a modified hcGAS polypeptide. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, have been grafted onto human framework sequences.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

As used herein, the term "isotype" refers to the antibody class (e.g., IgM, IgG1, IgG2C, and the like) that is encoded by heavy chain constant region genes.

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenstram's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "inhibiting" and grammatical equivalents thereof refer decrease, limiting, and/or blocking a particular action, function, or interaction. A reduced level of a given output or parameter need not, although it may, mean an absolute absence of the output or parameter. The invention does not require, and is not limited to, methods that wholly eliminate the output or parameter. The given output or parameter can be determined using methods well-known in the art, including, without limitation, immunohistochemical, molecular biological, cell biological, clinical, and biochemical assays, as discussed herein and in the examples. The opposite terms "promoting," "increasing," and grammatical equivalents thereof refer to the increase in the level of a given output or parameter that is the reverse of that described for inhibition or decrease.

As used herein, the term "interacting" or "interaction" means that two molecules (e.g., protein, nucleic acid), or fragments thereof, exhibit sufficient physical affinity to each other so as to bring the two interacting molecules, or fragments thereof, physically close to each other. An extreme case of interaction is the formation of a chemical bond that results in continual and stable proximity of the two entities. Interactions that are based solely on physical affinities, although usually more dynamic than chemically bonded interactions, can be equally effective in co-localizing two molecules. Examples of physical affinities and chemical bonds include but are not limited to, forces caused by electrical charge differences, hydrophobicity, hydrogen bonds, Van der Waals force, ionic force, covalent linkages, and combinations thereof. The state of proximity between the interaction domains, fragments, proteins or entities may be transient or permanent, reversible or irreversible. In any event, it is in contrast to and distinguishable from contact caused by natural random movement of two entities. Typically, although not necessarily, an "interaction" is exhibited by the binding between the interaction domains, fragments, proteins, or entities. Examples of interactions include specific interactions between antigen and antibody, ligand and receptor, enzyme and substrate, and the like.

Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

An "interaction" between two molecules, or fragments thereof, can be determined by a number of methods. For example, an interaction can be determined by functional assays. Such as the two-hybrid Systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, (1995) *Microbiol. Rev.*, 59:94-123.

As used herein, a "kit" is any manufacture (e.g. a package or container) comprising at least one reagent, e.g. a probe, for specifically detecting or modulating the expression of a modified human cGAS polypeptide of the present invention. The kit may be promoted, distributed, or sold as a unit for performing the methods of the present invention.

As used herein, the term "modulate" includes up-regulation and down-regulation, e.g., enhancing or inhibiting the expression and/or acticity of the modified hcGAS polypeptide of the present invention.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a polypeptide or fragment thereof, in which the protein is separated from cellular components of the cells from which it is isolated or recombinantly produced. In one embodiment, the language "substantially free of cellular material" includes preparations of a modified hcGAS polypeptide or fragment thereof, having less than about 30% (by dry weight) of non-hcGAS protein (also referred to herein as a "contaminating protein"), more preferably less than about 20% of non-hcGAS protein, still more preferably less than about 10% of non-hcGAS protein, and most preferably less than about 5% non-hcGAS protein.

When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" is intended to refer to a nucleic acid molecule in which the nucleotide sequences are free of other nucleotide sequences, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the present invention. BLAST protein searches can be performed with the XBLAST program, score=50, wordlength=3 to obtain amino acid sequences homologous to the protein molecules of the present invention. To obtain gapped alignments for comparison purposes, Gapped BLAST can be utilized as described in Altschul et al., (1997) *Nucleic Acids Res.* 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well-known in the art (see, F. Ausubel, et al., ed. *Current Protocols in Molecular Biology, Greene Publishing and* Wiley Interscience, *New York* (1987)).

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a modified hcGAS nucleic acid and normal post-transcriptional processing (e.g. splicing), if any, of the RNA transcript, and reverse transcription of the RNA transcript.

An "RNA interfering agent" as used herein, is defined as any agent which interferes with or inhibits expression of a target gene by RNA interference (RNAi). Such RNA interfering agents include, but are not limited to, nucleic acid molecules including RNA molecules which are homologous to a modified hcGAS nucleic acid of the present invention, or a fragment thereof, short interfering RNA (siRNA), and small molecules which interfere with or inhibit expression of a target modified hcGAS nucleic acid by RNA interference (RNAi).

"RNA interference (RNAi)" is an evolutionarily conserved process whereby the expression or introduction of RNA of a sequence that is identical or highly similar to a target modified hcGAS nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target modified hcGAS nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target modified hcGAS nucleic acids. As used herein, "inhibition of a modified hcGAS nucleic acid expression" or "inhibition of modified hcGAS gene expression" includes any decrease in expression or protein activity or level of the modified hcGAS nucleic acid or protein encoded by the modified hcGAS nucleic acid. The decrease may be of at least 30%, 40%, 50%, 60%, 70%, 80%, 90%, 95% or 99% or more as compared to the expression of a modified hcGAS nucleic acid or the activity or level of the protein encoded by a modified hcGAS nucleic acid which has not been targeted by an RNA interfering agent.

In addition to RNAi, genome editing can be used to modulate the copy number or genetic sequence of a protein of interest, such as constitutive or induced knockout or mutation of a protein of interest, such as a modified hcGAS polypeptide of the present invention. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47).

Such genetic strategies can use constitutive expression systems or inducible expression systems according to well-known methods in the art. "Piwi-interacting RNA (piRNA)" is the largest class of small non-coding RNA molecules. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. However, like other small RNAs, piRNAs are thought to be involved in gene silencing, specifically the silencing of transposons. The majority of piRNAs are antisense to transposon sequences, indicating that transposons are the piRNA target. In mammals it appears that the activity of piRNAs in transposon silencing is most important during the development of the embryo, and in both *C. elegans* and humans, piRNAs are necessary for spermatogenesis. piRNA has a role in RNA silencing via the formation of an RNA-induced silencing complex (RISC).

"Aptamers" are oligonucleotide or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. The "Affimer protein", an evolution of peptide aptamers, is a small, highly stable protein engineered to display peptide loops which provides a high affinity binding surface for a specific target protein. It is a protein of low molecular weight, 12-14 kDa, derived from the cysteine protease inhibitor family of cystatins. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

"Short interfering RNA" (siRNA), also referred to herein as "small interfering RNA" is defined as an agent which functions to inhibit expression of a modified hcGAS nucleic acid, e.g., by RNAi. A siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, a siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a host cell or organism, to inhibit expression of a modified hsGAS polypeptide of the present invention and thereby inhibit the expression and/or activity of hsGAS.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

As used herein, the term "molecular complex" means a composite unit that is a combination of two or more molecular components (e.g., protein, nucleic acid, nucleotide, compound) formed by interaction between the molecular components. Typically, but not necessarily, a "molecular complex" is formed by the binding of two or more molecular components together through specific non-covalent binding interactions. However, covalent bonds may also be present between the interacting partners. For instance, the two interacting partners can be covalently crosslinked so that the molecular complex becomes more stable. The molecular complex may or may not include and/or be associated with other molecules such as nucleic acid, such as RNA or DNA, or lipids or further cofactors or moieties selected from a metal ions, hormones, second messengers, phosphate, sugars. A "molecular complex" of the invention may also be part of or a unit of a larger physiological molecular complex assembly.

The term "isolated molecular complex" means a molecular complex present in a composition or environment that is different from that found in nature, in its native or original cellular or body environment. Preferably, an "isolated molecular complex" is separated from at least 50%, more preferably at least 75%, most preferably at least 90% of other naturally co-existing cellular or tissue components. Thus, an "isolated molecular complex" may also be a naturally existing molecular complex in an artificial preparation or a non-native host cell. An "isolated molecular complex" may also be a "purified molecular complex", that is, a substantially purified form in a substantially homogenous preparation substantially free of other cellular components, other polypeptides, viral materials, or culture medium, or, when the components in the molecular complex are chemically synthesized, free of chemical precursors or by-products associated with the chemical synthesis. A "purified molecular complex" typically means a preparation containing preferably at least 75%, more preferably at least 85%, and most preferably at least 95% of a particular molecular complex. A "purified molecular complex" may be obtained from natural or recombinant host cells or other body samples by standard purification techniques, or by chemical synthesis.

The term "modified molecular complex" means a molecular complex present in a composition that is different from that found in nature, in its native or original cellular or body environment. The term "modification" as used herein refers to all modifications of a protein, DNA, or protein-DNA complex of the invention including cleavage and addition or removal of a group. In some embodiments, the "modified molecular complex" comprises at least one modified hcGAS polypeptide, i.e., different from that found in nature, in its native or original cellular or body environment. The "modified hcGAS polypeptide" of this invention may be, e.g., homolog, derivative, or fragment of native human cGAS polypeptide having an amino acid sequence of SEQ ID NO: 1 that comprises amino acid substitutions at positions corresponding to K187 and L195 of SEQ ID NO: 1. Preferably, the "modified hcGAS polypeptide" has one or more following biologically activities: a) increased 2'3' cGAMP synthesis compared to human cGAS; b) increased repression of *V. cholera* chemotaxis compared to human cGAS; c) similar enzyme kinetics to mouse cGAS; d) recognizing DNA shorter than 45 bp; e) stabilized active enzyme conformation; f) stabilized interactions with DNA; and g) increased minimal cGAS-DNA complex formation compared to human cGAS. The term "modified hcGAS nucleic acid" refers to nucleic acid (e.g., DNA, mRNA) that encodes the modified hcGAS polypeptide of described herein.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

If not stated otherwise, the term "compound" as used herein are include but are not limited to peptides, nucleic acids, carbohydrates, natural product extract libraries, organic molecules, preferentially small organic molecules, inorganic molecules, including but not limited to chemicals, metals and organometallic molecules.

The terms "derivatives", "analogs" or "variants" as used herein include, but are not limited to molecules comprising regions that are substantially homologous to the modified hcGAS polypeptide, in various embodiments, by at least 30%, 40%, 50%, 60%, 70%, 80%, 90%, 95% or 99% identity over an amino acid sequence of identical size or when compared to an aligned sequence in which the alignment is done by a computer homology program known in the art, or whose encoding nucleic acid is capable of hybridizing to a sequence encoding the component protein under stringent, moderately stringent, or nonstringent conditions. It means a protein which is the outcome of a modification of the naturally occurring protein, by amino acid substitutions, deletions and additions, respectively, which derivatives still exhibit the biological function of the naturally occurring protein although not necessarily to the same degree. The biological function of such proteins can e.g. be examined by suitable available in vitro assays as provided in the invention.

The term "functionally active" as used herein refers to a polypeptide, namely a fragment or derivative, having structural, regulatory, or biochemical functions of the protein according to the embodiment of which this polypeptide, namely fragment or derivative is related to.

"Function-conservative variants" are those in which a given amino acid residue in a protein or enzyme has been changed without altering the overall conformation and function of the polypeptide, including, but not limited to, replacement of an amino acid with one having similar properties (e.g., polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGA-LIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxyl-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non- antibody, polypeptide, peptide or fusion protein chemicals.

The term "activity" when used in connection with proteins or molecular complexes means any physiological or biochemical activities displayed by or associated with a particular protein or molecular complex including but not limited to activities exhibited in biological processes and cellular functions, ability to interact with or bind another molecule or a moiety thereof, binding affinity or specificity to certain molecules, in vitro or in vivo stability (e.g., protein degradation rate, or in the case of molecular complexes ability to maintain the form of molecular complex), antigenicity and immunogenecity, enzymatic activities, etc. Such activities may be detected or assayed by any of a variety of suitable methods as will be apparent to skilled artisans.

As used herein, the term "interaction antagonist" means a compound that interferes with, blocks, disrupts or destabilizes a protein-protein interaction or a protein-DNA interaction; blocks or interferes with the formation of a molecular complex, or destabilizes, disrupts or dissociates an existing molecular complex.

The term "interaction agonist" as used herein means a compound that triggers, initiates, propagates, nucleates, or otherwise enhances the formation of a protein-protein interaction or a protein-DNA interaction; triggers, initiates, propagates, nucleates, or otherwise enhances the formation of a molecular complex; or stabilizes an existing molecular complex.

The terms "polypeptides" and "proteins" are, where applicable, used interchangeably herein. They may be chemically modified, e.g. post-translationally modified. For example, they may be glycosylated or comprise modified amino acid residues. They may also be modified by the addition of a signal sequence to promote their secretion from a cell where the polypeptide does not naturally contain such a sequence. They may be tagged with a tag. They may be tagged with different labels which may assists in identification of the proteins in a molecular complex. Polypeptides/proteins for use in the invention may be in a substantially isolated form. It will be understood that the polypeptide/protein may be mixed with carriers or diluents which will not interfere with the intended purpose of the polypeptide and still be regarded as substantially isolated. A polypeptide/protein for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

The terms "hybrid protein", "hybrid polypeptide," "hybrid peptide", "fusion protein", "fusion polypeptide", and "fusion peptide" are used herein interchangeably to mean a non-naturally occurring protein having a specified polypeptide molecule covalently linked to one or more polypeptide molecules that do not naturally link to the specified polypeptide. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or fused together by a peptide bond forming a single non-branched polypeptide chain.

The term "tag" as used herein is meant to be understood in its broadest sense and to include, but is not limited to any suitable enzymatic, fluorescent, or radioactive labels and suitable epitopes, including but not limited to HA-tag, Myc-tag, T7, His-tag, FLAG® tag, Calmodulin binding proteins, glutathione-S-transferase, strep-tag, KT3-epitope, EEF-epitopes, green-fluorescent protein and variants thereof.

The term "structure coordinates" refers to mathematical detercoordinates derived from mathematical equations related to the patterns obtained on diffraction of a monochromatic beam of X-rays by the atoms (scattering centers) of a molecule or molecule complex in crystal form. The diffraction data are used to calculate an electron density map of the repeating unit of the crystal. The electron density maps are used to establish the positions of the individual atoms within the unit cell of the crystal.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of human cGAS or a binding pocket portion thereof, as defined by the structure coordinates of human cGAS described herein.

The term "binding pocket," as used herein, refers to a region of a molecule or molecular complex, which, as a result of its shape, favorably associates with another chemical entity. Thus, a binding pocket may include or consist of features such as cavities, surfaces, or interfaces between domains. Chemical entities that may associate with a binding pocket include, but are not limited to, cofactors, substrates, modifiers, agonists, and antagonists.

The term "unit cell" refers to a basic parallelipiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal.

The term "molecular replacement" refers to a method that involves generating a preliminary model of an hcGAS crystal whose structure coordinates are unknown, by orienting and positioning a molecule whose structure coordinates are known (e.g., hcGAS coordinates from Table 3) within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal (Lattman et al. (1985) *Methods in Enzymology* 115:55-77; M. G.

Rossmann, ed., "The Molecular Replacement Method", Int. Sci. Rev. Ser., No. 13, Gordon & Breach, New York, (1972)). Using the structure coordinates of hcGAS provided by this invention, molecular replacement may be used to determine the structure coordinates of a crystalline mutant or homologue of hcGAS or of a different crystal form of hcGAS.

In the context of this invention, the term "crystal" refers to a regular assemblage of a modified human cGAS polypeptide or a complex of a modified human cGAS polypeptide for X-ray crystallography. That is, the assemblage produces an X-ray diffraction pattern when illuminated with a beam of X-rays. Thus, a crystal is distinguished from an agglomeration or other complex of hcGAS that does not give a diffraction pattern.

The term "STING" or "stimulator of interferon genes", also known as transmembrane protein 173 (TMEM173), refers to a five transmembrane protein that functions as a major regulator of the innate immune response to viral and bacterial infections. STING is a cytosolic receptor that senses both exogenous and endogenous cytosolic cyclic dinucleotides (CDNs), activating TBK1/IRF3 (interferon regulatory factor 3), NF-κB (nuclear factor KB), and STAT6 (signal transducer and activator of transcription 6) signaling pathways to induce robust type I interferon and proinflammatory cytokine responses. The term "STING" is intended to include fragments, variants (e.g., allelic variants) and derivatives thereof. Representative human STING cDNA and human STING protein sequences are well-known in the art and are publicly available from the National Center for Biotechnology Information (NCBI). Human STING isoforms include the longer isoform 1 (NM_198282.3 and NP_938023.1), and the shorter isoform 2 (NM_001301738.1 and NP_001288667.1; which has a shorter 5' UTR and lacks an exon in the 3' coding region which results in a shorter and distinct C-terminus compared to variant 1). Nucleic acid and polypeptide sequences of STING orthologs in organisms other than humans are well-known and include, for example, chimpanzee STING (XM_016953921.1 and XP_016809410.1; XM_009449784.2 and XP_009448059.1; XM_001135484.3 and XP_001135484.1), monkey STING (XM_015141010.1 and XP_014996496.1), dog STING (XM_022408269.1 and XP_022263977.1; XM_005617260.3 and XP_005617317.1; XM_022408249.1 and XP_022263957.1; XM_005617262.3 and XP_005617319.1; XM_005617258.3 and XP_005617315.1; XM_022408253.1 and XP_022263961.1; XM_005617257.3 and XP_005617314.1; XM_022408240.1 and XP_022263948.1; XM_005617259.3 and XP_005617316.1; XM_022408259.1 and XP_022263967.1; XM_022408265.1 and XP_022263973.1), cattle STING (NM_001046357.2 and NP_001039822.1), mouse STING (NM_001289591.1 and NP_001276520.1; NM_001289592.1 and NP_001276521.1; NM_028261.1 and NP_082537.1), and rat STING (NM_001109122.1 and NP_001102592.1).

STING agonists have been shown as useful therapies to treat cancer. Agonists of STING well-known in the art and include, for example, MK-1454, STING agonist-1 (MedChem Express Cat No. HY-19711), cyclic dinucleotides (CDNs) such as cyclic di-AMP (c-di-AMP), cyclic-di-GMP (c-di-GMP), cGMP-AMP (2'3'cGAMP or 3'3'cGAMP), or 10-carboxymethyl-9-acridanone (CMA) (Ohkuri et al. (2015) *Oncoimmunology* 4(4):e999523), rationally designed synthetic CDN derivative molecules (Fu et al. (2015) *Sci Transl Med.* 7(283):283ra52. doi: 10.1126/scitranslmed.aaa4306), and 5,6-dimethyl-xanthenone-4-acetic acid (DMXAA) (Corrales et al. (2015) *Cell Rep.* 11(7):1018-1030). These agonists bind to and activate STING, leading to a potent type I IFN response. On the other hand, targeting the cGAS-STING pathway with small molecule inhibitors would benefit for the treatment of severe debilitating diseases such as inflammatory and autoimmune diseases associated with excessive type I IFNs production due to aberrant DNA sensing and signaling. STING inhibitors are also known and include, for example, CCCP (MedChem Express, Cat No. HY-100941) and 2-bromopalmitate (Tao et al. (2016) *IUBMB Life.* 68(11):858-870). It is to be noted that the term can further be used to refer to any combination of features described herein regarding STING molecules. For example, any combination of sequence composition, percentage identify, sequence length, domain structure, functional activity, etc. can be used to describe a STING molecule of the present invention.

The term "STING pathway" or "cGAS-STING pathway" refers to a STING-regulated innate immune pathway, which mediates cytosolic DNA-induced signalling events. Cytosolic DNA binds to and activates cGAS, which catalyzes the synthesis of 2'3'-cGAMP from ATP and GTP. 2'3'-cGAMP binds to the ER adaptor STING, which traffics to the ER-Golgi intermediate compartment (ERGIC) and the Golgi apparatus. STING then activates IKK and TBK1. TBK1 phosphorylates STING, which in turn recruits IRF3 for phosphorylation by TBK1. Phosphorylated IRF3 dimerizes and then enters the nucleus, where it functions with NF-kB to turn on the expression of type I interferons and other immunomodulatory molecules. The cGAS-STING pathway not only mediates protective immune defense against infection by a large variety of DNA-containing pathogens but also detects tumor-derived DNA and generates intrinsic antitumor immunity. However, aberrant activation of the cGAS-STING pathway by self DNA can also lead to autoimmune and inflammatory disease.

The term "cGAS" or "Cyclic GMP-AMP Synthase", also known as Mab-21 Domain-Containing Protein 1, refers to nucleotidyltransferase that catalyzes the formation of cyclic GMP-AMP (cGAMP) from ATP and GTP (Sun et al. (2013) *Science* 339:786-791; Krazusch et al. (2013) *Cell Rep* 3:1362-1368; Civril et al. (2013) *Nature* 498:332-227; Ablasser et al. (2013) *Nature* 503:530-534; Kranzusch et al. (2014) *Cell* 158:1011-1021). cGAS involves both the formation of a 2,5 phosphodiester linkage at the GpA step and the formation of a 3,5 phosphodiester linkage at the ApG step, producing c[G(2,5)pA(3,5)p](Tao et al. (2017) *J Immunol* 198:3627-3636; Lee et al. (2017) *FEBS Lett.* 591:954-961). cGAS acts as a key cytosolic DNA sensor, the presence of double-stranded DNA (dsDNA) in the cytoplasm being a danger signal that triggers the immune responses (Tao et al. (2017) *J Immunol* 198:3627-3636). cGAS binds cytosolic DNA directly, leading to activation and synthesis of cGAMP, a second messenger that binds to and activates TMEM173/STING, thereby triggering type-I interferon production (Tao et al. (2017) *J Immunol* 198:3627-3636; Wang et al. (2017) *Immunity* 46:393-404). cGAS has antiviral activity by sensing the presence of dsDNA from DNA viruses in the cytoplasm (Tao et al. (2017) *J Immunol* 198:3627-3636). cGAS also acts as an innate immune sensor of infection by retroviruses, such as HIV-1, by detecting the presence of reverse-transcribed DNA in the cytosol (Gao et al. (2013) *Science* 341:903-906). The detection of retroviral reverse-transcribed DNA in the cytosol may be indirect and be mediated via interaction with PQBP1, which directly binds reverse-transcribed retroviral DNA (Yoh et al. (2015) *Cell* 161:1293-1305). cGAS also detects the presence of DNA from bacteria, such as *M. tuberculosis* (Wassermann et al. (2015) *Cell Host Microbe* 17:799-810). cGAMP can be transferred from producing cells to neighboring cells through gap junctions, leading to promote TMEM173/STING activation and convey immune response to connecting cells (Ablasser et al. (2013) *Nature* 503:530-534). cGAMP can also be transferred between cells by virtue of packaging within viral particles contributing to IFN-induction in newly infected cells in a cGAS-independent but TMEM173/STING-dependent manner (Gentili et al. (2015) *Science* 349:1232-1236). In addition to antiviral activity, cGAS is also involved in the response to cellular stresses, such as senescence, DNA damage or genome instability (Mackenzie et al. (2017) *Nature* 548:461-465; Harding et al. (2017) *Nature* 548:466-470). cGAS acts as a regulator of cellular senescence by binding to cytosolic chromatin fragments that are present in senescent cells, leading to trigger type-I interferon production via TMEM173/STING and promote cellular senescence. cGAS is also involved in the inflammatory response to genome instability and double-stranded DNA breaks. cGAS acts by localizing to micronuclei arising from genome instability (PubMed:28738408; Harding et al. (2017) *Nature* 548:466-470). Micronuclei, which is frequently found in cancer cells, is consist of chromatin surrounded by its own nuclear membrane. Following breakdown of the micronuclear envelope, a process associated with chromothripsis, MB21D1/cGAS binds self- DNA exposed to the cytosol, leading to cGAMP synthesis and subsequent activation of TMEM173/STING and type-I interferon production (Mackenzie et al. (2017) *Nature* 548: 461-465; Harding et al. (2017) *Nature* 548:466-470). In one embodiment, human cGAS has 522 amino acids with a molecular mass of 58814 Da. cGAS is a monomer in the absence of DNA and when bound to dsDNA (Tao et al. (2017) *J Immunol* 198:3627-3636). cGAS interacts with PQBP1 (via WW domain) (Yoh et al. (2015) *Cell* 161:1293-1305). cGAS also interacts with TRIM14 and this interaction stabilizes cGAS/MB21D1 and promotes type I interferon production (Chen et al. (2016) *Mol Cell* 64:105-119). cGAS also interacts with herpes virus 8/HHV-8 protein ORF52, and this interaction inhibits cGAS enzymatic activity.

The term "cGAS" is intended to include fragments, variants (e.g., allelic variants) and derivatives thereof. Representative human cGAS cDNA and human cGAS protein sequences are well-known in the art and are publicly available from the National Center for Biotechnology Information (NCBI). Human cGAS isoforms include the protein (NP_612450.2) encoded by the transcript (NM_138441.2). Nucleic acid and polypeptide sequences of cGAS orthologs in organisms other than humans are well-known and include, for example, chimpanzee cGAS (XM_009451553.3 and XP_009449828.1; and XM_009451552.3 and XP_009449827.1), Monkey cGAS (NM_001318175.1 and NP_001305104.1), cattle cGAS (XM_024996918.1 and XP_024852686.1, XM_005210662.4 and XP_005210719.2, and XM_002690020.6 and XP_002690066.3), mouse cGAS (NM_173386.5 and NP_775562.2), rat cGAS (XM_006243439.3 and XP_006243501.2), and chicken cGAS (XM_419881.6 and XP_419881.4).

Anti-cGAS antibodies suitable for detecting cGAS protein are well-known in the art and include, for example, antibody TA340293 (Origene), antibodies NBP1-86761 and NBP1-70755 (Novus Biologicals, Littleton, CO), antibodies ab224144 and ab176177 (AbCam, Cambridge, MA), antibody 26-664 (ProSci), etc. In addition, reagents are well-known for detecting cGAS. Multiple clinical tests of cGAS are available in NIH Genetic Testing Registry (GTR®) (e.g., GTR Test ID: GTR000540854.2, offered by Fulgent Clinical Diagnostics Lab (Temple City, CA)). Moreover, multiple siRNA, shRNA, CRISPR constructs for reducing cGAS expression can be found in the commercial product lists of the above-referenced companies, such as siRNA product #sc-95512 from Santa Cruz Biotechnology, RNAi products SR314484 and TL305813V, and CRISPR product KN212386 (Origene), and multiple CRISPR products from GenScript (Piscataway, NJ). It is to be noted that the term can further be used to refer to any combination of features described herein regarding cGAS molecules. For example, any combination of sequence composition, percentage identify, sequence length, domain structure, functional activity, etc. can be used to describe a cGAS molecule encompassed by the present invention.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a modified hcGAS polypeptide nucleic acid (or any portion thereof) can be used to derive the modified hcGAS polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the modified human cGAS polypeptide of the present invention are well-known in the art and readily available on publicly available databases, such as the National Center for Biotechnology Information (NCBI). For example, exemplary nucleic acid and amino acid sequences derived from publicly available sequence databases are provided in Table 1, Table 2 and Table 2.1 below.

TABLE 1 amino acid sequences of human cGAS polypeptides

SEQ ID NO: 1 Human cGAS amino acid sequence
```
  1    MQPWHGKAMQ RASEAGATAP KASARNARGA PMDPTESPAA PEAALPKAGK FGPARKSGSR
 61    QKKSAPDTQE RPPVRATGAR AKKAPQRAQD TQPSDATSAP GAEGLEPPAA REPALSRAGS
121    CRQRGARCST KPRPPPGPWD VPSPGLPVSA PILVRRDAAP GASKLRAVLE KLKLSRDDIS
181    TAAGMVKGVV DHLLLRLKCD SAFRGVGLLN TGSYYEHVKI SAPNEFDVMF KLEVPRIQLE
241    EYSNTRAYYF VKFKRNPKEN PLSQFLEGEI LSASKMLSKF RKIIKEEIND IKDTDVIMKR
301    KRGGSPAVTL LISEKISVDI TLALESKSSW PASTQEGLRI QNWLSAKVRK QLRLKPFYLV
361    PKHAKEGNGF QEETWRLSFS HIEKEILNNH GKSKTCCENK EEKCCRKDCL KLMKYLLEQL
421    KERFKDKKHL DKFSSYHVKT AFFHVCTQNP QDSQWDRKDL GLCFDNCVTY FLQCLRTEKL
481    ENYFIPEFNL FSSNLIDKRS KEFLTKQIEY ERNNEFPVFD EF
```

SEQ ID NO: 2 Human cGAS (residues 157-522) amino acid sequence
```
157              DAAP GASKLRAVLE KLKLSRDDIS
181    TAAGMVKGVV DHLLLRLKCD SAFRGVGLLN TGSYYEHVKI SAPNEFDVMF KLEVPRIQLE
241    EYSNTRAYYF VKFKRNPKEN PLSQFLEGEI LSASKMLSKF RKIIKEEIND IKDTDVIMKR
301    KRGGSPAVTL LISEKISVDI TLALESKSSW PASTQEGLRI QNWLSAKVRK QLRLKPFYLV
361    PKHAKEGNGF QEETWRLSFS HIEKEILNNH GKSKTCCENK EEKCCRKDCL KLMKYLLEQL
421    KERFKDKKHL DKFSSYHVKT AFFHVCTQNP QDSQWDRKDL GLCFDNCVTY FLQCLRTEKL
481    ENYFIPEFNL FSSNLIDKRS KEFLTKQIEY ERNNEFPVFD EF
```

TABLE 2 cDNA sequences of human cGAS

SEQ ID NO: 3 Human cGAS cDNA sequence
```
   1   atgcagcctt ggcacggaaa ggccatgcag agagcttccg aggccggagc cactgccccc
  61   aaggcttccg cacggaatgc cagggggcgcc ccgatggatc ccaccgagtc tccggctgcc
 121   cccgaggccg ccctgcctaa ggcgggaaag ttcggccccg ccaggaagtc gggatcccgg
 181   cagaaaaaga gcgccccgga cacccaggag aggccgcccg tccgcgcaac tggggcccgc
 241   gccaaaaagg cccctcagcg cgcccaggac acgcagccgt ctgacgccac cagcgcccct
 301   ggggcagagg ggctggagcc tcctgcggct cgggagccgg ctctttccag ggctggttct
 361   tgccgccaga ggggcgcgct gctccacg aagccaagac ctccgcccgg ccctgggac
 421   gtgcccagcc ccggcctgcc ggtctcggcc ccattctcg tacgaggga tgcggcgcct
 481   ggggcctcga agctccgggc ggttttggag aagttgaagc tcagccgcga tgatatctcc
 541   acggcggcgg ggatggtgAA Aggggttgtg gaccacctgc tgCTCagact gaagtgcgac
 601   tccgcgttca gaggcgtcgg gctgctgaac accgggagct actatgagca cgtgaagatt
 661   tctgcaccta atgaatttga tgtcatgttt aaactggaag tccccagaat tcaactagaa
 721   gaatattcca acactcgtgc atattacttt gtgaaattta aagaaatccc aaagaaaat
 781   cctctgagtc agtttttaga aggtgaaata ttatcagctt ctaagatgct gtcaaagttt
 841   aggaaaatca ttaaggaaga aattaacgac attaaagata cagatgtcat catgaagagg
 901   aaaagaggag ggagccctgc tgtaacactt cttattagtg aaaaaatatc tgtggatata
 961   accctggctt tggaatcaaa aagtagctgg cctgctagca cccaagaagg cctgcgcatt
1021   caaaactggc tttcagcaaa agttaggaag caactacgac taaagccatt ttaccttgta
```

TABLE 2-continued cDNA sequences of human cGAS

```
1081  cccaagcatg caaaggaagg aaatggtttc caagaagaaa catggcggct atccttctct
1141  cacatcgaaa aggaaatttt gaacaatcat ggaaaatcta aaacgtgctg tgaaaacaaa
1201  gaagagaaat gttgcaggaa agattgttta aaactaatga ataccttttt agaacagctg
1261  aaagaaaggt ttaaagacaa aaaacatctg gataaattct cttcttatca tgtgaaaact
1321  gccttctttc acgtatgtac ccagaaccct caagacagtc agtgggaccg caaagacctg
1381  ggcctctgct ttgataactg cgtgacatac tttcttcagt gcctcaggac agaaaaactt
1441  gagaattatt ttattcctga attcaatcta ttctctagca acttaattga caaagaagt
1501  aaggaatttc tgacaaagca aattgaatat gaaagaaaca atgagtttcc agtttttgat
1561  gaattttga
```

SEQ ID NO: 4 Human cGAS (residues 157-522) cDNA sequence

```
 469                                                       ga tgcggcgcct
 481  ggggcctcga agctccgggc ggttttggag aagttgaagc tcagccgcga tgatatctcc
 541  acggcggcgg ggatggtgAA Aggggttgtg gaccacctgc tgCTCagact gaagtgcgac
 601  tccgcgttca gaggcgtcgg gctgctgaac accgggagct actatgagca cgtgaagatt
 661  tctgcaccta atgaatttga tgtcatgttt aaactggaag tccccagaat tcaactagaa
 721  gaatattcca acactcgtgc atattacttt gtgaaattta aagaaatccc gaaagaaaat
 781  cctctgagtc agttttaga aggtgaaata ttatcagctt ctaagatgct gtcaaagttt
 841  aggaaaatca ttaaggaaga aattaacgac attaaagata cagatgtcat catgaagagg
 901  aaaagaggag ggagccctgc tgtaacactt cttattagtg aaaaaatatc tgtggatata
 961  accctggctt tggaatcaaa aagtagctgg cctgctagca cccaagaagg cctgcgcatt
1021  caaaactggc tttcagcaaa agttaggaag caactacgac taaagccatt ttaccttgta
1081  cccaagcatg caaaggaagg aaatggtttc caagaagaaa catggcggct atccttctct
1141  cacatcgaaa aggaaatttt gaacaatcat ggaaaatcta aaacgtgctg tgaaaacaaa
1201  gaagagaaat gttgcaggaa agattgttta aaactaatga ataccttttt agaacagctg
1261  aaagaaaggt ttaaagacaa aaaacatctg gataaattct cttcttatca tgtgaaaact
1321  gccttctttc acgtatgtac ccagaaccct caagacagtc agtgggaccg caaagacctg
1381  ggcctctgct ttgataactg cgtgacatac tttcttcagt gcctcaggac agaaaaactt
1441  gagaattatt ttattcctga attcaatcta ttctctagca acttaattga caaagaagt
1501  aaggaatttc tgacaaagca aattgaatat gaaagaaaca atgagtttcc agtttttgat
1561  gaattttga
```

TABLE 2.1 amino acid sequences of mouse cGAS polypeptides

SEQ ID NO: 5 Mouse cGAS amino acid sequence

```
  1  medprrrtta prakkpsakr aptqpsrtra haescgpqrg arsrraerdg dttekprapg
 61  prvhparate ltkdaqpsam daagatarpa vrvpqqqail dpelpavrep qppadpeark
121  vvrgpshrrg arstgqprap rgsrkepdkl kkvldklrlk rkdiseaaet vnkvverllr
181  rmqkresefk gveqlntgsy yehvkisapn efdvmfklev prielqeyye tgafylvkfk
241  riprgnplsh flegevlsat kmlskfrkii keevkeikdi dvsvekekpg spavtllirn
301  peeisvdiil aleskgswpi stkeglpiqg wlgtkvrtnl rrepfylvpk nakdgnsfqg
```

TABLE 2.1-continued amino acid sequences of mouse cGAS polypeptides

```
361  etwrlsfsht ekyilnnhgi ektccessga kccrkeclkl mkylleqlkk efgeldafcs 421  yhvktaifhm wtqdpqdsqw dprnlsscfd kllafflecl rtekldhyfi pkfnlfsgel 481  idrkskefls kkieyernng fpifdkl
```

\* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

\* Included in Table 2 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 2, or a portion thereof. Such nucleic acid molecules can have a function of the full-length nucleic acid as described further herein.

II. Agents and Compositions a. Isolated Nucleic Acids

One aspect of the present invention pertains to isolated nucleic acid molecules that encode an isolated polypeptide that binds double-stranded DNA and catalyzes production of 2'-5'/3'-5' cyclic GMP-AMP (2'3' cGAMP), wherein said polypeptide comprises an amino acid sequence having at least 70% identity to the human cGAS (hcGAS) amino acid sequence of any one of SEQ ID NOs: 1-2 and further comprises amino acid substitutions at positions corresponding to K187 and L195 of SEQ ID NO: 1.

As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule that encodes a modified hcGAS polypeptide, or biologically active portions thereof, can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule that encodes a modified human cGAS polypeptide, or biologically active portions thereof, of the present invention, e.g., a nucleic acid molecule having the nucleotide sequence shown in Table 2, or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in Table 2, or a portion thereof (i.e., 100, 200, 300, 400, 450, 500, or more nucleotides), wherein the polypeptide encoded by the nucleic acid molecule further comprises amino acid substitutions at positions corresponding to K187 and L195 of SEQ ID NO: 1, can be isolated using standard molecular biology techniques and the sequence information provided herein. For example, a modified human hcGAS polypeptide cDNA can be isolated from a human cell line using all or portion of the nucleotide sequence shown in Table 2, or fragment thereof, as a hybridization probe and standard hybridization techniques (i.e., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N Y, 1989). Moreover, a nucleic acid molecule encompassing all or a portion of the nucleotide sequence shown in Table 2, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in Table 2, or fragment thereof, wherein the polypeptide encoded by the nucleic acid molecule further comprises amino acid substitutions at positions corresponding to K187 and L195 of SEQ ID NO: 1, can be isolated by the polymerase chain reaction using oligonucleotide primers designed based upon the sequence of the nucleotide sequence shown in Table 2, or fragment thereof, or the homologous nucleotide sequence. For example, mRNA can be isolated from human cancer cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, MD; or AMV reverse transcriptase, available from Seikagaku America, Inc., St. Petersburg, FL). Synthetic oligonucleotide primers for PCR amplification can be designed based upon the nucleotide sequence shown in Table 2, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. In addition, a nucleic acid of the invention can be generated by site-directed mutagenesis technique using cDNA, or genomic DNA of wild-type hcGAS as a template and specific oligonucleotide primers that contain the intended mutation. The nucleic acid so amplified or generated can be cloned into an appropriate vector and characterized by DNA sequence analysis. Furthermore, oligonucleotides corresponding to a modified hcGAS polypeptide nucleotide sequence can be prepared by standard synthetic techniques, i.e., using an automated DNA synthesizer.

Probes based on the modified hcGAS polypeptide nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a modified hcGAS polypeptide, such as by measuring a level of a modified hcGAS polypeptide-encoding nucleic acid in a sample of cells from a subject, i.e., detecting mRNA levels of modified hcGAS polypeptides.

Nucleic acid molecules encoding other modified hcGAS polypeptides and thus having a nucleotide sequence which differs from the nucleotide sequences shown in Table 2, or fragment thereof, are contemplated. Moreover, nucleic acid molecules encoding modified hcGAS polypeptides from different species, preferably from hominoids, and thus which have a nucleotide sequence which differs from the nucleotide sequences shown in Table 2 are also intended to be within the scope of the present invention. For example, a modified chimpanzee cGAS cDNA can be identified based on the nucleotide sequence of a modified human hcGAS.

In one embodiment, the nucleic acid molecule(s) of the invention encodes a protein or portion thereof which includes an amino acid sequence which is sufficiently homologous to an amino acid sequence shown in Table 1 and further comprises amino acid substitutions at positions corresponding to K187 and L195 of SEQ ID NO: 1, or fragment thereof, such that the protein or portion thereof has one or more biological activities selected from the group consisting of: a) increased 2'3' cGAMP synthesis compared to human cGAS; b) increased repression of *V. cholera* chemotaxis compared to human cGAS; c) similar enzyme kinetics to mouse cGAS; d) recognizing DNA shorter than 45 bp; e) stabilized active enzyme conformation; f) stabilized interactions with DNA; and g) increased minimal cGAS-DNA complex formation compared to human cGAS. Methods and assays for measuring each such biological activity are well-known in the art and representative, non-limiting embodiments are described in the Examples below and Definitions above.

As used herein, the language "sufficiently homologous" refers to proteins or portions thereof which have amino acid sequences which include a minimum number of identical or equivalent (e.g., an amino acid residue which has a similar side chain as an amino acid residue in an amino acid sequence shown in Table 1, or fragment thereof) amino acid residues to an amino acid sequence shown in Table 1, or fragment thereof, such that the protein or portion thereof has one or more biological activities selected from the group consisting of: a) increased 2'3' cGAMP synthesis compared to human cGAS; b) increased repression of *V. cholera* chemotaxis compared to human cGAS; c) similar enzyme kinetics to mouse cGAS; d) recognizing DNA shorter than 45 bp; e) stabilized active enzyme conformation; f) stabilized interactions with DNA; and g) increased minimal cGAS-DNA complex formation compared to human cGAS.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of an amino acid sequence shown in Table 1, or a fragment thereof.

Portions of proteins encoded by the modified hcGAS nucleic acid molecule of the present invention are preferably biologically active portions of the modified hcGAS polypeptide. As used herein, the term "biologically active portion of the modified hcGAS polypeptide" is intended to include a portion, e.g., a domain/motif, of the modified hcGAS polypeptide that has one or more of the biological activities of the full-length modified hcGAS polypeptide, respectively.

Standard binding assays, e.g., immunoprecipitations and yeast two-hybrid assays, as described herein, or functional assays, e.g., RNAi or overexpression experiments, can be performed to determine the ability of a modified hcGAS polypeptide or a biologically active fragment thereof to maintain a biological activity of the full-length modified hcGAS polypeptide.

The invention further encompasses nucleic acid molecules that differ from the nucleotide sequences shown in Table 2, or fragment thereof due to degeneracy of the genetic code and thus encode the same modified hcGAS polypeptide, or fragment thereof. In another embodiment, an isolated nucleic acid molecule of the invention has a nucleotide sequence encoding a protein having an amino acid sequence shown in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to an amino acid sequence shown in Table 1, or fragment thereof, or differs by at least 1, 2, 3, 5 or 10 amino acids but not more than 30, 20, 15 amino acids from an amino acid sequence shown in Table 1, wherein the protein further comprises amino acid substitutions at positions corresponding to K187 and L195 of SEQ ID NO: 1. In another embodiment, a nucleic acid encoding a modified hcGAS polypeptide consists of nucleic acid sequence encoding a portion of a full-length modified hcGAS polypeptide of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the modified hcGAS polypeptides may exist within a population (e.g., a human population). Such genetic polymorphism in the modified hcGAS gene may exist among individuals within a population due to natural allelic variation. As used herein, the terms "gene" and "recombinant gene" refer to nucleic acid molecules comprising an open reading frame encoding a modified hcGAS protein. Such natural allelic variations can typically result in 1-5% variance in the nucleotide sequence of the modified hcGAS gene. Any and all such nucleotide variations and resulting amino acid polymorphisms in the modified hcGAS polypeptide that are the result of natural allelic variation and that do not alter the functional activity of the modified hcGAS polypeptide are intended to be within the scope of the invention. Nucleic acid molecules corresponding to natural allelic variants and homologues of the modified human cGAS cDNAs of the present invention can be isolated based on their homology to the modified human cGAS nucleic acid sequences disclosed herein using the human cDNA, or a portion thereof, as a hybridization probe according to standard hybridization techniques under stringent hybridization conditions (as described herein).

In addition to naturally-occurring allelic variants of the modified hcGAS polypeptide sequence that may exist in the population, the skilled artisan will further appreciate that changes can be introduced by mutation into the nucleotide sequences shown in Table 2, or fragment thereof, thereby leading to changes in the amino acid sequence of the encoded modified hcGAS polypeptide, without altering the functional ability of the modified polypeptide. For example, nucleotide substitutions leading to amino acid substitutions at "non-essential" amino acid residues can be made in the sequence shown in Table 2, or fragment thereof. A "non-essential" amino acid residue is a residue that can be altered from the sequence of the modified hcGAS polypeptide (e.g., the sequence shown in Table 1, or fragment thereof) without significantly altering the activity of the modified hcGAS polypeptide, whereas an "essential" amino acid residue is required for the modified hcGAS polypeptide activity. Other amino acid residues, however, (e.g., those that are not conserved or only semi-conserved between mouse and human) may not be essential for activity and thus are likely to be amenable to alteration without altering the modified hcGAS polypeptide activity.

Accordingly, another aspect of the present invention pertains to nucleic acid molecules encoding modified hcGAS polypeptides that contain changes in amino acid residues that are not essential for the modified hcGAS polypeptide activity. Such modified hcGAS polypeptides differ in amino acid sequence from an amino acid sequence shown in Table 1, or fragment thereof, yet retain at least one of the modified hcGAS polypeptide activities described herein. In one embodiment, the isolated nucleic acid molecule comprises a nucleotide sequence encoding a protein, wherein the protein lacks one or more modified hcGAS polypeptide domains. As stated in the Definitions section, the structure-function relationship of hcGAS polypeptide is known such that the ordinarily skilled artisan readily understands the regions that may be mutated or otherwise altered while preserving at least one biological activity of the modified hcGAS polypeptide.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared ×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a modified hcGAS polypeptide homologous to the protein show in Table 1 and further comprising amino acid substitutions at positions corresponding to K187 and L195 of SEQ ID NO: 1, or fragment thereof, can be created by introducing one or more nucleotide substitutions, additions or deletions into the nucleotide sequences shown in Table 2, or fragment thereof, or a homologous nucleotide sequence such that one or more amino acid substitutions, additions or deletions are introduced into the encoded protein. Mutations can be introduced into a nucleotide sequence shown in Table 2, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in the modified hcGAS polypeptide is preferably replaced with another amino acid residue from the same side chain family. Alternatively, in another embodiment, mutations can be introduced randomly along all or part of a modified hcGAS polypeptide coding sequence, such as by saturation mutagenesis, and the resultant mutants can be screened for the modified hcGAS polypeptide activity described herein to identify mutants that retain the modified hcGAS polypeptide activity. Following mutagenesis of a nucleotide sequence shown in Table 2, or fragment thereof, the encoded protein can be expressed recombinantly (as described herein) and the activity of the protein can be determined using, for example, assays described herein.

The levels of the modified hcGAS polypeptides may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of the modified hcGAS polypeptides are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the modified hcGAS polypeptide mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the modified hcGAS mRNA expression levels.

An alternative method for determining the modified hcGAS mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the modified hcGAS polypeptide mRNA.

As an alternative to making determinations based on the absolute the modified hcGAS polypeptide expression level, determinations may be based on the normalized modified hcGAS polypeptide expression level. Expression levels are normalized by correcting the absolute modified hcGAS polypeptide expression level by comparing its expression to the expression of a non-hcGAS polypeptide gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a modified hcGAS polypeptide can also be detected and/or quantified by detecting or quantifying the expressed polypeptide. The modified hcGAS polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the modified hcGAS polypeptide.

b. Recombinant Expression Vectors and Host Cells

Another aspect of the invention pertains to the use of vectors, preferably expression vectors, containing a nucleic acid encoding a modified hcGAS polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a modified hcGAS nucleic acid molecule are used.

The recombinant expression vectors of the present invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of the modified hcGAS polypeptide in prokaryotic or eukaryotic cells. For example, the modified hcGAS polypeptide can be expressed in bacterial cells such as $E.\ coli$, insect cells (using baculovirus expression vectors) yeast cells or mammalian cells. Suitable host cells are discussed further in Goeddel, Gene Expression Technology: Methods in Enzymology 185, Academic Press, San Diego, CA (1990). Alternatively, the recombinant expression vector can be transcribed and translated in vitro, for example using T7 promoter regulatory sequences and T7 polymerase.

Expression of proteins in prokaryotes is most often carried out in $E.\ coli$ with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein. In one embodiment, the coding sequence of the modified hcGAS polypeptide is cloned into a pGEX expression vector to create a vector encoding a fusion protein comprising, from the N-terminus to the C-terminus, GST-thrombin cleavage site-modified hcGAS polypeptide. The fusion protein can be purified by affinity chromatography using glutathione-agarose resin. Recombinant modified hcGAS polypeptide unfused to GST can be recovered by cleavage of the fusion protein with thrombin.

Examples of suitable inducible non-fusion $E.\ coli$ expression vectors include pTrc (Amann et al., (1988) *Gene* 69:301-315) and pET 11d (Studier et al., Gene Expression Technology: Methods in Enzymology 185, Academic Press, San Diego, California (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in $E.\ coli$ is to express the protein in a host bacteria with an impaired capacity to proteolytically cleave the recombinant protein (Gottesman, S., Gene Expression Technology: Methods in Enzymology 185, Academic Press, San Diego, California (1990) 119-128). Another strategy is to alter the nucleic acid sequence of the nucleic acid to be inserted into an expression vector so that the individual codons for each amino acid are those preferentially utilized in $E.\ coli$ (Wada et al. (1992) *Nucleic Acids Res.* 20:2111-2118). Such alteration of nucleic acid sequences of the invention can be carried out by standard DNA synthesis techniques.

In another embodiment, the modified hcGAS polypeptide expression vector is a yeast expression vector. Examples of vectors for expression in yeast S. cerivisae include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, CA).

Alternatively, the modified hcGAS polypeptide can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., *Cold Spring*

*Harbor Laboratory*, Cold Spring Harbor Laboratory Press, Cold Spring Harbor, N Y, 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the a-fetoprotein promoter (Campes and Tilghman (1989) *Genes Dev.* 3:537-546).

Another aspect of the present invention pertains to host cells into which a recombinant expression vector or nucleic acid of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the modified hcGAS polypeptide can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N Y, 1989), and other laboratory manuals.

A cell culture includes host cells, media and other byproducts. Suitable media for cell culture are well known in the art. A modified hcGAS polypeptide or fragment thereof, may be secreted and isolated from a mixture of cells and medium containing the polypeptide. Alternatively, a modified hcGAS polypeptide or fragment thereof, may be retained cytoplasmically and the cells harvested, lysed and the protein or molecular complex isolated. A modified hcGAS polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of the modified hcGAS polypeptide or a fragment thereof.

In some embodiments, the modified hcGAS polypeptide, or biologically active fragment thereof, and may be fused to a heterologous polypeptide. In certain embodiments, the fused polypeptide has greater half-life and/or cell permeability than the corresponding unfused modified hcGAS polypeptide, or biologically active fragment thereof. For example, the modified hcGAS polypeptide may be fused to a cell permeable peptide to facilitate the delivery of the modified hcGAS polypeptide into the intact cells. Cell Permeable Peptides, also known as Protein Transduction Domains (PTDs), are carriers with small peptide domains that can freely cross cell membranes. Several PTDs have been identified that allow a fused protein to efficiently cross cell membranes in a process known as protein transduction. Studies have demonstrated that a TAT peptide derived from the HIV TAT protein has the ability to transduce peptides or proteins into various cells. PTDs have been utilized in anticancer strategy, for example, a cell permeable Bcl-2 binding peptide, cpm1285, shows activity in slowing human myeloid leukemia growth in mice. Cell-permeable phospho-peptides, such as FGFR730pY, which mimics receptor binding sites for specific SH2 domain-containing proteins are potential tools for cancer research and cell signaling mechanism studies. In other embodiments, heterologous tags can be used for purification purposes (e.g., epitope tags and Fc fusion tags), according to standards methods known in the art.

Thus, a nucleotide sequence encoding all or a selected portion of the modified hcGAS polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant modified hcGAS polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the modified hcGAS polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., (1993) *Curr. Opin. Biotech.*: vol. 4, p 420; M. Miller, et al., (1989) Science: vol. 246, p 1149; A. Wlodawer, et al., (1989) Science: vol. 245, p 616; L. H. Huang, et al., (1991) Biochemistry: vol. 30, p 7402; M. Sclmolzer, et al., (1992) *Int. J. Pept. Prot. Res.*: vol. 40, p 180-193; K. Rajarathnam, et al., (1994) *Science*: vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., (1992) *J. Biol. Chem.*: vol. 267, p 3852; L. Abrahmsen, et al., (1991) *Biochemistry*: vol. 30, p 4151; T. K. Chang, et al., (1994) *Proc. Natl. Acad. Sci. USA* 91: 12544-12548; M. Schnlzer, et al., (1992) Science: vol., 3256, p 221; and K. Akaji, et al., (1985) *Chem. Pharm. Bull.* (Tokyo) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the modified hcGAS polypeptide or can be introduced on a separate vector. Cells stably transfected with the introduced nucleic acid can be identified by drug selection (e.g., cells that have incorporated the selectable marker gene will survive, while the other cells die).

A host cell of the present invention, such as a prokaryotic or eukaryotic host cell in culture, can be used to produce (i.e., express) the modified hcGAS polypeptide. Accordingly, the invention further provides methods for producing the modified hcGAS polypeptide using the host cells of the invention. In one embodiment, the method comprises culturing the host cell of invention (into which a recombinant expression vector encoding the modified hcGAS polypeptide has been introduced) in a suitable medium until the modified hcGAS polypeptide is produced. In another embodiment, the method further comprises isolating the modified hcGAS polypeptide from the medium or the host cell.

The host cells of the invention can also be used to produce human or non-human transgenic animals and/or cells that, for example, overexpress the modified hcGAS polypeptide or oversecrete the modified hcGAS polypeptide. The non-human transgenic animals can be used in screening assays designed to identify agents or compounds, e.g., drugs, pharmaceuticals, etc., which are capable of ameliorating detrimental symptoms of selected disorders such as diffuse gastric cancer (DGC), lobular breast cancer, or other types of EMT cancers. For example, in one embodiment, a host cell of the present invention is a fertilized oocyte or an embryonic stem cell into which the modified hcGAS polypeptide-encoding sequences, or fragments thereof, have been introduced. Such host cells can then be used to create non-human transgenic animals in which exogenous modified hcGAS polypeptide sequences have been introduced into their genome or homologous recombinant animals in which endogenous cGAS sequences have been altered. Such animals are useful for studying the function and/or activity of the modified hcGAS polypeptide, or fragments thereof, and for identifying and/or evaluating modulators of the modified hcGAS polypeptide activity. As used herein, a "transgenic animal" is a non-human animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous cGAS gene has been altered by homologous recombination between the endogenous gene and an exogenous DNA molecule introduced into a cell of the animal, e.g., an embryonic cell of the animal, prior to development of the animal.

A transgenic animal of the present invention can be created by introducing nucleic acids encoding the modified hcGAS polypeptide, or a fragment thereof, into the male pronuclei of a fertilized oocyte, e.g., by microinjection, retroviral infection, and allowing the oocyte to develop in a pseudopregnant female foster animal. The modified human cGAS cDNA sequence can be introduced as a transgene into the genome of a nonhuman animal. Alternatively, a nonhuman homologue of the modified human cGAS gene can be used as a transgene. Intronic sequences and polyadenylation signals can also be included in the transgene to increase the efficiency of expression of the transgene. A tissue-specific regulatory sequence(s) can be operably linked to the modified human cGAS transgene to direct expression of the modified human cGAS polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the modified human cGAS transgene in its genome and/or expression of the modified human cGAS mRNA in tissues or cells of the animals. A transgenic founder animal can then be used to breed additional animals carrying the transgene. Moreover, transgenic animals carrying a transgene encoding the modified hcGAS polypeptide can further be bred to other transgenic animals carrying other transgenes.

To create a homologous recombinant animal, a vector is prepared which contains at least a portion of a modified human cGAS gene. For example, a modified human cGAS gene can be used to construct a homologous recombination vector suitable for altering an endogenous cGAS gene, in the mouse genome. In the homologous recombination vector, the modified human cGAS gene is flanked at its 5' and 3' ends by additional nucleic acid of the cGAS gene to allow for homologous recombination to occur between the exogenous modified hcGAS gene carried by the vector and an endogenous cGAS gene in an embryonic stem cell. The additional flanking cGAS nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the modified hcGAS gene has homologously recombined with the endogenous cGAS gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

c. Modified hcGAS Polypeptides

The present invention also provides soluble, purified and/or isolated forms of modified hcGAS polypeptides that binds double-stranded DNA and catalyzes production of 2'-5'/3'-5' cyclic GMP-AMP (2'3' cGAMP), wherein said polypeptide comprises an amino acid sequence having at least 70% identity to the human cGAS (hcGAS) amino acid sequence of any one of SEQ ID NOs: 1-2 and further comprises amino acid substitutions at positions corresponding to K187 and L195 of SEQ ID NO: 1, for use according to methods described herein.

In one aspect, a modified hcGAS polypeptide may comprise a human cGAS amino acid sequence of any one of SEQ ID NOs: 1-2 and further comprising amino acid substitutions at positions corresponding to K187 and L195 of SEQ ID NO: 1, or a human cGAS amino acid sequence of any one of SEQ ID NOs: 1-2 and further comprising amino acid substitutions at positions corresponding to K187 and L195 of SEQ ID NO: 1 with 1 to about 20 additional conservative amino acid substitutions. Amino acid sequence of any modified hcGAS polypeptide described herein can also be at least 50, 55, 60, 65, 70, 75, 80, 85, 90, 91, 92, 93, 94, 95, 96, 97, 98, 99, or 99.5% identical to a human cGAS amino acid sequence of any one of SEQ ID NOs: 1-2 with amino acid substitutions at positions corresponding to K187 and L195 of SEQ ID NO: 1, or a fragment thereof.

In one embodiment, the residue corresponding to K187 is substituted with a residue that is capable of making direct contact with the DNA phosphate backbone. Such residue could be a polar residue selected from the group consisting of tyrosine, serine, threonine, asparagine, glutamine and cysteine. For example, the residue corresponding to K187 may be substituted with an asparagine residue. In another embodiment, the residue corresponding to L195 is substituted with a residue that increases the overall positive charge of the A-site DNA-binding surface. The residue corresponding to L195 may be substituted with a basic residue selected from the group consisting of lysine, arginine and histidine. For example, the residue corresponding to L195 may be substituted with an arginine residue. In still another embodiment, the modified hcGAS polypeptide further comprises amino acid substitutions at positions corresponding to S328, K350 and/or L354 of SEQ ID NO: 1. In specific embodiments, the modified hcGAS polypeptide further comprises S328G, K350T, and/or L354R amino acid substitutions.

In addition, any modified hcGAS polypeptide, or fragment thereof, described herein can have one or more of the following biological properties: a) increased 2'3' cGAMP synthesis compared to human cGAS having the amino acid sequence of SEQ ID NO: 1; b) increased repression of *V. cholera* chemotaxis compared to human cGAS having the amino acid sequence of SEQ ID NO: 1; c) similar enzyme kinetics to mouse cGAS having the amino acid sequence of SEQ ID NO: 5; d) recognizing DNA shorter than 45 bp; e) stabilized active enzyme conformation; f) stabilized interactions with DNA; and g) increased minimal cGAS-DNA complex formation compared to human cGAS having the amino acid sequence of SEQ ID NO: 1.

In certain embodiments, the activities of the modified hcGAS is increased by at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3.0-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4.0-fold, at least 4.1-fold, at least 4.2-fold, at least 4.3-fold, at least 4.4-fold, at least 4.5-fold, at least 4.6-fold, at least 4.7-fold, at least 4.8-fold, at least 4.9-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, at least 25-fold, at least 26-fold, at least 27-fold, at least 28-fold, at least 29-fold, at least 30-fold, at least 31-fold, at least 32-fold, at least 33-fold, at least 34-fold, at least 35-fold, at least 36-fold, at least 37-fold, at least 38-fold, at least 39-fold, at least 40-fold, at least 41-fold, at least 42-fold, at least 43-fold, at least 44-fold, at least 45-fold, at least 46-fold, at least 47-fold, at least 48-fold, at least 49-fold, at least 50-fold, at least 51-fold, at least 52-fold, at least 53-fold, at least 54-fold, at least 55-fold, at least 56-fold, at least 57-fold, at least 58-fold, at least 59-fold, at least 60-fold, at least 61-fold, at least 62-fold, at least 63-fold, at least 64-fold, at least 65-fold, at least 66-fold, at least 67-fold, at least 68-fold, at least 69-fold, at least 70-fold, at least 71-fold, at least 72-fold, at least 73-fold, at least 74-fold, at least 75-fold, at least 76-fold, at least 77-fold, at least 78-fold, at least 79-fold, at least 80-fold, at least 81-fold, at least 82-fold, at least 83-fold, at least 84-fold, at least 85-fold, at least 86-fold, at least 87-fold, at least 88-fold, at least 89-fold, at least 90-fold, at least 91-fold, at least 92-fold, at least 93-fold, at least 94-fold, at least 95-fold, at least 96-fold, at least 97-fold, at least 98-fold, at least 99-fold, at least 100-fold, or any range inclusive, such as 5-fold to 20-fold. The fold change of the activities of the modified hcGAS may be compared with human cGAS having the amino acid sequence of SEQ ID NO: 1, or mouse cGAS having the amino acid sequence of SEQ ID NO: 5. The activities of the modified hcGAS include but are not limited to 2'3' cGAMP synthesis, repression of *V. cholera* chemotaxis, enzyme kinetics, DNA interactions, nucleotide coordination, and protein stability.

In another aspect, the present invention contemplates a composition comprising an isolated modified hcGAS polypeptide described herein and less than about 25%, or alternatively 15%, or alternatively 5%, contaminating biological macromolecules or polypeptides.

The present invention further provides compositions related to producing, detecting, or characterizing a modified hcGAS polypeptide, or fragment thereof, such as nucleic acids, vectors, host cells, and the like. Such compositions may serve as compounds that modulate a modified hcGAS polypeptide's expression and/or activity, such as antisense nucleic acids.

In certain embodiments, a modified hcGAS polypeptide of the invention may be a fusion protein containing a domain which increases its solubility and bioavailability and/or facilitates its purification, identification, detection, and/or structural characterization. In some embodiments, it may be useful to express a modified hcGAS polypeptide in which the fusion partner enhances fusion protein stability in blood plasma and/or enhances systemic bioavailability. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG® fusion proteins and tags. Additional exemplary domains include domains that alter protein localization in vivo, such as signal peptides, type 21 secretion system-targeting peptides, transcytosis domains, nuclear localization signals, etc. In various embodiments, a modified hcGAS polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, the modified hcGAS polypeptides, or fragments thereof, are fused to an antibody (e.g., IgG1, IgG2, IgG3, IgG4) fragment (e.g., Fc polypeptides). Techniques for preparing these fusion proteins are known, and are described, for example, in WO 99/31241 and in Cosman et. al. (2001) *Immunity* 14:123-133. Fusion to an Fc polypeptide offers the additional advantage of facilitating purification by affinity chromatography over Protein A or Protein G columns.

In still another embodiment, a modified hcGAS polypeptide may be labeled with a fluorescent label to facilitate their detection, purification, or structural characterization. In an exemplary embodiment, a modified hcGAS polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

In preferred embodiments, the modified hcGAS polypeptide or portion thereof comprises an amino acid sequence which is sufficiently homologous to an amino acid sequence shown in Table 1 or fragment thereof and further comprises amino acid substitutions at positions corresponding to K187 and L195 of SEQ ID NO: 1, such that the modified hcGAS polypeptide or portion thereof has one or more of the following biological properties: a) increased 2'3' cGAMP synthesis compared to human cGAS; b) increased repression of *V. cholera* chemotaxis compared to human cGAS; c) similar enzyme kinetics to mouse cGAS; d) recognizing DNA shorter than 45 bp; e) stabilized active enzyme conformation; f) stabilized interactions with DNA; and g) increased minimal cGAS-DNA complex formation compared to human cGAS. The portion of the protein is preferably a biologically active portion as described herein. In another preferred embodiment, the modified hcGAS polypeptides has an amino acid sequence shown in Table 1, or fragment thereof, and further comprises amino acid substitutions at positions corresponding to K187 and L195 of SEQ ID NO: 1, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in Table 1, or fragment thereof, and further comprises amino acid substitutions at positions corresponding to K187 and L195 of SEQ ID NO: 1. In yet another preferred embodiment, the modified human cGAS polypeptide has an amino acid sequence which is encoded by a nucleotide sequence which hybridizes, e.g., hybridizes under stringent conditions, to the nucleotide sequence shown in Table 2, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in Table 2, or fragment thereof. The preferred modified hcGAS polypeptides of the present invention also preferably possess at least one of the modified hcGAS polypeptide biological activities described herein.

Biologically active portions of a modified hcGAS polypeptide include peptides comprising amino acid sequences derived from the amino acid sequence of the modified hcGAS protein, or the amino acid sequence of a protein homologous to the modified hcGAS protein, which include fewer amino acids than the full-length modified hcGAS protein or the full-length polypeptide which is homologous to the modified hcGAS protein, and exhibit at least one activity of the modified hcGAS protein. Typically, biologically active portions (peptides, e.g., peptides which are, for example, 50, 55, 60, 65, 70, 75, 80, 85, 90, 95, 100 or more amino acids in length) comprise a domain or motif, (e.g., the full-length protein minus the signal peptide). In a preferred embodiment, the biologically active portion of the protein which includes one or more the domains/motifs described herein have one or more following biologically activities: a) increased 2'3' cGAMP synthesis compared to human cGAS; b) increased repression of V. cholera chemotaxis compared to human cGAS; c) similar enzyme kinetics to mouse cGAS; d) recognizing DNA shorter than 45 bp; e) stabilized active enzyme conformation; f) stabilized interactions with DNA; and g) increased minimal cGAS-DNA complex formation compared to human cGAS. Moreover, other biologically active portions, in which other regions of the protein are deleted, can be prepared by recombinant techniques and evaluated for one or more of the activities described herein. Preferably, the biologically active portions of the modified hcGAS protein include one or more selected domains/motifs or portions thereof having biological activity. In one embodiment, a modified hcGAS polypeptide fragment of interest consists of a portion of a full-length modified hcGAS polypeptide that is less than 240, 230, 220, 210, 200, 195, 190, 185, 180, 175, 170, 165, 160, 155, 150, 145, 140, 135, 130, 125, 120, 115, 110, 105, 100, 95, 90, 85, 80, 75, or 70 amino acids in length.

The modified human cGAS polypeptides of the percent invention can be produced by recombinant DNA techniques. For example, a nucleic acid molecule encoding the protein is cloned into an expression vector (as described above), the expression vector is introduced into a host cell (as described above) and the modified hcGAS polypeptide is expressed in the host cell. The modified hcGAS polypeptide can then be isolated from the cells by an appropriate purification scheme using standard protein purification techniques. Alternative to recombinant expression, a modified hcGAS protein, polypeptide, or peptide can be synthesized chemically using standard peptide synthesis techniques. Moreover, modified hcGAS protein can be isolated from cells (e.g., engineered cells that harboring hcGAS mutations), for example using an anti-hcGAS antibody.

The invention also provides modified hcGAS chimeric or fusion proteins. As used herein, a modified hcGAS "chimeric protein" or "fusion protein" comprises a modified hcGAS polypeptide operatively linked to a non-hcGAS polypeptide. A "modified human cGAS polypeptide" refers to a polypeptide having an amino acid sequence corresponding to human cGAS with amino acid substitutions at positions of K187 and L195, whereas a "non-hcGAS polypeptide" refers to a polypeptide having an amino acid sequence corresponding to a protein which is not substantially homologous to the modified hcGAS protein, e.g., a protein which is different from the modified hcGAS protein and which is derived from the same or a different organism. Within the fusion protein, the term "operatively linked" is intended to indicate that the modified hcGAS polypeptide and the non-hcGAS polypeptide are fused in-frame to each other. The non-hcGAS polypeptide can be fused to the N-terminus or C-terminus of the modified hcGAS polypeptide. For example, in one embodiment the fusion protein is a modified hcGAS-GST and/or modified hcGAS-Fc fusion protein in which the modified hcGAS sequences, respectively, are fused to the N-terminus of the GST or Fc sequences. Such fusion proteins can be made using the modified hcGAS polypeptides. Such fusion proteins can also facilitate the purification, expression, and/or bioavailability of recombinant modified hcGAS polypeptides. In another embodiment, the fusion protein is a modified hcGAS protein containing a heterologous signal sequence at its C-terminus. In certain host cells (e.g., mammalian host cells), expression and/or secretion of the modified hcGAS polypeptides can be increased through use of a heterologous signal sequence.

Preferably, a modified hcGAS chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A modified hcGAS-encoding nucleic acid can be cloned into such an expression vector such that the fusion moiety is linked in-frame to the modified human cGAS protein.

The present invention also pertains to homologues of the modified human cGAS proteins. Homologues of the modified human cGAS protein can be generated by mutagenesis, e.g., discrete point mutation or truncation of the modified human cGAS protein, respectively. As used herein, the term "homologue" refers to a variant form of the modified human cGAS protein. In one embodiment, treatment of a subject with a homologue having a subset of the biological activities of the naturally occurring form of the protein has fewer side effects in a subject relative to treatment with the naturally occurring form of the modified human cGAS protein.

In an alternative embodiment, homologues of the modified human cGAS protein can be identified by screening combinatorial libraries of mutants, e.g., truncation mutants, of the modified human cGAS protein. In one embodiment, a variegated library of the modified human cGAS variants is generated by combinatorial mutagenesis at the nucleic acid level and is encoded by a variegated gene library. A variegated library of the modified human cGAS variants can be produced by, for example, enzymatically ligating a mixture of synthetic oligonucleotides into gene sequences such that a degenerate set of potential modified human cGAS sequences is expressible as individual polypeptides, or alternatively, as a set of larger fusion proteins (e.g., for phage display) containing the set of the modified human cGAS sequences therein. There are a variety of methods which can be used to produce libraries of potential modified human cGAS homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential modified human cGAS sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the modified human cGAS protein coding can be used to generate a variegated population of the modified human cGAS fragments for screening and subsequent selection of homologues of a modified human cGAS protein. In one embodiment, a library of coding sequence fragments can be generated by treating a double stranded PCR fragment of a modified hcGAS coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the modified hcGAS protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of the modified hcGAS homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify modified hcGAS homologues (Arkin and Youvan (1992) *Proc. Natl. Acad. Sci. USA* 89:7811-7815).

d. Modified hcGAS-DNA and hcGAS-DNA-ATP Complexes

In one aspect, the present invention relates, in part, to a modified hcGAS-DNA complex wherein (a) the complex comprises at least one double-stranded DNA and at least one human cGAS polypeptide or biologically active fragment thereof, (b) at least one human cGAS polypeptide or biologically active fragment thereof comprises amino acid substitutions at positions K187 and L195. In another aspect, the present invention relates, in part, to a modified hcGAS-DNA-ATP complex, wherein (a) the complex comprises at least one double-stranded DNA, at least one human cGAS polypeptide or biologically active fragment thereof, and at least one ATP molecule, (b) at least one human cGAS polypeptide or biologically active fragment thereof comprises amino acid substitutions at positions K187 and L195. In one embodiment, the residue at position K187 is substituted with a lysine residue and the residue at position L195 is substituted with an arginine residue. In another embodiment, the human cGAS polypeptide or biologically active fragment in the modified complex further comprises amino acid substitutions at positions S328, K350 and/or L354.

In certain embodiments, at least one modified hcGAS of a complex of the invention is a homolog, a derivative, e.g., a functionally active derivative, a fragment, e.g., a functionally active fragment, of the modified hcGAS polypeptide of the present invention. In certain embodiments of the invention, a homolog, derivative or fragment of a modified hcGAS polypeptide of a molecular complex of the invention is still capable of forming a complex with the other component(s). Complex-formation can be tested by any method known to the skilled artisan. Such methods include, but are not limited to, non-denaturing PAGE, FRET, EMSA, and Fluorescence Polarization Assay.

Homologs (e.g., nucleic acids encoding polypeptides from other species) or other related sequences (e.g., paralogs) which are members of a native cellular complex can be identified and obtained by low, moderate or high stringency hybridization with all or a portion of the particular nucleic acid sequence as a probe, using methods well known in the art for nucleic acid hybridization and cloning.

Exemplary moderately stringent hybridization conditions are as follows: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 pg/ml denatured salmon sperm DNA. Filters are hybridized for 48 hours at 65° C. in prehybridization mixture containing 100 pg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 min before autoradiography. Alternatively, exemplary conditions of high stringency are as follows: e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel et al., eds., 1989, *Current Protocols in Molecular Biology*, Vol. I, Green Publishing Associates, Inc., and John Wiley & sons, Inc., New York, at p. 2.10.3). Other conditions of high stringency which may be used are well known in the art. Exemplary low stringency hybridization conditions comprise hybridization in a buffer comprising 35% formamide, 5×SSC, 50 mM Tris-HCl (pH 7.5), 5 mM EDTA, 0.02% PVP, 0.02% Ficoll, 0.2% BSA, 100 pg/ml denatured salmon sperm DNA, and 1 0% (wt/vol) dextran sulfate for 18-20 hours at 40° C., washing in a buffer consisting of 2×SSC, 25 mM Tris-HCl (pH 7.4), 5 mM EDTA, and 0.1% SDS for 1.5 hours at 55° C., and washing in a buffer consisting of 2×SSC, 25 mM Tris-HCl (pH 7.4), 5 mM EDTA, and 0.1% SDS for 1.5 hours at 60° C.

In certain embodiments, a homolog of a modified hcGAS polypeptide binds to the same binding partners to which the modified hcGAS polypeptide binds. In certain, more specific embodiments, a homolog of a modified hcGAS polypeptide binds to the same binding partners to which the modified hcGAS polypeptide binds wherein the binding affinity between the homolog and the binding partner of the modified hcGAS polypeptide is at least 10%, at least 20%, at least 30%, at least 40%, at least 50%, at least 60%, at least 70%, at least 80%, at least 90%, at least 95% or at least 98% of the binding affinity between the modified hcGAS polypeptide and the binding partner. Binding affinities between proteins, or between protein and nucleic acid (e.g., DNA) can be determined by any method known to the skilled artisan.

In certain embodiments, a fragment of the modified hcGAS polypeptide of the complex consists of at least 6 (continuous) amino acids, of at least 10, at least 20 amino acids, at least 30 amino acids, at least 40 amino acids, at least 50 amino acids, at least 75 amino acids, at least 100 amino acids, at least 150 amino acids, at least 200 amino acids, at least 250 amino acids, at least 300 amino acids, at least 400 amino acids, or at least 500 amino acids of the modified hcGAS polypeptide comprising amino acid substitutions at positions K187 and L195. In specific embodiments, such fragments are not larger than 40 amino acids, 50 amino acids, 75 amino acids, 100 amino acids, 150 amino acids, 200 amino acids, 250 amino acids, 300 amino acids, 400 amino acids, or than 500 amino acids. In more specific embodiments, the functional fragment is capable of forming a complex of the invention, i.e., the fragment can still bind to at least one other binding partner to form a complex of the invention. In some embodiments, the fragment has at least one or more biological properties selected from the group consisting of: a) increased 2'3' cGAMP synthesis compared to human cGAS; b) increased repression of *V. cholera* chemotaxis compared to human cGAS; c) similar enzyme kinetics to mouse cGAS; d) recognizing DNA shorter than 45 bp; e) stabilized active enzyme conformation; f) stabilized interactions with DNA; and g) increased minimal cGAS-DNA complex formation compared to human cGAS.

Derivatives or analogs of the modified hcGAS protein include, but are not limited, to molecules comprising regions that are substantially homologous to the modified hcGAS protein, in various embodiments, by at least 30%, 40%, 50%, 60%, 70%, 80%, 90% or 95% identity over an amino acid sequence of identical size or when compared to an aligned sequence in which the alignment is done by a computer homology program known in the art, or whose encoding nucleic acid is capable of hybridizing to a sequence encoding the modified hcGAS polypeptide under stringent, moderately stringent, or nonstringent conditions. In certain embodiments, the modified human cGAS, or biologically active fragment thereof, further comprises one or more conservative amino acid substitutions.

Derivatives of a modified hcGAS polypeptide include, but are not limited to, fusion proteins of a modified hcGAS polypeptide to a heterologous amino acid sequence, mutant forms of a modified hcGAS polypeptide of a complex of the invention, and chemically modified forms of a modified hcGAS polypeptide of a complex of the invention. In a specific embodiment, the functional derivative of a modified hcGAS polypeptide of a complex of the invention is capable of forming a complex of the invention, i.e., the derivative can still bind to at least one other binding partner to form a complex of the invention.

In certain embodiments of the invention, at least two components of a complex of the invention are linked to each other via at least one covalent bond. A covalent bond between components of a complex of the invention increases the stability of the complex of the invention because it prevents the dissociation of the components. Any method known to the skilled artisan can be used to achieve a covalent bond between at least two components of a complex of the invention.

In specific embodiments, covalent cross-links are introduced between adjacent components. Such cross-links can be between the side chains of amino acids at opposing sides of the dimer interface. Any functional groups of amino acid residues at the dimer interface in combination with suitable cross-linking agents can be used to create covalent bonds between the components at the dimer interface. Existing amino acids at the dimer interface can be used or, alternatively, suitable amino acids can be introduced by site-directed mutagenesis.

In exemplary embodiments, cysteine residues at opposing sides of the dimer interface are oxidized to form disulfide bonds. See, e.g., Reznik et al., (1996) *Nat Bio Technol* 14:1007-1011, at page 1008. 1,3-dibromoacetone can also be used to create an irreversible covalent bond between two sulfhydryl groups at the dimer interface. In certain other embodiments, lysine residues at the dimer inter face are used to create a covalent bond between the components of the complex. Crosslinkers that can be used to create covalent bonds between the epsilon amino groups of lysine residues are, e.g., but are not limited to, bis(sulfosuccinimidyl)suberate; dimethyladipimidate-2HD1; disuccinimidyl glutarate; N-hydroxysuccinimidyl 2,3-dibromoproprionate.

In other specific embodiments, two or more interacting components, or homologues, derivatives or fragments thereof, are directly fused together, or covalently linked together through a peptide linker, forming a hybrid protein having a single unbranched polypeptide chain. Thus, the complex may be formed by intramolecular interactions between two portions of the hybrid protein. In still another embodiment, at least one of the fused or linked interacting components in this complex is a homologue, derivative or fragment of hcGAS polypeptide with amino acid substitutions at positions K187 and L195.

In specific embodiments, at least one hcGAS polypeptide, or a homologue, derivative or fragment thereof, may be expressed as fusion or chimeric protein comprising the modified hcGAS polypeptide, homologue, derivative or fragment, joined via a peptide bond to a heterologous amino acid sequence.

As used herein, a "chimeric protein" or "fusion protein" comprises all or part (preferably a biologically active part) of a polypeptide corresponding to a modified hcGAS polypeptide or a fragment, homologue or derivative thereof, operably linked to a heterologous polypeptide (i.e., a polypeptide other than the polypeptide corresponding to the modified hcGAS polypeptide or a fragment, homologue or derivative thereof). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

In one embodiment, the heterologous amino acid sequence comprises an affinity tag that can be used for affinity purification. In another embodiment, the heterologous amino acid sequence includes a fluorescent label. In still another embodiment, the fusion protein contains a heterologous signal sequence, immunoglobulin fusion protein, toxin, or other useful protein sequences.

A variety of peptide tags known in the art may be used to generate fusion proteins of the modified hcGAS polypeptide of a complex of the invention, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST: Smith, 1993, *Methods Mol. Cell Bio.* 4:220-229), the *E. coli* maltose binding protein (Guanetal., 1987, *Gene* 67:21-30), and various cellulose binding domains (U.S. Pat. Nos. 5,496,934: 5,202,247; 5,137,819; Tomme et al., 1994, *Protein Eng.* 7:117-123), etc.

One possible peptide tags are short amino acid sequences to which monoclonal antibodies are available, such as but not limited to the following well known examples, the FLAG® epitope, the myc epitope at amino acids 408-439, the influenza virus hemaglutinin (HA) epitope. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

In certain embodiments, a combination of different peptide tags is used for the purification of the modified hcGAS polypeptide of a complex of the invention or for the purification of a complex. In certain embodiments, at least one modified hcGAS polypeptide has at least two peptide tags, e.g., a FLAG® tag and a His tag. The different tags can be fused together or can be fused in different positions to the modified hcGAS polypeptide. In the purification procedure, the different peptide tags are used subsequently or concurrently for purification. In certain embodiments, at least two different components are fused to a peptide tag, wherein the peptide tags of the two components can be identical or different. Using different tagged components for the purification of the molecular complex ensures that only complex will be purified and minimizes the amount of uncomplexed components.

Various leader sequences known in the art can be used for the efficient secretion of a modified hcGAS polypeptide of a complex of the invention from bacterial and mammalian cells (von Heijne, 1985, *J. Mol. Biol.* 184:99-105). Leader peptides are selected based on the intended host cell, and may include bacterial, yeast, viral, animal, and mammalian sequences. For example, the herpes virus glycoprotein D leader peptide is suitable for use in a variety of mammalian cells. A preferred leader peptide for use in mammalian cells can be obtained from the V-J2-C region of the mouse immunoglobulin kappa chain (Bernard et al., 1981. *Proc. Natl. Acad. Sci.* 78:5812-5816).

DNA sequences encoding desired peptide tag or leader peptide which are known or readily available from libraries or commercial suppliers are suitable in the practice of this invention.

In certain embodiments, DNA of a complex of the invention is a double-stranded DNA. In one embodiment, DNA of a complex of the invention is at least 45 bp, e.g., at least 100 bp, at least 200 bp, at least 400 bp, at least 800 bp, at least 1 kb, at least 2 kb, at least 4 kb, at least 8 kb, at least 10 kb, at least 20 kb, at least 40 kb, at least 80 kb, at least 100 kb, at least 200 kb, at least 400 kb, at least 800 kb, at least 1 Mb, at least 2 Mb, at least 4 Mb, at least 8 Mb, at least 10 Mb, or at least 20 Mb, or any range in between, inclusive, such as 45 bp to 10 Mb. In certain embodiments, DNA of a complex of the invention is a genomic DNA. In another embodiment, DNA of a complex of the invention is less than 45 bp, e.g., less than 40 bp, less than 35 bp, less than 30 bp, less than 25 bp, less than 20 bp, less than 15 bp, or less than 10 bp. In a specific embodiment, DNA of a complex of the invention is 17 bp. DNA of a complex of the invention may be isolated from a cell or an organism using any methods described above. Alternatively, DNA of a complex of the invention may be synthesized by conventional techniques including automated DNA synthesizers.

In certain embodiments, DNA of a complex of the invention is an activating DNA. The "activating DNA" herein refers to DNA which is capable of binding to the hcGAS or modified hcGAS polypeptide and converting the conformation of the hcGAS or modified hcGAS polypeptide to an active conformation. The activating DNA can be of any length or comprise any sequences. In one specific embodiment, the activating DNA comprises a sense sequence of SEQ ID NO: 6 and an antisense sequence of SEQ ID NO: 7. In another specific embodiment, the activating DNA comprises a sense sequence of 8, or an antisense sequence of SEQ ID NO: 9.

The modified hcGAS polypeptide and DNA fragment may form various modified hcGAS-DNA complexes, all of which fall in the scope of the present invention. In certain embodiments, the human cGAS oligomerizes on the DNA and therefore forms a high-order oligomerized hcGAS-DNA complex. In other embodiment, a minimal hcGAS-DNA complex may be formed. In a specific embodiment, the minimal hcGAS-DNA complex comprises two molecules of human cGAS and two molecules of double-stranded DNA. In a more specific embodiment, each hcGAS polypeptide binds to one double-stranded DNA. Either the high-order oligomerized hcGAS-DNA complex or the minimal hcGAS-DNA complex may further comprises nucleotide (e.g., ATP), metal, and/or additional molecules (e.g., testing compound).

In certain embodiments, the components of a complex of the invention are derived from the same species. In more specific embodiments, the components are all derived from human. In another specific embodiment, the components are all derived from a mammal.

Included within the scope of the invention is a modified hcGAS complex in which the components, or homologs, derivatives, or fragments thereof, are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH4, acetylation, formylation, oxidation, reduction, metabolic synthesis in the presence of tunicamycin, etc. In still another embodiment, the protein sequences are modified to have a heterofunctional reagent; such heterofunctional reagents can be used to crosslink the members of the complex.

The complexes of the present invention can also be in a modified form. For example, an antibody selectively immunoreactive with the complex can be bound to the complex. In another example, a non-antibody modulator capable of enhancing the interaction between the interacting partners in the complex may be included.

The above-described modified hcGAS complexes may further include any additional components, e.g., other proteins, nucleic acids, lipid molecules, monosaccharides or polysaccharides, ions, etc.

III. Identification of Compounds that Modulate hcGAS

The modified hcGAS nucleic acid and polypeptide molecules described herein may be used to design and/or screen for modulators of one or more of biological activities of hcGAS polypeptides or complexes. In particular, information useful for the design of therapeutic and diagnostic molecules, including, for example, the protein domain, structural information, and the like for modified hcGAS polypeptides of the invention is now available or attainable as a result of the ability to prepare, purify and characterize the modified hcGAS polypeptides and complexes, and domains, fragments, variants and derivatives thereof.

Therefore, one aspect of the present invention pertains to methods of screening for modulators of the modified hcGAS nucleic acid and polypeptide molecules. For example, in one such method, a modified hcGAS nucleic acid and/or polypeptide, is contacted with a test compound, and the activity of the modified hcGAS nucleic acid and/or polypeptide is determined in the presence of the test compound, wherein a change in the activity of the modified hcGAS nucleic acid and/or polypeptide in the presence of the compound as compared to the activity in the absence of the compound (or in the presence of a control compound) indicates that the test compound modulates the activity of the modified hcGAS nucleic acid and/or polypeptide. The modulators of the invention may elicit a change in one or more of the following activities: (a) a change in the level and/or rate of formation of a hcGAS-DNA complex and/or a hcGAS-DNA-ATP complex, (b) a change in the activity of a hcGAS nucleic acid and/or polypeptide, including, e.g., 2'3' cGAMP synthesis, repression of *V. cholera* chemotaxis, enzyme kinetics, DNA-length specificity, STING pathway activation, etc., (c) a change in the stability of a hcGAS nucleic acid and/or polypeptide, (d) a change in the conformation of a hcGAS nucleic acid and/or polypeptide, or (e) a change in the activity of at least one component contained in a hcGAS-DNA complex and/or a hcGAS-DNA-ATP complex.

The modulators of the invention may be employed, for instance, to prevent and/or treat hcGAS-mediated diseases or disorders. In one aspect, inhibitors or antagonists against the modified hcGAS polypeptides of the invention, biological complexes containing them, or orthologues thereof, may be used to treat any disease or other treatable condition of a patient (including humans and animals), including, for example, autoimmune disorders. In another aspect, agonists of the modified hcGAS polypeptides of the invention, biological complexes containing them, or orthologues thereof, may be used to treat any disease or other treatable condition of a patient (including humans and animals), including, for example, cancer.

Compounds to be tested for their ability to act as modulators of hcGAS nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is a siRNA. In certain embodiments, the compound comprises a biologically active fragment of an hcGAS polypeptide (e.g., a dominant negative form that binds to DNA and ATP, but does not activate, 2'3' cGAMP synthesis).

A variety of assay formats will suffice and, in light of the present disclosure, those not expressly described herein may nevertheless be comprehended by one of ordinary skill in the art based on the teachings herein. Assay formats for analyzing modified hcGAS-DNA complex formation and/or activity of a modified hcGAS nucleic acid and/or polypeptide, may be generated in many different forms, and include assays based on cell-free systems, e.g. purified proteins or cell lysates, as well as cell-based assays which utilize intact cells. Simple binding assays can also be used to detect agents which modulate a modified hcGAS, for example, by enhancing the binding of a modified hcGAS polypeptide to DNA, and/or by enhancing the binding of the modified hcGAS-DNA complex to a substrate. Another example of an assay useful for identifying a modulator of hcGAS is a competitive assay that combines one or more modified hcGAS polypeptides with a potential modulator, such as, for example, polypeptides, nucleic acids, natural substrates or ligands, or substrate or ligand mimetics, under appropriate conditions for a competitive inhibition assay. The modified hcGAS polypeptides can be labeled, such as by radioactivity or a colorimetric compound, such that hcGAS-DNA complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting the modified hcGAS polypeptide, or complexes thereof, as described above.

Complex formation between a modified hcGAS polypeptide, or fragment thereof, and a binding partner (e.g., DNA) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying hcGAS-DNA complexes described above may be incorporated into the detection methods.

In certain embodiments, it may be desirable to immobilize a modified hcGAS polypeptide to facilitate separation of modified hcGAS complexes from uncomplexed forms of modified hcGAS polypeptides, DNA fragments, and/or ATP, as well as to accommodate automation of the assay. Binding of a modified hcGAS polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of the modified hcGAS polypeptides found in the bead fraction quantified from the gel using standard electrophoretic techniques such as described in the appended examples.

Other techniques for immobilizing proteins on matrices are also available for use in the subject assay. For instance, a modified hcGAS polypeptide may be immobilized utilizing conjugation of biotin and streptavidin. For instance, biotinylated polypeptide molecules may be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the modified hcGAS polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of the modified hcGAS polypeptide trapped in the modified hcGAS-DNA complex and/or hcGAS-DNA-ATP complex may be assessed with a chromogenic substrate of the enzyme, e.g. 3,3'-diamino-benzadine terahydrochloride or 4-chloro-1-napthol. Likewise, a fusion protein comprising the modified hcGAS polypeptide and glutathione-S-transferase may be provided, and the modified hcGAS-DNA complex and/or hcGAS-DNA-ATP complex formation may be quantified by detecting the GST activity using 1-chloro-2,4-dinitrobenzene (Habig et al (1974) *J Biol Chem* 249:7130).

Antibodies against the modified hcGAS polypeptide can be used for immunodetection purposes. Alternatively, the modified hcGAS polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) *J Biol Chem* 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In another embodiment, the modified hcGAS polypeptide, or complexes thereof, of interest may be generated in whole cells, taking advantage of cell culture techniques to support the subject assay. For example, the modified hcGAS polypeptide, or complexes thereof, may be constituted in a prokaryotic or eukaryotic cell culture system. Advantages to generating the modified hcGAS polypeptide, or complexes thereof, in an intact cell includes the ability to screen for modulators of the level and/or activity of the modified hcGAS polypeptide, or complexes thereof, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The modified hcGAS nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of a modified hcGAS may be detected in a cell-free assay generated by constitution of a functional modified hcGAS in a cell lysate. In an alternate format, the assay can be derived as a reconstituted protein mixture which, as described below, offers a number of benefits over lysate-based assays.

The activity of a modified hcGAS nucleic acid and/or polypeptide may be identified and/or assayed using a variety of methods well known to the skilled artisan. For example, the activity of a modified hcGAS nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes. In another embodiment, the biological activity of a modified hcGAS nucleic acid and/or polypeptide may be assessed by monitoring the modification of the substrate. For example, the synthesis of 2'3' cGAMP may be monitored as described in the examples herein.

In yet another embodiment, the biological activity of a modified hcGAS nucleic acid and/or polypeptide may be assessed by monitoring changes in the phenotype of a targeted cell. For example, the repression of *V. cholera* chemotaxis may be detected as described in the examples herein. The detection means can also include a reporter gene construct which includes a transcriptional regulatory element that is dependent in some form on the level and/or activity of a modified hcGAS nucleic acid and/or polypeptide. The modified hcGAS nucleic acid and/or polypeptide may be provided as a fusion protein with a domain that binds to a DNA element of a reporter gene construct. The added domain of the fusion protein can be one which, through its DNA-binding ability, increases or decreases transcription of the reporter gene. Whichever the case may be, its presence in the fusion protein renders it responsive to a modified hcGAS nucleic acid and/or polypeptide. Accordingly, the level of expression of the reporter gene will vary with the level of expression of a modified hcGAS nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a modified hcGAS nucleic acid and/or polypeptide present in the cell. Such embodiments of the subject assay are particularly amenable to high through-put analysis in that proliferation of the cell can provide a simple measure of inhibition of the modified hcGAS nucleic acid and/or polypeptide.

IV. Structure of hcGAS-DNA Complexes

The present invention provides, crystals of human cGAS-DNA complex and human cGAS-DNA-ATP complex, as well as structure of active human cGAS determined therefrom. In one aspect, the invention relates to a crystal of an hcGAS-DNA complex comprising an hcGAS polypeptide and a double-stranded DNA, wherein the crystal effectively diffracts X-rays for the determination of the atomic coordinates of the hcGAS-DNA-ATP complex to a resolution of greater than 5.0 Angstroms, alternatively greater than 3.0 Angstroms, or alternatively greater than 2.0 Angstroms. In one embodiment, the crystal of an hcGAS-DNA complex has a hexagonal space group P $6_1$ 2 2. In another embodiment, the crystal of an hcGAS-DNA complex has a unit cell of dimensions of a=b=101.17 Å, and c=241.06 Å. In yet another embodiment, the crystal has the set of structural coordinates as given in Table 3+/−the root mean square deviation from the backbone atoms of the hcGAS-DNA complex of less than 2 Angstroms, e.g., less than 1.5 Angstroms, less than 1.25 Angstroms, less than 1.0 Angstroms, less than 0.75 Angstroms, less than 0.5 Angstroms, less than 0.45 Angstroms, less than 0.4 Angstroms, less than 0.35 Angstroms, less than 0.3 Angstroms, less than 0.25 Angstroms, or less than 0.2 Angstroms.

In another aspect, the invention relates to a crystal of an hcGAS-DNA-ATP complex comprising an hcGAS polypeptide, an ATP, and a double-stranded DNA, wherein the crystal effectively diffracts X-rays for the determination of the atomic coordinates of the hcGAS-DNA-ATP complex to a resolution of greater than 5.0 Angstroms, alternatively greater than 3.0 Angstroms, or alternatively greater than 2.0 Angstroms. In one embodiment, the crystal of an hcGAS-DNA-ATP complex has a hexagonal space group P 61 2 2. In another embodiment, the crystal of an hcGAS-DNA-ATP complex has a unit cell of dimensions of a=b=100.49 Å, and c=236.75 Å. In yet another embodiment, the crystal has the set of structural coordinates as given in Table 3+/−the root mean square deviation from the backbone atoms of the hcGAS-DNA-ATP complex of less than 2 Angstroms, e.g., less than 1.5 Angstroms, less than 1.25 Angstroms, less than 1.0 Angstroms, less than 0.75 Angstroms, less than 0.5

Angstroms, less than 0.45 Angstroms, less than 0.4 Angstroms, less than 0.35 Angstroms, less than 0.3 Angstroms, less than 0.25 Angstroms, or less than 0.2 Angstroms.

In one embodiment, human cGAS in the crystals of the present invention is a modified hcGAS polypeptide having at least 70% identity to the human cGAS (hcGAS) amino acid sequence of any one of SEQ ID NOs: 1-2 and further comprising amino acid substitutions at positions corresponding to K187 and L195 of SEQ ID NO: 1. In a specific embodiment, the residue at position K187 is substituted with a lysine residue and the residue at position L195 is substituted with an arginine residue. In another embodiment, the modified hcGAS is a fragment of human cGAS, e.g., a biologically active fragment of human cGAS. In a specific embodiment, the modified hcGAS consists of residues 157-522 of a full-length native hcGAS. In yet another embodiment, the DNA in the crystals of the present invention is an activating DNA. In a specific embodiment, the DNA is a 17 bp activating DNA. In a more specific embodiment, DNA is a 17 bp activating DNA used in the examples described below.

In one embodiment, the structure of human cGAS-DNA complex reveals a minimal 2:2 complex of two molecules of cGAS bound to two molecules of double-stranded DNA. In another embodiment, hcGAS bound to DNA using two separate DNA-binding surfaces. In a specific embodiment, the crystals of the present invention have hcGAS and DNA contacts as those shown in FIGS. 6B and/or 7C. In yet another embodiment, hcGAS is in an active conformation. In still another embodiment, the conformation of the hcGAS-DNA complex is the conformation shown in FIGS. 5B, 6A, 6C, 6D, 7D and/or 7E. In one embodiment, the conformation of the human cGAS-DNA-ATP complex is the conformation shown in FIGS. 5C, 6D, 10A, and/or 10B.

X-ray structure coordinates define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the scalable three-dimensional configuration of points derived from the structure coordinates of at least a portion of a human cGAS molecule or molecular complex, as listed in Table 3, as well as structurally equivalent configurations, as described below. Preferably, the scalable three-dimensional configuration includes points derived from structure coordinates representing the locations of a plurality of the amino acids defining a human cGAS binding pocket.

In certain embodiments, the structure coordinates of human cGAS-DNA complex and human cGAS-DNA-ATP complex, as determined by X-ray crystallography, are listed in Table 3. Slight variations in structure coordinates can be generated by mathematically manipulating the human cGAS-DNA complex or the human cGAS-DNA-ATP complex structure coordinates. For example, the structure coordinates set forth in Table 3 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent.

It should be noted that slight variations in individual structure coordinates of the human cGAS-DNA complex or the human cGAS-DNA-ATP complex would not be expected to significantly alter the nature of chemical entities such as modulators that could associate with the binding pockets. In this context, the phrase "associating with" refers to a condition of proximity between a chemical entity, or portions thereof, and a human cGAS molecule or portions thereof. The association may be non-covalent, wherein the juxtaposition is energetically favored by hydrogen bonding, van der Waals forces, or electrostatic interactions, or it may be covalent. Thus, for example, a modulator that bound to a binding pocket of human cGAS would also be expected to bind to or interfere with a structurally equivalent binding pocket.

For the purpose of this invention, any molecule or molecular complex or binding pocket thereof, or any portion thereof, that has a root mean square deviation of conserved residue backbone atoms (N, Ca, C, O) of less than about 0.75 Å, when superimposed on the relevant backbone atoms described by the reference structure coordinates listed in Table 3, is considered "structurally equivalent" to the reference molecule. That is to say, the crystal structures of those portions of the two molecules are substantially identical, within acceptable error. As used herein, "residue" refers to one or more atoms. Particularly preferred structurally equivalent molecules or molecular complexes are those that are defined by the entire set of structure coordinates listed in Table 3±a root mean square deviation from the conserved backbone atoms of those amino acids of less than about 0.45 Å. More preferably, the root mean square deviation is at most about 0.35 Å, and most preferably at most about 0.2 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of human cGAS or a binding pocket portion thereof, as defined by the structure coordinates of human cGAS described herein.

Likewise, the invention also includes the scalable three-dimensional configuration of points derived from structure coordinates of molecules or molecular complexes that are structurally homologous to hcGAS, as well as structurally equivalent configurations. Structurally homologous molecules or molecular complexes are defined below. Advantageously, structurally homologous molecules can be identified using the structure coordinates of human hcGAS according to a method of the invention.

Various computational analyses can be used to determine whether a molecule or a binding pocket portion thereof is "structurally equivalent," defined in terms of its three-dimensional structure, to all or part of human cGAS or its binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures).

Since atom equivalency within QUANTA is defined by user input, for the purpose of this invention equivalent atoms are defined as protein backbone atoms (N, Ca, C, and O) for all conserved residues between the two structures being compared. A conserved residue is defined as a residue which is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

The configurations of points in space derived from structure coordinates according to the invention can be visualized as, for example, a holographic image, a stereodiagram, a model, or a computer-displayed image, and the invention thus includes such images, diagrams or models.

In one aspect, the invention relates to methods of producing crystals of an hcGAS-DNA complex or an hcGAS-DNA-ATP complex. Crystals of the hcGAS-DNA complex or the hcGAS-DNA-ATP complex can be produced or grown by a number of techniques including batch crystallization, vapor diffusion (either by sitting drop or hanging drop), soaking, and by microdialysis. Seeding of the crystals in some instances is required to obtain X-ray quality crystals. Standard micro and/or macro seeding of crystals may therefore be used. Preferably, the crystal effectively diffracts X-rays for the determination of the atomic coordinates of the protein-ligand complex to a resolution greater than 5.0 Angstroms, alternatively greater than 3.0 Angstroms, or alternatively greater than 2.0 Angstroms. Exemplified in the Examples section below is the hanging-drop vapor diffusion procedure.

Once a crystal of the present invention is produced, X-ray diffraction data can be collected. The example below used standard cryogenic conditions for such X-ray diffraction data collection though alternative methods may also be used. For example, diffraction data can be collected by using X-rays produced in a conventional source (such as a sealed tube or rotating anode) or using a synchrotron source. Methods of X-ray data collection include, but are not limited to, precession photography, oscillation photography and diffractometer data collection. Data can be processed using packages including, for example, DENZO and SCALPACK (Z. Otwinowski and W. Minor) and the like.

The three-dimensional structure of the hcGAS-DNA complex or the hcGAS-DNA-ATP complex constituting the crystal may be determined by conventional means as described herein. Where appropriate, the structure factors from the three-dimensional structure coordinates of a related cGAS-DNA complex may be utilized to aid the structure determination of the hcGAS-DNA complex. Structure factors are mathematical expressions derived from three-dimensional structure coordinates of a molecule. These mathematical expressions include, for example, amplitude and phase information. The term "structure factors" is known to those of ordinary skill in the art. Alternatively, the three-dimensional structure of the protein-ligand complex may be determined using molecular replacement analysis. This analysis utilizes a known three-dimensional structure as a search model to determine the structure of a closely related protein-ligand complex. The measured X-ray diffraction intensities of the crystal are compared with the computed structure factors of the search model to determine the position and orientation of the hcGAS in the hcGAS-ligand complex crystal. Computer programs that can be used in such analyses include, for example, X-PLOR and AmoRe (J. Navaza, *Acta Crystallographics* ASO, 157-163 (1994)). Once the position and orientation are known, an electron density map may be calculated using the search model to provide X-ray phases. The electron density can be inspected for structural differences and the search model may be modified to conform to the new structure. Using this approach, one may use the structure of the hcGAS-DNA complex or hcGAS-DNA-ATP complex described herein to solve other hcGAS-DNA complex crystal structures, or other polypeptide crystal structures, particularly where the polypeptide is homologous to hcGAS. Computer programs that can be used in such analyses include, for example, QUANTA and the like.

V. Uses of the Structure Coordinates of hcGAS-DNA Complexes

The present invention permits the use of molecular design techniques to design, select and synthesize chemical entities and compounds, including agonist and antagonist, capable of binding to hcGAS and/or modulating hcGAS.

One approach enabled by this invention, is to use the structure coordinates of human cGAS-DNA complex and human cGAS-DNA-ATP complex to design compounds that bind to the active enzyme conformation of hcGAS and alter the physical properties of the compounds in different ways, e.g., solubility. For example, this invention enables the design of compounds that act as inhibitors of the human cGAS protein by binding to, all or a portion of, the inhibitor packet above the ATP donor site in the active enzyme conformation of hcGAS. In certain embodiments, this invention also enables the design of compounds that act as modulators of hcGAS by binding to, all or a portion of, residues involved in DNA-binding, nucleotide coordination, and/or overall protein stability.

Another design approach is to probe a crystal of human cGAS-DNA complex or human cGAS-DNA-ATP complex with molecules composed of a variety of different chemical entities to determine optimal sites for interaction between candidate hcGAS modulators and the enzyme. For example, high resolution X-ray diffraction data collected from crystals saturated with solvent allows the determination of where each type of solvent molecule sticks. Small molecules that bind tightly to those sites can then be designed and synthesized and tested for their effects on modulating activity of hcGAS (see, e.g., Travis et al. (1993) *Science* 262:1374).

This invention also enables the development of compounds that can isomerize to short-lived reaction intermediates in the chemical reaction of a substrate or other compound that binds to hcGAS, with hcGAS. Thus, the time-dependent analysis of structural changes in hcGAS during its interaction with other molecules is enabled. The reaction intermediates of hcGAS can also be deduced from the reaction product in co-complex with hcGAS. Such information is useful to design improved analogues of known hcGAS modulators or to design novel classes of modulators based on the reaction intermediates of the hcGAS enzyme and hcGAS-modulator co-complex. This provides a novel route for designing hcGAS modulators with both high specificity and stability.

Another approach made possible and enabled by this invention, is to screen computationally small molecule data bases for chemical entities or compounds that can bind in whole, or in part, to the hcGAS enzyme. In this screening, the quality of fit of such entities or compounds to the binding site may be judged either by shape complementarity or by estimated interaction energy (see, e.g., Meng et al. (1992) *J. Camp. Chem.* 13:505-524). Because hcGAS-DNA complex or hcGAS-DNA-ATP complex may crystallize in more than one crystal form, the structure coordinates, or portions thereof, as provided by this invention are particularly useful to solve the structure of those other crystal forms of hcGAS-DNA complex or hcGAS-DNA-ATP complex. They may also be used to solve the structure of hcGAS mutants, hcGAS co-complexes, or of the crystalline form of any other protein with significant amino acid sequence homology to any functional domain of hcGAS.

One method that may be employed for this purpose is molecular replacement. In this method, the unknown crystal structure, whether it is another crystal form of hcGAS, an hcGAS mutant, or an hcGAS co-complex, or the crystal of some other protein with significant amino acid sequence homology to any functional domain of hcGAS, may be determined using the hcGAS structure coordinates of this invention as provided in Table 3. This method may provide an accurate structural form for the unknown crystal more quickly and efficiently than attempting to determine such information ab initio.

In addition, in accordance with this invention, hcGAS mutants may be crystallized in co-complex with known hcGAS modulators. The crystal structures of a series of such complexes may then be solved by molecular replacement and compared with that of wild-type hcGAS. Potential sites for modification within the various binding sites of the enzyme may thus be identified. This information may provide an additional tool for determining the most efficient binding interactions, for example, increased hydrophobic interactions, between hcGAS and a chemical entity or compound.

All of the complexes referred to above may be studied using well-known X-ray diffraction techniques and may be refined versus 2-3A resolution X-ray data to an R value of about 0.20 or less using computer software, such as X-PLOR (Yale University, ©1992, distributed by Molecular Simulations, Inc.). See, e.g., Blundel & Johnson, supra; *Methods in Enzymology*, vol. 114 & 115, H. W. Wyckoff et al., eds., Academic Press (1985). This information may thus be used to optimize known classes of hcGAS modultors, and more importantly, to design and synthesize novel classes of hcGAS modulators.

The structure coordinates of hcGAS mutants provided in this invention also facilitate the identification of related proteins or enzymes analogous to hcGAS in function, structure or both, thereby further leading to novel therapeutic modes for treating or preventing hcGAS-mediated diseases, such as cancer and autoimmune diseases.

The design of compounds that bind to or modulate hcGAS according to this invention may involve consideration of two factors. First, the compound may be capable of physically and structurally associating with hcGAS. Noncovalent molecular interactions important in the association of hcGAS with its substrate include hydrogen bonding, van der Waals and hydrophobic interactions. Second, the compound may be able to assume a conformation that allows it to associate with hcGAS. Although certain portions of the compound will not directly participate in this association with hcGAS, those portions may still influence the overall conformation of the molecule. This, in turn, may have a significant impact on potency. Such conformational requirements include the overall three-dimensional structure and orientation of the chemical entity or compound in relation to all or a portion of the binding site of ICE, or the spacing between functional groups of a compound comprising several chemical entities that directly interact with hcGAS.

The potential modulatory or binding effect of a chemical compound on hcGAS may be analyzed prior to its actual synthesis and testing by the use of computer modelling techniques. If the theoretical structure of the given compound indicates insufficient interaction and association between it and hcGAS, synthesis and testing of the compound may be obviated. However, if computer modelling indicates a strong interaction, the molecule may then be synthesized and tested for its ability to bind to hcGAS and modulate activity of hcGAS, e.g., by measuring 2'3' cGAMP synthesis. In this manner, synthesis of inoperative compounds may be avoided.

A modulatory or other binding compound of hcGAS may be computationally evaluated and designed by means of a series of steps in which chemical entities or fragments are screened and selected for their ability to associate with the individual binding pockets or other areas of hcGAS. One skilled in the art may use one of several methods to screen chemical entities or fragments for their ability to associate with hcGAS and more particularly with the individual binding pockets of the hcGAS active site. This process may begin by visual inspection of, for example, the active site on the computer screen based on the coordinates of the hcGAS-DNA complex or the hcGAS-DNA-ATP complex in Table 3. Selected fragments or chemical entities may then be positioned in a variety of orientations, or docked, within an individual binding pocket of hcGAS as defined supra. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. For example, these may include:
1. GRID (Goodford, P. J., "A Computational Procedure for Determining Energetically Favorable Binding Sites on Biologically Important Macromolecules", *J. Med.* Chem., 28, pp. 849-857 (1985)). GRID is available from Oxford University, Oxford, UK.
2. MCSS (Miranker, A and M. Karplus, "Functionality Maps of Binding Sites: A Multiple Copy Simultaneous Search Method." Proteins: Structure. Function and Genetics, 11, pp. 29-34 (1991)). MCSS is available from Molecular Simulations, Burlington, Mass.
3. AUTO DOCK (Goodsell, D. S. and A J. Olsen, "Automated Docking of Substrates to Proteins by Simulated Annealing", Proteins: Structure. Function, and Genetics, 8, pp. 195-202 (1990)). AUTODOCK is available from Scripps Research Institute, La Jolla, Calif.

4. DOCK (Kuntz, I. D. et al., "A Geometric Approach to Macromolecule-Ligand Interactions", *J. Mol. Biol.*, 161, pp. 269-288 (1982)). DOCK is available from University of California, San Francisco, Calif.

Once suitable chemical entities or fragments have been selected, they can be assembled into a single compound or inhibitor. Assembly may be proceed by visual inspection of the relationship of the fragments to each other on the three-dimensional image displayed on a computer screen in relation to the structure coordinates of the hcGAS-DNA complex or the hcGAS-DNA-ATP complex. This would be followed by manual model building using software such as Quanta or Sybyl.

For example, useful programs to aid one of skill in the art in connecting the individual chemical entities or fragments may include:

1. CAVEAT (Bartlett, P. A et al, "CAVEAT: A Program to Facilitate the Structure-Derived Design of Biologically Active Molecules". In "*Molecular Recognition in Chemical and Biological Problems*", Special Pub., Royal Chern. Soc., 78, pp. 182-196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", *J. Med. Chern.*, 35, pp. 2145-2154 (1992)).
3. HOOK (available from Molecular Simulations, Burlington, Mass.).

Instead of proceeding to build a hcGAS modulator in a step-wise fashion one fragment or chemical entity at a time as described above, modulatory or other hcGAS binding compounds may be designed as a whole or "de novo" using either an empty active site or optionally including some portion(s) of a known modulator(s). For example, these methods may include:

1. LUDI (Bohm, H.-J., "The Computer Program LUDI: A New Method for the De Novo Design of Enzyme Inhibitors", J. Camp. Aid. Malec. Design, 6, pp. 61-78 (1992)). LUDI is available from Biosym Technologies, San Diego, Calif.
2. LEGEND (Nishibata, Y. and A Itai, *Tetrahedron*, 47, p. 8985 (1991)). LEGEND is available from Molecular Simulations, Burlington, Mass.
3. LeapFrog (available from Tripos Associates, St. Louis, Mo.).

Other molecular modelling techniques may also be employed in accordance with this invention. See, e.g., Cohen, N. C. et al., "Molecular Modeling Software and Methods for Medicinal Chemistry", *J. Med. Chem.*, 33, pp. 883-894 (1990). See also, Navia, M. A and M. A Murcko, "The Use of Structural Information in Drug Design", *Current Opinions in Structural Biology*, 2, pp. 202-210 (1992).

Once a compound has been designed or selected by the above methods, the efficiency with which that compound may bind to hcGAS may be tested and optimized by computational evaluation. For example, a compound that has been designed or selected to function as an hcGAS-modulator may also preferably traverse a volume not overlapping that occupied by the active site when it is bound to the native substrate. An effective hcGAS modulator may preferably demonstrate a relatively small difference in energy between its bound and free states (i.e., a small deformation energy of binding). Thus, the most efficient hcGAS modulators may preferably be designed with a deformation energy of binding of not greater than about 10 kcal/mole, preferably, not greater than 7 kcal/mole. hcGAS modulators may interact with the enzyme in more than one conformation that is similar in overall binding energy. In those cases, the deformation energy of binding is taken to be the difference between the energy of the free compound and the average energy of the conformations observed when the modulator binds to the enzyme.

A compound designed or selected as binding to hcGAS may be further computationally optimized so that in its bound state it would preferably lack repulsive electrostatic interaction with the target enzyme. Such non-complementary (e.g., electrostatic) interactions include repulsive charge-charge, dipole-dipole and charge-dipole interactions. Specifically, the sum of all electrostatic interactions between the modulator and the enzyme when the modulator is bound to hcGAS, preferably make a neutral or favorable contribution to the enthalpy of binding.

Specific computer software is available in the art to evaluate compound deformation energy and electrostatic interaction. Examples of programs designed for such uses may include: Gaussian 92, revision C (M. J. Frisch, Gaussian, Inc., Pittsburgh, Pa. ©1992); AMBER, version 4.0 (P. A Kollman, University of California at San Francisco, ©1994); QUANTA/CHARMM (Molecular Simulations, Inc., Burlington, Mass. ©1994); and Insight 11/Discover (Biosysm Technologies Inc., San Diego, Calif. ©1994). These programs may be implemented, for instance, using a Silicon Graphics workstation, IRIS 4D/35 or IBM RISC/6000 workstation model 550. Other hardware systems and software packages will be known to those skilled in the art.

Once an hcGAS-binding compound has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to hcGAS by the same computer methods described in detail, above.

The present invention also enables mutants of ICE and the solving of their crystal structure. More particularly, by virtue of the present invention, the location of the active site and interface of hcGAS based on its crystal structure permits the identification of desirable sites for mutation.

For example, mutation may be directed to a particular site or combination of sites of wild-type hcGAS, i.e., the active site, or a location on the interface site may be chosen for mutagenesis. Similarly, only a location on, at or near the enzyme surface may be replaced, resulting in an altered surface charge of one or more charge units, as compared to the wild-type enzyme. Alternatively, an amino acid residue in hcGAS may be chosen for replacement based on its hydrophilic or hydrophobic characteristics.

Such mutants may be characterized by any one of several different properties as compared with wild-type hcGAS. For example, such mutants may have altered surface charge of one or more charge units, or have an increased stability to component dissociation. Or such mutants may have an altered substrate specificity in comparison with, or a higher specific activity than, wild-type hcGAS.

The mutants of hcGAS prepared by this invention may be prepared in a number of ways as discussed above. Once the hcGAS mutants have been generated in the desired location, i.e., active site or DNA binding interface, the mutants may be tested for any one of several properties of interest. For example, one or more of the following activities may be tested: a) 2'3' cGAMP synthesis; b) repression of *V. cholera* chemotaxis; c) enzyme kinetics; d) nucleotide coordination; e) protein stability; f) interactions with DNA; g) DNA-length specificity; h) enzyme conformation; and i) STING pathway activation.

VI. Pharmaceutical Compositions

In another aspect, the present invention provides pharmaceutically acceptable compositions which comprise a modified human cGAS polypeptide comprising an amino acid sequence that has at least 70% identity to the amino acid sequence of human cGAS (hcGAS) and further comprising amino acid substitutions at positions corresponding to K187 and L195 of human cGAS, formulated together with one or more pharmaceutically acceptable carriers (additives) and/or diluents.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits or enhances) expression and/or activity of the modified hcGAS which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances or inhibits) modified hcGAS polypeptide expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a modified hcGAS polypeptide of the present invention. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a modified hcGAS polypeptide of the present invention, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a modified hcGAS polypeptide of the present invention include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a modified hcGAS polypeptide, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Figure 4A:
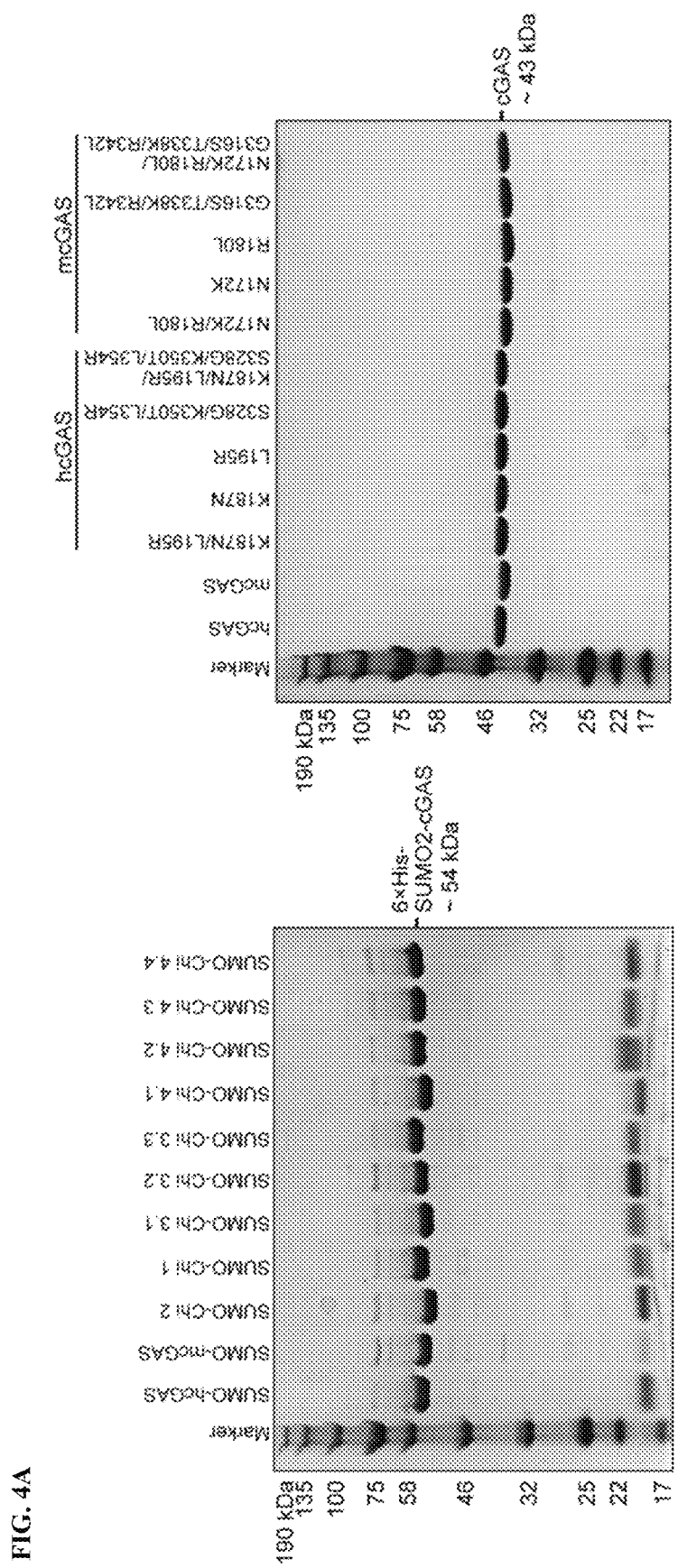
FIG. 4A-FIG. 4B show that in vitro analysis of hcGAS chimeras confirms genetic mapping.
Figure 4B:
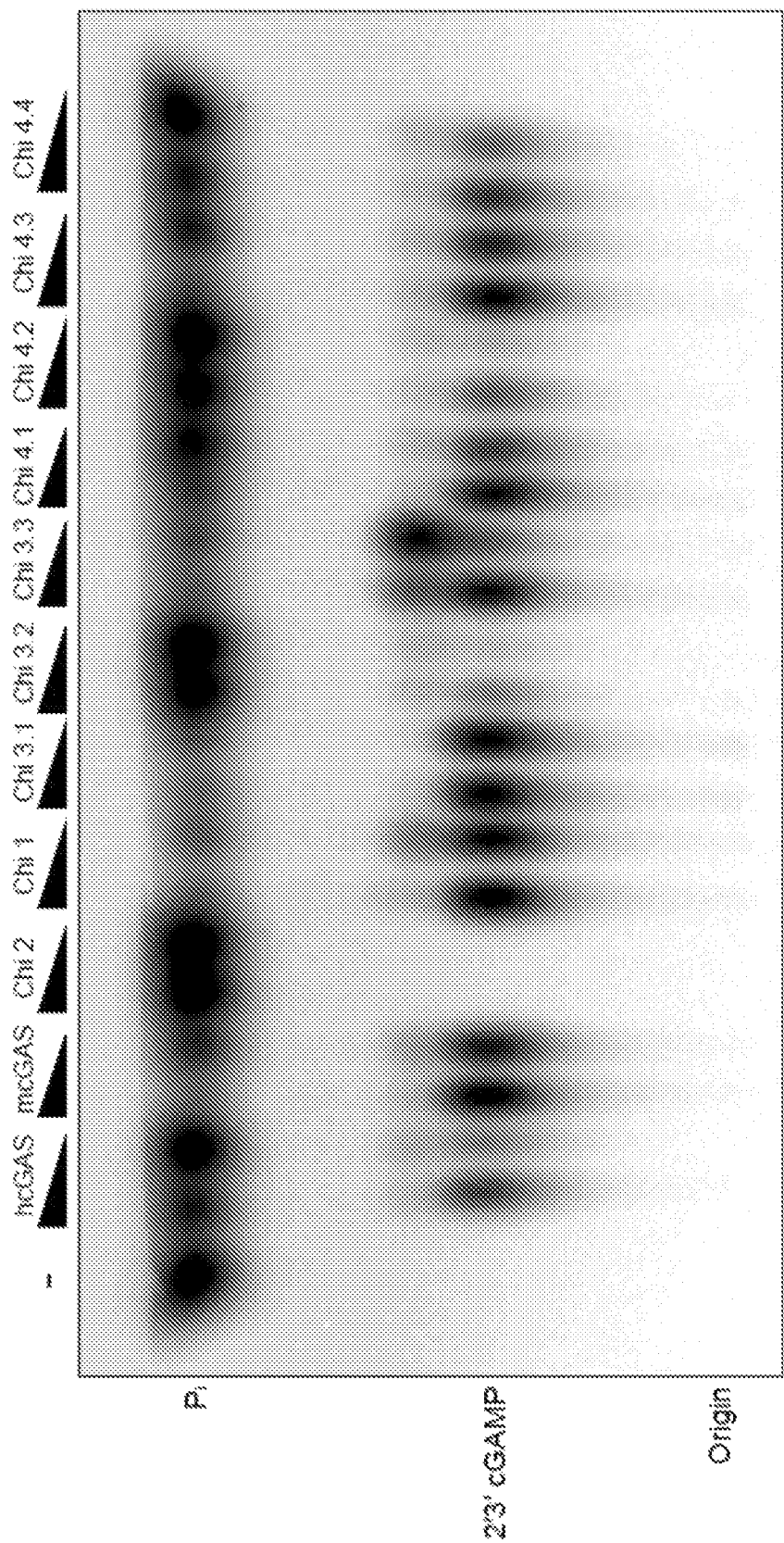

The modified hcGAS polypeptide, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a modified hcGAS polypeptide, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

This invention is further illustrated by the following examples which should not be construed as limiting. The contents of all references, patents and published patent applications cited throughout this application, as well as the Figures, are incorporated herein by reference.

EXAMPLES

Example 1: Materials and Methods for Examples 2-6 a. Protein Expression and Purification

Human cGAS (encoding residues 157-522) and mouse cGAS truncations (encoding residues147-507) were PCR amplified from previously described plasmids (Diner et al. (2013) *Cell Rep* 3:1355-1361; Kranzusch et al. (2013) *Cell Rep* 3:1362-1368) and cloned into a custom pET vector for expression of an N-terminal 6×His-SUMO2 ("6×His" disclosed as SEQ ID NO: 50) fusion protein in *E. coli*. *E. coli* BL21-RIL DE3 (Stratagene) bacteria harboring a pRARE2 tRNA plasmid were transformed with a pET cGAS plasmid. Transformations and starter cultures were grown in MDG media (0.5% glucose, 25 mM $Na_2HPO_4$, 25 mM $KH_2PO_4$, 50 mM $NH_4Cl$, 5 mM $Na_2SO_4$, 2 mM $MgSO_4$, 0.25% aspartic acid, 100 μg $ml^{-1}$ ampicillin, 34 μg $ml^{-1}$ chloramphenicol, and trace metals) overnight at 37° C. and used to seed 1 L cultures grown in M9ZB media (0.5% glycerol, 1% Cas-Amino Acids, 47.8 mM Na$_2$HPO$_4$, 22 mM KH$_2$PO$_4$, 18.7 mM H$_4$Cl, 85.6 mM NaCl, 2 mM MgSO$_4$, 100 µg ml$^{-1}$ ampicillin, 34 µg ml$^{-1}$ chloramphenicol, and trace metals) (Studier et al. (2005) *Protein Expr Purif* 41:207-234). M9ZB cultures were cultivated at 37° C. until OD$_{600}$ of ~1.5-2.5, cooled on ice for 20 min, and then recombinant protein synthesis was induced by supplementation with 0.5 mM IPTG. Cultures were placed at 16° C. with shaking for ~16 h. Bacteria were pelleted, washed with 1×PBS, and flash-frozen in LiN2 at −80° C. storage until lysis and purification. Recombinant cGAS was purified as previously described (Kranzusch et al. (2014) *Cell* 158:1011-1021) with modifications specific to SUMO2 tag removal. Bacterial pellets from 2×1 L M9ZB cultures were re-suspend in lysis buffer (20 mM HEPES-KOH pH 7.5, 400 mM NaCl, 30 mM imidazole, 10% glycerol, 1 mM DTT) chilled on ice and lysed by sonication. Lysate was clarified by centrifugation and subsequent filtration through glass-wool. 6×His-SUMO2-cGAS ("6×His" disclosed as SEQ ID NO: 50) was purified from clarified lysate by binding to Ni-NTA (Qiagen) and gravity chromatography. Resin was washed with lysis buffer supplemented to 1 M NaCl, and 6×His-SUMO2-cGAS was eluted with lysis buffer supplemented to 300 mM imidazole. The elution fraction was supplemented with ~250 µg of human SENP2 protease, and dialyzed overnight at 4° C. in dialysis buffer (20 mM HEPES-KOH pH 7.5, 300 mM NaCl, 1 mM DTT). Untagged cGAS was further purified by binding to 2×5 ml Heparin HP ion-exchange columns connected in tandem (GE Healthcare) and eluting with a gradient of 300-1000 mM NaCl followed by subsequent size-exclusion chromatography using a 16/600 SUPERDEX® S75 column (GE Healthcare) equilibrated with storage buffer (20 mM HEPES-KOH pH 7.5, 250 mM KCl, 1 mM TCEP). Final cGAS protein was concentrated to ~10 mg/ml, flash-frozen in liquid nitrogen, and stored at −80° C. for crystallography and biochemical experiments. Mutant cGAS variants were generated using standard cloning techniques. cGAS variants were purified as described above, except initial chimera cGAS screen variants in FIG. 4 that were dialyzed after Ni-NTA purification without SUMO2 tag removal for direct use in biochemistry experiments.

b. In Vitro cGAS 2'3' cGAMP Synthesis Assays cGAS activation and 2'3' cGAMP synthesis was performed in vitro using purified components and measured with thin-layer chromatography as previously described (Kranzusch et al. (2014) *Cell* 158:1011-1021). Briefly, 1 µM cGAS (or other concentration as indicated) was incubated with a 45 bp double-stranded interferon stimulatory DNA (sense: 5'-TACAGATCTACTAGTGATCTATGACT-GATCTGTACATGATCTACA-3', SEQ ID NO: 6; antisense: 5'-TGTAGATCATGTACAGATCAGTCATAGAT-CACTAGTAGATCTGTA-3', SEQ ID NO: 7) (Stetson and Medzhitov (2006) *Immunity* 24:93-103) in the 20 µl reaction buffer containing 50 mM Tris-HCl pH 7.5, 35 mM KCl, 5 mM Mg(OAc)$_2$, 1 mM DTT, 25 µM ATP, 25 µM GTP, and [α-$^{32}$P] ATP (~1 µCi) at 37° C. for 30 min. Reactions were terminated by heating at 95° C. for 3 min, and subsequently incubated with 4 U of alkaline phosphatase (New England Biolabs) at 37° C. for 30 min to hydrolyze unreacted NTPs. One microliter of each reaction was spotted on a PEI-Cellulose F thin-layer chromatography plate (EMD Biosciences) developed with 1.5 M KH$_2$PO$_4$ (pH 3.8) as a running buffer. Radiolabeled products were detected by Typhoon Trio Variable Mode Imager system (GE Healthcare) and quantified with ImageQuant 5.2. The relative activity of cGAS was determined based on the ratio of radiolabeled 2'3' cGAMP to the total radiolabeled products. cGAS activation in response to bacterial DNA was tested using wildtype *V. cholerae* genomic DNA isolated with a DNA Extraction Kit (DNeasy® Blood & Tissue, Qiagen), and supplemented in reactions as above using a final DNA concentration of 55 ng µl$^{-1}$ (equivalent to 1 µM of 45 bp DNA). cGAS enzyme kinetics were measured as a function of varying ATP concentration, and 2'3' cGAMP product formation was quantified with phosphorimaging and fit according to Michaelis-Menten kinetics. Briefly, ATP/GTP titrations (0, 5, 10, 25, 50, 100, 200, 400, 800, and 1000 µM) were performed in the presence of fixed cGAS (1 µM) and 45 bp dsDNA concentration (1.5 µM) in 10 µl of reaction buffer containing 50 mM Tris-HCl pH 7.5, 35 mM KCl, 5 mM Mg(OAc)$_2$, 1 mM DTT, and [α-$^{32}$P] ATP (~1 µCi) at 37° C. for 5 min. Reactions were terminated and analyzed using thin layer chromatography as indicated above. The ATP-dependent cGAS enzyme kinetics were plotted and fitted according to Michaelis-Menten substrate inhibition analysis in GraphPad Prism (version 7.0c).

c. *V. cholerae* Strain Construction and Chemotaxis Assay

*V. cholerae* strains were cultured at 37° C. on LB media (1% tryptone, 0.5% yeast extract, 0.5% NaCl w/v), stored at −80° C. in LB supplemented with 30% glycerol, and were all derivatives of streptomycin resistant C6706 dncV: Tn (to remove endogenous 3'3' cGAMP synthesis) (Davies et al. (2012) *Cell* 149:358-370). Where appropriate, antibiotics and supplemented nutrients were used at the following concentrations: streptomycin (100 µg ml$^{-1}$), carbenicillin (100 µg ml$^{-1}$), and diaminopimelic acid (300 µg ml$^{-1}$). hcGAS (D157-F522) and mcGAS (P147-L507) were codon optimized for bacterial expression (Genscript and IDT respectively), and all cGAS enzymes and control genes were overexpressed from a custom plasmid pBAD24T, a conjugation-proficient version of pBAD24 that harbors an arabinose inducible promoter and a strong ribosomal binding site (Guzman et al. (1995) *J Bacteriol* 177:4121-4130) that was further modified to include a new multiple cloning site. All genes overexpressed in *V. cholera* were encoded as MBP N-terminal fusions except the MBP alone negative control vector (Table 5).

Plasmids were introduced into *V. cholerae* by conjugation using MFDlpir *E. coli* as the plasmid donor and diaminopimelic acid auxotrophy for counter selection (Ferrieres et al. (2010) *J Bacteriol* 192:6418-6427). *V. cholerae* chemotaxis assays were performed as previously described (Davies et al. (2012) *Cell* 149:358-370). Briefly, chemotaxis medium (1% tryptone, 0.5% NaCl, 0.3% agar w/v) was prepared, autoclaved, and stored at 2x concentration; and chemotaxis plates were prepared 2-24 h prior to inoculation. 2x medium was melted, diluted to 1× with sterile water, and supplemented with 0.2% (w/v) arabinose. Deep-well plates (OmniTray w/Lid, Thermo Fisher) were poured at 40 ml/plate. Overnight, stationary phase cultures (16-24 h post inoculation) were diluted 10-fold with fresh LB, arrayed in a 96-well plate, then applied to the surface of a chemotaxis plate via pinning with a 96-pin, floating pin replicator (VP 408FH, V&P Scientific). Alternatively, 1 µl of diluted culture was applied to the surface of chemotaxis agar by pipetting. Chemotaxis plates were incubated at 30° C. for 16-24 h.

Chemotaxis was quantified by imaging plates at 16-24 h post inoculation and digitally measuring the area of motile bacteria using ImageJ (Schneider et al. (2012) *Nat Methods* 9:671-675). Chemotaxis area was normalized to MBP alone vector for each experiment for expression of "chemotaxis as a % of MBP". Values were transformed into "chemotaxis repression" by calculating (chemotaxis as a % of MBP)-1, then normalizing this value to dncV. Chemotaxis repression was determined and used to simplify a direct relationship between cGAMP levels and plotted values.

d. *V. cholerae* cGAS Expression Analysis

Log phase cultures of *V. cholerae* growing in LB medium were induced for 1 h with 0.2% (w/v) arabinose, and cultures were harvested by centrifugation at 8,000×g for 5 min. Pellets were re-suspended in 1×LDS loading buffer plus reducing agent (Life Technologies) equivalent to an OD of 2.5, and boiled for 10 min. Samples were separated by SDS-PAGE using 4%-12% bis-tris gels (Life Technologies). Proteins were transferred to nitrocellulose membranes and probed with primary antibodies: rabbit anti-MBP at 1:5,000 (polyclonal, catalog #AB3596, Millipore Sigma) and mouse anti-RNA polymerase beta at 1:5,000 (monoclonal 8RB13, catalog #MA1-25425, Thermo Fisher Scientific). Secondary antibodies: IRDyes 800CW goat anti-rabbit IgG at 1:10,000 (polyclonal, catalog #925-32211, LiCor), IRDyea 680LT goat anti-mouse IgG at 1:10,000 (polyclonal, catalog #926-68020, LiCor). Membranes were imaged using a Licor ODYSSEY® CLx imager.

e. Crystallization and Structure Determination

For crystallization, purified human cGAS K187N/L195R (residues 157-522) was mixed with 17 bp DNA (sense: 5'-AAATTGCCGAAGACGAA-3', SEQ ID NO: 8; anti-sense: 5'-TTTCGTCTTCGGCAATT-3', SEQ ID NO: 9) in a molar ratio of 1:1.25 protein:DNA in a buffer containing 20 mM HEPES-KOH pH 7.5, 125 mM KCl, 5 mM ATP, 0.5 mM Gpcpp, and 10.5 mM $MgCl_2$, incubated at room-temperature for 30 min, and centrifuged to pellet precipitation prior to crystallization trials. Crystals were obtained with hanging drop vapor diffusion in drops mixed 1:1 over a reservoir of 0.1 M HEPES-NaOH pH 7.0, 1.4 M sodium citrate after 3 days of growth at 18° C. Crystals were cryo-protected using reservoir solution supplemented with 10% glycerol and flash-frozen in $LiN_2$. Sodium citrate in the crystallization buffer chelated $Mg^{2+}$ and prevented NTP incorporation in the cGAS active site. To overcome this problem, fully-grown crystals were transferred to a soaking solution without citrate (0.1 M sodium succinate, 35% PEG-5000 MME, 3 mM ATP, 0.3 mM Gpcpp, 6.3 mM $MgCl_2$, 10% glycerol) for 10 min and then harvested and flash-frozen as above. Crystallization drops additionally included 0.5 mM nonhydrolyzable GTP, but no clear density was observed.

X-ray diffraction data were collected at the Advanced Photon Source (Beamlines 24-IE-E and 24-IE-C) and then processed with XDS and AIMLESS (Kabsch, 2010) using the SSRL autoxds script (A. Gonzalez, Stanford SSRL). Crystals for both complexes were indexed according to the hexagonal spacegroup P $6_1$ 2 2, and contain one copy of the hcGAS-DNA complex in the asymmetric unit. Phases were determined with molecular replacement using Phaser in PHENIX (Adams et al. (2010) *Acta Crystallogr D Biol Crystallogr* 66:213-221) and the apo human cGAS structure (PDB 4KM5) as a search model. Structure determination was completed with iterative model building and refinement using Coot (Emsley and Cowtan (2004) *Acta Crystallogr D Biol Crystallogr* 60:2126-2132) and PHENIX, respectively. Data collection and refinement statistics are listed in Table 3.

TABLE 3

Crystallographic Statistics

| | hcGAS-DNA | hcGAS-DNA ATP |
|---|---|---|
| Data Collection | | |
| Resolution (Å)[a] | 48.21-2.30 | 49.15-2.79 |
| | (2.38-2.30) | (2.95-2.79) |
| Wavelength (Å) | 0.97918 | 0.97918 |
| Space group | P $6_1$2 2 | P $6_1$2 2 |
| Unit cell: a, b, c (Å) | 101.17, 101.17, 241.06 | 100.49, 100.49, 236.75 |
| Unit cell: α, β, γ (°) | 90.0, 90.0, 120.0 | 90.0, 90.0, 120.0 |
| Molecules per ASU | 1 | 1 |
| No. reflections: total | 438690 | 356853 |
| No. reflections: unique | 33460 | 18321 |
| Completeness (%)[a] | 99.6 (96.4) | 99.8 (98.5) |
| Multiplicity[a] | 13.1 (12.1) | 19.5 (18.2) |
| I/σI[a] | 10.9 (1.1) | 10.0 (1.6) |
| CC(1/2)[b] (%)[a] | 99.8 (31.7) | 99.8 (31.9) |
| Rpim[c] (%)[a] | 4.5 (79.6) | 8.6 (118.0) |
| Refinement | | |
| Resolution (Å) | 48.21-2.30 | 49.15-2.79 |
| Free reflections (%) | 10 | 10 |
| R-factor/R-free | 19.9/22.8 | 21.1/24.6 |
| Bond distance (RMS Å) | 0.006 | 0.002 |
| Bond angles (RMS °) | 0.720 | 0.543 |
| Structure/Stereochemistry | | |
| No. atoms: protein | 2859 | 2826 |
| No. atoms: DNA | 592 | 592 |
| No. atoms: ligand | 1 (Zn) | 34 (ATP, Mg, Zn) |
| No. atoms: water | 103 | 21 |
| Average B-factor: protein | 57.0 | 66.1 |
| Average B-factor: DNA | 98.2 | 103.3 |
| Average B-factor: ligand | 43.4 | 56.3 |
| Average B-factor: water | 53.7 | 61.3 |
| Ramachandran plot: favored | 97.93% | 96.71% |
| Ramachandran plot: allowed | 1.77% | 2.99% |
| Ramachandran plot: outliers | 0.30% | 0.30% |
| Rotamer outliers: | 1.87% | 1.57% |
| MolProbity[d] score | 1.52 | 1.46 |
| Protein Data Bank ID | 6CT9 | 6CTA |

[a]Highest resolution shell values in parenthesis
[b](Karplus and Diederichs, 2012)
[c](Weiss, 2001)
[d](Chen et al., 2010)

Figure 8A:
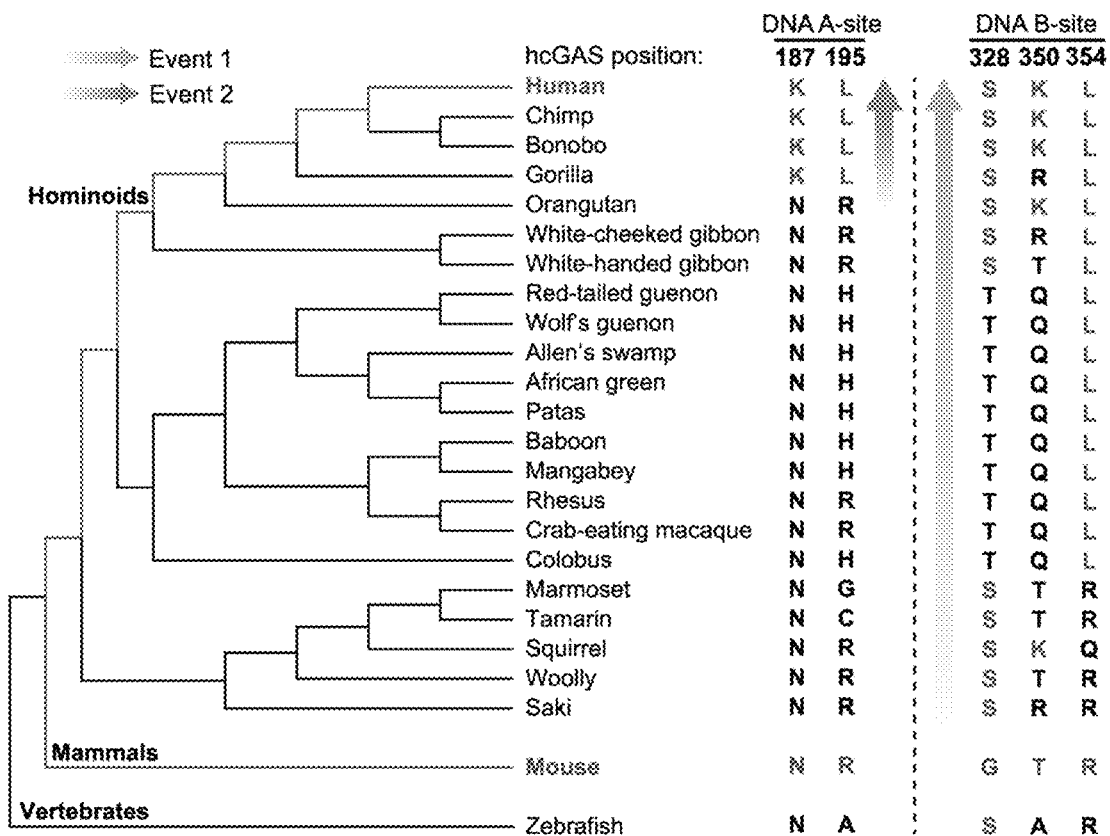
Figure 8B:
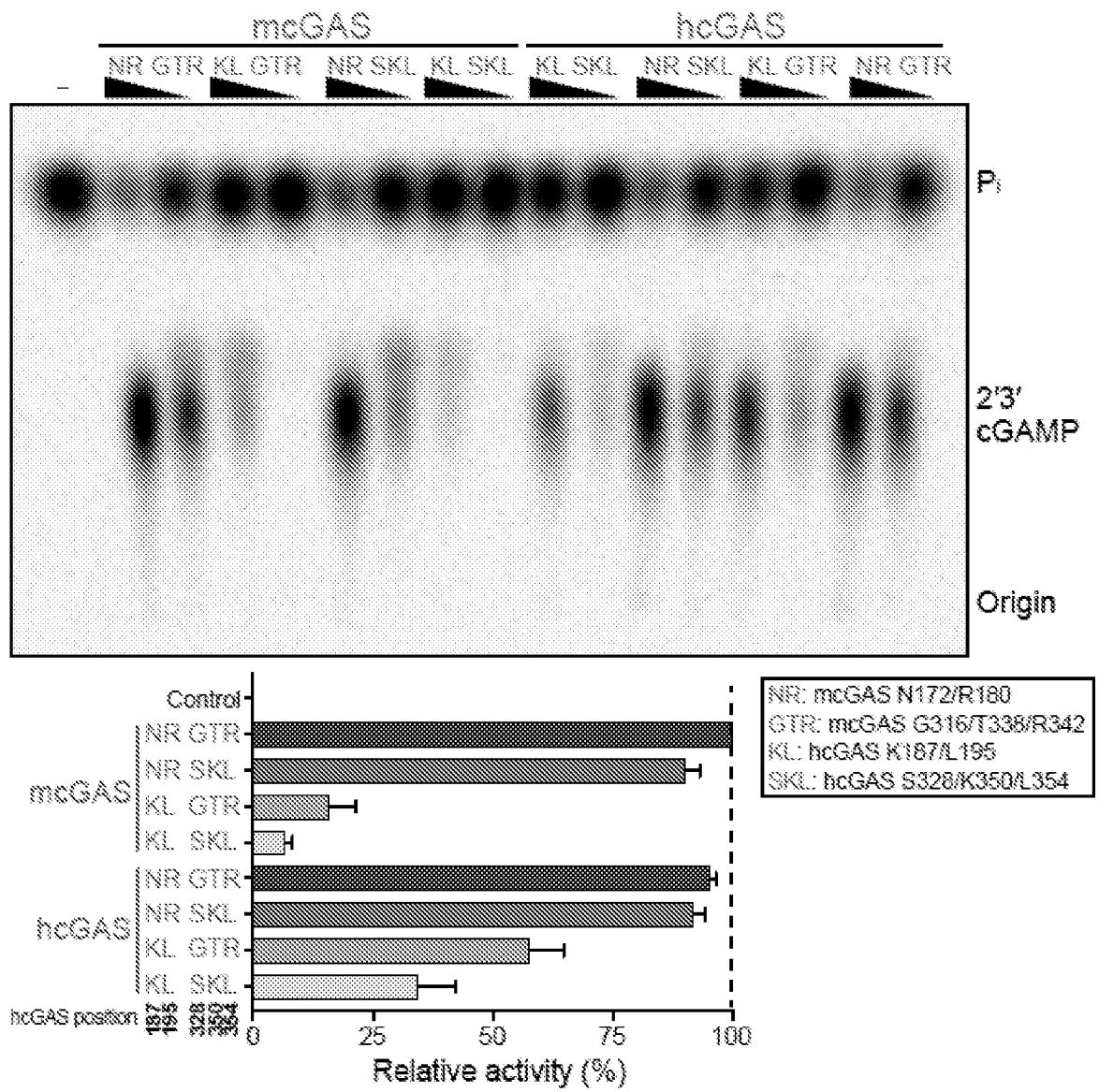
Figure 8D:
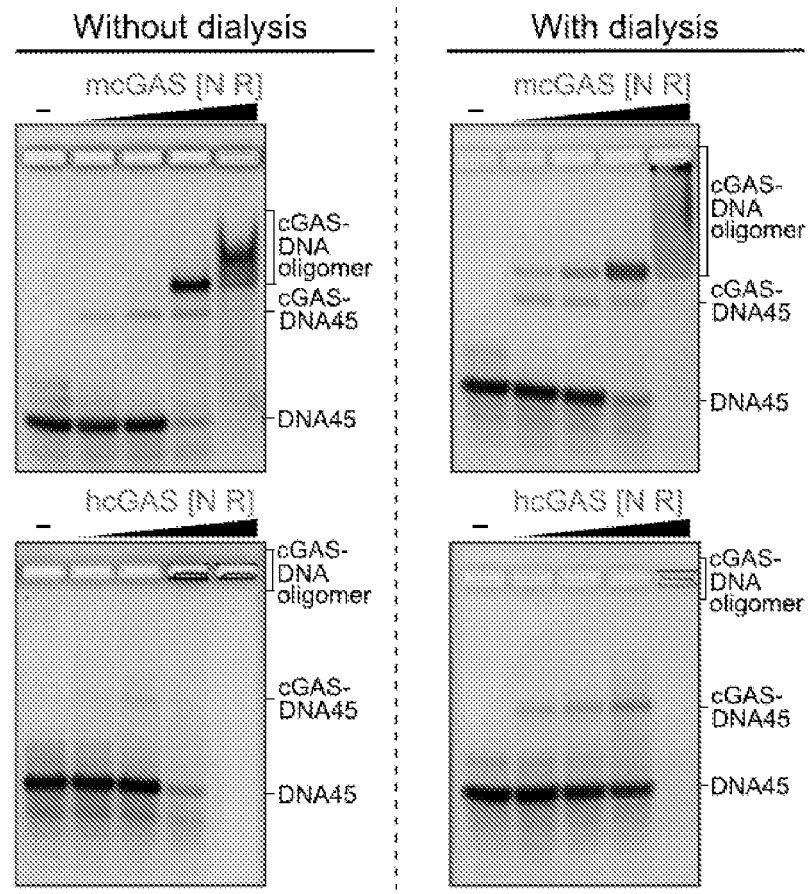
Figure 8E:
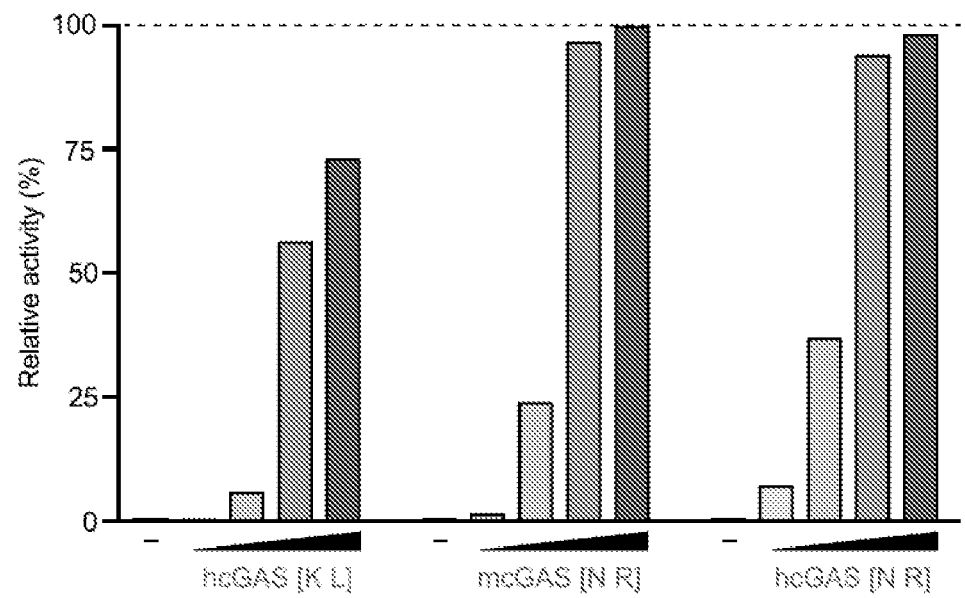

(see also Chen et al. (2010) *Acta Crystallogr D Biol Crystallogr* 66:12-21; Karplus and Diederichs (2012) *Science* 336:1030-1033; Weiss (2001) *Journal of Applied Crystallography* 34:130-135).

f. In vitro cGAS-DNA Complex Formation Analysis cGAS-DNA complexes were stably assembled using a method adapted from a nucleosome assembly gradient dialysis protocol (Lee and Narlikar (2001) Current protocols in molecular biology Chapter 21, Unit 21.26), and complex formation was measured by electrophoretic mobility shift analysis. Briefly, a concentration gradient of recombinant protein (0.2, 0.4, 2, 10 μM) was incubated with 45 bp dsDNA (2 μM) in a high-salt buffer containing 20 mM HEPES-NaOH pH 7.8, 75 mM KCl, 1 mM DTT at 4° C. for 20 min. The reconstitution mixture was then transferred into 8-10 kDa molecular weight cut-off dialysis tubing (Spectrum Labs), and placed into a beaker of the high-salt buffer. The KCl concentration was reduced gradually by slowly replacing high-salt buffer with low-salt buffer (20 mM HEPES-KOH pH 7.5, 50 mM KCl, 1 mM DTT) with a peristaltic pump (Bio-Rad) at a rate of 200 ml min$^{-1}$ for 48 hr at 4° C. After gradient dialysis, reactions were supplemented to 5% glycerol, and subsequently separated on a 2% agarose gel in 0.5×TBE buffer at 4° C. Agarose gels were stained in a solution containing 10 μg ml$^{-1}$ ethidium bromide and visualized with a ChemiDoc™ MP Imaging System (Bio-Rad). Alternatively, where indicated in FIGS. 8A and 8C, cGAS-DNA complexes were assembled by incubating directly in reaction buffer containing 20 mM HEPES-NaOH pH 7.8, 75 mM KCl, 1 mM DTT at 4° C. for 20 min and analyzed by electrophoretic mobility shift analysis as indicated above.

g. Accession Numbers

Coordinates of human cGAS-DNA binary complex and human cGAS-DNA-ATP ternary complex have been deposited in the RCSB Protein Data Bank under accession numbers 6CT9 and 6CTA.

h. Experimental Model and Subject Details

*Vibrio cholerae* Strains

*V. cholerae* strains were all derivatives of streptomycin resistant C6706 dncV::Tn (to remove endogenous 3030 cGAMP synthesis) (Davies et al. (2012) *Cell* 149:358-370). *V. cholerae* were cultured at 37° C. on LB media (1% tryptone, 0.5% yeast extract, 0.5% NaCl w/v), stored at −80° C. in LB supplemented with 30% glycerol. Where appropriate, antibiotics and supplemented nutrients were used at the following concentrations: streptomycin (100 mg mL$^{-1}$), carbenicillin (100 mg mL$^{-1}$), and diaminopimelic acid (300 mg mL$^{-1}$).

*Escherichia coli* Strains

Recombinant cGAS enzymes were expressed in *E. coli* BL21-RIL DE3 (Agilent) bacteria harboring a pRARE2 tRNA plasmid. Transformations and starter cultures were grown in MDG media (0.5% glucose, 25 mM Na$_2$HPO$_4$, 25 mM KH$_2$PO$_4$, 50 mM NH$_4$Cl, 5 mM Na$_2$SO$_4$, 2 mM MgSO$_4$, 0.25% aspartic acid, 100 mg mL$^{-1}$ ampicillin, 34 mg mL$^{-1}$ chloramphenicol, and trace metals) overnight at 37° C. and used to seed 1 L cultures grown in M9ZB media (0.5% glycerol, 1% Cas-Amino Acids, 47.8 mM Na$_2$HPO$_4$, 22 mM KH$_2$PO$_4$, 18.7 mM NH$_4$Cl, 85.6 mM NaCl, 2 mM MgSO$_4$, 100 mg mL$^{-1}$ ampicillin, 34 mg mL$^{-1}$ chloramphenicol, and trace metals) (Studier et al. (2005) *Protein Expr Purif* 41:207-234). M9ZB cultures were cultivated at 37° C. until OD600 of ~1.5-2.5, cooled on ice for 20 min, and then recombinant protein synthesis was induced by supplementation with 0.5 mM IPTG. Cultures were incubated at 16° C. with shaking for ~16 hr before harvest.

i. Molecular Docking Analysis

The crystal structures of RU.521 bound to the mcGAS-DNA complex (PDB: 5XZG), PF-06928215 bound to inactive hcGAS (PDB: 5V8N), and the active hcGAS-DNA complex were prepared using the Protein Preparation Wizard in Maestro (Maestro v. 11.5.011). Default settings were used, except that all crystallographic water molecules >5 A from heteroatom groups were removed. The docking receptor grid was created using the Receptor Grid Generation module in Glide (Maestro v. 11.5.011). The grid box and center were set to default by using the active site ligand, with the active site ligand excluded from the grid. The ligands were prepared using the LigPrep module with OPLS3 force field and default settings (Maestro v. 11.5.011). The docking poses were generated using the LigandDocking protocol as implemented in Schrodinger Suite 2018-1. All default settings were used, except that the Standard Precision (SP) or Extra Precision (XP) scoring functions were used with flexible ligand sampling. Briefly, the grid box and center were set at default using the active site ligand, and no constraints were defined. The default set of ligand poses with the lowest Glide SP score is shown for hcGAS-DNA docking of RU.521 and PF-06928215, eight and four respectively, and two ligand poses each for mcGAS-DNA docking of RU.521 (XP score) and inactive hcGAS (XP and SP score). Alignment of the mcGAS-DNA bound RU.521 (PDB: 5XZG) and inactive hcGAS bound PF-06928215 (PDB: 5V8N) to hcGAS-DNA in FIGS. 10G and 10H was generated in PyMOL (The PyMOL Molecular Graphics System, version 1.8.6.0 Schrodinger, LLC).

j. Small-Molecule cGAS Inhibition Assays

The cGAS small-molecule inhibitors PF-06928215 (Sigma) (Hall et al. (2017) *PLoS One* 12: e0184843) and RU.521 (Aobious) (Vincent et al. (2017) *Nat Commun* 8:750) were prepared as ~10 mM and ~20 mM stocks respectively in 100% dimethyl sulfoxide (DMSO). Liquid chromatography, mass-spectrometry analysis of the RU.521 manufacturer preparation revealed the additional presence of lower-molecular weight byproducts, and the effective RU.521 stock concentration was adjusted accordingly. cGAS inhibition was measured as a function of varying small-molecule concentration compared to DMSO alone. Briefly, small-molecule titrations (0.02-100 mM) were performed in the presence of cGAS (1 mM) and 45 bp dsDNA concentration (1 mM) in 20 ml of reaction buffer containing 50 mM Tris-HCl pH 7.5, 35 mM KCl, 10 mM Mg(OAc)2, 1 mM DTT, 100 mM ATP, 100 mM GTP, [α-32P] ATP (~1 μCi), and 1% final DMSO concentration at 37° C. for 30 min. Reactions were terminated and analyzed using thin layer chromatography as indicated above. 2'3' cGAMP product formation was quantified with phosphorimaging and the inhibitor dose response curves for RU.521 and PF-06928215 were plotted and fit according to standard "log(inhibitor) vs. response—Variable slope (four parameters)" equation in GraphPad Prism (version 7.0c).

k. Quantification and Statistical Analysis

Statistical details for each experiment can be found in the figure legends, and outlined in the corresponding methods details section. *V. cholerae* chemotaxis data are plotted with error bars representing the standard error of the mean (SEM), all other data are plotted with error bars representing as the standard deviation of the mean (SD).

l. Data and Software Availability

The accession numbers for the hcGAS-DNA and hcGAS-DNA-ATP crystal structure data reported in this paper have been deposited in the Protein Data Bank under ID codes PDB: 6CT9 and 6CTA.

TABLE 4

KEY RESOURCES TABLE

| REAGENT or RESOURCE | SOURCE | IDENTIFIER |
|---|---|---|
| Antibodies | | |
| Polyclonal anti-MBP antibody produced in rabbit | Millipore Sigma | AB3596 |

TABLE 4-continued

KEY RESOURCES TABLE

| REAGENT or RESOURCE | SOURCE | IDENTIFIER |
|---|---|---|
| Monoclonal anti-RNA polymerase beta produced in mouse | Thermo Fisher Scientific | MA1-25425 |
| IRDye® 800CW goat anti-rabbit IgG | LiCor | 925-32211 |
| IRDye® 680LT goat anti-mouse IgG | LiCor | 926-68020 |
| Bacterial Strains | | |
| E. coli BL21-RIL DE3 | Agilent | 230245 |
| Vibrio cholerae C6706 dncV::Tn | Davies et al. (2012) Cell 149:358-370 | N/A |
| Reagent | | |
| Ni-NTA Agarose | Qiagen | 30250 |
| HiTrap® Heparin HP Column | GE Healthcare | 17040703 |
| HiLoad® 16/600 SUPERDEX® 75 pg Column | GE Healthcare | 28989333 |
| [$\alpha$-$^{32}$P] ATP | Perkin Elmer | BLU003H250UC |
| Alkaline phosphatase | New England Biolabs | M0290L |
| PEI-Cellulose F TLC plate | EMD Biosciences | EM1.05579.0001 |
| DNA Extraction Kit | Qiagen | 69504 |
| ATP, GTP | New England Biolabs | N0450S |
| HEPES | VWR | 97061-824 |
| Sodium citrate | VWR | BDH9288-500G |
| Sodium succinate | Sigma-Aldrich | S2378-100G |
| PEG-5000 | Sigma-Aldrich | 81323-250G |
| RU.521 | Aobious | AOB37877 (Lot #7263M) |
| PF-06928215 | Sigma-Aldrich | PZ038-5MG (Lot #0000027198) |
| Oligonucleotides | | |
| 5'-AAATTGCCGAAGACGAA-3' (SEQ ID NO: 8) | Integrated DNA Technologies | DNA17 sense |
| 5'-TTTCGTCTTCGGCAATT-3' (SEQ ID NO: 9) | Integrated DNA Technologies | DNA17 antisense |
| 5'-TACAGATCTACTAGTGATCTATGACTGATCTGTACATGATCTACA-3' (SEQ ID NO: 6) | Integrated DNA Technologies | DNA45 sense |
| 5'-TGTAGATCATGTACAGATCAGTCATAGATCACTAGTAGATCTGTA-3' (SEQ ID NO: 7) | Integrated DNA Technologies | DNA45 antisense |
| Deposited Data | | |
| Human cGAS-DNA complex | This paper | PDB: 6CT9 |
| Human cGAS-DNA-ATP complex | This paper | PDB: 6CTA |
| Software and Algorithms | | |
| Phenix 1.13-2998 | Adams et al. (2010) Acta Crystallogr D Biol Crystallogr 66:213-221 | available on the World Wide Web at phenix-online.org/ |

TABLE 4-continued

KEY RESOURCES TABLE

| REAGENT or RESOURCE | SOURCE | IDENTIFIER |
|---|---|---|
| Coot 0.8.9 | Emsley and Cowtan (2004) Acta Crystallogr D Biol Crystallogr 60:2126-2132 | available on the World Wide Web at 2.mrc-lmb.cam.ac.uk/personal/pemsley/coot/ |
| Pymol v1.7.4.4 | Schrödinger, LLC | available on the World Wide Web at pymol.org/ |
| Prism 7.0d | GraphPad Software | available on the World Wide Web at graphpad.com/scientific-software/prism/ |
| ImageJ | NIH | available on the World Wide Web at imagej.nih.gov/ij/index.html |
| ImageQuant 5.2 | GE Healthcare | available on the World Wide Web at gelifesciences.com/en/us/shop/protein-analysis/molecular-imaging-for-proteins/imaging-software/imagequant-tl-8-1-p-00110?current=29000605 |
| Maestro | Schrödinger, LLC | available on the World Wide Web at schrodinger.com/maestro |

TABLE 5

Plasmid and insert sequences.

DncV (pAW1004-pBAD24-MBP-dncV) Insert Nucleotide Sequence (SEQ ID NO: 10)
gtgagaatgacttggaactttcaccagtactacacaaaccgaaatgatggcttgatgggcaagctagttcttacagacgaggagaag
aacaatctaaaggcattgcgtaagatcatccgcttaagaacacgagatgtatttgaagaagctaagggtattgccaaggctgtgaaa
aaaagtgctcttacgtttgaaattattcaggaaaaggtgtcaacgacccaaattaagcaccttctgacagcgaacaacgagaagtgg
ctaagatatttacgagatggatgatgatgctcgtgatgagtttttgggattgacacctcgcttttgacctcagggaagctttcagtatga
cacgctgaatcgcccgtttcagcctggtcaagaaatggatattgatgatggaacctatatgccaatgcctattttttgagtcagagccta
agattggtcattctttactaattcttcttgttgacgcgtcacttaagtcacttgtagctgaaaatcatggctggaaatttgaagctaagcag
acttgtgggaggattaagattgaggcagagaaaacatattgatgtaccaatgtatgcaatccctaaagatgagttccagaaaaag
caaatagcttagaagcaaatagatcatttgttaaaggtgccattttttgaatcatatgttgcagatttcaattactgacgatagtgaaacttat
gaattagattcagaaaacgtaaaccttgctcttcgtgaaggtgatcggaagtggatcaatagcgaccccaaaatagttgaagattggt
tcaacgatagttgtatacgtattggtaaacatcttcgtaaggtttgtcgctttatgaaagcgtggagagatgcgcagtgggatgttggag
gtccgtcatcgattagtcttatggctgcaacggtaaatattcttgatagcgttgctcatgatgctagtgatctcggagaaacaatgaaga
taattgctaagcatttacctagtgagtttgctagggagtagagagcgcctgacagtaccgattgaaaagccactcttcccaccctcttat
aagcatggccctcgggagatggacattatgagcaaactagagcgtttgccagagattctgtcatctgctgagtcagctgactctaagt
cagaggccttgaaaagattaatatggcgtttgggaatcgtgttactaatagcgagcttattgttttggcaaaggctttaccggctttcg
ctcaagaacctagttcagcctcgaaacctgaaaaaatcagcagcacaatggtaagtggc DncV (pAW1004-pBAD24-MBP-dncV) Insert Amino Acid Sequence (SEQ ID NO: 11)
VRMTWNFHQYYTNRNDGLMGKLVLTDEEKNNLKALRKIIRLRTRDVFEEAKGIAK
AVKKSALTFEIIQEKVSTTQIKHLSDSEQREVAKLIYEMDDDARDEFLGLTPRFWTQ
GSFQYDTLNRPFQPGQEMDIDDGTYMPMPIFESEPKIGHSLLILLVDASLKSLVAEN
HGWKFEAKQTCGRIKIEAEKTHIDVPMYAIPKDEFQKKQIALEANRSFVKGAIFESY
VADSITDDSETYELDSENVNLALREGDRKWINSDPKIVEDWFNDSCIRIGKHLRKV
CRFMKAWRDAQWDVGGPSSISLMAATVNILDSVAHDASDLGETMKIIAKHLPSEF
ARGVESPDSTDEKPLFPPSYKHGPREMDIMSKLERLPEILSSAESADSKSEALKKIN
MAFGNRVTNSELIVLAKALPAFAQEPSSASKPEKISSTMVSG hcGAS (pAW1106-pBAD24T-MBP-hcGAS) Insert Nucleotide Sequence (SEQ ID NO: 12)
gacgcagctccgggtgcttctaaactgcgtgcggtcctggaaaaactgaaactgagccgcgatgacatttctaccgcgcggccggcat
ggtgaaaggtgtggttgatcatctgctgctgcgtctgaaatgcgactcagccttcgcggcgttggtctgctgaacacgggtagctatt
acgaacacgtcaaatctctgcaccgaacgaattcgatgtatgtttcaaactggaagtcccgcgtattcagctggaagaatatagcaa
cacccgtgcctattactttgttaaattcaaacgcaacccgaaagaaaatccgctgagtcagtttctggaaggcgaaatcctgagtgcg
tccaaaatgctgtccaaattccgcaaaatcatcaaagaagaaatcaacgatatcaaagataccgacgtcattatgaaacgtaaacgc
ggcggtagtccggcagtcaccctgctgatttcagaaaaaatctcggtggactaccgctggctctggaatcaaaaagctcttggccg
gcgagcacccaggaaggcctgcgtattcaaaactggctgtccgctaaagtgcgtaaacagctgcgcctgaaaccgttttacctggtt
ccgaaacatgcgaaagaaggcaatggttttcaagaagaaacctggcgcctgtcattctcgcatatcgaaaaagaaatcctgaacaa
ccacggtaaaagtaaaacgtgctgtgaaaacaaagaagaaaatgctgtcgtaaagattgtctgaaactgatgaaatatctgctgga
acagctgaaagaaccgcttcaaagataaaaaacacctggacaatcttcctaccatgtgaaaaccgcgttttttccacgttttgcacg
caaaatccgcaggatagccaatgggatcgtaaagacctgggtctgtgctttgacaactgtgtgacctatttcctgcagtgtctgcgca
cggaaaaactgaaaattactttatcccggaatttaacctgttctcatcgaatctgattgataaacgttctaaagaattcctgacgaaaca
gattgaatacgaacgcaacaacgaatttccggtctttgacgaattt TABLE 5-continued Plasmid and insert sequences.

hcGAS (pAW1106-pBAD24T-MBP-hcGAS) Insert Amino Acid Sequence (SEQ ID NO: 13)
DAAPGASKLRAVLEKLKLSRDDISTAAGMVKGVVDHLLLRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF mcGAS (pAW1013-pBAD24T-MBP-mcGAS) Insert Nucleotide Sequence (SEQ ID NO: 14)
ccggacaagctgaaaaaagtgctcgacaagcttcggctgaaacggaaagatatcagtgaagctgcagagaccgtgaacaaggtg
gtcgagcggttactgcgtcggatgcaaaagagagagtcagagtttaagggcgtcgagcaacttaacacaggatcctattacgaaca
cgttaaaatctctgcccctaatgagttcgacgtgatgtttaagttggaagttccgcgtatagaattacaagaatattatgagacgggagc
cttctacttggtgaaatttaaacgcattccgcggggtaatcctctgagtcacttcttagagggtgaagtgctgtctgctacgaaaatgtta
agtaagtttcggaagatcatcaaggaggaagtaaaggaaatcaaagacattgacgttagcgtggagaaggaaaaaccaggctccc
cggcggtaacacttttaattagaaatcctgaggaaattagcgtagatattatactcgcgctggagtctaagggatcctggccgattagt
accaaagagggcttacctatccagggatggctggagcaaaggtacgtacaaatctccgtcgcgaaccattctaccttgtaccgaag
aacgctaaagatggtaactccttccaaggggagacttggcgtcttttcattttcccacaccgagaagtacattttaaataatcatgggatc
gaaaagacatgctgtgagtcaagtggtgccaaatgttgtcgcaaagagtgcttgaagttaatgaaatatttactggagcagctgaaga
aagagttccaggagttagacgctttctgtagctatcatgttaagacggccatatttcacatgtggacgcaggatccacaggattctcaa
tgggatccacgcaacctgtccagttgttttgacaaactgctcgcgttttttttagaatgcctgcggaccgagaagttggatcattacttca
tccctaaattcaacctgtttagtcaagagttgattgatcgcaaatctaaagagtttctgtctaaaaaaatcgaatatgagcgcaataacg
ggttcccgatatttgacaaactt mcGAS (pAW1013-pBAD24T-MBP-mcGAS) Insert Amino Acid Sequence (SEQ ID NO: 15)
PDKLKKVLDKLRLKRKDISEAAETVNKVVERLLRRMQKRESEFKGVEQLNTGSYY
EHVKISAPNEFDVMFKLEVPRIELQEYYETGAFYLVKFKRIPRGNPLSHFLEGEVLS
ATKMLSKFRKIIKEEVKEIKDIDVSVEKEKPGSPAVTLLIRNPEEISVDIILALESKGS
WPISTKEGLPIQGWLGTKVRTNLRREPFYLVPKNAKDGNSFQGETWRLSFSHTEKY
ILNNHGIEKTCCESSGAKCCRKECLKLMKYLLEQLKKEFQELDAFCSYHVKTAIFH
MWTQDPQDSQWDPRNLSSCFDKLLAFFLECLRTEKLDHYFIPKFNLFSQELIDRKS
KEFLSKKIEYERNNGFPIFDKL Chimera 1 (pBAD24T-MBP-cGAS m-P147-K372 h-E385-F522) Insert Nucleotide
Sequence (SEQ ID NO: 16)
ccggacaagctgaaaaaagtgctcgacaagcttcggctgaaacggaaagatatcagtgaagctgcagagaccgtgaacaaggtg
gtcgagcggttactgcgtcggatgcaaaagagagagtcagagtttaagggcgtcgagcaacttaacacaggatcctattacgaaca
cgttaaaatctctgcccctaatgagttcgacgtgatgtttaagttggaagttccgcgtatagaattacaagaatattatgagacgggagc
cttctacttggtgaaatttaaacgcattccgcggggtaatcctctgagtcacttcttagagggtgaagtgctgtctgctacgaaaatgtta
agtaagtttcggaagatcatcaaggaggaagtaaaggaaatcaaagacattgacgttagcgtggagaaggaaaaaccaggctccc
cggcggtaacacttttaattagaaatcctgaggaaattagcgtagatattatactcgcgctggagtctaagggatcctggccgattagt
accaaagagggcttacctatccagggatggctgggacaaaggtacgtacaaatctccgtcgcgaaccattctaccttgtaccgaag
aacgctaaagatggtaactccttccaaggggagacttggcgtcttttcattttcccacaccgagaaggtacattctgaacaaccacggt
aaaagtaaaacgtgctgtgaaaacaaagaagaaaaatgctgtcgtaaagattgtctgaaactgatgaaatatctgctggaacagctg
aaagaacgcttcaaagataaaaaacacctggacaaattcagttcctaccatgtgaaaaccgcgttttttccacgtttgcacgcaaaatc
cgcaggatagccaatgggatcgtaaagacctgggtctgtgctttgacaactgtgtgacctatttcctgcagtgtctgcgcacggaaaa
actggaaaattactttatccccggaatttaacctgttctcatcgaatctgattgataaacgttctaaagaattcctgacgaaacagattgaat
acgaacgcaacaacgaatttccggtctttgacgaattt Chimera 1 (pBAD24T-MBP-cGAS m-P147-K372 h-E385-F522) Insert Amino Acid
Sequence (SEQ ID NO: 17)
PDKLKKVLDKLRLKRKDISEAAETVNKVVERLLRRMQKRESEFKGVEQLNTGSYY
EHVKISAPNEFDVMFKLEVPRIELQEYYETGAFYLVKFKRIPRGNPLSHFLEGEVLS
ATKMLSKFRKIIKEEVKEIKDIDVSVEKEKPGSPAVTLLIRNPEEISVDIILALESKGS
WPISTKEGLPIQGWLGTKVRTNLRREPFYLVPKNAKDGNSFQGETWRLSFSHTEKE
ILNNHGKSKTCCENKEEKCCRKDCLKLMKYLLEQLKERFKDKKHLDKFSSYHVKT
AFFHVCTQNPQDSQWDRKDLGLCFDNCVTYFLQCLRTEKLENYFIPEFNLFSSNLID
KRSKEFLTKQIEYERNNEFPVFDEF Chimera 2 (pBAD24T-cGAS h-D157-K384 m-Y373-L507) Insert Nucleotide Sequence
(SEQ ID NO: 18)
gacgcagctccgggtgcttctaaactgcgtgcggtcctggaaaaactgaaactgagccgcgatgacatttctaccgcggccggcat
ggtgaaaggtgtggttgatcatctgctgctgcgtctgaaatgcgactcagcctttcgcggcgttggtctgctgaacacgggtagctatt
acgaacacgtcaaaatctctgcaccgaacgaattcgatgttatgttcaaactggaagtcccgcgtattcagctggaagaatatagcaa
caccctgtgcctattactttgttaaattcaaacgcaaccccgaaagaaaatccgctgagtcagtttctggaaggcgaaatcctgagtcg
tccaaaatgctgtccaaattccgcaaaatcatcaaagaagaaatcaacgatatcaaagataccgacgtcattatgaaacgtaaacgc
ggcggtagtccggcagtcaccctgctgatttcagaaaaaatctcggtggacattacgctggctctgaatcaaaaagctcttggccg
cgagcacccaggaaggcctgcgtattcaaaactggctgtccgctaaagtgcgtaaacagctgcgcctgaaaccgttttacctggtt
ccgaaacatgcgaaagaaggcaatggttttcaagaagaaacctggcgcctgtcattctcgcatattcgaaaaatacatttaaataatc
atgggatcgaaaagacatgctgtgagtcaagtggtgccaaatgttgtcgcaaagagtgcttgaagttaatgaaatatttactggagca
gctgaagaaagagttccaggagttagacgctttctgtagctatcatgttaagacggccatatttcacatgtggacgcaggatccacag
gattctcaatgggatccacgcaacctgtccagttgttttgacaaactgctcgcgttttttttagaatgcctgcggaccgagaagttggat
cattacttcatccctaaattcaacctgtttagtcaagagttgattgatcgcaaatctaaagagtttctgtctaaaaaaatcgaatatgagcg
caataacgggttcccgatatttgacaaactt TABLE 5-continued Plasmid and insert sequences.

Chimera 2 (pBAD24T-cGAS h-D157-K384 m-Y373-L507) Insert Amino Acid Sequence
(SEQ ID NO: 19)
DAAPGASKLRAVLEKLKLSRDDISTAAGMVKGVVDHLLLRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKYILNNHGIEKTCCESSGAKCCRKECLKLMKYLLEQLKKEFQELDAFCSYHVKTA
IFHMWTQDPQDSQWDPRNLSSCFDKLLAFFLECLRTEKLDHYFIPKFNLFSQELIDR
KSKEFLSKKIEYERNNGFPIFDKL Chimera 3.1 (pBAD24T-cGAS m-P147-Q194 [m hh]) Insert Nucleotide Sequence (SEQ ID
NO: 20)
ccggacaagctgaaaaaagtgctcgacaagcttcggctgaaacggaaagatatcagtgaagctgcagagaccgtgaacaaggtg
gtcgagcggttactgcgtcggatgcaaaagagagagtcagagtttaaggggcgtcgagcaactgaacacgggtagctattacgaac
acgtcaaaatctctgcaccgaacgaattcgatgttatgttcaaactggaagtcccgcgtattcagctggaagaatatagcaacacccg
tgcctattactttgttaaattcaaacgcaacccgaaagaaaatccgctgagtcagtttctggaaggcgaaatcctgagtgcgtccaaaa
tgctgtccaaattccgcaaaatcatcaaagaagaaatcaacgatatcaaagataccgacgtcattatgaaacgtaaacgcggcggta
gtccggcagtcaccctgctgatttcagaaaaaatctcggtggacattacgctggctgtcggaatcaaaaagctcttggccggcgagca
cccaggaaggcctgcgtattcaaaactggctgtccgctaaagtgcgtaaacagctgcgcctgaaaccgttttacctggttccgaaac
atgcgaaagaaggcaatggttttcaagaagaaacctggcgcctgtcattctcgcatatcgaaaaagaaatcctgaacaaccacggta
aaagtaaaacgtgctgtgaaaacaaagaagaaaaatgctgtcgtaaagattgtctgaaactgatgaaatatctgctggaacagctga
aagaacgcttcaaagataaaaaaacacctggacaaattcagttcctaccatgtgaaaaccgcgttttccacgtttgcacgcaaaatcc
gcaggatagccaatgggatcgtaaagacctgggtctgtgctttgacaactgtgtgacctatttcctgcagtgtctgcgcacgcagaaaa
ctggaaaattactttatcccggaatttaaccgttctcatcgaatctgattgataaacgttctaaagaattcctgacgaaacagattgaata
cgaacgcaacaacgaatttccggtctttgacgaattt Chimera 3.1 (pBAD24T-cGAS m-P147-Q194 [m hh]) Insert Amino Acid Sequence (SEQ
ID NO: 21)
PDKLKKVLDKLRLKRKDISEAAETVNKVVERLLRRMQKRESEFKGVEQLNTGSYY
EHVKISAPNEFDVMFKLEVPRIQLEEYSNTRAYYFVKFKRNPKENPLSQFLEGEILS
ASKMLSKFRKIIKEEINDIKDTDVIMKRKRGGSPAVTLLISEKISVDITLALESKSSWP
ASTQEGLRIQNWLSAKVRKQLRLKPFYLVPKHAKEGNGFQEETWRLSFSHIEKEIL
NNHGKSKTCCENKEEKCCRKDCLKLMKYLLEQLKERFKDKKHLDKFSSYHVKTA
FFHVCTQNPQDSQWDRKDLGLCFDNCVTYFLQCLRTEKLENYFIPEFNLFSSNLIDK
RSKEFLTKQIEYERNNEFPVFDEF Chimera 3.2 (pBAD24T-cGAS m-L195-E273 [h m h]) Insert Nucleotide Sequence (SEQ
ID NO: 22)
gacgcagctccgggtgcttctaaactgcgtgcggtcctggaaaaaactgaaactgagccgcgatgacatttctaccgcggccggcat
ggtgaaaggtgtggttgatcatctgctgctgcgtctgaaatgcgactcagcctttcgcggcgttggtctgcttaacacaggatcctatt
acgaacacgttaaaatctctgcccctaatgagttcgacgtgatgtttaagttggaagttccgcgtatagaattacaagaatattatgaga
cgggagccttctacttggtgaaatttaaacgcattccgcggggtaatcctctgagtcacttcttagagggtgaagtgctgtctgctacg
aaaatgttaagtaagtttcggaagatcatcaaggaggaaatcaacgatatcaaagataccgacgtcattatgaaacgtaaacgcggc
ggtagtccggcagtcaccctgctgatttcagaaaaaatctcggtggacattacgctggctgtcggaatcaaaaagctcttggccggcg
agcacccaggaaggcctgcgtattcaaaactggctgtccgctaaagtgcgtaaacagctgcgcctgaaaccgttttacctggttccg
aaacatgcgaaagaaggcaatggttttcaagaagaaacctggcgcctgtcattctcgcatatcgaaaaagaaatcctgaacaacca
cggtaaaagtaaaacgtgctgtgaaaacaaagaagaaaaatgctgtcgtaaagattgtctgaaactgatgaaatatctgctggaaca
gctgaaagaacgcttcaaagataaaaaaacacctggacaaattcagttcctaccatgtgaaaaccgcgttttccacgttgcacgcaa
atccgcaggatagccaatgggatcgtaaagacctgggtctgtgctttgacaactgtgtgacctatttcctgcagtgtctgcgcacgg
aaaaactggaaaattactttatcccggaatttaaccgttctcatcgaatctgattgataaacgttctaaagaattcctgacgaaacagat
tgaatacgaacgcaacaacgaatttccggtctttgacgaattt Chimera 3.2 (pBAD24T-cGAS m-L195-E273 [h m h]) Insert Amino Acid Sequence (SEQ
ID NO: 23)
DAAPGASKLRAVLEKLKLSRDDISTAAGMVKGVVDHLLLRLKCDSAFRGVGLLNT
GSYYEHVKISAPNEFDVMFKLEVPRIELQEYYETGAFYLVKFKRIPRGNPLSHFLEG
EVLSATKMLSKFRKIIKEEINDIKDTDVIMKRKRGGSPAVTLLISEKISVDITLALESK
SSWPASTQEGLRIQNWLSAKVRKQLRLKPFYLVPKHAKEGNGFQEETWRLSFSHIE
KEILNNHGKSKTCCENKEEKCCRKDCLKLMKYLLEQLKERFKDKKHLDKFSSYHV
KTAFFHVCTQNPQDSQWDRKDLGLCFDNCVTYFLQCLRTEKLENYFIPEFNLFSSN
LIDKRSKEFLTKQIEYERNNEFPVFDEF Chimera 3.3 (pBAD24T-cGAS m-V274-K372 [hh m]) Insert Nucleotide Sequence (SEQ
ID NO: 24)
gacgcagctccgggtgcttctaaactgcgtgcggtcctggaaaaaactgaaactgagccgcgatgacatttctaccgcggccggcat
ggtgaaaggtgtggttgatcatctgctgctgcgtctgaaatgcgactcagcctttcgcggcgttggtctgctgaacacgggtagctatt
acgaacacgtcaaaatctctgcaccgaacgaattcgatgttatgttcaaactggaagtcccgcgtattcagctggaagaatatagcaa
cacccgtgcctattactttgttaaattcaaacgcaacccgaaagaaaatccgctgagtcagtttctggaaggcgaaatcctgagtgcg
tccaaaatgctgtccaaattccgcaaaatcatcaaagaagaagtaaagaaatcaaagacattgacgttagcgtggagaaggaaaa
accaggctcccggcggtaacacttttaattagaaatcctgaggaaattagcgtagatattatactcgcgctggagtctaagggatcct
ggccgattagtaccaaagagggcttacctatccagggatggcttgggacaaaggtacgtacaaatctccgtcgcgaaccattctacc
ttgtaccgaagaacgctaaagatggtaactccttccaagggagacttggcgtcttcattttcccacaccgagaaggaaatcctgaa
caaccacggtaaaagtaaaacgtgctgtgaaaacaaagaagaaaaatgctgtcgtaaagattgtctgaaactgatgaaatatctgct
ggaacagctgaaagaacgcttcaaagataaaaaaacacctggacaaattcagttcctaccatgtgaaaaccgcgttttccacgtttgc
acgcaaaatccgcaggatagccaatgggatcgtaaagacctgggtctgtgctttgacaactgtgtgacctatttcctgcagtgtctgc
gcacggaaaaactggaaaattactttatcccggaatttaaccgttctcatcgaatctgattgataaacgttctaaagaattcctgacga
aacagattgaatacgaacgcaacaacgaatttccggtctttgacgaattt TABLE 5-continued Plasmid and insert sequences.

Chimera 3.3 (pBAD24T-cGAS m-V274-K372 [hh m]) Insert Amino Acid Sequence (SEQ
ID NO: 25)
DAAPGASKLRAVLEKLKLSRDDISTAAGMVKGVVDHLLLRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEVKEIKDIDVSVEKEKPGSPAVTLLIRNPEEISVDIILALE
SKGSWPISTKEGLPIQGWLGTKVRTNLRREPFYLVPKNAKDGNSFQGETWRLSFSH
TEKEILNNHGKSKTCCENKEEKCCRKDCLKLMKYLLEQLKERFKDKKHLDKFSSY
HVKTAFFHVCTQNPQDSQWDRKDLGLCFDNCVTYFLQCLRTEKLENYFIPEFNLFS
SNLIDKRSKEFLTKQIEYERNNEFPVFDEF Chimera 4.1 (pAW1102-pBAD24T-cGAS m-P147-K160 [m hhh]) Insert Nucleotide
Sequence (SEQ ID NO: 26)
ccggacaagctgaaaaaagtgctcgacaagcttcggctgaaacgcgatgacatttctaccgcggccggcatggtgaaaggtgtgg
ttgatcatctgctgctgcgtctgaaatgcgactcagccttttcgcggcgttggtctgctgaacacgggtagctattacgaacacgtcaaa
atctctgcaccgaacgaattcgatgttatgttcaaactggaagtcccgcgtattcagctggaagaatatagcaacacccgtgcctatta
ctttgttaaattcaaacgcaacccgaaagaaaatccgctgagtcagtttctggaaggcgaaatcctgagtgcgtccaaaatgctgtcc
aaattccgcaaaatcatcaaagaagaaatcaacgatatcaaagataccgacgtcattatgaaacgtaaacgcggcggtagtccggc
agtcaccctgctgatttcagaaaaaatctcggtggacattacgctggctctggaatcaaaaagctcttggccggcgagcacccagga
aggcctgcgtattcaaaactggctgtccgctaaagtgcgtaaacagctgcgcctgaaaccgttttacctggttccgaaacatgcgaa
agaaggcaatggttttcaagaagaaacctggcgcctgtcattctcgcatatcgaaaaagaaatcctgaacaaccacggtaaaagtaa
aacgtgctgtgaaaacaaagaagaaaaatgctgtcgtaaagattgtctgaaactgatgaaatatctgctggaacagctgaaagaacg
cttcaaagataaaaaacacctggacaaattcagttcctaccatgtgaaaaccgcgttttttccacgtttgcacgcaaaatccgcaggata
gccaatgggatcgtaaagacctgggtctgtgctttgacaactgtgtgacctatttcctgcagtgtctgcgcacggaaaaactggaaaa
ttactttatcccggaatttaacctgttctcatcgaatctgattgataaacgttctaaagaattcctgacgaaacagattgaatacgaacgc
aacaacgaatttccggtctttgacgaatt Chimera 4.1 (pAW1102-pBAD24T-cGAS m-P147-K160 [m hhh]) Insert Amino Acid
Sequence (SEQ ID NO: 27)
PDKLKKVLDKLRLKRDDISTAAGMVKGVVDHLLLRLKCDSAFRGVGLLNTGSYY
EHVKISAPNEFDVMFKLEVPRIQLEEYSNTRAYYFVKFKRNPKENPLSQFLEGEILS
ASKMLSKFRKIIKEEINDIKDTDVIMKRKRGGSPAVTLLISEKISVDTLALESKSSWP
ASTQEGLRIQNWLSAKVRKQLRLKPFYLVPKHAKEGNGFQEETWRLSFSHIEKEIL
NNHGKSKTCCENKEEKCCRKDCLKLMKYLLEQLKERFKDKKHLDKFSSYHVKTA
FFHVCTQNPQDSQWDRKDLGLCFDNCVTYFLQCLRTEKLENYFIPEFNLFSSNLIDK
RSKEFLTKQIEYERNNEFPVFDEF Chimera 4.2 (pAW1103-pBAD24T-cGAS m-R161-V171 [h m hh]) Insert Nucleotide
Sequence (SEQ ID NO: 28)
gacgcagctccgggtgcttctaaactgcgtgcggtcctggaaaaaactgaaactgagccggaaagatatcagtgaagctgcagaga
ccgtgaaaggtgtggttgatcatctgctgctgcgtctgaaatgcgactcagcctttcgcggcgttggtctgctgaacacgggtagcta
ttacgaacacgtcaaaatctctgcaccgaacgaattcgatgttatgttcaaactggaagtcccgcgtattcagctggaagaatatagca
acacccgtgcctattactttgttaaattcaaacgcaacccgaaagaaaatccgctgagtcagtttctggaaggcgaaatcctgagtgc
gtccaaaatgctgtccaaattccgcaaaatcatcaaagaagaaatcaacgatatcaaagataccgacgtcattatgaaacgtaaacg
cggcggtagtccggcagtcaccctgctgatttcagaaaaaatctcggtggacattacgctggctctggaatcaaaaagctcttggcc
ggcgagcacccaggaaggcctgcgtattcaaaactggctgtccgctaaagtgcgtaaacagctgcgcctgaaaccgttttacctgg
ttccgaaacatgcgaaagaaggcaatggttttcaagaagaaacctggcgcctgtcattctcgcatatcgaaaaagaaatcctgaaca
accacggtaaaagtaaaacgtgctgtgaaaacaaagaagaaaaatgctgtcgtaaagattgtctgaaactgatgaaatatctgctgg
aacagctgaaagaacgcttcaaagataaaaaacacctggacaaattcagttcctaccatgtgaaaaccgcgttttttccacgtttgcac
gcaaaatccgcaggatagccaatgggatcgtaaagacctgggtctgtgctttgacaactgtgtgacctatttcctgcagtgtctgcgc
acggaaaaactggaaaattactttatcccggaatttaacctgttctcatcgaatctgattgataaacgttctaaagaattcctgacgaaac
agattgaatacgaacgcaacaacgaatttccggtctttgacgaatt Chimera 4.2 (pAW1103-pBAD24T-cGAS m-R161-V171 [h m hh]) Insert Amino Acid
Sequence (SEQ ID NO: 29)
DAAPGASKLRAVLEKLKLSRKDISEAAETVKGVVDHLLLRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 4.3 (pAW1104-pBAD24T-cGAS m-N172-R181 [hh m h]) Insert Nucleotide
Sequence (SEQ ID NO: 30)
gacgcagctccgggtgcttctaaactgcgtgcggtcctggaaaaaactgaaactgagccgcgatgacatttctaccgcggccggcat
ggtgaacaaggtggtcgagcggttactgcgtcggctgaaatgcgactcagcctttgcgggcgttggtctgctgaacacgggtagct
attacgaacacgtcaaaatctctgcaccgaacgaattcgatgttatgttcaaactggaagtcccgcgtattcagctggaagaatatagc
aacacccgtgcctattactttgttaaattcaaacgcaacccgaaagaaaatccgctgagtcagtttctggaaggcgaaatcctgagtg
cgtccaaaatgctgtccaaattccgcaaaatcatcaaagaagaaatcaacgatatcaaagataccgacgtcattatgaaacgtaaac
gcggcggtagtccggcagtcaccctgctgatttcagaaaaaatctcggtggacattacgctggctctggaatcaaaaagctcttggc
cggcgagcacccaggaaggcctgcgtattcaaaactggctgtccgctaaagtgcgtaaacagctgcgcctgaaaccgttttacctg
gttccgaaacatgcgaaagaaggcaatggttttcaagaagaaacctggcgcctgtcattctcgcatatcgaaaaagaaatcctgaac
aaccacggtaaaagtaaaacgtgctgtgaaaacaaagaagaaaaatgctgtcgtaaagattgtctgaaactgatgaaatatctgctg
gaacagctgaaagaacgcttcaaagataaaaaacacctggacaaattcagttcctaccatgtgaaaaccgcgttttttccacgtttgca
cgcaaaatccgcaggatagccaatgggatcgtaaagacctgggtctgtgctttgacaactgtgtgacctatttcctgcagtgtctgcg
cacggaaaaactggaaaattactttatcccggaatttaacctgttctcatcgaatctgattgataaacgttctaaagaattcctgacgaaa
cagattgaatacgaacgcaacaacgaatttccggtctttgacgaatt TABLE 5-continued Plasmid and insert sequences.

Chimera 4.3 (pAW1104-pBAD24T-cGAS m-N172-R181 [hh m h]) Insert Amino Acid
Sequence (SEQ ID NO: 31)
DAAPGASKLRAVLEKLKLSRDDISTAAGMVNKVVERLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 4.4 (pAW1105-pBAD24T-cGAS m-M182-Q194 [hhh m]) Insert Nucleotide
Sequence (SEQ ID NO: 32)
gacgcagctccgggtgcttctaaactgcgtgcggtcctggaaaaactgaaactgagccgcgatgacatttctaccgcggccggcat
ggtgaaaggtgtggttgatcatctgctgctgcgtatgcaaaagagagtcagagtttaagggcgtcgagcaactgaacacgggta
gctattacgaacacgtcaaaatctctgcaccgaacgaattcgatgttatgttcaaactggaagtcccgcgtattcagctggaagaatat
agcaacacccgtgcctattactttgttaaattcaaacgcaacccgaaagaaaatccgctgagtcagtttctggaaggcgaaatcctga
gtgcgtccaaaatgctgtccaaattccgcaaaatcatcaaagaagaaatcaacgatatcaaagataccgacgtcattatgaaacgtaa
acgcggcggtagtccggcagtcaccctgctgatttcagaaaaaatctcggtgcattacgctggctctggaatcaaaaagctcttg
gccggcgagcacccaggaaggcctgcgtattcaaaactggctgtccgctaaagtgcgtaaacagctgcgcctgaaaccgttttacc
tggttccgaaacatgcgaaagaaggcaatggttttcaagaagaaacctggcgcctgtcattctcgcatatcgaaaaagaaatcctga
caaccacggtaaaagtaaaacgtgctgtgaaaacaaagaagaaaaatgctgtcgtaaagattgtctgaaactgatgaaatatctgc
tggaacagctgaaagaacgcttcaaagataaaaaacacctggacaaattcagttcctaccatgtgaaaaccgcgttttccacgttg
cacgcaaaatccgcaggatagccaatgggatcgtaaagacctgggtctgtgctttgacaactgtgtgacctatttcctgcagtgtctg
cgcacggaaaaactggaaaattactttatcccggaatttaacctgttctcatcgaatctgattgataaacgttctaaagaattcctgacg
aaacagattgaatacgaacgcaacaacgaatttccggtctttgacgaattt Chimera 4.4 (pAW1105-pBAD24T-cGAS m-M182-Q194[hhh m]) Insert Amino Acid
Sequence (SEQ ID NO: 33)
DAAPGASKLRAVLEKLKLSRDDISTAAGMVKGVVDHLLLRMQKRESEFKGVEQL
NTGSYYEHVKISAPNEFDVMFKLEVPRIQLEEYSNTRAYYFVKFKRNPKENPLSQF
LEGEILSASKMLSKFRKIIKEEINDIKDTDVIMKRKRGGSPAVTLLISEKISVDITLALE
SKSSWPASTQEGLRIQNWLSAKVRKQLRLKPFYLVPKHAKEGNGFQEETWRLSFS
HIEKEILNNHGKSKTCCENKEEKCCRKDCLKLMKYLLEQLKERFKDKKHLDKFSS
YHVKTAFFHVCTQNPQDSQWDRKDLGLCFDNCVTYFLQCLRTEKLENYFIPEFNLF
SSNLIDKRSKEFLTKQIEYERNNEFPVFDEF Chimera 5.1 (pAW1096-pBAD24T-cGAS Chi4.3 N187K) Insert Nucleotide Sequence
(SEQ ID NO: 34)
gacgcagctccgggtgcttctaaactgcgtgcggtcctggaaaaactgaaactgagccgcgatgacatttctaccgcggccggcat
ggtgaaaaaggtggtcgagcggttactgcgtcggctgaaatgcgactcagcctttcgcggcgttggtctgctgaacacgggtagct
attacgaacacgtcaaaatctctgcaccgaacgaattcgatgttatgttcaaactggaagtcccgcgtattcagctggaagaatatagc
aacacccgtgcctattactttgttaaattcaaacgcaacccgaaagaaaatccgctgagtcagtttctggaaggcgaaatcctgagtg
cgtccaaaatgctgtccaaattccgcaaaatcatcaaagaagaaatcaacgatatcaaagataccgacgtcattatgaaacgtaaac
gcggcggtagtccggcagtcaccctgctgatttcagaaaaaatctcggtggacattacgctggctctggaatcaaaaagctcttggc
cggcgagcacccaggaaggcctgcgtattcaaaactggctgtccgctaaagtgcgtaaacagctgcgcctgaaaccgttttacctg
gttccgaaacatgcgaaagaaggcaatggttttcaagaagaaacctggcgcctgtcattctcgcatatcgaaaaagaaatcctgaac
aaccacggtaaaagtaaaacgtgctgtgaaaacaaagaagaaaaatgctgtcgtaaagattgtctgaaactgatgaaatatctgctg
gaacagctgaaagaacgcttcaaagataaaaaacacctggacaaattcagttcctaccatgtgaaaaccgcgttttccacgtttgca
cgcaaaatccgcaggatagccaatgggatcgtaaagacctgggtctgtgctttgacaactgtgtgacctatttcctgcagtgtctgcg
cacggaaaaactggaaaattactttatcccggaatttaacctgttctcatcgaatctgattgataaacgttctaaagaattcctgacgaaa
cagattgaatacgaacgcaacaacgaatttccggtctttgacgaattt Chimera 5.1 (pAW1096-pBAD24T-cGAS Chi4.3 N187K) Insert Amino Acid Sequence
(SEQ ID NO: 35)
DAAPGASKLRAVLEKLKLSRDDISTAAGMVKKVVERLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 5.2 (pAW1097-pBAD24T-cGAS Chi4.3 K188G) Insert Nucleotide Sequence
(SEQ ID NO: 36)
gacgcagctccgggtgcttctaaactgcgtgcggtcctggaaaaactgaaactgagccgcgatgacatttctaccgcggccggcat
ggtgaacggtgtggtcgagcggttactgcgtcggctgaaatgcgactcagcctttcgcggcgttggtctgctgaacacgggtagct
attacgaacacgtcaaaatctctgcaccgaacgaattcgatgttatgttcaaactggaagtcccgcgtattcagctggaagaatatagc
aacacccgtgcctattactttgttaaattcaaacgcaacccgaaagaaaatccgctgagtcagtttctggaaggcgaaatcctgagtg
cgtccaaaatgctgtccaaattccgcaaaatcatcaaagaagaaatcaacgatatcaaagataccgacgtcattatgaaacgtaaac
gcggcggtagtccggcagtcaccctgctgatttcagaaaaaatctcggtggacattacgctggctctggaatcaaaaagctcttggc
cggcgagcacccaggaaggcctgcgtattcaaaactggctgtccgctaaagtgcgtaaacagctgcgcctgaaaccgttttacctg
gttccgaaacatgcgaaagaaggcaatggttttcaagaagaaacctggcgcctgtcattctcgcatatcgaaaaagaaatctgaac
aaccacggtaaaagtaaaacgtgctgtgaaaacaaagaagaaaaatgctgtcgtaaagattgtctgaaactgatgaaatatctgctg
gaacagctgaaagaacgcttcaaagataaaaaacacctggacaaattcagttcctaccatgtgaaaaccgcgttttccacgtttgca
cgcaaaatccgcaggatagccaatgggatcgtaaagacctgggtctgtgctttgacaactgtgtgacctatttcctgcagtgtctgcg
cacggaaaaactggaaaattactttatcccggaatttaacctgttctcatcgaatctgattgataaacgttctaaagaattcctgacgaaa
cagattgaatacgaacgcaacaacgaatttccggtctttgacgaattt TABLE 5-continued Plasmid and insert sequences.

Chimera 5.2 (pAW1097-pBAD24T-cGAS Chi4.3 K188G) Insert Amino Acid Sequence
(SEQ ID NO: 37)
DAAPGASKLRAVLEKLKLSRDDISTAAGMVNGVVERLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 5.3 (pAW1098-pBAD24T-cGAS Chi4.3 E191D) Insert Nucleotide Sequence
(SEQ ID NO: 38)
gacgcagctccgggtgcttctaaactgcgtgcggtcctggaaaaactgaaactgagccgcgatgacatttctaccgcggccggcat
ggtgaacaaggtggtcgatcggttactgcgtcggctgaaatgcgactcagcctttcgcggcgttggtctgctgaacacgggtagcta
ttacgaacacgtcaaaatctctgcaccgaacgaattcgatgttatgttcaaactggaagtcccgcgtattcagctggaagaatatagca
acacccgtgcctattactttgttaaattcaaacgcaacccgaaagaaaatccgctgagtcagtttctggaaggcgaaatcctgagtgc
gtccaaaatgctgtccaaattccgcaaaatcatcaaagaagaaatcaacgatatcaaagataccgacgtcattatgaaacgtaaacg
cggcggtagtccggcagtcaccctgctgatttcagaaaaaatctcggtggacattacgctggctctggaatcaaaaagctcttggcc
ggcgagcacccaggaaggcctgcgtattcaaaactggctgtccgctaaagtgcgtaaacagctgcgcctgaaaccgttttacctgg
ttccgaaacatgcgaaagaaggcaatggttttcaagaagaaacctggcgcctgtcattctcgcatatcgaaaaagaaatcctgaaca
accacggtaaaagtaaaacgtgctgtgaaaacaaagaagaaaaatgctgtcgtaaagattgtctgaaactgatgaaatatctgctgg
aacagctgaaagaacgcttcaaagataaaaaaaacacctggacaaattcagttcctaccatgtgaaaaccgcgttttttccacgtttgcac
gcaaaatccgcaggatagccaatgggatcgtaaagacctgggtctgtgctttgacaactgtgtgacctattttcctgcagtgtctgcgc
acggaaaaactggaaaattactttatcccggaatttaacctgttctcatcgaatctgattgataaacgttctaaagaattcctgacgaaac
agattgaatacgaacgcaacaacgaatttccggtctttgacgaattt Chimera 5.3 (pAW1098-pBAD24T-cGAS Chi4.3 E191D) Insert Amino Acid Sequence
(SEQ ID NO: 39)
DAAPGASKLRAVLEKLKLSRDDISTAAGMVNKVVDRLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 5.4 (pAW1099-pBAD24T-cGAS Chi4.3 R192H) Insert Nucleotide Sequence
(SEQ ID NO: 40)
gacgcagctccgggtgcttctaaactgcgtgcggtcctggaaaaactgaaactgagccgcgatgacatttctaccgcggccggcat
ggtgaacaaggtggtcgagcatttactgcgtcggctgaaatgcgactcagcctttcgcggcgttggtctgctgaacacgggtagcta
ttacgaacacgtcaaaatctctgcaccgaacgaattcgatgttatgttcaaactggaagtcccgcgtattcagctggaagaatatagca
acacccgtgcctattactttgttaaattcaaacgcaacccgaaagaaaatccgctgagtcagtttctggaaggcgaaatcctgagtgc
gtccaaaatgctgtccaaattccgcaaaatcatcaaagaagaaatcaacgatatcaaagataccgacgtcattatgaaacgtaaacg
cggcggtagtccggcagtcaccctgctgatttcagaaaaaatctcggtggacattacgctggctctggaatcaaaaagctcttggcc
ggcgagcacccaggaaggcctgcgtattcaaaactggctgtccgctaaagtgcgtaaacagctgcgcctgaaaccgttttacctgg
ttccgaaacatgcgaaagaaggcaatggttttcaagaagaaacctggcgcctgtcattctcgcatatcgaaaaagaaatcctgaaca
accacggtaaaagtaaaacgtgctgtgaaaacaaagaagaaaaatgctgtcgtaaagattgtctgaaactgatgaaatatctgctgg
aacagctgaaagaacgcttcaaagataaaaaaaacacctggacaaattcagttcctaccatgtgaaaaccgcgttttttccacgtttgcac
gcaaaatccgcaggatagccaatgggatcgtaaagacctgggtctgtgctttgacaactgtgtgacctattttcctgcagtgtctgcgc
acggaaaaactggaaaattactttatcccggaatttaacctgttctcatcgaatctgattgataaacgttctaaagaattcctgacgaaac
agattgaatacgaacgcaacaacgaatttccggtctttgacgaattt Chimera 5.4 (pAW1099-pBAD24T-cGAS Chi4.3 R192H) Insert Amino Acid Sequence
(SEQ ID NO: 41)
DAAPGASKLRAVLEKLKLSRDDISTAAGMVNKVVEHLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 5.5 (pAW1100-pBAD24T-cGAS Chi4.3 R195L) Insert Nucleotide Sequence
(SEQ ID NO: 42)
gacgcagctccgggtgcttctaaactgcgtgcggtcctggaaaaactgaaactgagccgcgatgacatttctaccgcggccggcat
ggtgaacaaggtggtcgagcggttactgctgcggctgaaatgcgactcagcctttcgcggcgttggtctgctgaacacgggtagct
attacgaacacgtcaaaatctctgcaccgaacgaattcgatgttatgttcaaactggaagtcccgcgtattcagctggaagaatatagc
aacacccgtgcctattactttgttaaattcaaacgcaacccgaaagaaaatccgctgagtcagtttctggaaggcgaaatcctgagtg
cgtccaaaatgctgtccaaattccgcaaaatcatcaaagaagaaatcaacgatatcaaagataccgacgtcattatgaaacgtaaac
gcggcggtagtccggcagtcaccctgctgatttcagaaaaaatctcggtggacattacgctggctctggaatcaaaaagctcttggc
cggcgagcacccaggaaggcctgcgtattcaaaactggctgtccgctaaagtgcgtaaacagctgcgcctgaaaccgttttacctg
gttccgaaacatgcgaaagaaggcaatggttttcaagaagaaacctggcgcctgtcattctcgcatatcgaaaaagaaatcctgctg
aaccacggtaaaagtaaaacgtgctgtgaaaacaaagaagaaaaatgctgtcgtaaagattgtctgaaactgatgaaatatctgctg
gaacagctgaaagaacgcttcaaagataaaaaaaacacctggacaaattcagttcctaccatgtgaaaaccgcgttttttccacgtttgca
cgcaaaatccgcaggatagccaatgggatcgtaaagacctgggtctgtgctttgacaactgtgtgacctattttcctgcagtgtctgcg
cacggaaaaactggaaaattactttatcccggaatttaacctgttctcatcgaatctgattgataaacgttctaaagaattcctgacgaaa
cagattgaatacgaacgcaacaacgaatttccggtctttgacgaattt TABLE 5-continued Plasmid and insert sequences.

Chimera 5.5 (pAW1100-pBAD24T-cGAS Chi4.3 R195L) Insert Amino Acid Sequence
(SEQ ID NO: 43)
DAAPGASKLRAVLEKLKLSRDDISTAAGMVNKVVERLLLRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 6.1 (pAW1107-pBAD24T-hcGAS K187N) Insert Nucleotide Sequence (SEQ ID
NO: 44)
gacgcagctccgggtgcttctaaactgcgtgcggtcctggaaaaactgaaactgagccgcgatgacatttctaccgcggccggcat
ggtgaacggtgtggttgatcatctgctgcgtcgtctgaaatgcgactcagcctttcgcggcgttggtctgctgaacacgggtagctatt
acgaacacgtcaaaatctctgcaccgaacgaattcgatgttatgttcaaactggaagtcccgcgtattcagctggaagaatatagcaa
cacccgtgcctattactttgttaaattcaaacgcaacccgaaagaaaatccgctgagtcagtttctggaaggcgaaatcctgagtgcg
tccaaaatgctgtccaaattccgcaaaatcatcaaagaagaaatcaacgatatcaaagataccgacgtcattatgaaacgtaaacgc
ggcggtagtccggcagtcaccctgctgatttcagaaaaaatctcggtggacattacgctggctctggaatcaaaaagctcttggccg
gcgagcacccaggaaggcctgcgtattcaaaactggctgtccgctaaagtgcgtaaacagctgcgcctgaaaccgttttacctggtt
ccgaaacatgcgaaagaaggcaatggttttcaagaagaaacctggcgcctgtcattctcgcatatcgaaaaagaaatcctgaacaa
ccacggtaaaagtaaaacgtgctgtgaaaacaaagaagaaaaatgctgtcgtaaagattgtctgaaactgatgaaatatctgctgga
acagctgaaagaacgcttcaaagataaaaaacacctggacaaatttcagttcctaccatgtgaaaaccgcgttttttccacgtttgcacg
caaaatccgcaggatagccaatgggatcgtaaagacctgggtctgtgctttgacaactgtgtgacctatttcctgcagtgtctgcgca
cggaaaaactggaaaattactttatcccggaatttaacctgttctcatcgaatctgattgataaacgttctaaagaattcctgacgaaaca
gattgaatacgaacgcaacaacgaatttccggtctttgacgaattt Chimera 6.1 (pAW1107-pBAD24T-hcGAS K187N) Insert Amino Acid Sequence (SEQ ID
NO: 45)
DAAPGASKLRAVLEKLKLSRDDISTAAGMVNGVVDHLLLRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 6.2 (pAW1111-pBAD24T-hcGAS L195R) Insert Nucleotide Sequence (SEQ ID
NO: 46)
gacgcagctccgggtgcttctaaactgcgtgcggtcctggaaaaactgaaactgagccgcgatgacatttctaccgcggccggcat
ggtgaaaggtgtggttgatcatctgctgcgtcgtctgaaatgcgactcagcctttcgcggcgttggtctgctgaacacgggtagctatt
acgaacacgtcaaaatctctgcaccgaacgaattcgatgttatgttcaaactggaagtcccgcgtattcagctggaagaatatagcaa
cacccgtgcctattactttgttaaattcaaacgcaacccgaaagaaaatccgctgagtcagtttctggaaggcgaaatcctgagtgcg
tccaaaatgctgtccaaattccgcaaaatcatcaaagaagaaatcaacgatatcaaagataccgacgtcattatgaaacgtaaacgc
ggcggtagtccggcagtcaccctgctgatttcagaaaaaatctcggtggacattacgctggctctggaatcaaaaagctcttggccg
gcgagcacccaggaaggcctgcgtattcaaaactggctgtccgctaaagtgcgtaaacagctgcgcctgaaaccgttttacctggtt
ccgaaacatgcgaaagaaggcaatggttttcaagaagaaacctggcgcctgtcattctcgcatatcgaaaaagaaatcctgaacaa
ccacggtaaaagtaaaacgtgctgtgaaaacaaagaagaaaaatgctgtcgtaaagattgtctgaaactgatgaaatatctgctgga
acagctgaaagaacgcttcaaagataaaaaacacctggacaaatttcagttcctaccatgtgaaaaccgcgttttttccacgtttgcacg
caaaatccgcaggatagccaatgggatcgtaaagacctgggtctgtgctttgacaactgtgtgacctatttcctgcagtgtctgcgca
cggaaaaactggaaaattactttatcccggaatttaacctgttctcatcgaatctgattgataaacgttctaaagaattcctgacgaaaca
gattgaatacgaacgcaacaacgaatttccggtctttgacgaattt Chimera 6.2 (pAW1111-pBAD24T-hcGAS L195R) Insert Amino Acid Sequence (SEQ ID
NO: 47)
DAAPGASKLRAVLEKLKLSRDDISTAAGMVKGVVDHLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF Chimera 7 (pAW1101-pBAD24T-hcGAS K187N, L195R) Insert Nucleotide Sequence
(SEQ ID NO: 48)
gacgcagctccgggtgcttctaaactgcgtgcggtcctggaaaaactgaaactgagccgcgatgacatttctaccgcggccggcat
ggtgaacggtgtggttgatcatctgctgcgtcgtctgaaatgcgactcagcctttcgcggcgttggtctgctgaacacgggtagctatt
acgaacacgtcaaaatctctgcaccgaacgaattcgatgttatgttcaaactggaagtcccgcgtattcagctggaagaatatagcaa
cacccgtgcctattactttgttaaattcaaacgcaacccgaaagaaaatccgctgagtcagtttctggaaggcgaaatcctgagtgcg
tccaaaatgctgtccaaattccgcaaaatcatcaaagaagaaatcaacgatatcaaagataccgacgtcattatgaaacgtaaacgc
ggcggtagtccggcagtcaccctgctgatttcagaaaaaatctcggtggacattacgctggctctggaatcaaaaagctcttggccg
gcgagcacccaggaaggcctgcgtattcaaaactggctgtccgctaaagtgcgtaaacagctgcgcctgaaaccgttttacctggtt
ccgaaacatgcgaaagaaggcaatggttttcaagaagaaacctggcgcctgtcattctcgcatatcgaaaaagaaatcctgaacaa
ccacggtaaaagtaaaacgtgctgtgaaaacaaagaagaaaaatgctgtcgtaaagattgtctgaaactgatgaaatatctgctgga
acagctgaaagaacgcttcaaagataaaaaacacctggacaaatttcagttcctaccatgtgaaaaccgcgttttttccacgtttgcacg
caaaatccgcaggatagccaatgggatcgtaaagacctgggtctgtgctttgacaactgtgtgacctatttcctgcagtgtctgcgca
cggaaaaactggaaaattactttatcccggaatttaacctgttctcatcgaatctgattgataaacgttctaaagaattcctgacgaaaca
gattgaatacgaacgcaacaacgaatttccggtctttgacgaattt TABLE 5-continued Plasmid and insert sequences.

Chimera 7 (pAW1101-pBAD24T-hcGAS K187N, L195R) Insert Amino Acid Sequence
(SEQ ID NO: 49)
DAAPGASKLRAVLEKLKLSRDDISTAAGMVNGVVDHLLRRLKCDSAFRGVGLLNT
GSYYEHVKISAPNEFDVMFKLEVPRIQLEEYSNTRAYYFVKFKRNPKENPLSQFLE
GEILSASKMLSKFRKIIKEEINDIKDTDVIMKRKRGGSPAVTLLISEKISVDITLALES
KSSWPASTQEGLRIQNWLSAKVRKQLRLKPFYLVPKHAKEGNGFQEETWRLSFSHI
EKEILNNHGKSKTCCENKEEKCCRKDCLKLMKYLLEQLKERFKDKKHLDKFSSYH
VKTAFFHVCTQNPQDSQWDRKDLGLCFDNCVTYFLQCLRTEKLENYFIPEFNLFSS
NLIDKRSKEFLTKQIEYERNNEFPVFDEF

Example 2: A Rapid Genetic Assay in Bacteria Maps the Molecular Determinant of Human-Specific cGAS Regulation to Two N-Terminal Substitutions Cyclic GMP-AMP synthase (cGAS) recognition of cytosolic DNA is critical for immune responses to pathogen replication, cellular stress, and cancer. Existing structures of the mouse cGAS-DNA complex provide a model for enzyme activation, but do not explain why human cGAS exhibits severely reduced levels of cyclic GMP-AMP (cGAMP) synthesis compared to other mammals. Previous results demonstrate that hcGAS produces less 2' 3' cGAMP than mcGAS (Sun et al. (2013) *Science* 339:786-791). A critical feature of human cGAS-STING signaling is the preferential response of human cells to long (>45 bp) cytosolic DNA (Andreeva et al. (2017) *Nature* 549:394-398; Karayel et al. (2009) *Eur J Immunol* 39:1929-1936; Luecke et al. (2017) *EMBO Rep* 18:1707-1715; Stetson and Medzhitov (2006) *Immunity* 24:93-103). To better understand human-specific regulation of cGAS activation, cGAS activation was reconstituted in vitro with purified components, and 2' 3' cGAMP production was directly measured by thin-layer chromatography. Purified hcGAS exhibited markedly reduced 2' 3' cGAMP production compared to mcGAS (FIG. 1A), demonstrating that altered regulation was an intrinsic feature of the hcGAS protein not shared with mammalian homologs.

Figure 1B:
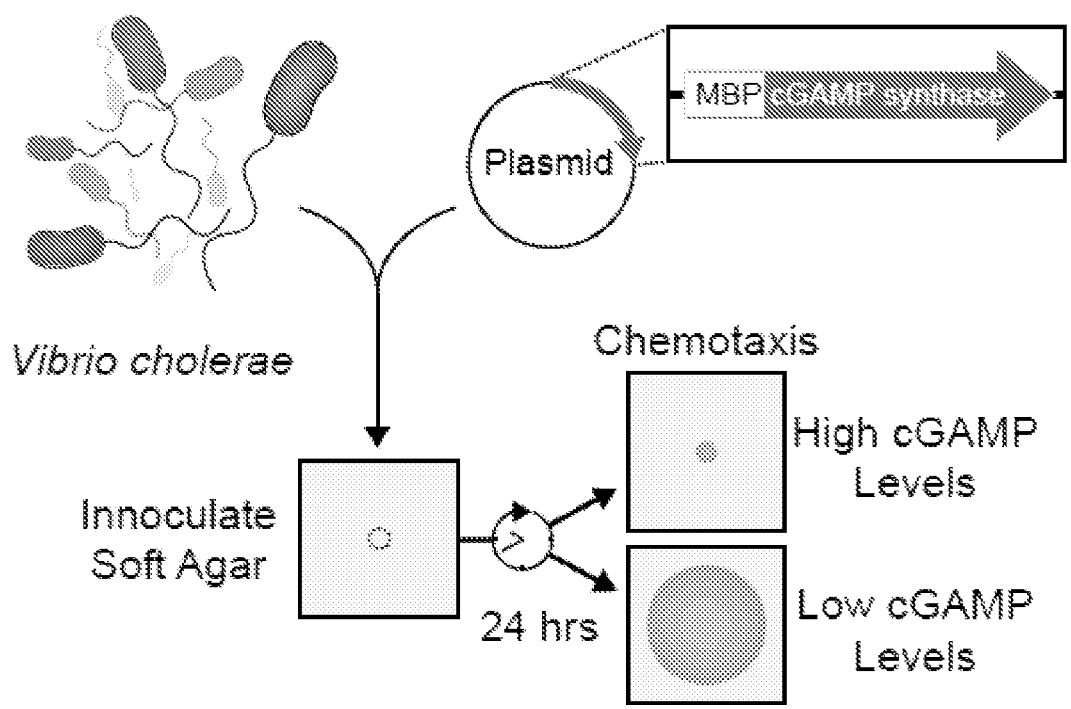
Figure 1C:
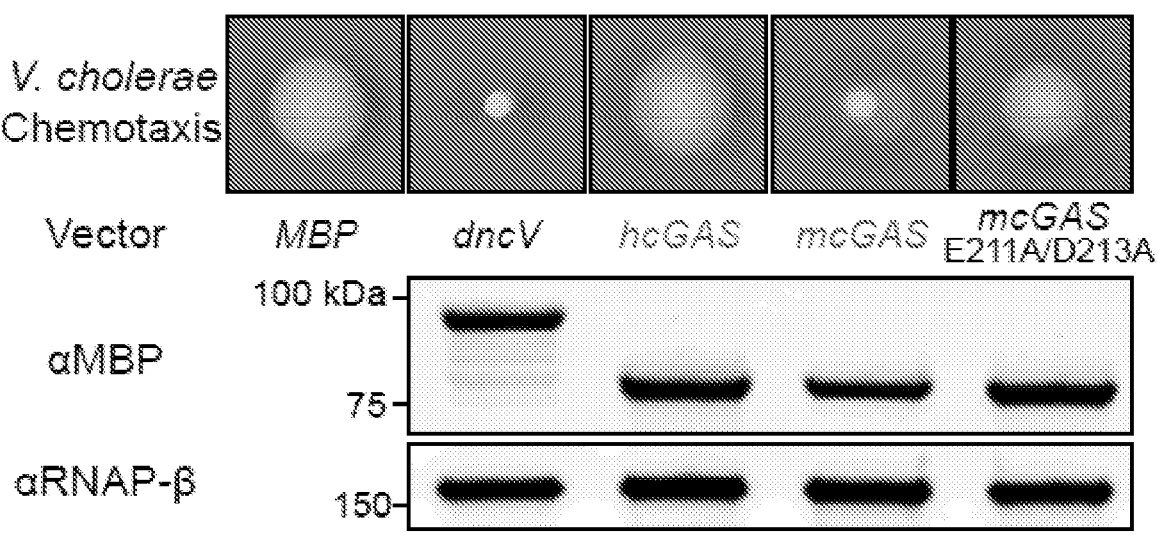
Figure 2:
FIG. 2 shows sequence alignment of human (SEQ ID NO: 1) and mouse (SEQ ID NO: 5) cGAS. Alignment of human and mouse cGAS amino acid sequences with known alpha-helix (magenta) and beta-strand (grey) secondary structure depicted below. Conserved residues are shaded in grey, residues mediating cGAS-DNA contacts are boxed in black, and the metal-coordinating active-site residues are marked with a red asterisk. Human-specific substitutions in DNA A-site and B-site binding surfaces are labeled in magenta and corresponding mouse residues are labeled in blue.
Figure 3A:
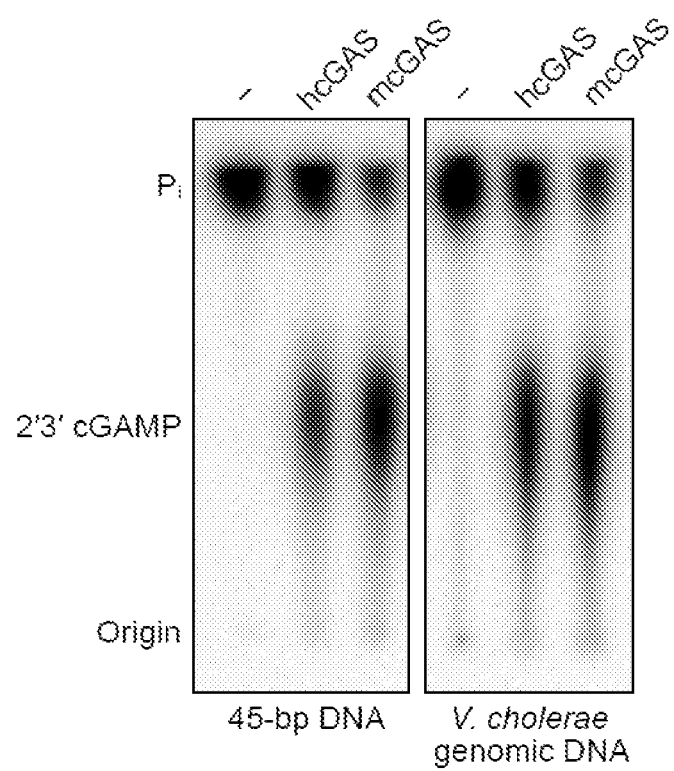
FIG. 3A-FIG. 3C show that reconstitution of cGAS 2'3' cGAMP signaling in bacteria allows genetic mapping of the human-specific regulatory element.
Figure 3B:
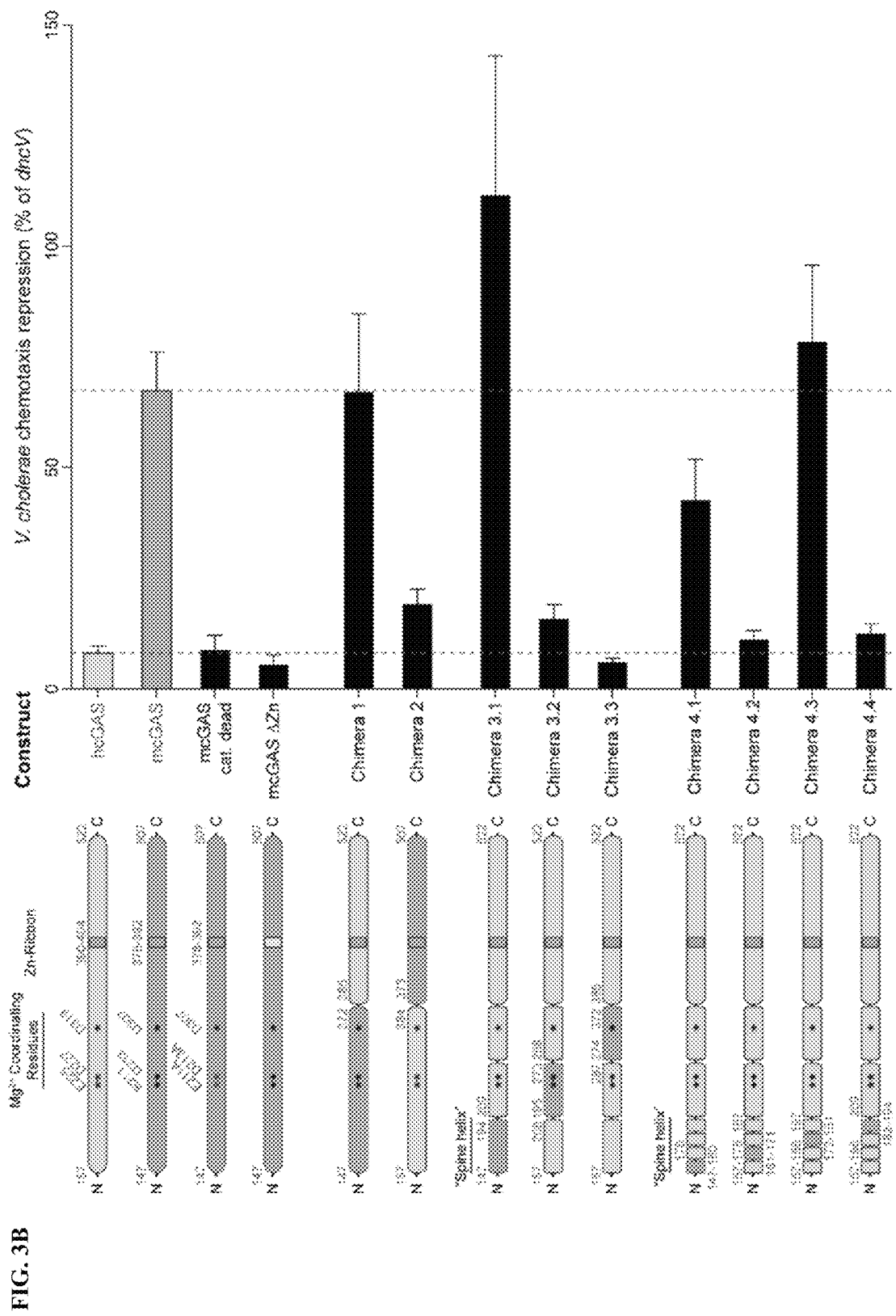
Figure 3C:
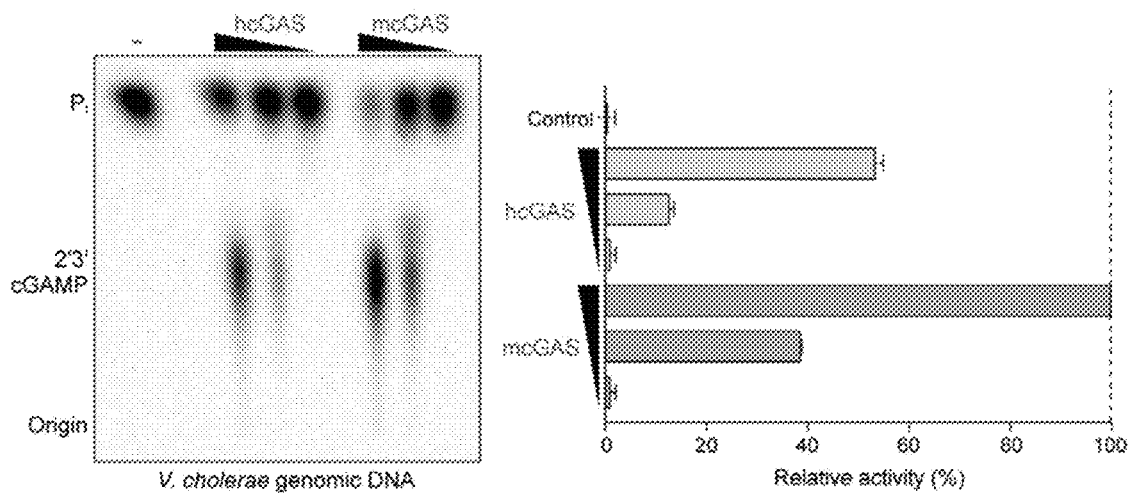

The human gene encoding cGAS (CGAS, MB21D1) is under intense positive selection (George et al. (2011) *Genome Res* 21:1686-1694; Hancks et al. (2015) *PLoS Genet* 11:e1005203; Mozzi et al. (2015) *Genome Biol Evol* 7:1016-1032), and there are 116 amino acid differences between the hcGAS and mcGAS enzymatic domains (FIG. 2). The resulting low sequence homology, and a complete lack of structural information for the active hcGAS-DNA complex, prevents rational determination of the key residues responsible for altered hcGAS function. To overcome this limitation, a bacterial assay was developed in *Vibrio cholerae* that monitors 2'3'GAMP synthesis and allows rapid determination of relative cGAS enzymatic activity (FIG. 1B). The *V. cholerae* enzyme dinucleotide cyclase in *Vibrio* (DncV) is a structural homolog of hcGAS that synthesizes a chemically-related second messenger 3'-5'/3'-5' cGAMP (3'3' cGAMP) to control host colonization and bacterial chemotaxis (Davies et al. (2012) *Cell* 149:358-370; Kranzusch et al. (2014) *Cell* 158:1011-1021; Zhu et al. (2014) *Mol Cell* 55:931-937). Increased levels of 3'3' cGAMP in *V. cholerae* arrest chemotaxis, and it was hypothesized that ectopic cGAS expression and 2'3' cGAMP production might also induce this phenotype. Indeed, overexpression of dncV inhibited chemotaxis, while the negative control *E. coli* maltose-binding protein (MBP) had no effect (FIG. 1C). In agreement with the hypothesis that 2'3' cGAMP could agonize the bacterial 3'3' cGAMP pathway, overexpression of mcGAS in *V. cholerae* potently arrested chemotaxis and phenocopied dncV. However, no loss of chemotaxis was observed upon expression of hcGAS (FIG. 1C). The *V. cholerae* genome was the likely source of cGAS-activating DNA in the bacterial cytosol, and it was confirmed in vitro that *V. cholerae* genomic DNA was capable of stimulating both hcGAS and mcGAS 2'3' cGAMP synthesis (FIG. 3A and FIG. 3C). In agreement with synthetic DNA experiments (FIG. 1A), mcGAS also produces more 2'3' cGAMP than hcGAS in response to bacterial genomic DNA (FIG. 3C). Additionally, hcGAS and mcGAS proteins are stable and express to similar levels, indicating that chemotaxis inhibition is most likely due to higher levels of 2'3' cGAMP produced by mcGAS compared to hcGAS (FIG. 1C). Mutations to the mcGAS active site that disrupt catalytic magnesium coordination (E211 Å/D213 Å) relieved chemotaxis inhibition, confirming that the *V. cholerae* phenotype observed with mcGAS was due to elevated 2'3' cGAMP production (FIG. 1C).

Figures 1D, 1E:
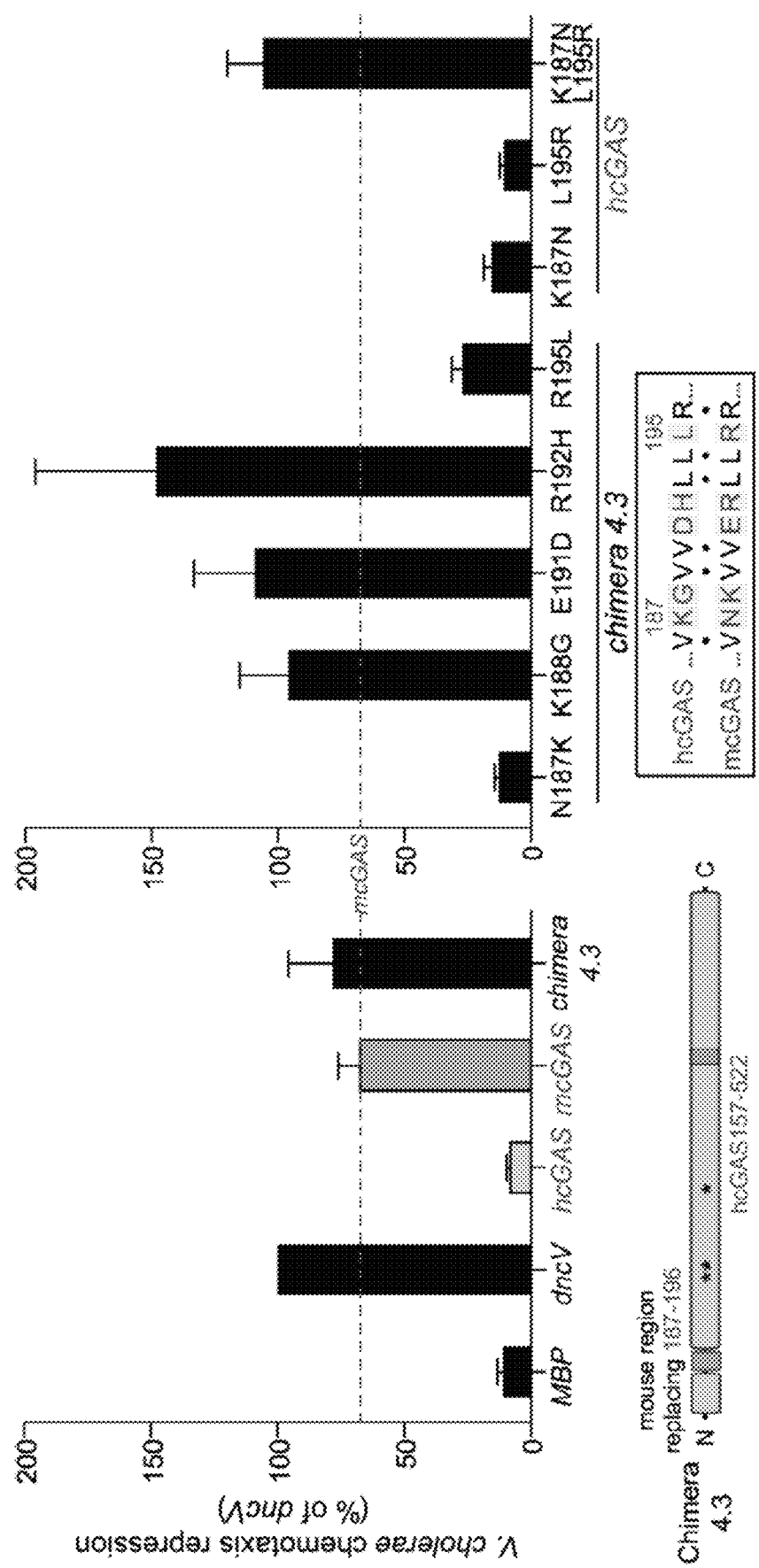
Figure 1F:
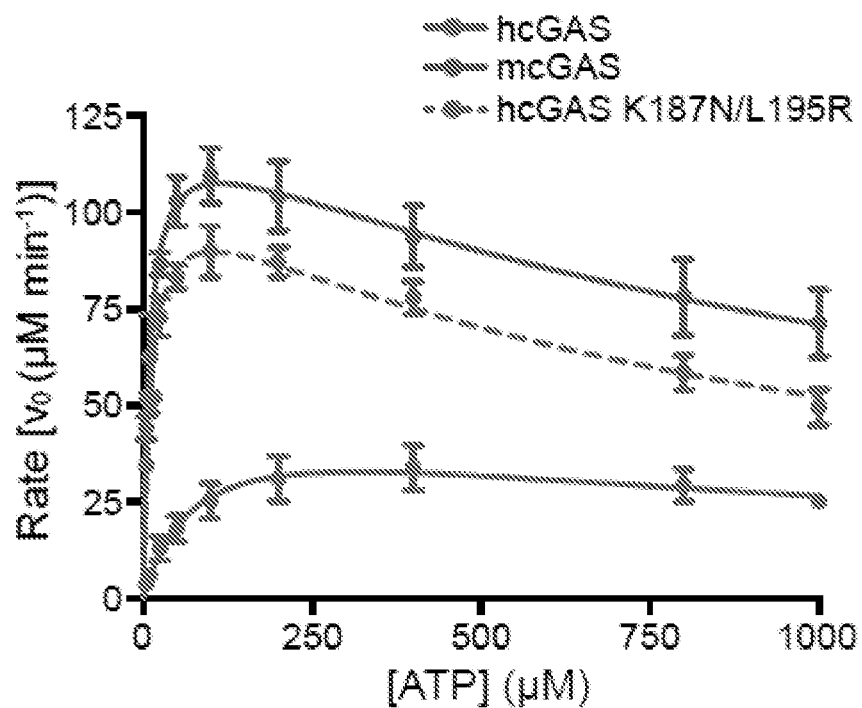

*V. cholerae* was used as a sensitive platform to rapidly screen cGAS activity, and a chimera approach was applied to map the genetic determinant of human-specific cGAS regulation. Based on the apo structure of hcGAS (PDB: 4KM5) (Kato et al. (2013) *PLoS One* 8:e76983; Kranzusch et al. (2013) *Cell Rep* 3:1362-1368; Li et al. (2013) *Immunity* 39:1019-1031; Zhang et al. (2014) *Cell Rep* 6:421-430), a construct encoding the first half of the mcGAS enzymatic domain fused to the second half from hcGAS (Chimera 1: mcGAS P147-K372, hcGAS E385-F522) was designed. This chimeric cGAS construct exhibited potent inhibition of *V. cholerae* chemotaxis equal to that of wildtype mcGAS, demonstrating that human-mouse cGAS chimeras retain enzymatic activity (FIG. 3B). The inverse construct encoding the mcGAS C-terminal half of the enzymatic domain (Chimera 2: hcGAS D157-K384, mcGAS Y373-L507) resulted in significantly weaker chemotaxis inhibition, indicating that the critical determinant of hcGAS regulation resides in the first ~220 amino acids of the catalytic domain. Through iterative rounds of structure-guided chimera design, the location of the human-specific regulatory element was mapped to a minimal region of 10 residues that contains five human-specific amino acid substitutions (Chimera 4.3: hcGAS, with K187-R196 replaced with mcGAS N172-R181) (FIGS. 1D and 3B).

Figure 7B:
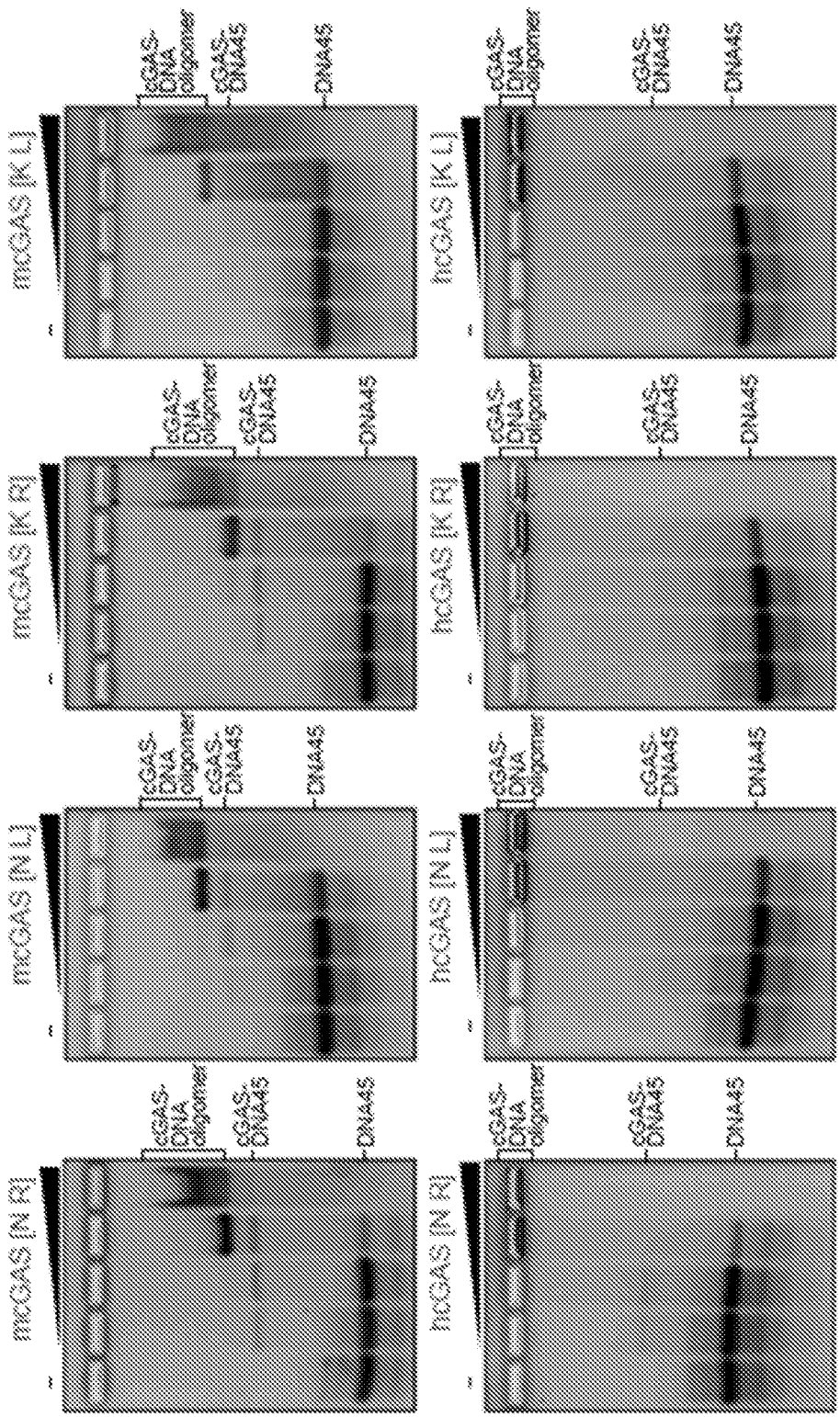
Figure 7C:
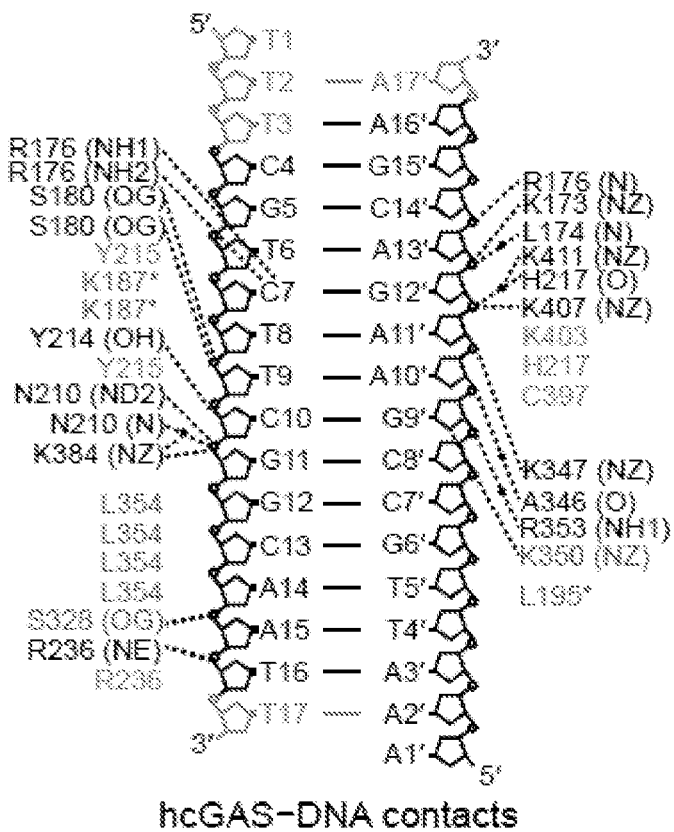
Figure 7D:
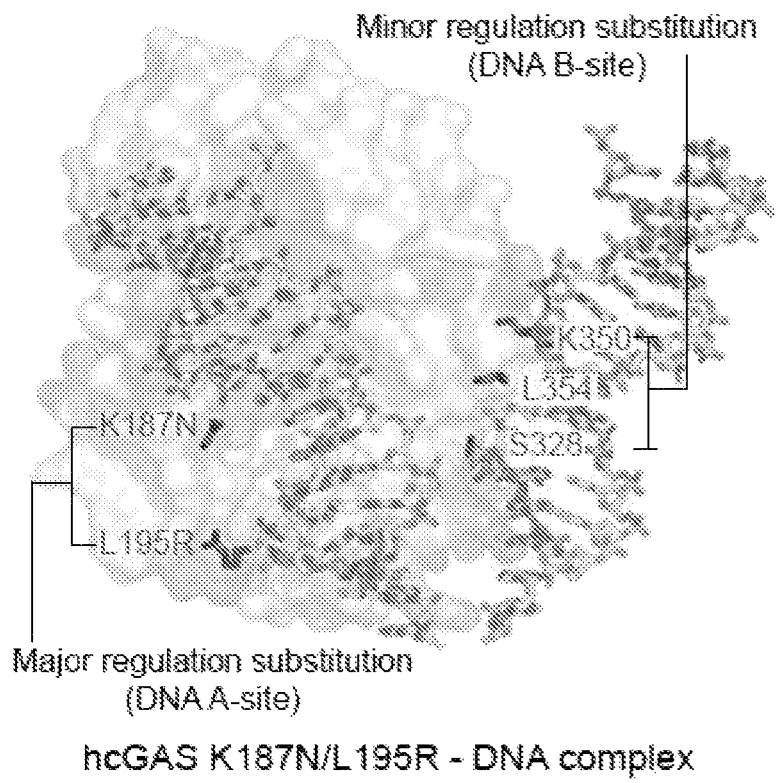
Figure 7E:
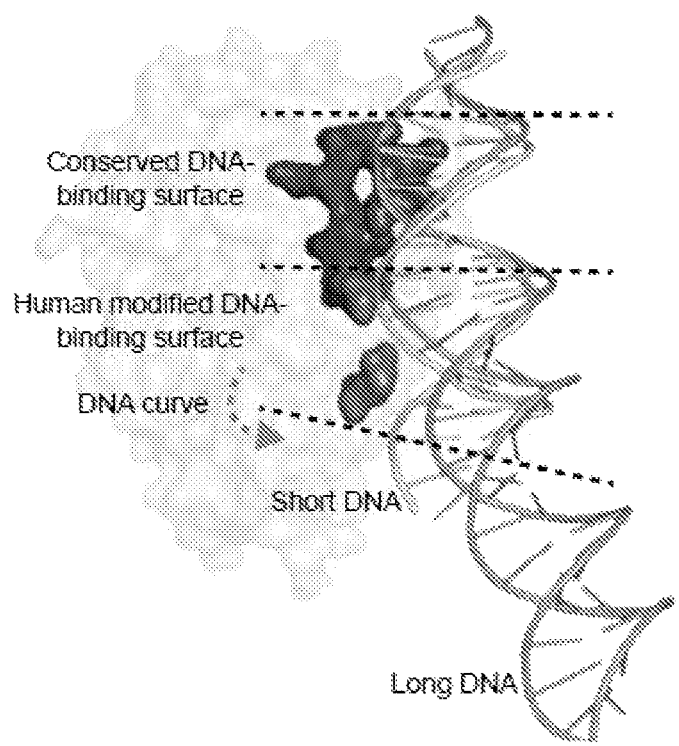

Using the highly active hcGAS Chimera 4.3 as a background, each of the unique amino acid substitutions were next reverted individually back to the wildtype human sequence and activity in *V. cholerae* was measured. Wild-type human sequence at hcGAS position K187 and L195 resulted in loss of chemotaxis inhibition, while individual substitutions at the remaining three positions had no effect (FIG. 1E). Neither K187N nor L195R alone was sufficient to enhance hcGAS activity. Instead, a K187N/L195R double-mutant potently inhibited *V. cholerae* chemotaxis, demonstrating that both amino acid substitutions were required and together were sufficient to elevate levels of 2'3' cGAMP synthesis (FIG. 1E). To confirm these results, recombinant cGAS chimera enzymes were purified from each stage of the genetic analysis and 2'3' cGAMP synthesis was directly quantified in vitro (FIG. 4). Measurement of the kinetics and catalytic efficiency of 2'3' cGAMP synthesis revealed that hcGAS is ~20-fold less efficient than mcGAS. Strikingly, the engineered hcGAS K187N/L195R variant exhibited elevated 2'3' cGAMP synthesis and enzyme kinetics nearly equal to mcGAS, indicating that these residues control the major regulatory difference between human and mouse enzyme activation (FIG. 1F). Together, these data demonstrated that two unique substitutions K187 and L195 in the N-terminus of hcGAS are responsible for human-specific control of 2'3' cGAMP synthesis.

Example 3: Structural Basis of K187 and L195 Substitutions Controlling hcGAS Activity The impact of hcGAS K187 and L195 substitution on enzyme activity was dissected using a panel of eight recombinant cGAS enzymes and direct measurement of 2'3' cGAMP synthesis. Analysis of all possible combinations of K187/N187 and L195/R195 substitutions in both hcGAS and mcGAS backgrounds revealed a clear pattern showing that human-specific substitutions reduced total 2'3' cGAMP output (FIG. 5A). The presence of K187 and L195 resulted in reduced enzyme activity (as compared to N187/R195) in both the hcGAS and mcGAS backgrounds, and a double K187/L195 mutation fully restrained mcGAS 2'3' cGAMP synthesis to human levels. The structural basis of how K187 and L195 controlled enzyme function was next determined. All previous efforts in the field to determine the structure of hcGAS bound to activating DNA have been unsuccessful. However, using hcGAS K187N/L195R and a 17 bp activating DNA, it was now able to identify conditions that allowed growth of crystals suitable for structure determination. Phase information obtained through molecular replacement with the apo structure of hcGAS was used, and the structure of the hcGAS-DNA binary complex to 2.3 A and the hcGAS-DNA-ATP ternary complex to 2.8 A (Table 3) was determined.

The structure of hcGAS K187N/L195R bound to activating DNA reveals a minimal 2:2 complex of two molecules of cGAS embracing two molecules of double-stranded DNA (FIG. 5B). The overall complex topology was similar to previous mcGAS- and *Sus scrofa* cGAS-DNA structures (Civril et al. (2013) *Nature* 498, 332-337; Gao et al. (2013) *Cell* 153:1094-1107; Li et al. (2013) *Immunity* 39:1019-1031; Zhang et al. (2014) *Cell Rep* 6:421-430), including two separate DNA-binding surfaces on each enzyme monomer designated the DNA "A-site" and "B-site," and a conserved mechanism of structural rearrangement induced by DNA-binding that allows competent active-site formation and initiation of 2'3' cGAMP synthesis (FIGS. 5B and 6). hcGAS K187 and L195 mapped to a long alpha-helix designated the "spine" that braced the back half of the enzyme nucleotidyltransferase domain and formed part of the A-site DNA-binding surface. The engineered hcGAS mutation K187N made direct contact with the DNA phosphate backbone. Likewise, L195R further stabilized DNA interactions and increased the overall positive charge of the A-site DNA-binding surface (FIG. 5C). Surprisingly, in both cases, the normal human-specific K187 and L195 substitutions must therefore remodel DNA contacts and alter the interaction between hcGAS and DNA. Additionally, the K187N substitution repositions Y215 and stabilizes a loop in the enzyme active site that is required for nucleotide coordination (FIG. 5C). Loss of Y215 stabilization in hcGAS provides a further structural explanation for why overall 2'3' cGAMP synthesis is restrained in hcGAS compared to the mouse enzyme. These results demonstrated that unique substitutions modify the hcGAS DNA-binding surface and create an unexpected layer of regulation that controls 2'3' cGAMP synthesis.

Example 4: Mechanism of Human-Specific cGAS-DNA Recognition

The structure of the hcGAS K187N/L195R-DNA complex revealed that the human substitutions K187 and L195 specifically alter the DNA-binding surface. These two hcGAS substitutions occurred ~10-15 million years ago, and are only present in humans and closely related hominoid species (FIG. 7A) (Scally et al. (2012) *Nature* 483:169-175), further highlighting that human cGAS-DNA recognition is controlled by distinct contacts not shared with other mammalian cGAS homologs. The impact of K187 and L195 on the ability of hcGAS and mcGAS to interact in vitro with a 45 bp immunostimulatory DNA sequence was next measured (Stetson and Medzhitov (2006) Immunity 24:93-103). Human cGAS quickly aggregates in the presence of DNA; however, a technique from the nucleosome assembly field was adapted (Lee and Narlikar (2001) Current protocols in molecular biology Chapter 21, Unit 21.26), and gradient dialysis was used to specifically generate and monitor stable cGAS-DNA complexes (FIG. 8D). It was observed that wildtype mcGAS formed two types of DNA complexes: (1) a lower molecular weight minimal cGAS-DNA complex, and (2) multiple slowly migrating protein-DNA complexes that are stabilized by increasing cGAS concentration and indicate higher-order oligomerization (FIG. 7B, Top). Notably, introduction of the human K187 and L195 mutations into mcGAS ablated all detectable formation of the lower-molecular-weight complex, but still permitted formation of higher-order oligomeric interactions (FIG. 7B, Top). Wild-type hcGAS preferentially formed higher-order oligomeric complexes that run near the top of the gel similar to the highest migrating mcGAS-DNA species (FIG. 7B, Bottom). It was verified that hcGAS and mcGAS robustly synthesize 2'3' cGAMP under these conditions used for cGAS-DNA complex formation, demonstrating that higher-order migration is due to functional cGAS-DNA oligomerization and not non-specific aggregation (FIG. 8E). Intriguingly, hcGAS-DNA higher-order complex formation is unaffected in the K187N/L195R variant, indicating that these mutations do not impact cGAS-DNA oligomerization. Instead, introduction of K187N and L195R mutations restored the ability of hcGAS to form a stable lower molecular weight protein-DNA complex (FIG. 7B, bottom). These results reveal that human-specific substitutions had a greater impact on minimal cGAS-DNA complex formation than on the ability of cGAS to oligomerize on a long DNA.

A defining feature of human cGAS-STING signaling is that activation is dependent on DNA length, and DNA >45 bp is required for efficient cGAS recognition and 2'3' cGAMP synthesis (Andreeva et al. (2017) *Nature* 549:394-398; Karayel et al. (2009) *Eur J Immunol* 39:1929-1936; Luecke et al. (2017) *EMBO Rep* 18:1707-1715; Stetson and Medzhitov (2006) Immunity 24:93-103). To explain why hcGAS substitutions may specifically impact length-dependent DNA recognition, all DNA contacts in hcGAS-DNA structure were compared with the DNA contacts in previously determined mcGAS-DNA structures. Human-specific substitutions S328, K350 and L354 in the DNA B-site surface form additional altered DNA contacts that can function cooperatively with the major K187/L195 substitutions to further regulate DNA recognition and 2'3' cGAMP synthesis (FIGS. 7C, 7D, and 8). A recent structure of mcGAS bound to a 39 bp DNA revealed that recognition of long DNA involves formation of a higher-order cGAS-DNA "ladder" complex where long DNA adopts a curved conformation between adjacent cGAS dimers (Andreeva et al. (2017) Nature 549:394-398). DNA curving in the mcGAS-39 bp structure reduces the overall contact between cGAS and DNA, indicating that fewer protein-DNA interactions are required in the context of long DNA recognition. Human K187, L195, and B-site substitutions are located within the small patch of the cGAS DNA- binding surface that corresponds to where long DNA begins to curve away and no longer contacts cGAS (FIG. 3E). Strikingly, these results indicated that human substitutions specifically weaken a portion of the cGAS DNA-binding surface that is not required during recognition of long DNAs, and indicated a mechanism where human cGAS DNA recognition is precisely altered to limit recognition of short DNAs. Together, structural and biochemical analysis of hcGAS-DNA complex formation revealed that unique alterations to the DNA-binding surface specifically inhibited minimal cGAS-DNA complex formation and underlined a key regulation controlling 2'3' cGAMP synthesis in human cells.

Example 5: Human cGAS Adaptations Re-Shape DNA Length Specificity

Figure 9C:
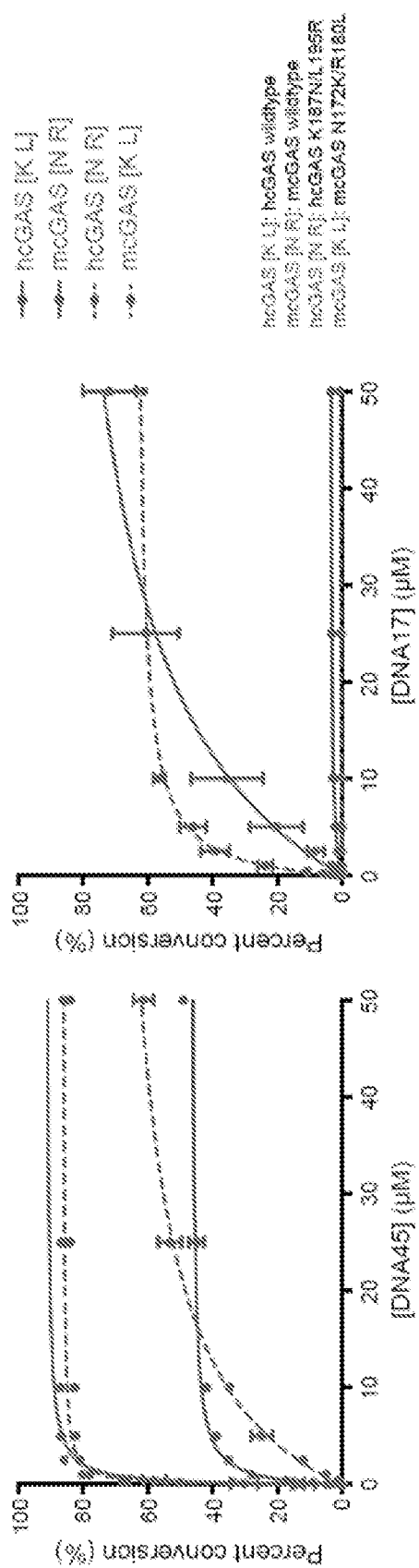
Figure 12A:
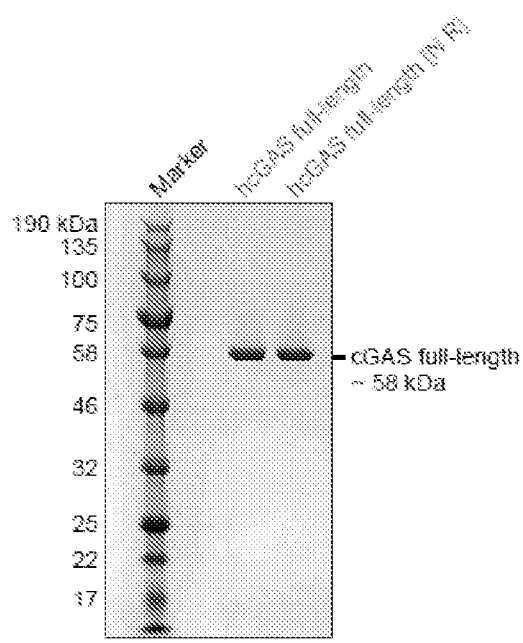
FIG. 12A-FIG. 12C show that hcGAS adaptations control DNA-length specificity in full-length hcGAS.
Figure 12B:
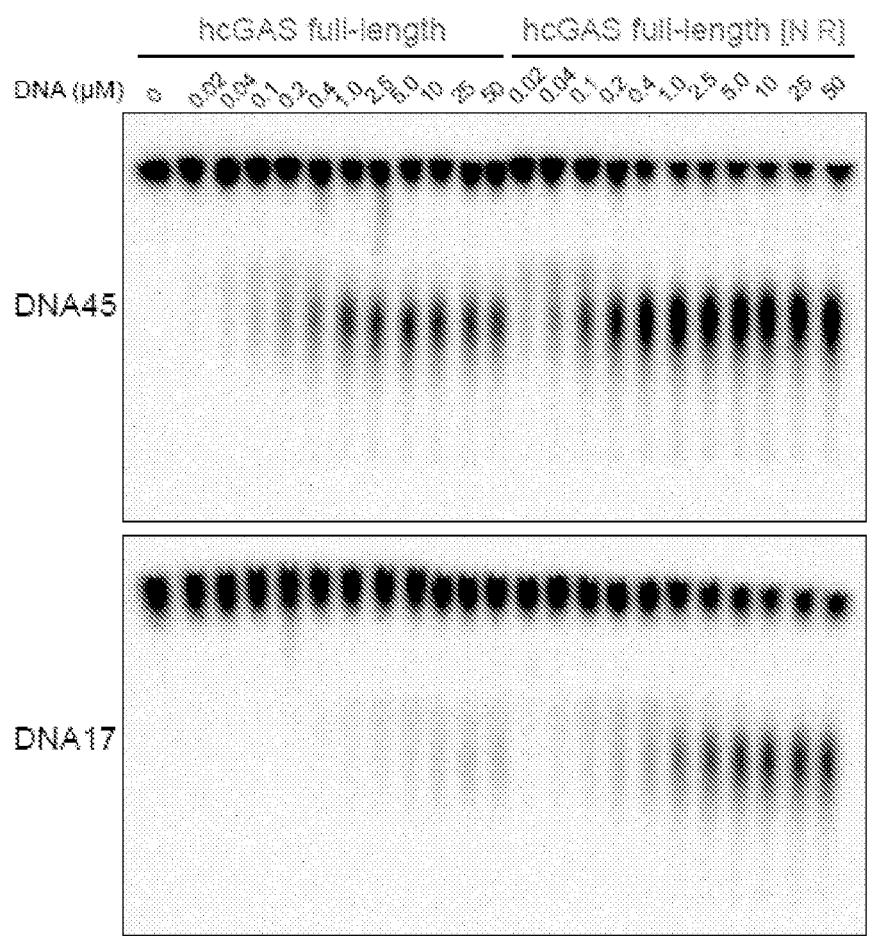
Figure 12C:
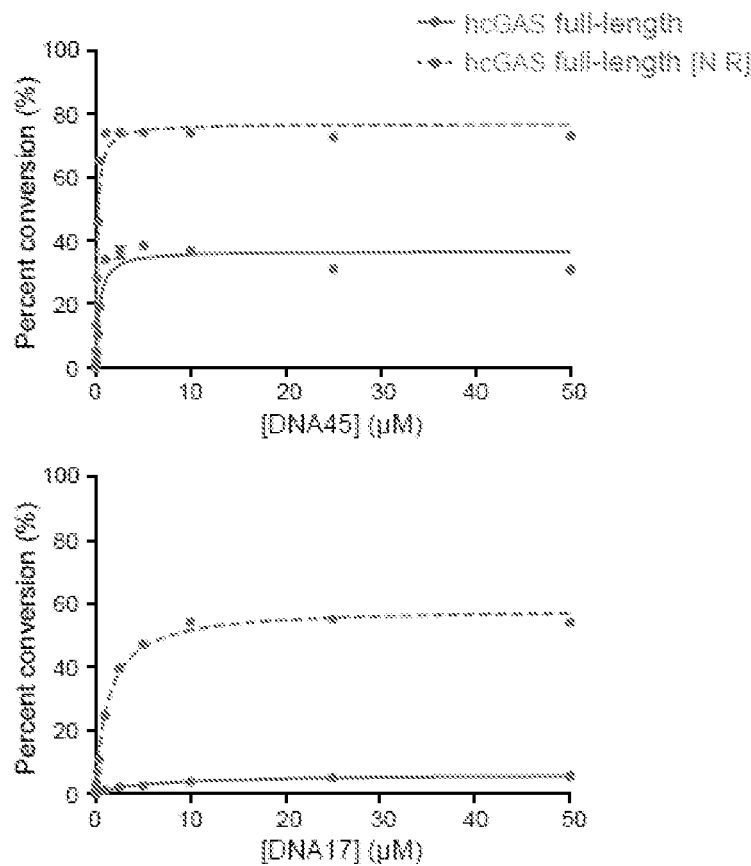

Biochemical and structural data indicated that human-specific cGAS regulation controlled enzyme activation by biasing cGAS-DNA interactions away from a minimal 2:2 complex and towards higher-order protein-DNA oligomerization. An important prediction of this model was that hcGAS K187 and L195 adaptations should specifically alter the ability of cGAS to respond to DNA in a length-dependent manner. To directly test this prediction, the ability of cGAS variants to respond to 17 and 45 bp DNA was compared. Wild-type hcGAS robustly synthesized 2'3' cGAMP in response to increasing concentrations of 45 bp DNA, but remained inactive in the presence of 17 bp DNA. In contrast, mcGAS recognized both 45 bp and 17 bp DNA with near equal efficiency, consistent with ability of mcGAS to stably form the minimal 2:2 complex required for short DNA recognition and enzyme activation (FIGS. 9A and 9C) (Andreeva et al. (2017) Nature 549:394-398). Strikingly, the contrasting ability of hcGAS and mcGAS to respond to short DNA was completely reversed through human-specific K187/L195 substitution. The hcGAS K187N/L195R variant exhibited full enzyme activation in the presence of 17 bp DNA, while the ability of humanized mcGAS K187/L195 to recognize 17 bp DNA was abolished (FIGS. 9B and 9C). The same phenotype was observed using full-length recombinant hcGAS including the unstructured N-terminal tail, further confirming the critical importance of positions K187 and L195 in specifically controlling discrimination of long and short DNAs (FIGS. 12A-12C). These data confirmed a mechanistic rationale for how human-specific cGAS adaptation allows enhanced control of length-dependent DNA recognition and immune surveillance.

Figure 5A:
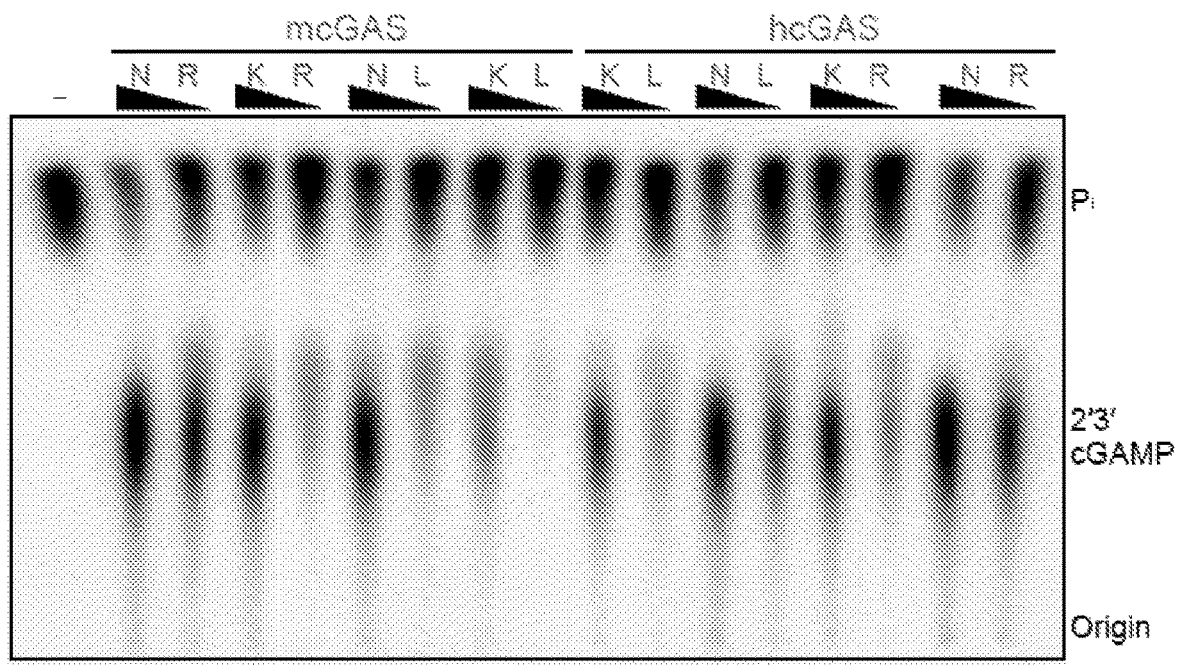
FIG. 5A-FIG. 5C show the structural basis of how K187 and L195 substitutions control hcGAS activity.
Figure 5A:
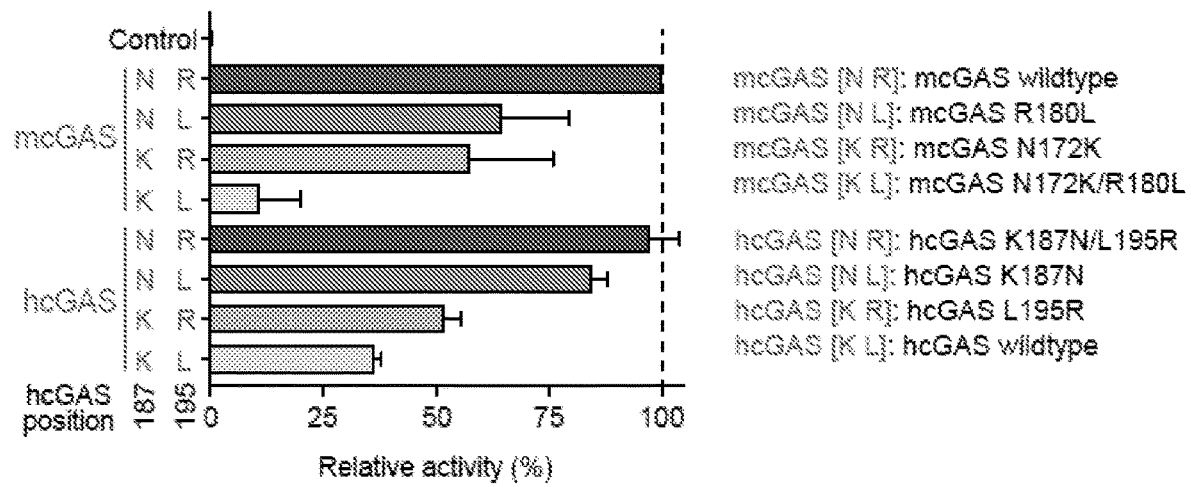
Figure 5B:
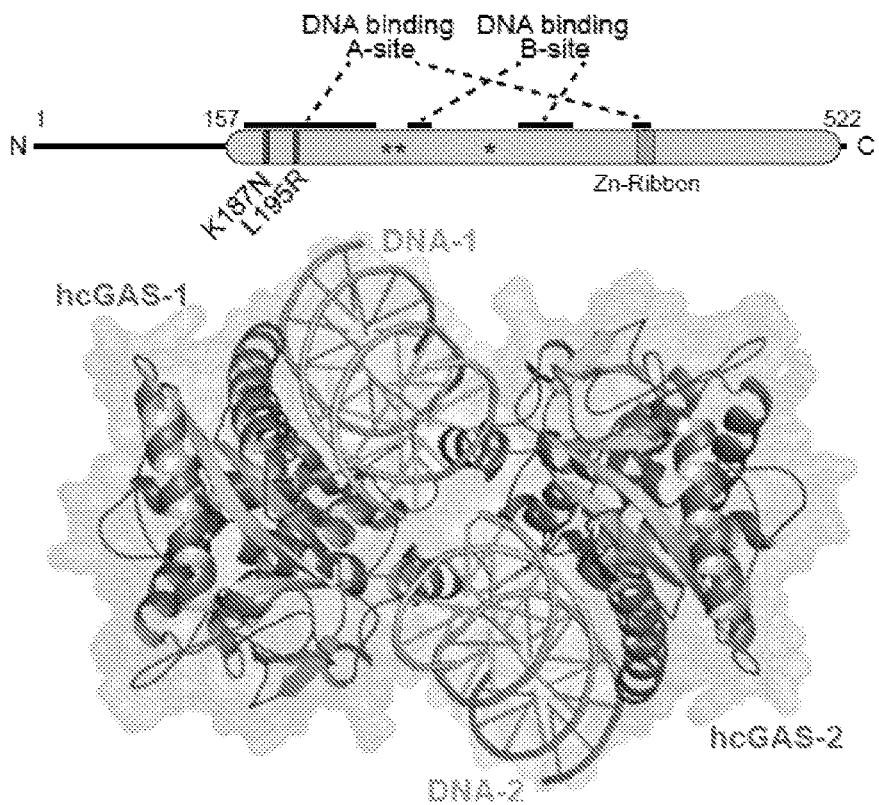
Figure 5C:
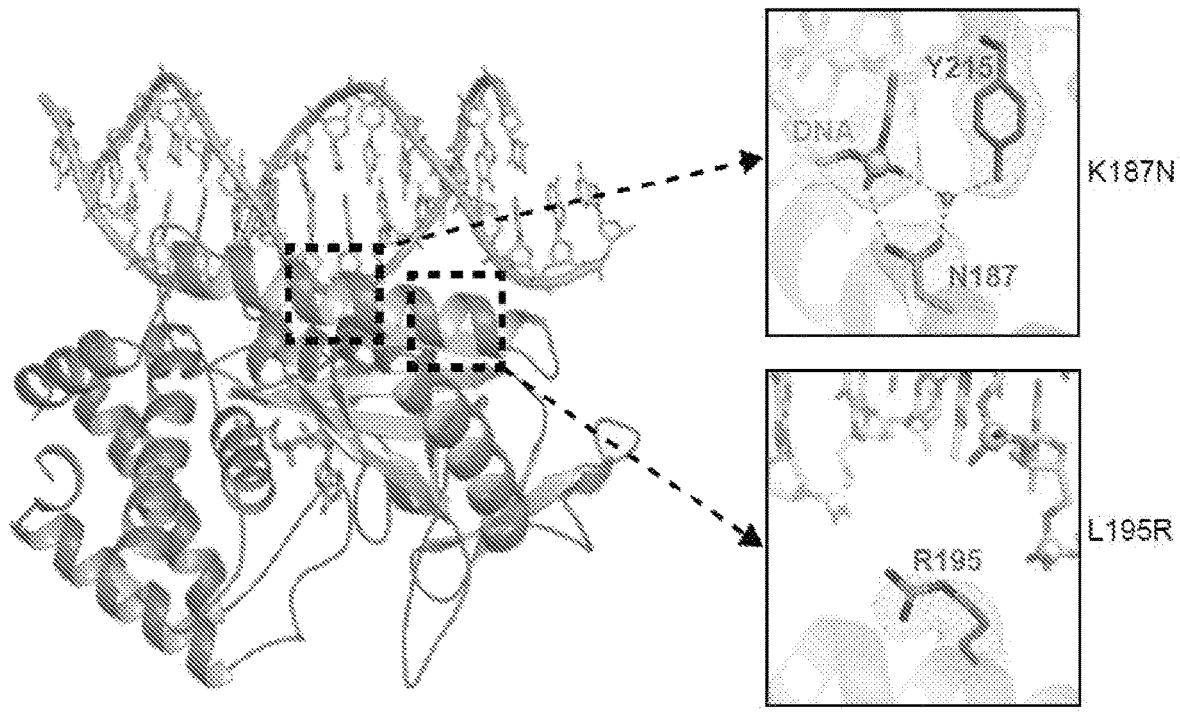
Figure 6A:
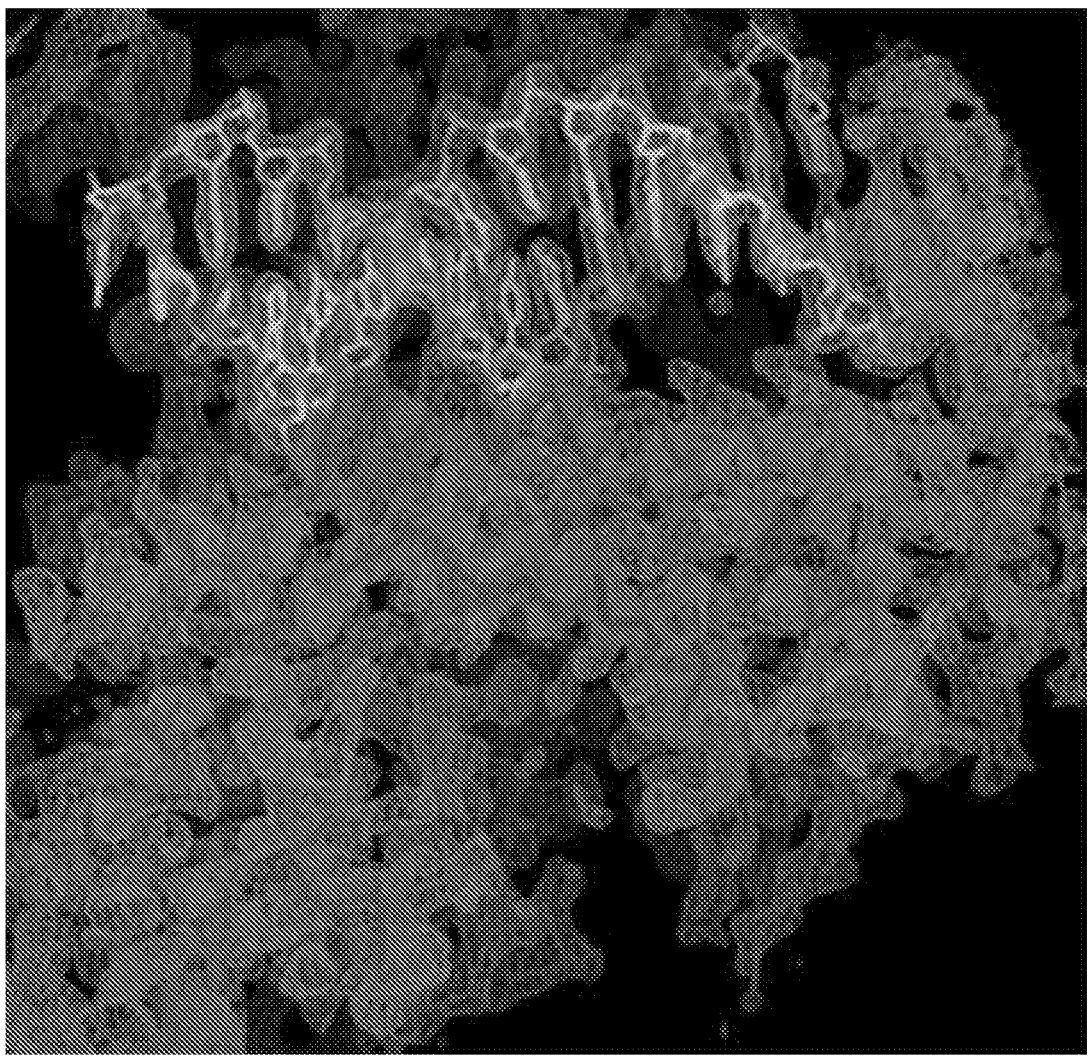
FIG. 6A-FIG. 6D shows that the structures of the hcGAS-DNA complex reveal a conserved mechanism of DNA stimulated active-site rearrangement.
Figure 6B:
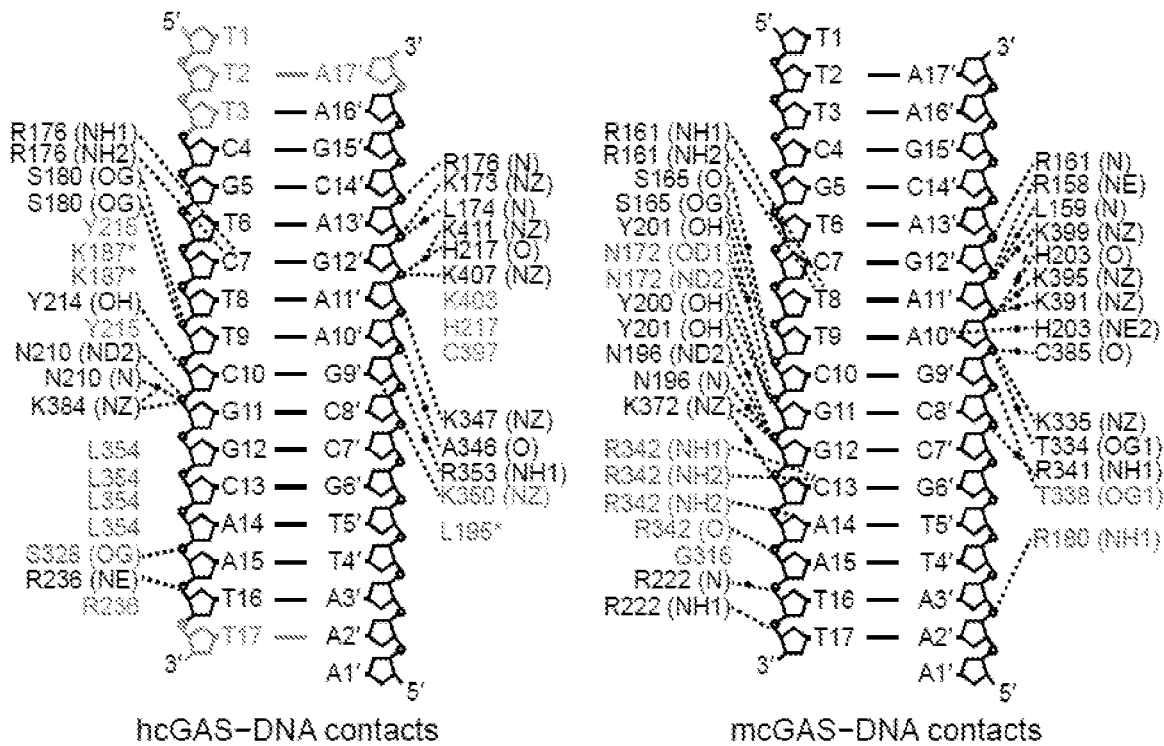
Figure 6C:
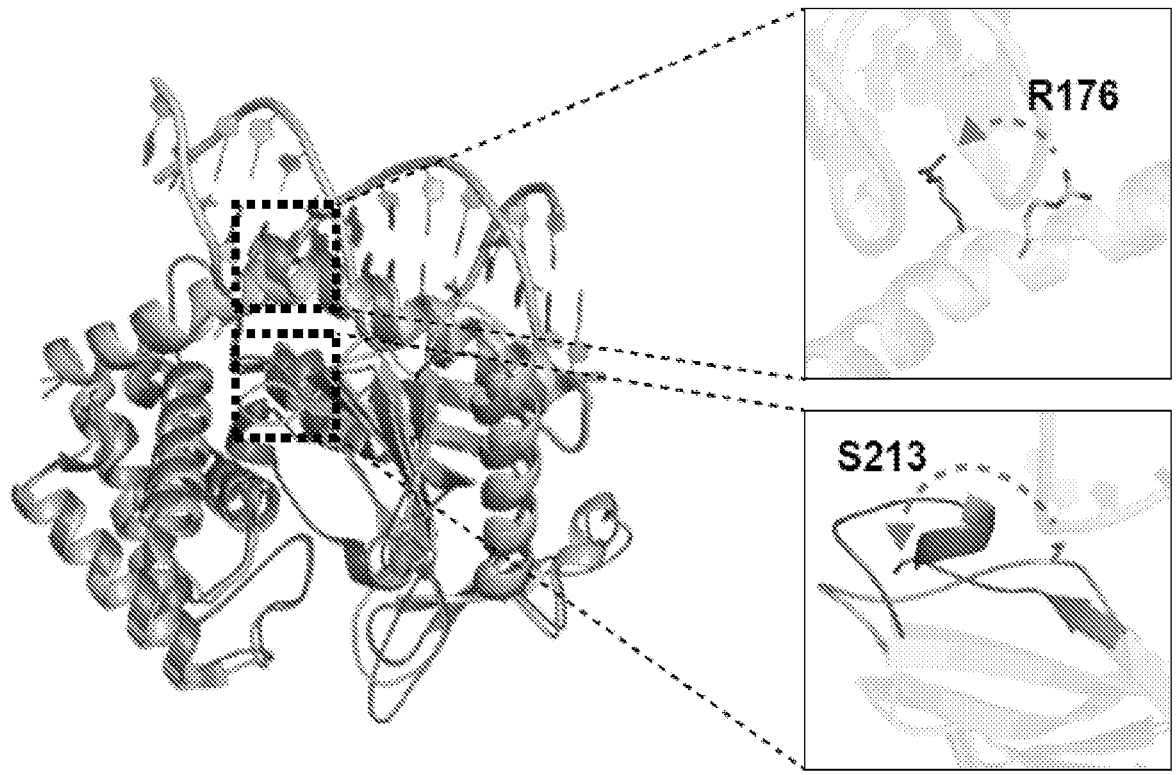
Figures 6D, 7A:
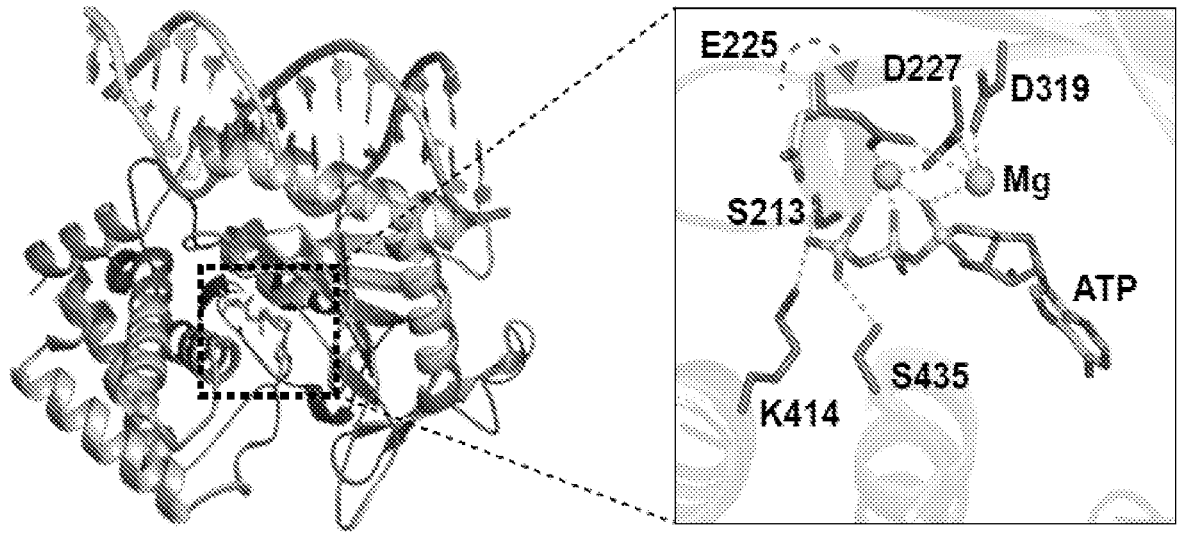
FIG. 7A-FIG. 7E shows the mechanism of human-specific cGAS-DNA recognition.

Example 6: The Structure of hcGAS in an Active Conformation Provides a Key Template to Understand cGAS Mutations and Guide Therapeutic Intervention The crystallized hcGAS-DNA complex contained no engineered mutations other than K187N and L195R in the DNA-binding surface, and presented an opportunity to analyze the human enzyme in an active conformation. cGAS mutations are frequently observed in cancers (Carami et al., 2012). It was next asked if the structure could explain the impact of cGAS mutations that are frequently observed in cancer (Konno et al. (2018) Oncogene 37:2037-2051). Consistent with the key role of cGAS-STING immunity in antitumor immunity (Bakhoum et al. (2018) Nature 553: 467-472; Deng et al. (2014) Immunity 41:843-852; Dou et al. (2017) Nature 550:402-406; Harding et al. (2017) Nature 548:466-470; Woo et al. (2014) Immunity 41:830-842), tumor-associated mutations have been predicted to impact cGAS function, but their exact structural role has remained unclear. Mapping these residues onto the active hcGAS-DNA structure revealed that 37 of the 60 tumor-associated mutations impacted key residues involved in DNA-binding, nucleotide coordination, and overall protein stability (FIGS. 5A and 5B). These results established a molecular explanation for how tumor-associated mutations impede cGAS function, and provided a structural correlate to recent experimental work confirming that many tumor-associated mutations negatively impact cGAS activity in cells (Konno et al. (2018) Oncogene 37:2037-2051).

The active human cGAS-DNA structure was next used to analyze existing small-molecule inhibitor data and provide insight into the specificity of cGAS inhibition. Recently, the discovery of small molecules targeting cGAS demonstrated that a pocket above the ATP donor site is critical for therapeutic inhibition of 2'3' cGAMP synthesis (Hall et al. (2017) PLoS One 12: e0184843; Hall et al. (2017) Protein Sci 26:2367-2380; Vincent et al. (2017) Nat Commun 8:750). In addition to the DNA-induced structural rearrangements that distinguish the hcGAS-DNA structure from the apo enzyme conformation, the hcGAS- DNA-ATP ternary complex revealed that human-specific residues S434 and N482 brace both sides of the inhibitor pocket and create an enzyme active-site that is structurally distinct from previously observed mouse cGAS-DNA structures (FIGS. 10C-10F). Structure-based molecular docking and virtual screening has become a critical component of drug development and high-throughput screening, but this analysis has not previously been possible for the active hcGAS conformational state. To understand how unique features of the hcGAS active site may impact interactions of currently available cGAS inhibitors, the mcGAS inhibitor RU.521 (Vincent et al. (2017) Nat Commun 8:750) and the hcGAS inhibitor PF-06928215 (Hall et al. (2017) PLoS One 12: e0184843) were analyzed with molecular docking. A validation experiment was first performed using RU.521 and the mcGAS-DNA complex (PDB 5XZG), or PF-06928215 and the previous inactive hcGAS complex (PDB 5V8N) confirming that the top small-molecule poses scored during molecular docking correctly identified the observed location and orientation within the inhibitor binding site (FIGS. 10G and 10H). However, molecular docking analysis of these inhibitors against the active hcGAS-DNA complex revealed that no accepted poses were compatible with previously observed binding conformations (FIGS. 10I-10J). In each case, the analysis demonstrated that the hcGAS-DNA complex active-site conformation is structurally distinct from previous apo hcGAS and mcGAS-DNA structures, and indicated incompatibilities that can may explain differences in hcGAS-specific targeting and inhibitor potency.

Figure 13A:
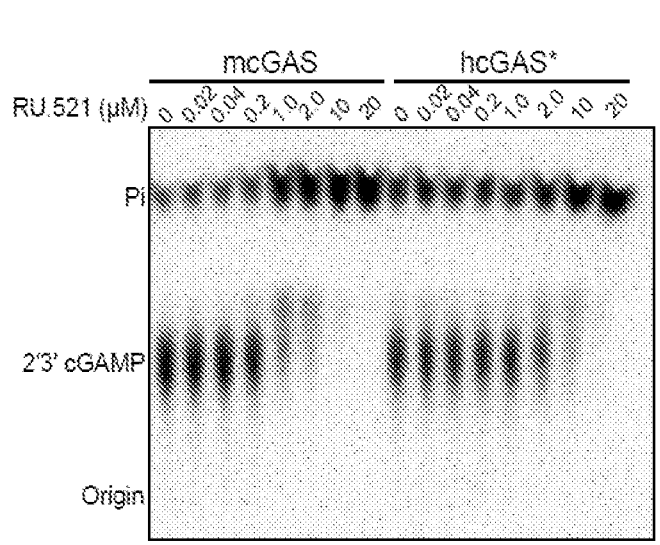
FIG. 13A-FIG. 13C show the molecular basis of cGAS inhibitor specificity.
Figure 13B:
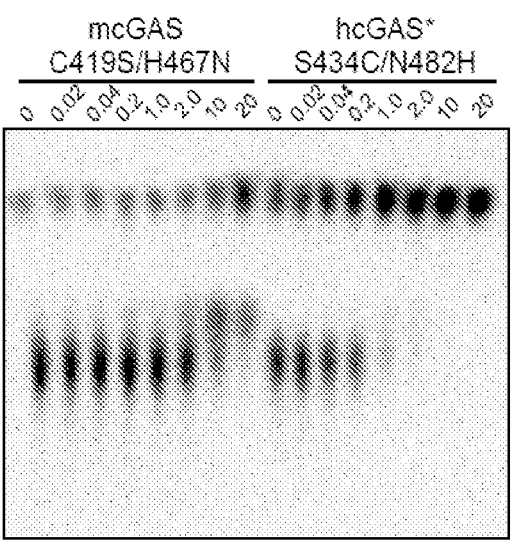
Figure 13C:
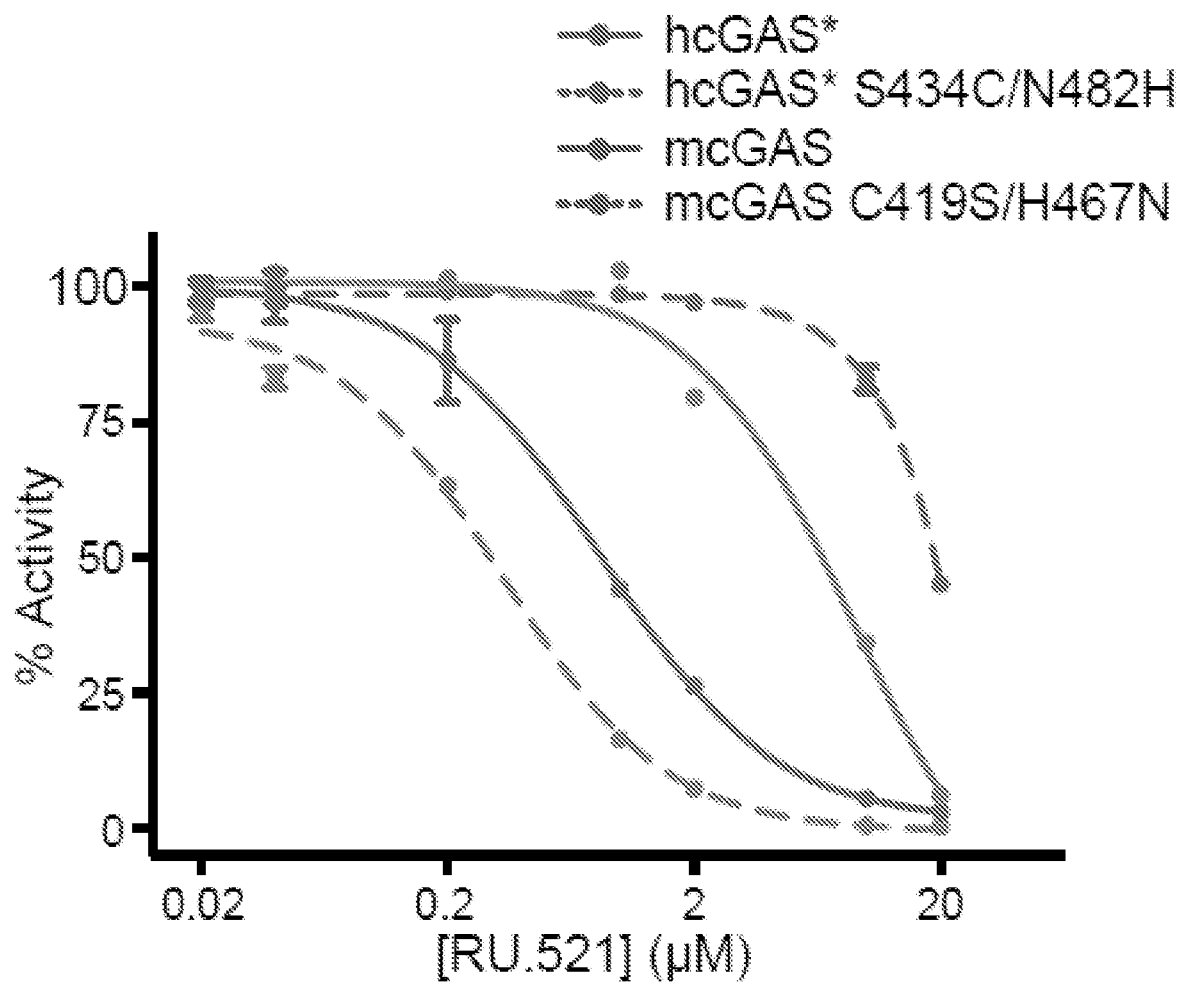
Figure 14C:
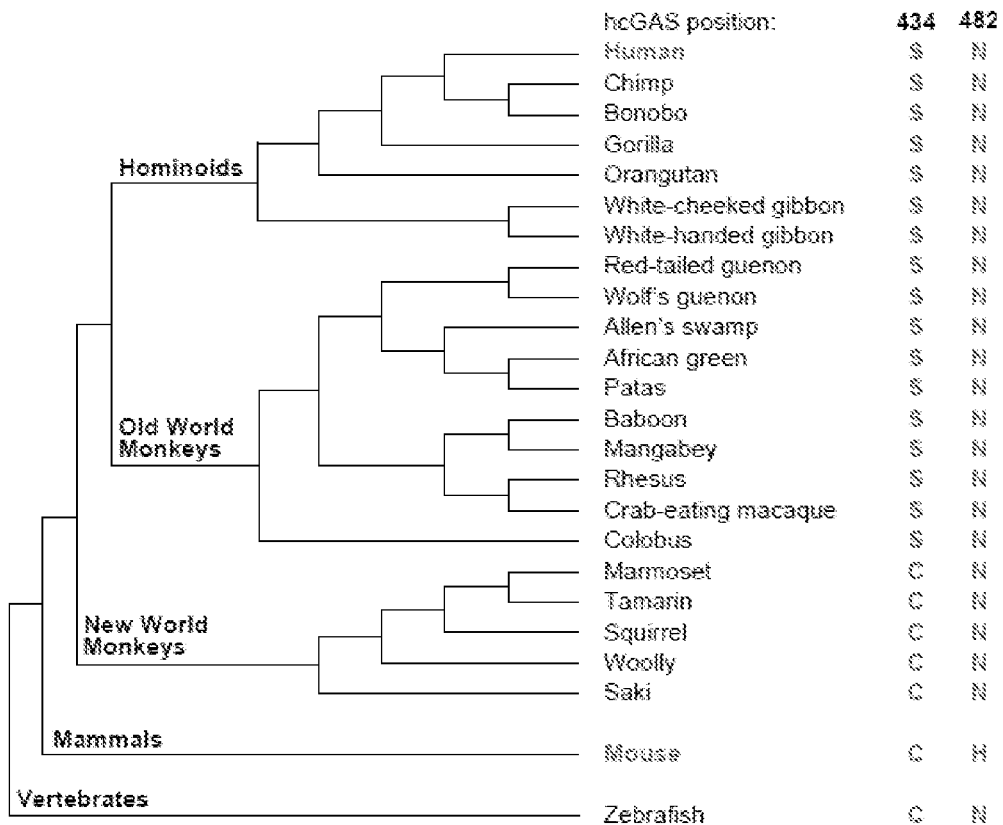
Figure 14D:
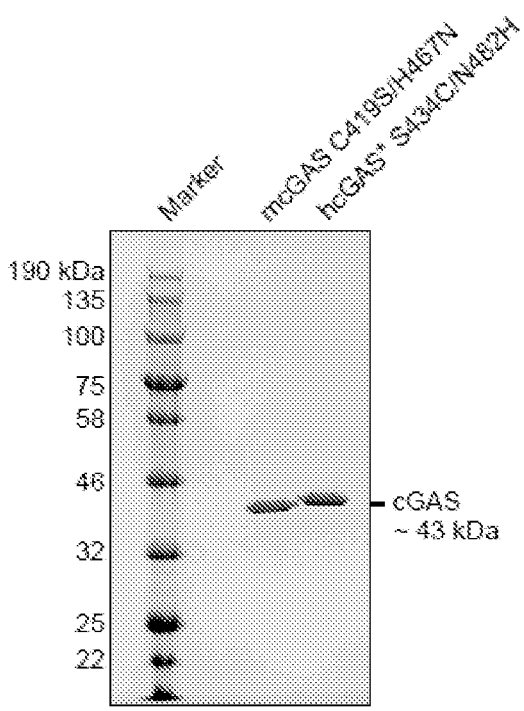

To validate the impact of the findings on inhibitor design, the human-specific substitutions in the inhibitor binding pocket on cGAS-inhibitor specificity was directly assessed. RU.521 more potently inhibits mcGAS, while PF-06928215 is a more potent inhibitor against hcGAS, demonstrating clear species-specificity of inhibitor interactions (FIGS. 13A and 14). Importantly, the reduced enzymatic activity of wildtype hcGAS, a significant barrier to drug design (Vincent et al. (2017) Nat Commun 8:750) was overcome by using the engineered hcGAS K187N/L195R enzyme discovered in the Vibrio genetic assay (hcGAS*). hcGAS* behaved similarly to wild type hcGAS but exhibits >15-fold enhanced 2'3' cGAMP synthesis with activity comparable to wildtype mcGAS (FIG. 14). The docking analysis of RU.521 indicated that the human residues at 434 and 482 play a crucial role in protein-inhibitor interactions and these positions explain the species-specificity of RU.521. Strikingly, the species-specificity of RU.521 is completely dependent on the hcGAS S434 and N482 substitutions. Purified mcGAS with humanizing C419S/H467N mutations was strongly resistant to RU.521, while hcGAS* with mouse-like S434C/N482H mutations gains susceptibility to RU.521 inhibition (FIGS. 13B and 13C). These results revealed that human-specific substitutions in the enzyme active site are necessary and sufficient to control susceptibility to the RU.521 cGAS inhibitor, and demonstrated the importance of the hcGAS-DNA structure to informing small-molecule design. Together with the discovery of the regulatory role of hcGAS K187 and L195 in controlling DNA-length specificity, these results revealed the structural basis of hcGAS activation and provided a critical model to guide development of small-molecules targeting cGAS activity (FIG. 11).

Finally, the diminished ability of hcGAS to synthesize 2'3' cGAMP in vitro has been an important limitation on high-throughput screens to identify small molecules targeting the human enzyme (Vincent et al. (2017) Nat Commun 8:750). The engineered hcGAS K187N/L195R discovered in the Vibrio genetics assay exhibited dramatically enhanced 2'3' cGAMP synthesis (FIG. 11) and allow robust high-throughput identification of small molecules capable of inhibiting or agonizing hcGAS activity. Together with the discovery of the regulatory role of hcGAS K187 and L195 in controlling DNA-length specificity, these results revealed the structural basis of hcGAS activation and provided a new model to understand hcGAS function and therapeutic inhibition.

Figure 11A:
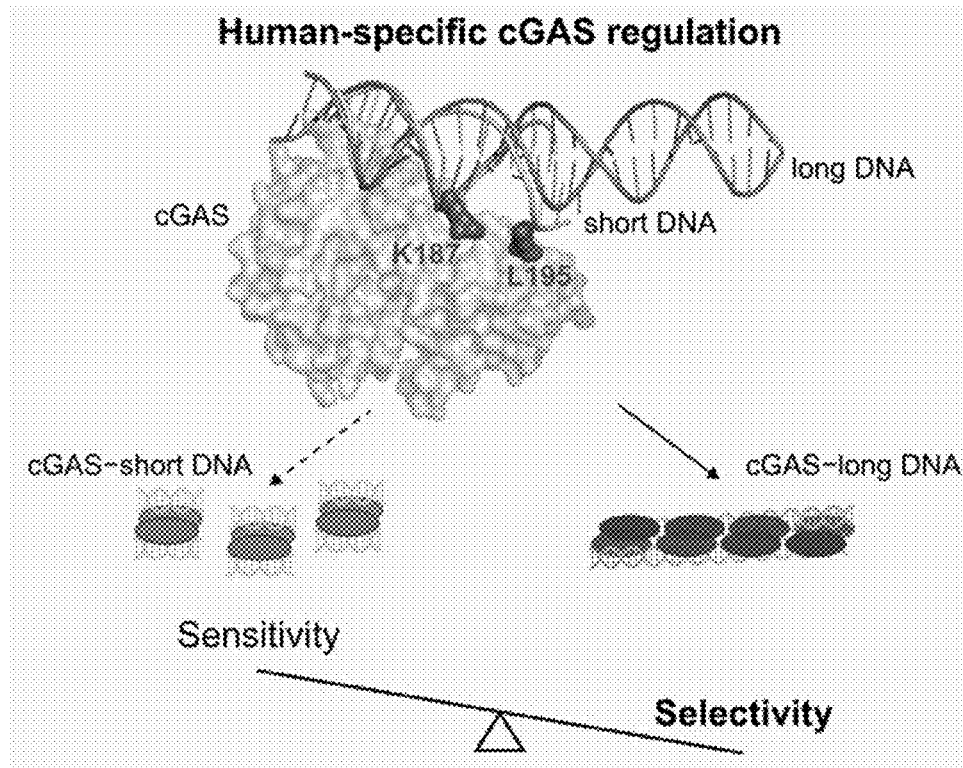
FIG. 11A-FIG. 11B show that determination of the hcGAS-DNA structure reveals that human-specific substitutions enhance regulation of cGAS activation.

The results revealed a new layer of regulation in cGAS-STING signaling, where human-specific adaptations in cGAS allowed enhanced control of DNA-sensing. Key substitutions in the DNA-binding surface refined protein-DNA interactions and directly augmented the ability of hcGAS to discriminate long DNAs. Human K187 and L195 substitutions were required for altered enzyme regulation, and were sufficient to confer human-like regulation to mcGAS. Mechanistically, it was demonstrated herein that K187 and L195 substitutions maped to a unique surface on cGAS that was critical for recognition of short DNA, but not required during higher-order cGAS-DNA recognition. Human-specific cGAS substitutions had two functional consequences. First, they restrained total 2'3' cGAMP production and therefore immune activation. Second, they dramatically enhanced the ability of cGAS to discriminate DNA in a length-dependent manner (FIG. 11A). Given the affinity of STING for 2'3' cGAMP is as strong as ~4 nM (Gao et al. (2013) Cell 154:748-762; Zhang et al. (2013) Mol Cell 51:226-235), the threshold of 2'3' cGAMP required for immune activation is extremely low and the major outcome of human-specific cGAS substitutions is the ability to accurately recognize long DNAs and tolerate shorter DNA fragments. Intriguingly, hcGAS variation mirrors a similar phenomenon in STING where emergence of a human-specific R232H mutation in the cyclic dinucleotide binding pocket increases specificity of STING for the cGAS product 2'3' cGAMP and limits recognition of bacterial-derived 3'3' linked cyclic dinucleotides (Ablasser et al. (2013) Nature 498:380-384; Diner et al. (2013) Cell Rep 3:1355-1361; Gao et al. (2013) Cell 154:748-762; Kranzusch et al. (2015) Mol Cell 59:891-903; Zhang et al. (2013) Mol Cell 51:226-235). Thus, in addition to post-translational modifications and binding partners (Chen et al. (2016) Mol Cell 64:105-119; Liang et al. (2014) Cell Host Microbe 15:228-238; Xia et al. (2016) Nat Immunol 17:369-378; Yoh et al. (2015) Cell 161:1293-1305), the results demonstrated that intrinsic substitutions in the hcGAS protein sequence played a key role in regulation of cGAS-STING signaling in human cells.

Substitutions in cGAS allowed cells to fine-tune a balance between specificity and sensitivity in innate immunity. Human-specific DNA A-site substitutions are evolutionarily more recent than the DNA B-site substitutions (FIG. 8C), indicating current human regulation has evolved as the result of at least two separate events. Interestingly, some of the hcGAS substitutions mapped in this study, including the major DNA A-site substitution L195, were previously demonstrated to be under strong positive selection (dN/dS>1), a genetic signature typically associated with rapid evolution (Hancks et al. (2015) PLoS Genet 11:e1005203; Mozzi et al. (2015) Genome Biol Evol 7:1016-1032). Unlike traditional examples of positive selection, such as an "arms race" at a host interface antagonized by a pathogen effector (Elde and Malik (2009) Nat Rev Microbiol 7:787-797), the results demonstrated that positive selection also mark protein surfaces that are modify regulation of innate immune signaling. The distribution of K187 and L195 suggests a genetic bottleneck in hominoid evolution where tolerance to smaller fragments of self-DNA in the cytosol provided a major selective advantage during a catastrophic event. Although tolerance to small fragments of self-DNA could decrease the occurrence of autoimmune disease and chronic inflammation, these do not consistent with the extreme penetrance of the key K187/L195 cGAS substitutions. Alternatively, DNA-length discrimination improve resistance to pathogens or disease tolerance. Intriguingly, hcGAS variation mirrors a similar phenomenon in STING where emergence of a human-specific R232H mutation in the cyclic dinucleotide binding pocket increases specificity of STING for the cGAS product 2'3' cGAMP and limits recognition of bacterial-derived 3'3' linked cyclic dinucleotides (Ablasser et al. (2013) Nature 498:380-384; Civril et al. (2013) Nature 498, 332-337; Diner et al. (2013) Cell Rep 3:1355-1361; Gao et al. (2013) Cell 153:1094-1107; Kranzusch et al. (2013) Cell Rep 3:1362-1368; Li et al. (2013) Immunity 39:1019-1031; Zhang et al. (2014) Cell Rep 6:421-430). The evolutionary pressures driving selection of human-specific mutations that reduce the affinity of STING for 3'3' linked cyclic dinucleotides while maintaining recognition of 2'3' cGAMP has been a topic for speculation (Danilchanka and Mekalanos (2013) Cell 154:962-970; Kranzusch et al. (2015) Mol Cell 59:891-903; Margolis et al. (2017) Trends Immunol 38:733-743) and potentially the same pressures have selected for the human allele that alters the responsiveness of cGAS to DNA fragment length. Substitutions in both cGAS and STING allow cells to fine-tune a balance between specificity and sensitivity in innate immune signaling.

Figure 11B:
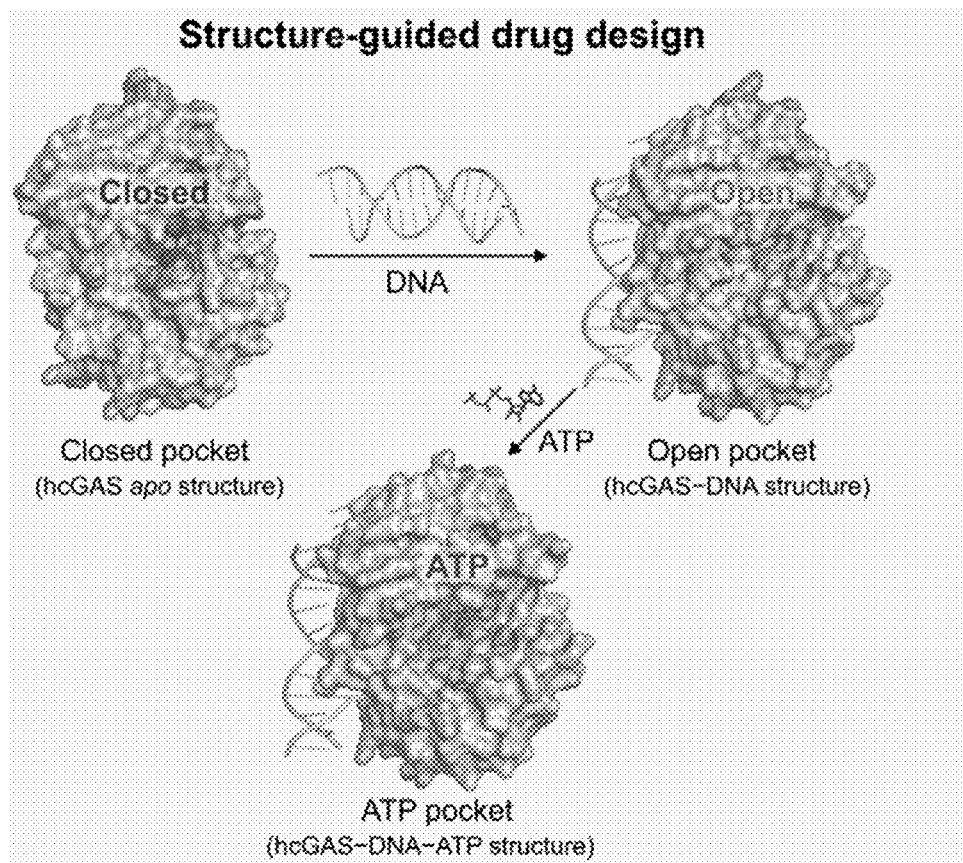

In addition to recognizing pathogen DNA, cGAS-STING immunity plays a key role in controlling responses to cellular stress and cancer. cGAS is critical for recognition of DNA released during mitochondrial damage (Rongvaux et al. (2014) Cell 159:1563-1577; White et al. (2014) Cell 159:1549-1562), aberrant chromosomal segregation (Dou et al. (2017) Nature 550:402-406; Gluck et al. (2017) Nat Cell Biol 19:1061-1070; Harding et al. (2017) Nature 548:466-470; Mackenzie et al. (2017) Nature 548:461-465; Yang et al. (2017) Proc Natl Acad Sci USA 114:E4612-E4620), and during the immune response to cancer cells and checkpoint blockade therapy (Bakhoum et al. (2018) Nature 553:467-472; Deng et al. (2014) Immunity 41:843-852; Dou et al. (2017) Nature 550:402-406; Harding et al. (2017) Nature 548:466-470; Woo et al. (2014) Immunity 41:830-842). Importantly, the structure of hcGAS in an active conformation removes the previous reliance on the mammalian homologs to understand enzyme activation, the mutational burden in cancer, and therapeutic design (FIG. 11B). Efforts to develop small molecule agonists and antagonists of cGAS-STING immunity have already identified 2'3' cGAMP analogues as new adjuvants for cancer immunotherapy (Corrales et al. (2015) Cell Rep 11:1018-1030; Fu et al. (2015) Sci Transl Med 7:283ra252), and small molecule cGAS inhibitors for the treatment of autoimmunity (Hall et al. (2017) PLoS One 12: e0184843; Hall et al. (2017) Protein Sci 26:2367-2380; Vincent et al. (2017) Nat Commun 8:750). Current cGAS inhibitors target a pocket above the ATP donor position in the enzyme active site. Notably, the hcGAS-DNA-ATP ternary complex revealed that additional human-specific substitutions in the enzyme active site line both sides of this pocket and alter the inhibitor binding interface (FIGS. 10 and 13). The structure of the active human cGAS-DNA complex, and discovery of key human-specific adaptations, provided a missing template required to guide development of cGAS therapeutics and established a complete model of DNA sensing in human cells.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide that binds double-stranded DNA and catalyzes production of 2'-5'/3'-5' cyclic GMP-AMP (2'3' cGAMP), wherein the polypeptide comprises an amino acid sequence having at least 90% identity to the human cyclic GMP-AMP synthase (hcGAS) amino acid sequence of SEQ ID NO: 1 and further comprises amino acid substitutions at positions corresponding to K187 and L195 of SEQ ID NO: 1.

2. The isolated polypeptide of claim 1, wherein the polypeptide comprises an amino acid sequence having at least 95% identity to the human cGAS (hcGAS) amino acid sequence of SEQ ID NO: 1 and further comprises amino acid substitutions at positions corresponding to K187 and L195 of SEQ ID NO: 1.

3. The isolated polypeptide of claim 1, wherein the polypeptide comprises an amino acid sequence having the amino acid sequence of SEQ ID NO: 1 and further comprises amino acid substitutions at positions corresponding to K187 and L195 of SEQ ID NO: 1.

4. The isolated polypeptide of claim 1, wherein the residue corresponding to K187 is substituted with a residue selected from the group consisting of a) a residue that makes direct contact with the DNA phosphate backbone; b) a polar residue selected from the group consisting of tyrosine, serine, threonine, asparagine, glutamine and cysteine; and c) an asparagine residue, and wherein the residue corresponding to L195 is substituted with a residue selected from the group consisting of i) a residue that increases the overall positive charge of the A-site DNA-binding surface; ii) a basic residue selected from the group consisting of lysine, arginine and histidine; and iii) an arginine residue.

5. The isolated polypeptide of claim 2, wherein the residue corresponding to K187 is substituted with a residue selected from the group consisting of a) a residue that makes direct contact with the DNA phosphate backbone; b) a polar residue selected from the group consisting of tyrosine, serine, threonine, asparagine, glutamine and cysteine; and c) an asparagine residue, and wherein the residue corresponding to L195 is substituted with a residue selected from the group consisting of i) a residue that increases the overall positive charge of the A-site DNA-binding surface; ii) a basic residue selected from the group consisting of lysine, arginine and histidine; and iii) an arginine residue.

6. The isolated polypeptide of claim 3, wherein the residue corresponding to K187 is substituted with a residue selected from the group consisting of a) a residue that makes direct contact with the DNA phosphate backbone; b) a polar residue selected from the group consisting of tyrosine, serine, threonine, asparagine, glutamine and cysteine; and c) an asparagine residue, and wherein the residue corresponding to L195 is substituted with a residue selected from the group consisting of i) a residue that increases the overall positive charge of the A-site DNA-binding surface; ii) a basic residue selected from the group consisting of lysine, arginine and histidine; and iii) an arginine residue.

7. The isolated polypeptide of claim 1, wherein the isolated polypeptide further comprises amino acid substitutions at positions corresponding to S328, K350 and/or L354 of SEQ ID NO: 1.

8. The isolated polypeptide of claim 1, wherein the isolated polypeptide has one or more biological properties selected from the group consisting of:
  i) increased 2'3' cGAMP synthesis compared to hcGAS having the amino acid sequence of SEQ ID NO: 1, optionally wherein the 2'3' cGAMP synthesis is increased by at least 5-fold;
  ii) increased repression of *Vibrio cholera* chemotaxis compared to hcGAS having the amino acid sequence of SEQ ID NO: 1;
  iii) similar enzyme kinetics to mouse cGAS having the amino acid sequence of SEQ ID NO: 5;
  iv) recognizing DNA shorter than 45 bp;
  v) stabilized active enzyme conformation;
  vi) stabilized interactions with DNA; and
  vii) increased minimal cGAS-DNA complex formation compared to hcGAS having the amino acid sequence of SEQ ID NO: 1.

9. The isolated polypeptide of claim 1, further comprising a heterologous polypeptide, optionally wherein the heterologous polypeptide is selected from the group consisting of a signal peptide, a peptide tag, a dimerization domain, an oligomerization domain, and an antibody.

10. A pharmaceutical composition comprising:
  an isolated polypeptide that binds double-stranded DNA and catalyzes production of 2'-5'/3'-5' cyclic GMP-AMP (2'3' cGAMP), wherein the polypeptide comprises an amino acid sequence having at least 90% identity to the human cyclic GMP-AMP synthase (hcGAS) amino acid sequence of SEQ ID NO: 1 and further comprises amino acid substitutions at positions corresponding to K187 and L195 of SEQ ID NO: 1; and
  a pharmaceutically acceptable excipient, diluent, or carrier.

11. An isolated polypeptide that binds double-stranded DNA and catalyzes production of 2'-5'/3'-5' cyclic GMP-AMP (2'3' cGAMP), wherein the polypeptide comprises an amino acid sequence having at least 90% identity to the human cyclic GMP-AMP synthase (hcGAS) amino acid sequence of SEQ ID NO: 2 and further comprises amino acid substitutions at positions corresponding to K31 and L39 of SEQ ID NO: 2.

12. The isolated polypeptide of claim 11, wherein the polypeptide comprises an amino acid sequence having at least 95% identity to the human cGAS (hcGAS) amino acid sequence of SEQ ID NO: 2 and further comprises amino acid substitutions at positions corresponding to K31 and L39 of SEQ ID NO: 2.

13. The isolated polypeptide of claim 11, wherein the polypeptide comprises an amino acid sequence having the amino acid sequence of SEQ ID NO: 2 and further comprises amino acid substitutions at positions corresponding to K31 and L39 of SEQ ID NO: 2.

14. The isolated polypeptide of claim 11, wherein the residue corresponding to K31 is substituted with a residue selected from the group consisting of a) a residue that makes direct contact with the DNA phosphate backbone; b) a polar residue selected from the group consisting of tyrosine, serine, threonine, asparagine, glutamine and cysteine; and c) an asparagine residue, and wherein the residue corresponding to L39 is substituted with a residue selected from the group consisting of i) a residue that increases the overall positive charge of the A-site DNA-binding surface; ii) a basic residue selected from the group consisting of lysine, arginine and histidine; and iii) an arginine residue.

15. The isolated polypeptide of claim 12, wherein the residue corresponding to K31 is substituted with a residue selected from the group consisting of a) a residue that makes direct contact with the DNA phosphate backbone; b) a polar residue selected from the group consisting of tyrosine, serine, threonine, asparagine, glutamine and cysteine; and c) an asparagine residue, and wherein the residue corresponding to L39 is substituted with a residue selected from the group consisting of i) a residue that increases the overall positive charge of the A-site DNA-binding surface; ii) a basic residue selected from the group consisting of lysine, arginine and histidine; and iii) an arginine residue.

16. The isolated polypeptide of claim 13, wherein the residue corresponding to K31 is substituted with a residue selected from the group consisting of a) a residue that makes direct contact with the DNA phosphate backbone; b) a polar residue selected from the group consisting of tyrosine, serine, threonine, asparagine, glutamine and cysteine; and c) an asparagine residue, and wherein the residue corresponding to L39 is substituted with a residue selected from the group consisting of i) a residue that increases the overall positive charge of the A-site DNA-binding surface; ii) a basic residue selected from the group consisting of lysine, arginine and histidine; and iii) an arginine residue.

17. The isolated polypeptide of claim 11, wherein the isolated polypeptide further comprises amino acid substitutions at positions corresponding to S172, K194 and/or L198 of SEQ ID NO: 2.

18. The isolated polypeptide of claim 11, wherein the isolated polypeptide has one or more biological properties selected from the group consisting of:
  i) increased 2'3' cGAMP synthesis compared to hcGAS having the amino acid sequence of SEQ ID NO: 1, optionally wherein the 2'3' cGAMP synthesis is increased by at least 5-fold;
  ii) increased repression of *Vibrio cholera* chemotaxis compared to hcGAS having the amino acid sequence of SEQ ID NO: 1;
  iii) similar enzyme kinetics to mouse cGAS having the amino acid sequence of SEQ ID NO: 5;
  iv) recognizing DNA shorter than 45 bp;
  v) stabilized active enzyme conformation;
  vi) stabilized interactions with DNA; and
  vii) increased minimal cGAS-DNA complex formation compared to hcGAS having the amino acid sequence of SEQ ID NO: 1.

19. The isolated polypeptide of claim 11, wherein the isolated polypeptide further comprises a heterologous polypeptide, optionally wherein the heterologous polypeptide is selected from the group consisting of a signal peptide, a peptide tag, a dimerization domain, an oligomerization domain, and an antibody.

20. A pharmaceutical composition comprising:
  an isolated polypeptide that binds double-stranded DNA and catalyzes production of 2'-5'/3'-5' cyclic GMP-AMP (2'3' cGAMP), wherein the polypeptide comprises an amino acid sequence having at least 90% identity to the human cyclic GMP-AMP synthase (hcGAS) amino acid sequence of SEQ ID NO: 2 and further comprises amino acid substitutions at positions corresponding to K31 and L39 of SEQ ID NO: 2; and
  a pharmaceutically acceptable excipient, diluent, or carrier.

* * * * *

SEQUENCE LISTING

<160> NUMBER OF SEQ ID NOS: 52

<210> SEQ ID NO 1
<211> LENGTH: 522
<212> TYPE: PRT
<213> ORGANISM: Homo sapiens

<400> SEQUENCE: 1

Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30

Asp Pro Thr Glu Ser Pro Ala Ala Pro Glu Ala Ala Leu Pro Lys Ala
        35                  40                  45

Gly Lys Phe Gly Pro Ala Arg Lys Ser Gly Ser Arg Gln Lys Lys Ser
    50                  55                  60

Ala Pro Asp Thr Gln Glu Arg Pro Pro Val Arg Ala Thr Gly Ala Arg
65                  70                  75                  80

Ala Lys Lys Ala Pro Gln Arg Ala Gln Asp Thr Gln Pro Ser Asp Ala
                85                  90                  95

Thr Ser Ala Pro Gly Ala Glu Gly Leu Glu Pro Pro Ala Ala Arg Glu
            100                 105                 110

Pro Ala Leu Ser Arg Ala Gly Ser Cys Arg Gln Arg Gly Ala Arg Cys
        115                 120                 125

Ser Thr Lys Pro Arg Pro Pro Gly Pro Trp Asp Val Pro Ser Pro
    130                 135                 140

```
Gly Leu Pro Val Ser Ala Pro Ile Leu Val Arg Asp Ala Ala Pro
145                 150                 155                 160

Gly Ala Ser Lys Leu Arg Ala Val Leu Glu Lys Leu Lys Leu Ser Arg
            165                 170                 175

Asp Asp Ile Ser Thr Ala Ala Gly Met Val Lys Gly Val Val Asp His
            180                 185                 190

Leu Leu Leu Arg Leu Lys Cys Asp Ser Ala Phe Arg Gly Val Gly Leu
            195                 200                 205

Leu Asn Thr Gly Ser Tyr Tyr Glu His Val Lys Ile Ser Ala Pro Asn
    210                 215                 220

Glu Phe Asp Val Met Phe Lys Leu Glu Val Pro Arg Ile Gln Leu Glu
225                 230                 235                 240

Glu Tyr Ser Asn Thr Arg Ala Tyr Tyr Phe Val Lys Phe Lys Arg Asn
                245                 250                 255

Pro Lys Glu Asn Pro Leu Ser Gln Phe Leu Glu Gly Glu Ile Leu Ser
            260                 265                 270

Ala Ser Lys Met Leu Ser Lys Phe Arg Lys Ile Ile Lys Glu Glu Ile
    275                 280                 285

Asn Asp Ile Lys Asp Thr Asp Val Ile Met Lys Arg Lys Arg Gly Gly
290                 295                 300

Ser Pro Ala Val Thr Leu Leu Ile Ser Glu Lys Ile Ser Val Asp Ile
305                 310                 315                 320

Thr Leu Ala Leu Glu Ser Lys Ser Ser Trp Pro Ala Ser Thr Gln Glu
                325                 330                 335

Gly Leu Arg Ile Gln Asn Trp Leu Ser Ala Lys Val Arg Lys Gln Leu
            340                 345                 350

Arg Leu Lys Pro Phe Tyr Leu Val Pro Lys His Ala Lys Glu Gly Asn
    355                 360                 365

Gly Phe Gln Glu Glu Thr Trp Arg Leu Ser Phe Ser His Ile Glu Lys
370                 375                 380

Glu Ile Leu Asn Asn His Gly Lys Ser Lys Thr Cys Cys Glu Asn Lys
385                 390                 395                 400

Glu Glu Lys Cys Cys Arg Lys Asp Cys Leu Lys Leu Met Lys Tyr Leu
                405                 410                 415

Leu Glu Gln Leu Lys Glu Arg Phe Lys Asp Lys Lys His Leu Asp Lys
            420                 425                 430

Phe Ser Ser Tyr His Val Lys Thr Ala Phe Phe His Val Cys Thr Gln
    435                 440                 445

Asn Pro Gln Asp Ser Gln Trp Asp Arg Lys Asp Leu Gly Leu Cys Phe
450                 455                 460

Asp Asn Cys Val Thr Tyr Phe Leu Gln Cys Leu Arg Thr Glu Lys Leu
465                 470                 475                 480

Glu Asn Tyr Phe Ile Pro Glu Phe Asn Leu Phe Ser Ser Asn Leu Ile
                485                 490                 495

Asp Lys Arg Ser Lys Glu Phe Leu Thr Lys Gln Ile Glu Tyr Glu Arg
            500                 505                 510

Asn Asn Glu Phe Pro Val Phe Asp Glu Phe
    515                 520

<210> SEQ ID NO 2
<211> LENGTH: 366
<212> TYPE: PRT
<213> ORGANISM: Homo sapiens
```

<400> SEQUENCE: 2

Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

Val Val Asp His Leu Leu Arg Leu Lys Cys Asp Ser Ala Phe Arg
        35                  40                  45

Gly Val Gly Leu Leu Asn Thr Gly Ser Tyr Tyr Glu His Val Lys Ile
        50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
                100                 105                 110

Glu Ile Leu Ser Ala Ser Lys Met Leu Ser Lys Phe Arg Lys Ile Ile
                115                 120                 125

Lys Glu Glu Ile Asn Asp Ile Lys Asp Thr Asp Val Ile Met Lys Arg
130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
                180                 185                 190

Arg Lys Gln Leu Arg Leu Lys Pro Phe Tyr Leu Val Pro Lys His Ala
                195                 200                 205

Lys Glu Gly Asn Gly Phe Gln Glu Glu Thr Trp Arg Leu Ser Phe Ser
210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
                260                 265                 270

His Leu Asp Lys Phe Ser Ser Tyr His Val Lys Thr Ala Phe Phe His
                275                 280                 285

Val Cys Thr Gln Asn Pro Gln Asp Ser Gln Trp Asp Arg Lys Asp Leu
290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
                340                 345                 350

Glu Tyr Glu Arg Asn Asn Glu Phe Pro Val Phe Asp Glu Phe
                355                 360                 365

<210> SEQ ID NO 3
<211> LENGTH: 1569
<212> TYPE: DNA
<213> ORGANISM: Homo sapiens

<400> SEQUENCE: 3

```
atgcagcctt ggcacggaaa ggccatgcag agagcttccg aggccggagc cactgccccc    60
aaggcttccg cacggaatgc caggggcgcc ccgatggatc ccaccgagtc tccggctgcc   120
cccgaggccg ccctgcctaa ggcgggaaag ttcggccccg ccaggaagtc gggatcccgg   180
cagaaaaaga gcgccccgga cacccaggag aggccgcccg tccgcgcaac tggggcccgc   240
gccaaaaagg cccctcagcg cgcccaggac acgcagccgt ctgacgccac cagcgcccct   300
ggggcagagg ggctggagcc tcctgcggct cgggagccgg ctctttccag ggctggttct   360
tgccgccaga ggggcgcgcg ctgctccacg aagccaagac ctccgcccgg gccctgggac   420
gtgcccagcc ccggcctgcc ggtctcggcc ccattctcg tacggaggga tgcggcgcct    480
ggggcctcga agctccgggc ggttttggag aagttgaagc tcagccgcga tgatatctcc   540
acggcggcgg ggatggtgaa aggggttgtg gaccacctgc tgctcagact gaagtgcgac   600
tccgcgttca gaggcgtcgg gctgctgaac accgggagct actatgagca cgtgaagatt   660
tctgcaccta atgaatttga tgtcatgttt aaactggaag tccccagaat tcaactagaa   720
gaatattcca cactcgtgc atattacttt gtgaaattta aaagaaatcc gaaagaaaat    780
cctctgagtc agttttttaga aggtgaaata ttatcagctt ctaagatgct gtcaaagttt   840
aggaaaatca ttaaggaaga aattaacgac attaaagata cagatgtcat catgaagagg   900
aaagaggag ggagccctgc tgtaacactt cttattagtg aaaaaatatc tgtggatata    960
accctggctt tggaatcaaa aagtagctgg cctgctagca cccaagaagg cctgcgcatt  1020
caaaactggc tttcagcaaa agttaggaag caactacgac taaagccatt ttaccttgta  1080
cccaagcatg caaggaagg aaatggtttc caagaagaaa catggcggct atccttctct   1140
cacatcgaaa aggaattttt gaacaatcat ggaaaatcta aaacgtgctg tgaaaacaaa  1200
gaagagaaat gttgcaggaa agattgttta aaactaatga ataccttttt agaacagctg  1260
aaagaaaggt ttaaagacaa aaaacatctg gataaattct cttcttatca tgtgaaaact  1320
gccttctttc acgtatgtac ccagaacct caagacagtc agtgggaccg caaagacctg   1380
ggcctctgct tgataactg cgtgacatac tttcttcagt gcctcaggac agaaaaactt   1440
gagaattatt ttattcctga attcaatcta ttctctagca acttaattga caaagaagt   1500
aaggaatttc tgacaaagca aattgaatat gaaagaaaca atgagtttcc agtttttgat   1560
gaatttttga                                                          1569
```

<210> SEQ ID NO 4
<211> LENGTH: 1101
<212> TYPE: DNA
<213> ORGANISM: Homo sapiens

<400> SEQUENCE: 4

```
gatgcggcgc ctgggccctc gaagctccgg gcggttttgg agaagttgaa gctcagccgc    60
gatgatatct ccacggcggc ggggatggtg aaaggggttg tggaccacct gctgctcaga   120
ctgaagtgcg actccgcgtt cagaggcgtc gggctgctga acaccgggag ctactatgag   180
cacgtgaaga tttctgcacc taatgaattt gatgtcatgt ttaaactgga agtccccaga   240
attcaactag aagaatattc caacactcgt gcatattact ttgtgaaatt taaaagaaat   300
ccgaaagaaa atcctctgag tcagttttta gaaggtgaaa tattatcagc ttctaagatg   360
ctgtcaaagt ttaggaaaat cattaaggaa gaaattaacg acattaaaga tacagatgtc   420
```

-continued

```
atcatgaaga ggaaaagagg agggagccct gctgtaacac ttcttattag tgaaaaaata    480
tctgtggata taaccctggc tttggaatca aaaagtagct ggcctgctag cacccaagaa    540
ggcctgcgca ttcaaaactg ctttcagca aaagttagga agcaactacg actaaagcca    600
ttttaccttg tacccaagca tgcaaaggaa ggaaatggtt tccaagaaga acatggcgg    660
ctatccttct ctcacatcga aaggaaatt ttgaacaatc atggaaaatc taaacgtgc    720
tgtgaaaaca aagaagagaa atgttgcagg aaagattgtt taaaactaat gaaatacctt    780
ttagaacagc tgaaagaaag gtttaaagac aaaaacatc tggataaatt ctcttcttat    840
catgtgaaaa ctgccttctt tcacgtatgt acccagaacc ctcaagacag tcagtgggac    900
cgcaaagacc tgggcctctg ctttgataac tgcgtgacat actttcttca gtgcctcagg    960
acagaaaaac ttgagaatta ttttattcct gaattcaatc tattctctag caacttaatt   1020
gacaaaagaa gtaaggaatt tctgacaaag caaattgaat atgaaagaaa caatgagttt   1080
ccagtttttg atgaattttg a                                              1101
```

<210> SEQ ID NO 5
<211> LENGTH: 507
<212> TYPE: PRT
<213> ORGANISM: Mus sp.

<400> SEQUENCE: 5

```
Met Glu Asp Pro Arg Arg Thr Thr Ala Pro Arg Ala Lys Lys Pro
1               5                   10                  15

Ser Ala Lys Arg Ala Pro Thr Gln Pro Ser Arg Thr Arg Ala His Ala
            20                  25                  30

Glu Ser Cys Gly Pro Gln Arg Gly Ala Arg Ser Arg Arg Ala Glu Arg
        35                  40                  45

Asp Gly Asp Thr Thr Glu Lys Pro Arg Ala Pro Gly Pro Arg Val His
    50                  55                  60

Pro Ala Arg Ala Thr Glu Leu Thr Lys Asp Ala Gln Pro Ser Ala Met
65                  70                  75                  80

Asp Ala Ala Gly Ala Thr Ala Arg Pro Ala Val Arg Val Pro Gln Gln
                85                  90                  95

Gln Ala Ile Leu Asp Pro Glu Leu Pro Ala Val Arg Glu Pro Gln Pro
            100                 105                 110

Pro Ala Asp Pro Glu Ala Arg Lys Val Val Arg Gly Pro Ser His Arg
        115                 120                 125

Arg Gly Ala Arg Ser Thr Gly Gln Pro Arg Ala Pro Arg Gly Ser Arg
    130                 135                 140

Lys Glu Pro Asp Lys Leu Lys Lys Val Leu Asp Lys Leu Arg Leu Lys
145                 150                 155                 160

Arg Lys Asp Ile Ser Glu Ala Ala Glu Thr Val Asn Lys Val Val Glu
                165                 170                 175

Arg Leu Leu Arg Arg Met Gln Lys Arg Glu Ser Glu Phe Lys Gly Val
            180                 185                 190

Glu Gln Leu Asn Thr Gly Ser Tyr Tyr Glu His Val Lys Ile Ser Ala
        195                 200                 205

Pro Asn Glu Phe Asp Val Met Phe Lys Leu Glu Val Pro Arg Ile Glu
    210                 215                 220

Leu Gln Glu Tyr Tyr Glu Thr Gly Ala Phe Tyr Leu Val Lys Phe Lys
225                 230                 235                 240

Arg Ile Pro Arg Gly Asn Pro Leu Ser His Phe Leu Glu Gly Glu Val
                245                 250                 255
```

```
Leu Ser Ala Thr Lys Met Leu Ser Lys Phe Arg Lys Ile Ile Lys Glu
            260                 265                 270

Glu Val Lys Glu Ile Lys Asp Ile Asp Val Ser Val Glu Lys Glu Lys
275                 280                 285

Pro Gly Ser Pro Ala Val Thr Leu Leu Ile Arg Asn Pro Glu Glu Ile
            290                 295                 300

Ser Val Asp Ile Ile Leu Ala Leu Glu Ser Lys Gly Ser Trp Pro Ile
305                 310                 315                 320

Ser Thr Lys Glu Gly Leu Pro Ile Gln Gly Trp Leu Gly Thr Lys Val
                325                 330                 335

Arg Thr Asn Leu Arg Arg Glu Pro Phe Tyr Leu Val Pro Lys Asn Ala
            340                 345                 350

Lys Asp Gly Asn Ser Phe Gln Gly Glu Thr Trp Arg Leu Ser Phe Ser
        355                 360                 365

His Thr Glu Lys Tyr Ile Leu Asn Asn His Gly Ile Glu Lys Thr Cys
    370                 375                 380

Cys Glu Ser Ser Gly Ala Lys Cys Cys Arg Lys Glu Cys Leu Lys Leu
385                 390                 395                 400

Met Lys Tyr Leu Leu Glu Gln Leu Lys Lys Glu Phe Gln Glu Leu Asp
                405                 410                 415

Ala Phe Cys Ser Tyr His Val Lys Thr Ala Ile Phe His Met Trp Thr
            420                 425                 430

Gln Asp Pro Gln Asp Ser Gln Trp Asp Pro Arg Asn Leu Ser Ser Cys
        435                 440                 445

Phe Asp Lys Leu Leu Ala Phe Phe Leu Glu Cys Leu Arg Thr Glu Lys
    450                 455                 460

Leu Asp His Tyr Phe Ile Pro Lys Phe Asn Leu Phe Ser Gln Glu Leu
465                 470                 475                 480

Ile Asp Arg Lys Ser Lys Glu Phe Leu Ser Lys Ile Glu Tyr Glu
                485                 490                 495

Arg Asn Asn Gly Phe Pro Ile Phe Asp Lys Leu
            500                 505

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tacagatcta ctagtgatct atgactgatc tgtacatgat ctaca            45

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtagatcat gtacagatca gtcatagatc actagtagat ctgta            45

<210> SEQ ID NO 8
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 8
aaattgccga agacgaa                                                        17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttcgtcttc ggcaatt                                                        17

<210> SEQ ID NO 10
<211> LENGTH: 1308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gtgagaatga cttggaactt tcaccagtac tacacaaacc gaaatgatgg cttgatgggc          60
aagctagttc ttacagacga ggagaagaac aatctaaagg cattgcgtaa gatcatccgc         120
ttaagaacac gagatgtatt tgaagaagct aagggtattg ccaaggctgt gaaaaaaagt         180
gctcttacgt ttgaaattat tcaggaaaag gtgtcaacga cccaaattaa gcacctttct         240
gacagcgaac aacgagaagt ggctaagctt atttacgaga tggatgatga tgctcgtgat         300
gagtttttgg gattgacacc tcgcttttgg actcagggaa gctttcagta tgacacgctg         360
aatcgcccgt ttcagcctgg tcaagaaatg gatattgatg atggaaccta tatgccaatg         420 cctattttg agtcagagcc taagattggt cattctttac taattcttct tgttgacgcg         480
tcacttaagt cacttgtagc tgaaaatcat ggctggaaat ttgaagctaa gcagacttgt         540
gggaggatta agattgaggc agagaaaaca catattgatg taccaatgta tgcaatccct         600
aaagatgagt tccagaaaaa gcaaatagct ttagaagcaa atagatcatt tgttaaaggt         660 gccattttg aatcatatgt tgcagattca attactgacg atagtgaaac ttatgaatta         720
gattcagaaa acgtaaacct tgctcttcgt gaaggtgatc ggaagtggat caatagcgac         780
cccaaaatag ttgaagattg gttcaacgat agttgtatac gtattggtaa acatcttcgt         840
aaggtttgtc gctttatgaa agcgtggaga gatgcgcagt gggatgttgg aggtccgtca         900
tcgattagtc ttatggctgc aacggtaaat attcttgata gcgttgctca tgatgctagt         960
gatctcggag aaacaatgaa gataattgct aagcatttac ctagtgagtt tgctagggga        1020
gtagagagcc ctgacagtac cgatgaaaag ccactcttcc caccctctta taagcatggc        1080
cctcgggaga tggacattat gagcaaacta gagcgtttgc cagagattct gtcatctgct        1140
gagtcagctg actctaagtc agaggccttg aaaaagatta atatggcgtt tgggaatcgt        1200
gttactaata gcgagcttat tgttttggca aaggctttac cggctttcgc tcaagaacct        1260
agttcagcct cgaaacctga aaaaatcagc agcacaatgg taagtggc                    1308

<210> SEQ ID NO 11
```

```
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val Arg Met Thr Trp Asn Phe His Gln Tyr Tyr Thr Asn Arg Asn Asp
1               5                   10                  15

Gly Leu Met Gly Lys Leu Val Leu Thr Asp Glu Glu Lys Asn Asn Leu
            20                  25                  30

Lys Ala Leu Arg Lys Ile Ile Arg Leu Arg Thr Arg Asp Val Phe Glu
        35                  40                  45

Glu Ala Lys Gly Ile Ala Lys Ala Val Lys Lys Ser Ala Leu Thr Phe
    50                  55                  60

Glu Ile Ile Gln Glu Lys Val Ser Thr Thr Gln Ile Lys His Leu Ser
65                  70                  75                  80

Asp Ser Glu Gln Arg Glu Val Ala Lys Leu Ile Tyr Glu Met Asp Asp
                85                  90                  95

Asp Ala Arg Asp Glu Phe Leu Gly Leu Thr Pro Arg Phe Trp Thr Gln
            100                 105                 110

Gly Ser Phe Gln Tyr Asp Thr Leu Asn Arg Pro Phe Gln Pro Gly Gln
        115                 120                 125

Glu Met Asp Ile Asp Asp Gly Thr Tyr Met Pro Met Pro Ile Phe Glu
    130                 135                 140

Ser Glu Pro Lys Ile Gly His Ser Leu Leu Ile Leu Leu Val Asp Ala
145                 150                 155                 160

Ser Leu Lys Ser Leu Val Ala Glu Asn His Gly Trp Lys Phe Glu Ala
                165                 170                 175

Lys Gln Thr Cys Gly Arg Ile Lys Ile Glu Ala Glu Lys Thr His Ile
            180                 185                 190

Asp Val Pro Met Tyr Ala Ile Pro Lys Asp Glu Phe Gln Lys Lys Gln
        195                 200                 205

Ile Ala Leu Glu Ala Asn Arg Ser Phe Val Lys Gly Ala Ile Phe Glu
    210                 215                 220

Ser Tyr Val Ala Asp Ser Ile Thr Asp Ser Glu Thr Tyr Glu Leu
225                 230                 235                 240

Asp Ser Glu Asn Val Asn Leu Ala Leu Arg Glu Gly Asp Arg Lys Trp
                245                 250                 255

Ile Asn Ser Asp Pro Lys Ile Val Glu Asp Trp Phe Asn Asp Ser Cys
            260                 265                 270

Ile Arg Ile Gly Lys His Leu Arg Lys Val Cys Arg Phe Met Lys Ala
        275                 280                 285

Trp Arg Asp Ala Gln Trp Asp Val Gly Pro Ser Ser Ile Ser Leu
    290                 295                 300

Met Ala Ala Thr Val Asn Ile Leu Asp Ser Val Ala His Asp Ala Ser
305                 310                 315                 320

Asp Leu Gly Glu Thr Met Lys Ile Ile Ala Lys His Leu Pro Ser Glu
                325                 330                 335

Phe Ala Arg Gly Val Glu Ser Pro Asp Ser Thr Asp Glu Lys Pro Leu
            340                 345                 350

Phe Pro Pro Ser Tyr Lys His Gly Pro Arg Glu Met Asp Ile Met Ser
        355                 360                 365
```

```
Lys Leu Glu Arg Leu Pro Glu Ile Leu Ser Ser Ala Glu Ser Ala Asp
        370                 375                 380

Ser Lys Ser Glu Ala Leu Lys Lys Ile Asn Met Ala Phe Gly Asn Arg
385                 390                 395                 400

Val Thr Asn Ser Glu Leu Ile Val Leu Ala Lys Ala Leu Pro Ala Phe
                405                 410                 415

Ala Gln Glu Pro Ser Ser Ala Ser Lys Pro Glu Lys Ile Ser Ser Thr
            420                 425                 430

Met Val Ser Gly
        435

<210> SEQ ID NO 12
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacgcagctc cgggtgcttc taaactgcgt gcggtcctgg aaaaactgaa actgagccgc      60
gatgacattt ctaccgcggc cggcatggtg aaaggtgtgg ttgatcatct gctgctgcgt     120
ctgaaatgcg actcagcctt tcgcggcgtt ggtctgctga acacgggtag ctattacgaa     180
cacgtcaaaa tctctgcacc gaacgaattc gatgttatgt tcaaactgga agtcccgcgt     240
attcagctgg aagaatatag caacacccgt gcctattact tgttaaaatt caaacgcaac     300
ccgaaagaaa atccgctgag tcagtttctg gaaggcgaaa tcctgagtgc gtccaaaatg     360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aaagtgcgta acagctgcg cctgaaaccg     600 tttttacctgg ttccgaaaca tgcgaaagaa ggcaatggtt ttcaagaaga aacctggcgc     660
ctgtcattct cgcatatcga aaagaaatc ctgaacaacc acggtaaaag taaacgtgc      720 tgtgaaaaca aagaagaaaa atgctgtcgt aaagattgtc tgaaactgat gaaatatctg     780
ctggaacagc tgaaagaacg cttcaaagat aaaaaacacc tggacaaatt cagttcctac     840
catgtgaaaa ccgcgttttt ccacgtttgc acgcaaaatc cgcaggatag ccaatgggat     900
cgtaaagacc tgggtctgtg ctttgacaac tgtgtgacct atttcctgca gtgtctgcgc     960
acggaaaaac tggaaaatta ctttatcccg gaatttaacc tgttctcatc gaatctgatt    1020
gataaacgtt ctaaagaatt cctgacgaaa cagattgaat acgaacgcaa caacgaattt    1080
ccggtctttg acgaattt                                                  1098

<210> SEQ ID NO 13
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ala Ala Pro Gly Ala Ser Lys Leu Arg Ala Val Leu Glu Lys Leu
1               5                   10                  15
```

Lys Leu Ser Arg Asp Asp Ile Ser Thr Ala Ala Gly Met Val Lys Gly
                20                  25                  30

Val Val Asp His Leu Leu Arg Leu Lys Cys Asp Ser Ala Phe Arg
         35                  40                  45

Gly Val Gly Leu Leu Asn Thr Gly Ser Tyr Tyr Glu His Val Lys Ile
 50                  55                  60

Ser Ala Pro Asn Glu Phe Asp Val Met Phe Lys Leu Glu Val Pro Arg
 65                  70                  75                  80

Ile Gln Leu Glu Glu Tyr Ser Asn Thr Arg Ala Tyr Tyr Phe Val Lys
                 85                  90                  95

Phe Lys Arg Asn Pro Lys Glu Asn Pro Leu Ser Gln Phe Leu Glu Gly
                100                 105                 110

Glu Ile Leu Ser Ala Ser Lys Met Leu Ser Lys Phe Arg Lys Ile Ile
                115                 120                 125

Lys Glu Glu Ile Asn Asp Ile Lys Asp Thr Asp Val Ile Met Lys Arg
130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
                180                 185                 190

Arg Lys Gln Leu Arg Leu Lys Pro Phe Tyr Leu Val Pro Lys His Ala
                195                 200                 205

Lys Glu Gly Asn Gly Phe Gln Glu Glu Thr Trp Arg Leu Ser Phe Ser
                210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
                260                 265                 270

His Leu Asp Lys Phe Ser Ser Tyr His Val Lys Thr Ala Phe Phe His
                275                 280                 285

Val Cys Thr Gln Asn Pro Gln Asp Ser Gln Trp Asp Arg Lys Asp Leu
                290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
                340                 345                 350

Glu Tyr Glu Arg Asn Asn Glu Phe Pro Val Phe Asp Glu Phe
                355                 360                 365

<210> SEQ ID NO 14
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
ccggacaagc tgaaaaaagt gctcgacaag cttcggctga acggaaaga tatcagtgaa        60
gctgcagaga ccgtgaacaa ggtggtcgag cggttactgc gtcggatgca aaagagagag      120
tcagagttta agggcgtcga gcaacttaac acaggatcct attacgaaca cgttaaaatc      180
tctgcccta atgagttcga cgtgatgttt aagttggaag ttccgcgtat agaattacaa       240
gaatattatg agacgggagc cttctacttg gtgaaattta aacgcattcc gcggggtaat      300
cctctgagtc acttcttaga gggtgaagtg ctgtctgcta cgaaaatgtt aagtaagttt      360
cggaagatca tcaaggagga agtaaaggaa atcaaagaca ttgacgttag cgtggagaag      420
gaaaaaccag gctccccggc ggtaacactt taattagaa atcctgagga aattagcgta       480
gatattatac tcgcgctgga gtctaaggga tcctggccga ttagtaccaa agagggctta      540
cctatccagg gatggcttgg gacaaaggta cgtacaaatc tccgtcgcga accattctac      600
cttgtaccga agaacgctaa agatggtaac tccttccaag gggagacttg gcgtctttca      660
ttttcccaca ccgagaagta cattttaaat aatcatggga tcgaaaagac atgctgtgag      720
tcaagtggtg ccaaatgttg tcgcaaagag tgcttgaagt taatgaaata tttactggag      780
cagctgaaga aagagttcca ggagttagac gctttctgta gctatcatgt taagacggcc      840
atatttcaca tgtggacgca ggatccacag gattctcaat gggatccacg caacctgtcc      900
agttgttttg acaaactgct cgcgttttt ttagaatgcc tgcggaccga aagttggat       960
cattacttca tccctaaatt caacctgttt agtcaagagt tgattgatcg caaatctaaa     1020
gagtttctgt ctaaaaaaat cgaatatgag cgcaataacg ggttcccgat atttgacaaa     1080
ctt                                                                   1083
```

<210> SEQ ID NO 15
<211> LENGTH: 361
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Pro Asp Lys Leu Lys Lys Val Leu Asp Lys Leu Arg Leu Lys Arg Lys
1               5                   10                  15

Asp Ile Ser Glu Ala Ala Glu Thr Val Asn Lys Val Val Glu Arg Leu
            20                  25                  30

Leu Arg Arg Met Gln Lys Arg Glu Ser Glu Phe Lys Gly Val Glu Gln
        35                  40                  45

Leu Asn Thr Gly Ser Tyr Tyr Glu His Val Lys Ile Ser Ala Pro Asn
    50                  55                  60

Glu Phe Asp Val Met Phe Lys Leu Glu Val Pro Arg Ile Glu Leu Gln
65                  70                  75                  80

Glu Tyr Tyr Glu Thr Gly Ala Phe Tyr Leu Val Lys Phe Lys Arg Ile
                85                  90                  95

Pro Arg Gly Asn Pro Leu Ser His Phe Leu Glu Gly Glu Val Leu Ser
            100                 105                 110

Ala Thr Lys Met Leu Ser Lys Phe Arg Lys Ile Ile Lys Glu Glu Val
        115                 120                 125

Lys Glu Ile Lys Asp Ile Asp Val Ser Val Glu Lys Glu Lys Pro Gly
    130                 135                 140

```
Ser Pro Ala Val Thr Leu Leu Ile Arg Asn Pro Glu Glu Ile Ser Val
145                 150                 155                 160

Asp Ile Ile Leu Ala Leu Glu Ser Lys Gly Ser Trp Pro Ile Ser Thr
                165                 170                 175

Lys Glu Gly Leu Pro Ile Gln Gly Trp Leu Gly Thr Lys Val Arg Thr
            180                 185                 190

Asn Leu Arg Arg Glu Pro Phe Tyr Leu Val Pro Lys Asn Ala Lys Asp
        195                 200                 205

Gly Asn Ser Phe Gln Gly Glu Thr Trp Arg Leu Ser Phe Ser His Thr
    210                 215                 220

Glu Lys Tyr Ile Leu Asn Asn His Gly Ile Glu Lys Thr Cys Cys Glu
225                 230                 235                 240

Ser Ser Gly Ala Lys Cys Cys Arg Lys Glu Cys Leu Lys Leu Met Lys
                245                 250                 255

Tyr Leu Leu Glu Gln Leu Lys Lys Glu Phe Gln Glu Leu Asp Ala Phe
            260                 265                 270

Cys Ser Tyr His Val Lys Thr Ala Ile Phe His Met Trp Thr Gln Asp
        275                 280                 285

Pro Gln Asp Ser Gln Trp Asp Pro Arg Asn Leu Ser Ser Cys Phe Asp
    290                 295                 300

Lys Leu Leu Ala Phe Phe Leu Glu Cys Leu Arg Thr Glu Lys Leu Asp
305                 310                 315                 320

His Tyr Phe Ile Pro Lys Phe Asn Leu Phe Ser Gln Glu Leu Ile Asp
                325                 330                 335

Arg Lys Ser Lys Glu Phe Leu Ser Lys Lys Ile Glu Tyr Glu Arg Asn
            340                 345                 350

Asn Gly Phe Pro Ile Phe Asp Lys Leu
        355                 360

<210> SEQ ID NO 16
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ccggacaagc tgaaaaaagt gctcgacaag cttcggctga acggaaaga tatcagtgaa      60 gctgcagaga ccgtgaacaa ggtggtcgag cggttactgc gtcggatgca aaagagagag    120
tcagagttta agggcgtcga gcaacttaac acaggatcct attacgaaca cgttaaaatc    180 tctgcccta atgagttcga cgtgatgttt aagttggaag ttccgcgtat agaattacaa     240
gaatattatg agacgggagc cttctacttg gtgaaattta acgcattcc gcggggtaat    300 cctctgagtc acttcttaga gggtgaagtg ctgtctgcta cgaaaatgtt aagtaagttt    360
cggaagatca tcaaggagga agtaaaggaa atcaaagaca ttgacgttag cgtggagaag    420
gaaaaaccag gctccccggc ggtaacactt ttaattagaa atcctgagga aattagcgta    480
gatattatac tcgcgctgga gtctaaggga tcctggccga ttagtaccaa agagggctta    540
cctatccagg gatggcttgg gacaaggta cgtacaaatc tccgtcgcga accattctac    600
cttgtaccga agaacgctaa agatggtaac tccttccaag gggagacttg gcgtctttca    660
ttttcccaca ccgagaagga atcctgaac aaccacggta aaagtaaaac gtgctgtgaa    720
aacaaagaag aaaaatgctg tcgtaaagat tgtctgaaac tgatgaaata tctgctggaa    780
```

```
cagctgaaag aacgcttcaa agataaaaaa cacctggaca aattcagttc ctaccatgtg    840
aaaaccgcgt ttttccacgt ttgcacgcaa atccgcagg atagccaatg ggatcgtaaa    900
gacctgggtc tgtgctttga caactgtgtg acctatttcc tgcagtgtct gcgcacggaa    960
aaactggaaa attactttat cccggaattt aacctgttct catcgaatct gattgataaa   1020
cgttctaaag aattcctgac gaaacagatt gaatacgaac gcaacaacga atttccggtc   1080
tttgacgaat tt                                                       1092
```

<210> SEQ ID NO 17
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Pro Asp Lys Leu Lys Lys Val Leu Asp Lys Leu Arg Leu Lys Arg Lys
1               5                   10                  15

Asp Ile Ser Glu Ala Ala Glu Thr Val Asn Lys Val Val Glu Arg Leu
            20                  25                  30

Leu Arg Arg Met Gln Lys Arg Glu Ser Glu Phe Lys Gly Val Glu Gln
        35                  40                  45

Leu Asn Thr Gly Ser Tyr Tyr Glu His Val Lys Ile Ser Ala Pro Asn
    50                  55                  60

Glu Phe Asp Val Met Phe Lys Leu Glu Val Pro Arg Ile Glu Leu Gln
65                  70                  75                  80

Glu Tyr Tyr Glu Thr Gly Ala Phe Tyr Leu Val Lys Phe Lys Arg Ile
                85                  90                  95

Pro Arg Gly Asn Pro Leu Ser His Phe Leu Glu Gly Glu Val Leu Ser
            100                 105                 110

Ala Thr Lys Met Leu Ser Lys Phe Arg Lys Ile Ile Lys Glu Glu Val
        115                 120                 125

Lys Glu Ile Lys Asp Ile Asp Val Ser Val Glu Lys Glu Lys Pro Gly
    130                 135                 140

Ser Pro Ala Val Thr Leu Leu Ile Arg Asn Pro Glu Glu Ile Ser Val
145                 150                 155                 160

Asp Ile Ile Leu Ala Leu Glu Ser Lys Gly Ser Trp Pro Ile Ser Thr
                165                 170                 175

Lys Glu Gly Leu Pro Ile Gln Gly Trp Leu Gly Thr Lys Val Arg Thr
            180                 185                 190

Asn Leu Arg Arg Glu Pro Phe Tyr Leu Val Pro Lys Asn Ala Lys Asp
        195                 200                 205

Gly Asn Ser Phe Gln Gly Glu Thr Trp Arg Leu Ser Phe Ser His Thr
    210                 215                 220

Glu Lys Glu Ile Leu Asn Asn His Gly Lys Ser Lys Thr Cys Cys Glu
225                 230                 235                 240

Asn Lys Glu Glu Lys Cys Cys Arg Lys Asp Cys Leu Lys Leu Met Lys
                245                 250                 255

Tyr Leu Leu Glu Gln Leu Lys Glu Arg Phe Lys Asp Lys Lys His Leu
            260                 265                 270

Asp Lys Phe Ser Ser Tyr His Val Lys Thr Ala Phe Phe His Val Cys
        275                 280                 285

Thr Gln Asn Pro Gln Asp Ser Gln Trp Asp Arg Lys Asp Leu Gly Leu
    290                 295                 300
```

Cys Phe Asp Asn Cys Val Thr Tyr Phe Leu Gln Cys Leu Arg Thr Glu
305                 310                 315                 320

Lys Leu Glu Asn Tyr Phe Ile Pro Glu Phe Asn Leu Phe Ser Ser Asn
                325                 330                 335

Leu Ile Asp Lys Arg Ser Lys Glu Phe Leu Thr Lys Gln Ile Glu Tyr
            340                 345                 350

Glu Arg Asn Asn Glu Phe Pro Val Phe Asp Glu Phe
        355                 360

<210> SEQ ID NO 18
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gacgcagctc cgggtgcttc taaactgcgt gcggtcctgg aaaaactgaa actgagccgc      60
gatgacattt ctaccgcggc cggcatggtg aaaggtgtgg ttgatcatct gctgctgcgt    120
ctgaaatgcg actcagcctt tcgcggcgtt ggtctgctga cacgggtag ctattacgaa     180 cacgtcaaaa tctctgcacc gaacgaattc gatgttatgt tcaaactgga agtcccgcgt    240
attcagctgg aagaatatag caacacccgt gcctattact ttgttaaatt caaacgcaac    300
ccgaaagaaa atccgctgag tcagtttctg gaaggcgaaa tcctgagtgc gtccaaaatg    360
ctgtccaaat tccgcaaaat catcaaagaa gaaatcaacg atatcaaaga taccgacgtc    420
attatgaaac gtaaacgcgg cggtagtccg gcagtcaccc tgctgatttc agaaaaaatc    480
tcggtggaca ttacgctggc tctggaatca aaaagctctt ggccggcgag cacccaggaa    540
ggcctgcgta ttcaaaactg gctgtccgct aaagtgcgta acagctgcg cctgaaaccg    600 ttttacctgg ttccgaaaca tgcgaaagaa ggcaatggtt tcaagaaga aacctggcgc    660 ctgtcattct cgcatatcga aaatacatt ttaaataatc atgggatcga aagacatgc     720 tgtgagtcaa gtggtgccaa atgttgtcgc aaagagtgct gaagttaat gaaatattta    780 ctggagcagc tgaagaaaga gttccaggag ttagacgctt tctgtagcta tcatgttaag    840
acggccatat ttcacatgtg gacgcaggat ccacaggatt ctcaatggga tccacgcaac    900
ctgtccagtt gttttgacaa actgctcgcg ttttttttag aatgcctgcg gaccgagaag    960
ttggatcatt acttcatccc taaattcaac ctgtttagtc aagagttgat tgatcgcaaa  1020
tctaaagagt ttctgtctaa aaaaatcgaa tatgagcgca ataacgggtt cccgatattt    1080
gacaaactt                                                           1089

<210> SEQ ID NO 19
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

Val Val Asp His Leu Leu Arg Leu Lys Cys Asp Ser Ala Phe Arg
 35                  40                  45

Gly Val Gly Leu Leu Asn Thr Gly Ser Tyr Tyr Glu His Val Lys Ile
 50                  55                  60

Ser Ala Pro Asn Glu Phe Asp Val Met Phe Lys Leu Glu Val Pro Arg
 65                  70                  75                  80

Ile Gln Leu Glu Glu Tyr Ser Asn Thr Arg Ala Tyr Tyr Phe Val Lys
                 85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
210                 215                 220

His Ile Glu Lys Tyr Ile Leu Asn Asn His Gly Ile Glu Lys Thr Cys
225                 230                 235                 240

Cys Glu Ser Ser Gly Ala Lys Cys Cys Arg Lys Glu Cys Leu Lys Leu
                245                 250                 255

Met Lys Tyr Leu Leu Glu Gln Leu Lys Lys Glu Phe Gln Glu Leu Asp
            260                 265                 270

Ala Phe Cys Ser Tyr His Val Lys Thr Ala Ile Phe His Met Trp Thr
        275                 280                 285

Gln Asp Pro Gln Asp Ser Gln Trp Asp Pro Arg Asn Leu Ser Ser Cys
290                 295                 300

Phe Asp Lys Leu Leu Ala Phe Phe Leu Glu Cys Leu Arg Thr Glu Lys
305                 310                 315                 320

Leu Asp His Tyr Phe Ile Pro Lys Phe Asn Leu Phe Ser Gln Glu Leu
                325                 330                 335

Ile Asp Arg Lys Ser Lys Glu Leu Ser Lys Ile Glu Tyr Glu
            340                 345                 350

Arg Asn Asn Gly Phe Pro Ile Phe Asp Lys Leu
        355                 360

<210> SEQ ID NO 20
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
ccggacaagc tgaaaaaagt gctcgacaag cttcggctga acggaaaga tatcagtgaa      60 gctgcagaga ccgtgaacaa ggtggtcgag cggttactgc gtcggatgca aaagagagag    120
tcagagttta agggcgtcga gcaactgaac acgggtagct attacgaaca cgtcaaaatc    180

```
tctgcaccga acgaattcga tgttatgttc aaactggaag tcccgcgtat tcagctggaa      240
gaatatagca acacccgtgc ctattacttt gttaaattca aacgcaaccc gaaagaaaat      300
ccgctgagtc agtttctgga aggcgaaatc ctgagtgcgt ccaaaatgct gtccaaattc      360
cgcaaaatca tcaaagaaga aatcaacgat atcaaagata ccgacgtcat tatgaaacgt      420
aaacgcggcg gtagtccggc agtcaccctg ctgatttcag aaaaaatctc ggtggacatt      480
acgctggctc tggaatcaaa aagctcttgg ccggcgagca cccaggaagg cctgcgtatt      540
caaaactggc tgtccgctaa agtgcgtaaa cagctgcgcc tgaaaccgtt ttacctggtt      600
ccgaaacatg cgaaagaagg caatggtttt caagaagaaa cctggcgcct gtcattctcg      660
catatcgaaa agaaatcct gaacaaccac ggtaaaagta aacgtgctg tgaaaacaaa      720 gaagaaaaat gctgtcgtaa agattgtctg aaactgatga atatctgct ggaacagctg      780 aaagaacgct tcaaagataa aaaacacctg gacaaattca gttcctacca tgtgaaaacc      840
gcgttttttc acgtttgcac gcaaaatccg caggatagcc aatgggatcg taaagacctg      900
ggtctgtgct ttgacaactg tgtgacctat ttcctgcagt gtctgcgcac ggaaaaactg      960
gaaaattact ttatcccgga atttaacctg ttctcatcga atctgattga taaacgttct      1020
aaagaattcc tgacgaaaca gattgaatac gaacgcaaca acgaatttcc ggtctttgac      1080
gaattt                                                                1086
```

<210> SEQ ID NO 21
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Pro Asp Lys Leu Lys Lys Val Leu Asp Lys Leu Arg Leu Lys Arg Lys
1               5                   10                  15

Asp Ile Ser Glu Ala Ala Glu Thr Val Asn Lys Val Val Glu Arg Leu
            20                  25                  30

Leu Arg Arg Met Gln Lys Arg Glu Ser Glu Phe Lys Gly Val Glu Gln
        35                  40                  45

Leu Asn Thr Gly Ser Tyr Tyr Glu His Val Lys Ile Ser Ala Pro Asn
    50                  55                  60

Glu Phe Asp Val Met Phe Lys Leu Glu Val Pro Arg Ile Gln Leu Glu
65                  70                  75                  80

Glu Tyr Ser Asn Thr Arg Ala Tyr Tyr Phe Val Lys Phe Lys Arg Asn
                85                  90                  95

Pro Lys Glu Asn Pro Leu Ser Gln Phe Leu Glu Gly Glu Ile Leu Ser
            100                 105                 110

Ala Ser Lys Met Leu Ser Lys Phe Arg Lys Ile Ile Lys Glu Glu Ile
        115                 120                 125

Asn Asp Ile Lys Asp Thr Asp Val Ile Met Lys Arg Lys Arg Gly Gly
    130                 135                 140

Ser Pro Ala Val Thr Leu Leu Ile Ser Glu Lys Ile Ser Val Asp Ile
145                 150                 155                 160

Thr Leu Ala Leu Glu Ser Lys Ser Ser Trp Pro Ala Ser Thr Gln Glu
                165                 170                 175

Gly Leu Arg Ile Gln Asn Trp Leu Ser Ala Lys Val Arg Lys Gln Leu
            180                 185                 190
```

Arg Leu Lys Pro Phe Tyr Leu Val Pro Lys His Ala Lys Glu Gly Asn
    195                 200                 205
Gly Phe Gln Glu Glu Thr Trp Arg Leu Ser Phe Ser His Ile Glu Lys
210                 215                 220
Glu Ile Leu Asn Asn His Gly Lys Ser Lys Thr Cys Cys Glu Asn Lys
225                 230                 235                 240
Glu Glu Lys Cys Cys Arg Lys Asp Cys Leu Lys Leu Met Lys Tyr Leu
                245                 250                 255
Leu Glu Gln Leu Lys Glu Arg Phe Lys Asp Lys Lys His Leu Asp Lys
            260                 265                 270
Phe Ser Ser Tyr His Val Lys Thr Ala Phe His Val Cys Thr Gln
        275                 280                 285
Asn Pro Gln Asp Ser Gln Trp Asp Arg Lys Asp Leu Gly Leu Cys Phe
    290                 295                 300
Asp Asn Cys Val Thr Tyr Phe Leu Gln Cys Leu Arg Thr Glu Lys Leu
305                 310                 315                 320
Glu Asn Tyr Phe Ile Pro Glu Phe Asn Leu Phe Ser Ser Asn Leu Ile
                325                 330                 335
Asp Lys Arg Ser Lys Glu Phe Leu Thr Lys Gln Ile Glu Tyr Glu Arg
            340                 345                 350
Asn Asn Glu Phe Pro Val Phe Asp Glu Phe
        355                 360

<210> SEQ ID NO 22
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gacgcagctc cgggtgcttc taaactgcgt gcggtcctgg aaaaactgaa actgagccgc        60
gatgacattt ctaccgcggc cggcatggtg aaaggtgtgg ttgatcatct gctgctgcgt       120
ctgaaatgcg actcagcctt tcgcggcgtt ggtctgctta acacaggatc ctattacgaa       180
cacgttaaaa tctctgcccc taatgagttc gacgtgatgt ttaagttgga agttccgcgt       240
atagaattac aagaatatta tgagacggga gccttctact tggtgaaatt taaacgcatt       300
ccgcggggta atcctctgag tcacttctta gagggtgaag tgctgtctgc tacgaaaatg       360
ttaagtaagt ttcggaagat catcaaggag gaaatcaacg atatcaaaga taccgacgtc       420
attatgaaac gtaaacgcgg cggtagtccg gcagtcaccc tgctgatttc agaaaaaatc       480
tcggtggaca ttacgctggc tctggaatca aaaagctctt ggccggcgag cacccaggaa       540
ggcctgcgta ttcaaaactg gctgtccgct aaagtgcgta acagctgcg cctgaaaccg        600 tttacctgg ttccgaaaca tgcgaaagaa ggcaatggtt tcaagaaga acctggcgc          660 ctgtcattct cgcatatcga aaagaaatc ctgaacaacc acggtaaaag taaacgtgc         720 tgtgaaaaca agaagaaaa atgctgtcgt aaagattgtc tgaaactgat gaaatatctg        780
ctggaacagc tgaaagaacg cttcaaagat aaaaacacc tggacaaatt cagttcctac       840
catgtgaaaa ccgcgttttt ccacgtttgc acgcaaaatc cgcaggatag ccaatgggat       900
cgtaaagacc tgggtctgtg ctttgacaac tgtgtgacct atttcctgca gtgtctgcgc       960
acggaaaaac tggaaaatta ctttatcccg gaatttaacc tgttctcatc gaatctgatt      1020

```
gataaacgtt ctaaagaatt cctgacgaaa cagattgaat acgaacgcaa caacgaattt    1080
ccggtctttg acgaattt                                                   1098
```

<210> SEQ ID NO 23
<211> LENGTH: 366
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

Val Val Asp His Leu Leu Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Glu Leu Gln Glu Tyr Tyr Glu Thr Gly Ala Phe Tyr Leu Val Lys
                85                  90                  95

Phe Lys Arg Ile Pro Arg Gly Asn Pro Leu Ser His Phe Leu Glu Gly
            100                 105                 110

Glu Val Leu Ser Ala Thr Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
    290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335
```

```
Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365

<210> SEQ ID NO 24
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gacgcagctc cgggtgcttc taaactgcgt gcggtcctgg aaaaactgaa actgagccgc      60
gatgacattt ctaccgcggc cggcatggtg aaaggtgtgg ttgatcatct gctgctgcgt     120
ctgaaatgcg actcagcctt tcgcggcgtt ggtctgctga acacgggtag ctattacgaa     180
cacgtcaaaa tctctgcacc gaacgaattc gatgttatgt tcaaactgga agtcccgcgt     240
attcagctgg aagaatatag caacacccgt gcctattact ttgttaaatt caaacgcaac     300
ccgaaagaaa tccgctgag tcagtttctg gaaggcgaaa tcctgagtgc gtccaaaatg     360
ctgtccaaat tccgcaaaat catcaaagaa gaagtaaagg aaatcaaaga cattgacgtt     420
agcgtggaga aggaaaaacc aggctccccg gcggtaacac ttttaattag aaatcctgag     480
gaaattagcg tagatattat actcgcgctg gagtctaagg gatcctggcc gattagtacc     540
aaagagggct tacctatcca gggatggctt gggacaaagg tacgtacaaa tctccgtcgc     600
gaaccattct accttgtacc gaagaacgct aaagatggta actccttcca aggggagact     660
tggcgtcttt cattttccca caccgagaag gaaatcctga caaccacgg taaaagtaaa      720 acgtgctgtg aaaacaaaga gaaaaatgc tgtcgtaaag attgtctgaa actgatgaaa     780
tatctgctgg aacagctgaa agaacgcttc aaagataaaa acacctgga caaattcagt     840 tcctaccatg tgaaaaccgc gttttttccac gtttgcacgc aaaatccgca ggatagccaa     900
tgggatcgta agacctggg tctgtgcttt gacaactgtg tgacctattt cctgcagtgt     960
ctgcgcacgg aaaaactgga aaattacttt atcccggaat ttaacctgtt ctcatcgaat    1020
ctgattgata aacgttctaa agaattcctg acgaaacaga ttgaatacga acgcaacaac    1080
gaatttccgg tctttgacga attt                                           1104

<210> SEQ ID NO 25
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

Val Val Asp His Leu Leu Leu Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60
```

| | | | | | | | | | | | | | | |
|---|---|---|---|---|---|---|---|---|---|---|---|---|---|---|
| Ser | Ala | Pro | Asn | Glu | Phe | Asp | Val | Met | Phe | Lys | Leu | Glu | Val | Pro | Arg |
| 65 | | | | 70 | | | | | 75 | | | | | 80 |

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
            115                 120                 125

Lys Glu Glu Val Lys Glu Ile Lys Asp Ile Asp Val Ser Val Glu Lys
130                 135                 140

Glu Lys Pro Gly Ser Pro Ala Val Thr Leu Leu Ile Arg Asn Pro Glu
145                 150                 155                 160

Glu Ile Ser Val Asp Ile Ile Leu Ala Leu Glu Ser Lys Gly Ser Trp
                165                 170                 175

Pro Ile Ser Thr Lys Glu Gly Leu Pro Ile Gln Gly Trp Leu Gly Thr
            180                 185                 190

Lys Val Arg Thr Asn Leu Arg Arg Glu Pro Phe Tyr Leu Val Pro Lys
            195                 200                 205

Asn Ala Lys Asp Gly Asn Ser Phe Gln Gly Glu Thr Trp Arg Leu Ser
210                 215                 220

Phe Ser His Thr Glu Lys Glu Ile Leu Asn Asn His Gly Lys Ser Lys
225                 230                 235                 240

Thr Cys Cys Glu Asn Lys Glu Lys Cys Cys Arg Lys Asp Cys Leu
                245                 250                 255

Lys Leu Met Lys Tyr Leu Leu Glu Gln Leu Lys Glu Arg Phe Lys Asp
            260                 265                 270

Lys Lys His Leu Asp Lys Phe Ser Ser Tyr His Val Lys Thr Ala Phe
            275                 280                 285

Phe His Val Cys Thr Gln Asn Pro Gln Asp Ser Gln Trp Asp Arg Lys
290                 295                 300

Asp Leu Gly Leu Cys Phe Asp Asn Cys Val Thr Tyr Phe Leu Gln Cys
305                 310                 315                 320

Leu Arg Thr Glu Lys Leu Glu Asn Tyr Phe Ile Pro Glu Phe Asn Leu
            325                 330                 335

Phe Ser Ser Asn Leu Ile Asp Lys Arg Ser Lys Glu Phe Leu Thr Lys
            340                 345                 350

Gln Ile Glu Tyr Glu Arg Asn Asn Glu Phe Pro Val Phe Asp Glu Phe
            355                 360                 365

<210> SEQ ID NO 26
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ccggacaagc tgaaaaaagt gctcgacaag cttcggctga acgcgatga catttctacc      60 gcggccggca tggtgaaagg tgtggttgat catctgctgc tgcgtctgaa atgcgactca    120
gcctttcgcg gcgttggtct gctgaacacg ggtagctatt acgaacacgt caaaatctct    180
gcaccgaacg aattcgatgt tatgttcaaa ctggaagtcc cgcgtattca gctggaagaa    240
tatagcaaca cccgtgccta ttactttgtt aaattcaaac gcaacccgaa agaaaatccg    300
ctgagtcagt ttctggaagg cgaaatcctg agtgcgtcca aaatgctgtc caaattccgc    360

```
aaaatcatca aagaagaaat caacgatatc aaagataccg acgtcattat gaaacgtaaa      420
cgcggcggta gtccggcagt caccctgctg atttcagaaa aaatctcggt ggacattacg      480
ctggctctgg aatcaaaaag ctcttggccg gcgagcaccc aggaaggcct gcgtattcaa      540
aactggctgt ccgctaaagt gcgtaaacag ctgcgcctga aaccgtttta cctggttccg      600
aaacatgcga agaaggcaa tggttttcaa gaagaaacct ggcgcctgtc attctcgcat       660
atcgaaaaag aaatcctgaa caaccacggt aaaagtaaaa cgtgctgtga aaacaaagaa      720
gaaaaatgct gtcgtaaaga ttgtctgaaa ctgatgaaat atctgctgga cagctgaaa      780 gaacgcttca agataaaaa acacctggac aaattcagtt cctaccatgt gaaaaccgcg      840
tttttccacg tttgcacgca aaatccgcag gatagccaat gggatcgtaa agacctgggt     900
ctgtgctttg acaactgtgt gacctatttc ctgcagtgtc tgcgcacgga aaaactggaa     960
aattacttta tcccggaatt taacctgttc tcatcgaatc tgattgataa acgttctaaa    1020
gaattcctga cgaaacagat tgaatacgaa cgcaacaacg aatttccggt ctttgacgaa    1080
ttt                                                                   1083
```

<210> SEQ ID NO 27
<211> LENGTH: 361
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Pro Asp Lys Leu Lys Lys Val Leu Asp Lys Leu Arg Leu Lys Arg Asp
1               5                   10                  15

Asp Ile Ser Thr Ala Ala Gly Met Val Lys Gly Val Val Asp His Leu
            20                  25                  30

Leu Leu Arg Leu Lys Cys Asp Ser Ala Phe Arg Gly Val Gly Leu Leu
        35                  40                  45

Asn Thr Gly Ser Tyr Tyr Glu His Val Lys Ile Ser Ala Pro Asn Glu
    50                  55                  60

Phe Asp Val Met Phe Lys Leu Glu Val Pro Arg Ile Gln Leu Glu Glu
65                  70                  75                  80

Tyr Ser Asn Thr Arg Ala Tyr Tyr Phe Val Lys Phe Lys Arg Asn Pro
                85                  90                  95

Lys Glu Asn Pro Leu Ser Gln Phe Leu Glu Gly Glu Ile Leu Ser Ala
            100                 105                 110

Ser Lys Met Leu Ser Lys Phe Arg Lys Ile Ile Lys Glu Glu Ile Asn
        115                 120                 125

Asp Ile Lys Asp Thr Asp Val Ile Met Lys Arg Lys Arg Gly Gly Ser
    130                 135                 140

Pro Ala Val Thr Leu Leu Ile Ser Glu Lys Ile Ser Val Asp Ile Thr
145                 150                 155                 160

Leu Ala Leu Glu Ser Lys Ser Ser Trp Pro Ala Ser Thr Gln Glu Gly
                165                 170                 175

Leu Arg Ile Gln Asn Trp Leu Ser Ala Lys Val Arg Lys Gln Leu Arg
            180                 185                 190

Leu Lys Pro Phe Tyr Leu Val Pro Lys His Ala Lys Glu Gly Asn Gly
        195                 200                 205

Phe Gln Glu Glu Thr Trp Arg Leu Ser Phe Ser His Ile Glu Lys Glu
    210                 215                 220
```

```
Ile Leu Asn Asn His Gly Lys Ser Lys Thr Cys Cys Glu Asn Lys Glu
225                 230                 235                 240

Glu Lys Cys Cys Arg Lys Asp Cys Leu Lys Leu Met Lys Tyr Leu Leu
            245                 250                 255

Glu Gln Leu Lys Glu Arg Phe Lys Asp Lys Lys His Leu Asp Lys Phe
        260                 265                 270

Ser Ser Tyr His Val Lys Thr Ala Phe Phe His Val Cys Thr Gln Asn
    275                 280                 285

Pro Gln Asp Ser Gln Trp Asp Arg Lys Asp Leu Gly Leu Cys Phe Asp
290                 295                 300

Asn Cys Val Thr Tyr Phe Leu Gln Cys Leu Arg Thr Glu Lys Leu Glu
305                 310                 315                 320

Asn Tyr Phe Ile Pro Glu Phe Asn Leu Phe Ser Ser Asn Leu Ile Asp
                325                 330                 335

Lys Arg Ser Lys Glu Phe Leu Thr Lys Gln Ile Glu Tyr Glu Arg Asn
                340                 345                 350

Asn Glu Phe Pro Val Phe Asp Glu Phe
                355                 360

<210> SEQ ID NO 28
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacgcagctc cgggtgcttc taaactgcgt gcggtcctgg aaaaactgaa actgagccgg     60
aaagatatca gtgaagctgc agagaccgtg aaaggtgtgg ttgatcatct gctgctgcgt    120
ctgaaatgcg actcagcctt tcgcggcgtt ggtctgctga acacgggtag ctattacgaa    180
cacgtcaaaa tctctgcacc gaacgaattc gatgttatgt tcaaactgga agtcccgcgt    240
attcagctgg aagaatatag caacacccgt gcctattact tgttaaaatt caaacgcaac    300
ccgaaagaaa atccgctgag tcagtttctg gaaggcgaaa tcctgagtgc gtccaaaatg    360
ctgtccaaat tccgcaaaat catcaaagaa gaaatcaacg atatcaaaga taccgacgtc    420
attatgaaac gtaaacgcgg cggtagtccg gcagtcaccc tgctgatttc agaaaaaatc    480
tcggtggaca ttacgctggc tctggaatca aaaagctctt ggccggcgag cacccaggaa    540
ggcctgcgta ttcaaaactg gctgtccgct aagtgcgta aacagctgcg cctgaaaccg    600
ttttacctgg ttccgaaaca tgcgaaagaa ggcaatggtt tcaagaaga acctggcgc    660 ctgtcattct cgcatatcga aaagaaatc ctgaacaacc acgtaaaag taaacgtgc    720 tgtgaaaaca agaagaaaa atgctgtcgt aaagattgtc tgaaactgat gaaatatctg    780
ctggaacagc tgaaagaacg cttcaaagat aaaaaacacc tggacaaatt cagttcctac    840
catgtgaaaa ccgcgttttt ccacgtttgc acgcaaaatc cgcaggatag ccaatgggat    900
cgtaaagacc tgggtctgtg ctttgacaac tgtgtgacct atttcctgca gtgtctgcgc    960
acggaaaaac tggaaaatta ctttatcccg gaatttaacc tgttctcatc gaatctgatt   1020
gataaacgtt ctaaagaatt cctgacgaaa cagattgaat acgaacgcaa caacgaattt   1080
ccggtctttg acgaattt                                                 1098

<210> SEQ ID NO 29
```

```
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ala Ala Pro Gly Ala Ser Lys Leu Arg Ala Val Leu Glu Lys Leu
1               5                   10                  15

Lys Leu Ser Arg Lys Asp Ile Ser Glu Ala Ala Glu Thr Val Lys Gly
            20                  25                  30

Val Val Asp His Leu Leu Leu Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
    290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365
```

<210> SEQ ID NO 30
<211> LENGTH: 1098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
gacgcagctc cgggtgcttc taaactgcgt gcggtcctgg aaaaactgaa actgagccgc      60
gatgacattt ctaccgcggc cggcatggtg aacaaggtgg tcgagcggtt actgcgtcgg     120
ctgaaatgcg actcagcctt tcgcggcgtt ggtctgctga acacgggtag ctattacgaa     180
cacgtcaaaa tctctgcacc gaacgaattc gatgttatgt tcaaactgga agtcccgcgt     240
attcagctgg aagaatatag caacacccgt gcctattact ttgttaaatt caaacgcaac     300
ccgaaagaaa atccgctgag tcagtttctg gaaggcgaaa tcctgagtgc gtccaaaatg     360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aaagtgcgta acagctgcg cctgaaaccg     600
ttttacctgg ttccgaaaca tgcgaaagaa ggcaatggtt ttcaagaaga acctggcgc     660
ctgtcattct cgcatatcga aaagaaatc ctgaacaacc acggtaaaag taaaacgtgc     720
tgtgaaaaca agaagaaaa atgctgtcgt aaagattgtc tgaaactgat gaaatatctg     780
ctggaacagc tgaaagaacg cttcaaagat aaaaaacacc tggacaaatt cagttcctac     840
catgtgaaaa ccgcgttttt ccacgtttgc acgcaaaatc cgcaggatag ccaatgggat     900
cgtaaagacc tgggtctgtg ctttgacaac tgtgtgacct atttcctgca gtgtctgcgc     960
acggaaaaac tggaaaatta ctttatcccg gaatttaacc tgttctcatc gaatctgatt    1020
gataaacgtt ctaaagaatt cctgacgaaa cagattgaat acgaacgcaa caacgaattt    1080
ccggtctttg acgaattt                                                  1098
```

<210> SEQ ID NO 31
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Asn Lys
            20                  25                  30

Val Val Glu Arg Leu Leu Arg Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110
```

Glu Ile Leu Ser Ala Ser Lys Met Leu Ser Lys Phe Arg Lys Ile Ile
            115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
            195                 200                 205

Lys Glu Gly Asn Gly Phe Gln Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
            275                 280                 285

Val Cys Thr Gln Asn Pro Gln Asp Ser Gln Trp Asp Arg Lys Asp Leu
            290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
            355                 360                 365

<210> SEQ ID NO 32
<211> LENGTH: 1101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gacgcagctc cgggtgcttc taaactgcgt gcggtcctgg aaaaactgaa actgagccgc      60
gatgacattt ctaccgcggc cggcatggtg aaaggtgtgg ttgatcatct gctgctgcgt     120
atgcaaaaga gagagtcaga gtttaagggc gtcgagcaac tgaacacggg tagctattac     180
gaacacgtca aaatctctgc accgaacgaa ttcgatgtta tgttcaaact ggaagtcccg     240
cgtattcagc tggaagaata tagcaacacc cgtgcctatt actttgttaa attcaaacgc     300
aacccgaaag aaaatccgct gagtcagttt ctggaaggcg aaatcctgag tgcgtccaaa     360
atgctgtcca aattccgcaa aatcatcaaa gaagaaatca cgatatcaa agataccgac      420 gtcattatga acgtaaacg cggcggtagt ccggcagtca ccctgctgat ttcagaaaaa     480
atctcggtgg acattacgct ggctctggaa tcaaaaagct cttggccggc gagcacccag     540
gaaggcctgc gtattcaaaa ctggctgtcc gctaaagtgc gtaaacagct cgcgctgaaa     600

```
ccgttttacc tggttccgaa acatgcgaaa gaaggcaatg gttttcaaga agaaacctgg    660
cgcctgtcat tctcgcatat cgaaaaagaa atcctgaaca accacggtaa agtaaaacg    720 tgctgtgaaa acaaagaaga aaaatgctgt cgtaaagatt gtctgaaact gatgaaatat    780
ctgctggaac agctgaaaga acgcttcaaa gataaaaaac acctggacaa attcagttcc    840
taccatgtga aaccgcgtt tttccacgtt tgcacgcaaa atccgcagga tagccaatgg    900
gatcgtaaag acctgggtct gtgctttgac aactgtgtga cctatttcct gcagtgtctg    960
cgcacggaaa aactggaaaa ttactttatc ccggaattta acctgttctc atcgaatctg   1020
attgataaac gttctaaaga attcctgacg aaacagattg aatacgaacg caacaacgaa   1080
tttccggtct ttgacgaatt t                                              1101
```

<210> SEQ ID NO 33
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

Val Val Asp His Leu Leu Leu Arg Met Gln Lys Arg Glu Ser Glu Phe
        35                  40                  45

Lys Gly Val Glu Gln Leu Asn Thr Gly Ser Tyr Tyr Glu His Val Lys
    50                  55                  60

Ile Ser Ala Pro Asn Glu Phe Asp Val Met Phe Lys Leu Glu Val Pro
65                  70                  75                  80

Arg Ile Gln Leu Glu Glu Tyr Ser Asn Thr Arg Ala Tyr Tyr Phe Val
                85                  90                  95

Lys Phe Lys Arg Asn Pro Lys Glu Asn Pro Leu Ser Gln Phe Leu Glu
            100                 105                 110

Gly Glu Ile Leu Ser Ala Ser Lys Met Leu Ser Lys Phe Arg Lys Ile
        115                 120                 125

Ile Lys Glu Glu Ile Asn Asp Ile Lys Asp Thr Asp Val Ile Met Lys
    130                 135                 140

Arg Lys Arg Gly Gly Ser Pro Ala Val Thr Leu Leu Ile Ser Glu Lys
145                 150                 155                 160

Ile Ser Val Asp Ile Thr Leu Ala Leu Glu Ser Lys Ser Ser Trp Pro
                165                 170                 175

Ala Ser Thr Gln Glu Gly Leu Arg Ile Gln Asn Trp Leu Ser Ala Lys
            180                 185                 190

Val Arg Lys Gln Leu Arg Leu Lys Pro Phe Tyr Leu Val Pro Lys His
        195                 200                 205

Ala Lys Glu Gly Asn Gly Phe Gln Glu Glu Thr Trp Arg Leu Ser Phe
    210                 215                 220

Ser His Ile Glu Lys Glu Ile Leu Asn Asn His Gly Lys Ser Lys Thr
225                 230                 235                 240

Cys Cys Glu Asn Lys Glu Glu Lys Cys Cys Arg Lys Asp Cys Leu Lys
                245                 250                 255
```

```
Leu Met Lys Tyr Leu Leu Glu Gln Leu Lys Glu Arg Phe Lys Asp Lys
        260                 265                 270

Lys His Leu Asp Lys Phe Ser Ser Tyr His Val Lys Thr Ala Phe Phe
        275                 280                 285

His Val Cys Thr Gln Asn Pro Gln Asp Ser Gln Trp Asp Arg Lys Asp
        290                 295                 300

Leu Gly Leu Cys Phe Asp Asn Cys Val Thr Tyr Phe Leu Gln Cys Leu
305                 310                 315                 320

Arg Thr Glu Lys Leu Glu Asn Tyr Phe Ile Pro Glu Phe Asn Leu Phe
                325                 330                 335

Ser Ser Asn Leu Ile Asp Lys Arg Ser Lys Glu Phe Leu Thr Lys Gln
                340                 345                 350

Ile Glu Tyr Glu Arg Asn Asn Glu Phe Pro Val Phe Asp Glu Phe
                355                 360                 365
```

<210> SEQ ID NO 34
<211> LENGTH: 1098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
gacgcagctc cgggtgcttc taaactgcgt gcggtcctgg aaaaactgaa actgagccgc      60
gatgacattt ctaccgcggc cggcatggtg aaaaaggtgg tcgagcggtt actgcgtcgg     120
ctgaaatgcg actcagcctt cgcggcgttg gtctgctga acacgggtag ctattacgaa     180
cacgtcaaaa tctctgcacc gaacgaattc gatgttatgt tcaaactgga agtcccgcgt     240
attcagctgg aagaatatag caacacccgt gcctattact tgttaaaatt caaacgcaac     300
ccgaaagaaa atccgctgag tcagtttctg gaaggcgaaa tcctgagtgc gtccaaaatg     360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aaagtgcgta acagctgcg cctgaaaccg     600
ttttacctgg ttccgaaaca tgcgaaagaa ggcaatggtt tcaagaaga aacctggcgc     660
ctgtcattct cgcatatcga aaagaaatc ctgaacaacc acggtaaaag taaaacgtgc     720
tgtgaaaaca aagaagaaaa atgctgtcgt aaagattgtc tgaaactgat gaaatatctg     780
ctggaacagc tgaaagaacg cttcaaagat aaaaacacc tggacaaatt cagttcctac     840
catgtgaaaa ccgcgttttt ccacgtttgc acgcaaaatc cgcaggatag ccaatgggat     900
cgtaaagacc tgggtctgtg ctttgacaac tgtgtgacct atttcctgca gtgtctgcgc     960
acggaaaaac tggaaaatta ctttatcccg gaatttaacc tgttctcatc gaatctgatt    1020
gataaacgtt ctaaagaatt cctgacgaaa cagattgaat acgaacgcaa caacgaattt    1080
ccggtctttg acgaattt                                                  1098
```

<210> SEQ ID NO 35
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Lys
            20                  25                  30

Val Val Glu Arg Leu Leu Arg Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
    290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365
```

<210> SEQ ID NO 36
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gacgcagctc cgggtgcttc taaactgcgt gcggtcctgg aaaaactgaa actgagccgc    60
gatgacattt ctaccgcggc cggcatggtg aacggtgtgg tcgagcggtt actgcgtcgg   120
ctgaaatgcg actcagcctt tcgcggcgtt ggtctgctga acacgggtag ctattacgaa   180
cacgtcaaaa tctctgcacc gaacgaattc gatgttatgt tcaaactgga agtcccgcgt   240
attcagctgg aagaatatag caacacccgt gcctattact ttgttaaatt caaacgcaac   300
ccgaaagaaa atccgctgag tcagtttctg gaaggcgaaa tcctgagtgc gtccaaaatg   360
ctgtccaaat tccgcaaaat catcaaagaa gaaatcaacg atatcaaaga taccgacgtc   420
attatgaaac gtaaacgcgg cggtagtccg gcagtcaccc tgctgatttc agaaaaaatc   480
tcggtggaca ttacgctggc tctggaatca aaaagctctt ggccggcgag cacccaggaa   540
ggcctgcgta ttcaaaactg gctgtccgct aaagtgcgta acagctgcg cctgaaaccg    600
ttttacctgg ttccgaaaca tgcgaaagaa ggcaatggtt ttcaagaaga aacctggcgc   660
ctgtcattct cgcatatcga aaagaaatc ctgaacaacc acggtaaaag taaacgtgc    720
tgtgaaaaca aagaagaaaa atgctgtcgt aaagattgtc tgaaactgat gaaatatctg   780
ctggaacagc tgaaagaacg cttcaaagat aaaaaacacc tggacaaatt cagttcctac   840
catgtgaaaa ccgcgttttt ccacgtttgc acgcaaaatc cgcaggatag ccaatgggat   900
cgtaaagacc tgggtctgtg ctttgacaac tgtgtgacct atttcctgca gtgtctgcgc   960
acggaaaaac tggaaaatta ctttatcccg gaatttaacc tgttctcatc gaatctgatt  1020
gataaacgtt ctaaagaatt cctgacgaaa cagattgaat acgaacgcaa caacgaattt  1080
ccggtctttg acgaattt                                                1098
```

<210> SEQ ID NO 37
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Asn Gly
            20                  25                  30

Val Val Glu Arg Leu Leu Arg Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125
```

```
Lys Glu Glu Ile Asn Asp Ile Lys Asp Thr Asp Val Ile Met Lys Arg
        130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
            195                 200                 205

Lys Glu Gly Asn Gly Phe Gln Glu Glu Thr Trp Arg Leu Ser Phe Ser
210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
            275                 280                 285

Val Cys Thr Gln Asn Pro Gln Asp Ser Gln Trp Asp Arg Lys Asp Leu
290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
            355                 360                 365

<210> SEQ ID NO 38
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gacgcagctc cgggtgcttc taaactgcgt gcggtcctgg aaaaactgaa actgagccgc      60
gatgacattt ctaccgcggc cggcatggtg aacaaggtgg tcgatcggtt actgcgtcgg     120
ctgaaatgcg actcagcctt tcgcggcgtt ggtctgctga acacgggtag ctattacgaa     180
cacgtcaaaa tctctgcacc gaacgaattc gatgttatgt tcaaactgga agtcccgcgt     240
attcagctgg aagaatatag caacacccgt gcctattact tgttaaaatt caaacgcaac     300
ccgaaagaaa atccgctgag tcagtttctg gaaggcgaaa tcctgagtgc gtccaaaatg     360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aaagtgcgta acagctgcg cctgaaaccg     600 ttttacctgg ttccgaaaca tgcgaaagaa ggcaatggtt tcaagaagaa acctggcgc     660 ctgtcattct cgcatatcga aaagaaatc ctgaacaacc acggtaaaag taaaacgtgc     720
```

-continued

```
tgtgaaaaca aagaagaaaa atgctgtcgt aaagattgtc tgaaactgat gaaatatctg    780
ctggaacagc tgaagaacg cttcaaagat aaaaaacacc tggacaaatt cagttcctac    840
catgtgaaaa ccgcgttttt ccacgtttgc acgcaaaatc cgcaggatag ccaatgggat    900
cgtaaagacc tgggtctgtg ctttgacaac tgtgtgacct atttcctgca gtgtctgcgc    960
acggaaaaac tggaaaatta ctttatcccg gaatttaacc tgttctcatc gaatctgatt   1020
gataaacgtt ctaaagaatt cctgacgaaa cagattgaat acgaacgcaa caacgaattt   1080
ccggtctttg acgaattt                                                  1098
```

<210> SEQ ID NO 39
<211> LENGTH: 366
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 39

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Asn Lys
            20                  25                  30

Val Val Asp Arg Leu Leu Arg Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285
```

Val Cys Thr Gln Asn Pro Gln Asp Ser Gln Trp Asp Arg Lys Asp Leu
           290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
            355                 360                 365

<210> SEQ ID NO 40
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gacgcagctc cgggtgcttc taaactgcgt gcggtcctgg aaaaactgaa actgagccgc      60
gatgacattt ctaccgcggc cggcatggtg aacaaggtgg tcgagcattt actgcgtcgg     120
ctgaaatgcg actcagcctt tcgcggcgtt ggtctgctga cacgggtag ctattacgaa      180 cacgtcaaaa tctctgcacc gaacgaattc gatgttatgt tcaaactgga agtcccgcgt     240
attcagctgg aagaatatag caacacccgt gcctattact ttgttaaatt caaacgcaac     300
ccgaaagaaa atccgctgag tcagtttctg gaaggcgaaa tcctgagtgc gtccaaaatg     360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aaagtgcgta acagctgcg cctgaaaccg      600 ttttacctgg ttccgaaaca tgcgaaagaa ggcaatggtt ttcaagaaga aacctggcgc     660
ctgtcattct cgcatatcga aaaagaaatc ctgaacaacc acggtaaaag taaaacgtgc     720
tgtgaaaaca aagaagaaaa atgctgtcgt aaagattgtc tgaaactgat gaaatatctg     780
ctggaacagc tgaaagaacg cttcaaagat aaaaaacacc tggacaaatt cagttcctac     840
catgtgaaaa ccgcgttttt ccacgtttgc acgcaaaatc cgcaggatag ccaatgggat     900
cgtaaagacc tgggtctgtg ctttgacaac tgtgtgacct atttcctgca gtgtctgcgc     960
acggaaaaac tggaaaatta ctttatcccg gaatttaacc tgttctcatc gaatctgatt    1020
gataaacgtt ctaagaatt cctgacgaaa cagattgaat acgaacgcaa caacgaattt     1080
ccggtctttg acgaattt                                                  1098

<210> SEQ ID NO 41
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ala Ala Pro Gly Ala Ser Lys Leu Arg Ala Val Leu Glu Lys Leu
1               5                   10                  15

-continued

Lys Leu Ser Arg Asp Asp Ile Ser Thr Ala Ala Gly Met Val Asn Lys
                20                  25                  30

Val Val Glu His Leu Leu Arg Arg Leu Lys Cys Asp Ser Ala Phe Arg
            35                  40                  45

Gly Val Gly Leu Leu Asn Thr Gly Ser Tyr Tyr Glu His Val Lys Ile
        50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
    290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365

<210> SEQ ID NO 42
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
gacgcagctc cgggtgcttc taaactgcgt gcggtcctgg aaaaactgaa actgagccgc    60
gatgacattt ctaccgcggc cggcatggtg aacaaggtgg tcgagcggtt actgctgcgg   120
ctgaaatgcg actcagcctt tcgcggcgtt ggtctgctga cacgggtag ctattacgaa    180
cacgtcaaaa tctctgcacc gaacgaattc gatgttatgt tcaaactgga agtcccgcgt   240
attcagctgg aagaatatag caacacccgt gcctattact ttgttaaatt caaacgcaac   300
ccgaaagaaa atccgctgag tcagtttctg gaaggcgaaa tcctgagtgc gtccaaaatg   360
ctgtccaaat tccgcaaaat catcaaagaa gaaatcaacg atatcaaaga taccgacgtc   420
attatgaaac gtaaacgcgg cggtagtccg gcagtcaccc tgctgatttc agaaaaaatc   480
tcggtggaca ttacgctggc tctggaatca aaaagctctt ggccggcgag cacccaggaa   540
ggcctgcgta ttcaaaactg gctgtccgct aaagtgcgta acagctgcg cctgaaaccg    600
ttttacctgg ttccgaaaca tgcgaaagaa ggcaatggtt ttcaagaaga aacctggcgc   660
ctgtcattct cgcatatcga aaaagaaatc ctgaacaacc acggtaaaag taaaacgtgc   720
tgtgaaaaca agaagaaaa atgctgtcgt aaagattgtc tgaaactgat gaaatatctg    780
ctggaacagc tgaaagaacg cttcaaagat aaaaaacacc tggacaaatt cagttcctac   840
catgtgaaaa ccgcgttttt ccacgtttgc acgcaaaatc cgcaggatag ccaatgggat   900
cgtaaagacc tgggtctgtg ctttgacaac tgtgtgacct atttcctgca gtgtctgcgc   960
acggaaaaac tggaaaatta ctttatcccg gaatttaacc tgttctcatc gaatctgatt  1020
gataaacgtt ctaaagaatt cctgacgaaa cagattgaat acgaacgcaa caacgaattt  1080
ccggtctttg acgaattt                                                1098
```

<210> SEQ ID NO 43
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Asp Ala Ala Pro Gly Ala Ser Lys Leu Arg Ala Val Leu Glu Lys Leu
1               5                   10                  15
Lys Leu Ser Arg Asp Asp Ile Ser Thr Ala Ala Gly Met Val Asn Lys
            20                  25                  30
Val Val Glu Arg Leu Leu Leu Arg Leu Lys Cys Asp Ser Ala Phe Arg
        35                  40                  45
Gly Val Gly Leu Leu Asn Thr Gly Ser Tyr Tyr Glu His Val Lys Ile
    50                  55                  60
Ser Ala Pro Asn Glu Phe Asp Val Met Phe Lys Leu Glu Val Pro Arg
65                  70                  75                  80
Ile Gln Leu Glu Glu Tyr Ser Asn Thr Arg Ala Tyr Tyr Phe Val Lys
                85                  90                  95
Phe Lys Arg Asn Pro Lys Glu Asn Pro Leu Ser Gln Phe Leu Glu Gly
            100                 105                 110
Glu Ile Leu Ser Ala Ser Lys Met Leu Ser Lys Phe Arg Lys Ile Ile
        115                 120                 125
Lys Glu Glu Ile Asn Asp Ile Lys Asp Thr Asp Val Ile Met Lys Arg
    130                 135                 140
```

```
Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
            165                 170                 175

Ser Thr Gln Glu Gly Leu Arg Ile Gln Asn Trp Leu Ser Ala Lys Val
        180                 185                 190

Arg Lys Gln Leu Arg Leu Lys Pro Phe Tyr Leu Val Pro Lys His Ala
    195                 200                 205

Lys Glu Gly Asn Gly Phe Gln Glu Thr Trp Arg Leu Ser Phe Ser
210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365
```

<210> SEQ ID NO 44
<211> LENGTH: 1098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
gacgcagctc cgggtgcttc taaactgcgt gcggtcctgg aaaaactgaa actgagccgc      60
gatgacattt ctaccgcggc cggcatggtg aacggtgtgg ttgatcatct gctgctgcgt     120
ctgaaatgcg actcagcctt tcgcggcgtt ggtctgctga cacgggtag ctattacgaa      180 cacgtcaaaa tctctgcacc gaacgaattc gatgttatgt tcaaactgga agtcccgcgt     240
attcagctgg aagaatatag caacacccgt gcctattact tgttaaaatt caaacgcaac     300
ccgaaagaaa atccgctgag tcagtttctg gaaggcgaaa tcctgagtgc gtccaaaatg     360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aagtgcgta acagctgcg cctgaaaccg       600 tttacctgg ttccgaaaca tgcgaaagaa ggcaatggtt tcaagaaga aacctggcgc       660 ctgtcattct cgcatatcga aaagaaatc ctgaacaacc acggtaaaag taaaacgtgc      720
tgtgaaaaca agaagaaaa atgctgtcgt aaagattgtc tgaaactgat gaaatatctg      780
```

```
ctggaacagc tgaaagaacg cttcaaagat aaaaaacacc tggacaaatt cagttcctac        840
catgtgaaaa ccgcgttttt ccacgtttgc acgcaaaatc cgcaggatag ccaatgggat        900
cgtaaagacc tgggtctgtg ctttgacaac tgtgtgacct atttcctgca gtgtctgcgc        960
acggaaaaac tggaaaatta ctttatcccg gaatttaacc tgttctcatc gaatctgatt       1020
gataaacgtt ctaaagaatt cctgacgaaa cagattgaat acgaacgcaa caacgaattt       1080
ccggtctttg acgaattt                                                     1098
```

<210> SEQ ID NO 45
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Asn Gly
            20                  25                  30

Val Val Asp His Leu Leu Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
    290                 295                 300
```

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365

<210> SEQ ID NO 46
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gacgcagctc cgggtgcttc taaactgcgt gcggtcctgg aaaaactgaa actgagccgc      60
gatgacattt ctaccgcggc cggcatggtg aaaggtgtgg ttgatcatct gctgcgtcgt     120
ctgaaatgcg actcagcctt tcgcggcgtt ggtctgctga cacgggtag ctattacgaa      180 cacgtcaaaa tctctgcacc gaacgaattc gatgttatgt tcaaactgga agtcccgcgt     240
attcagctgg aagaatatag caacacccgt gcctattact tgttaaaatt caaacgcaac     300
ccgaaagaaa atccgctgag tcagtttctg aaggcgaaa tcctgagtgc gtccaaaatg      360
ctgtccaaat tccgcaaaat catcaaagaa gaaatcaacg atatcaaaga taccgacgtc     420
attatgaaac gtaaacgcgg cggtagtccg gcagtcaccc tgctgatttc agaaaaaatc     480
tcggtggaca ttacgctggc tctggaatca aaaagctctt ggccggcgag cacccaggaa     540
ggcctgcgta ttcaaaactg gctgtccgct aaagtgcgta acagctgcg cctgaaaccg      600 ttttacctgg ttccgaaaca tgcgaaagaa ggcaatggtt tcaagaaga acctggcgc      660 ctgtcattct cgcatatcga aaagaaatc ctgaacaacc acggtaaag taaaacgtgc      720 tgtgaaaaca agaagaaaa atgctgtcgt aaagattgtc tgaaactgat gaaatatctg     780
ctggaacagc tgaaagaacg cttcaaagat aaaaaacacc tggacaaatt cagttcctac     840
catgtgaaaa ccgcgttttt ccacgtttgc acgcaaaatc cgcaggatag ccaatgggat     900
cgtaaagacc tgggtctgtg ctttgacaac tgtgtgacct atttcctgca gtgtctgcgc     960
acggaaaaac tggaaaatta ctttatcccg gaatttaacc tgttctcatc gaatctgatt    1020
gataaacgtt ctaaagaatt cctgacgaaa cagattgaat acgaacgcaa caacgaattt    1080
ccggtctttg acgaattt                                                   1098

<210> SEQ ID NO 47
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

| | | | | | | | | | | | |
|---|---|---|---|---|---|---|---|---|---|---|---|
|Val|Val|Asp|His|Leu|Leu|Arg|Arg|Leu|Lys|Cys|Asp|Ser|Ala|Phe|Arg|
| | |35| | | |40| | | |45| |

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe His
        275                 280                 285

Val Cys Thr Gln Asn Pro Gln Asp Ser Gln Trp Asp Arg Lys Asp Leu
290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365

<210> SEQ ID NO 48
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gacgcagctc cgggtgcttc taaactgcgt gcggtcctgg aaaaactgaa actgagccgc      60
gatgacattt ctaccgcggc cggcatggtg aacggtgtgg ttgatcatct gctgcgtcgt     120
ctgaaatgcg actcagcctt tcgcggcgtt ggtctgctga acacgggtag ctattacgaa     180

```
cacgtcaaaa tctctgcacc gaacgaattc gatgttatgt tcaaactgga agtcccgcgt    240
attcagctgg aagaatatag caacacccgt gcctattact ttgttaaatt caaacgcaac    300
ccgaaagaaa atccgctgag tcagtttctg gaaggcgaaa tcctgagtgc gtccaaaatg    360
ctgtccaaat tccgcaaaat catcaaagaa gaaatcaacg atatcaaaga taccgacgtc    420
attatgaaac gtaaacgcgg cggtagtccg gcagtcaccc tgctgatttc agaaaaaatc    480
tcggtggaca ttacgctggc tctggaatca aaaagctctt ggccggcgag cacccaggaa    540
ggcctgcgta ttcaaaactg gctgtccgct aaagtgcgta acagctgcg cctgaaaccg    600 ttttacctgg ttccgaaaca tgcgaaagaa ggcaatggtt ttcaagaaga aacctggcgc    660
ctgtcattct cgcatatcga aaagaaatc ctgaacaacc acggtaaaag taaaacgtgc    720
tgtgaaaaca aagaagaaaa atgctgtcgt aaagattgtc tgaaactgat gaaatatctg    780
ctggaacagc tgaaagaacg cttcaaagat aaaaaacacc tggacaaatt cagttcctac    840
catgtgaaaa ccgcgttttt ccacgtttgc acgcaaaatc cgcaggatag ccaatgggat    900
cgtaaagacc tgggtctgtg ctttgacaac tgtgtgacct atttcctgca gtgtctgcgc    960
acggaaaaac tggaaaatta ctttatcccg gaatttaacc tgttctcatc gaatctgatt   1020
gataaacgtt ctaaagaatt cctgacgaaa cagattgaat acgaacgcaa caacgaattt   1080
ccggtctttg acgaattt                                                1098
```

<210> SEQ ID NO 49
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Asn Gly
            20                  25                  30

Val Val Asp His Leu Leu Arg Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95

Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190
```

```
Arg Lys Gln Leu Arg Leu Lys Pro Phe Tyr Leu Val Pro Lys His Ala
            195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
            275                 280                 285

Val Cys Thr Gln Asn Pro Gln Asp Ser Gln Trp Asp Arg Lys Asp Leu
    290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
            355                 360                 365

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 50

His His His His His His
1               5

<210> SEQ ID NO 51
<211> LENGTH: 11
<212> TYPE: PRT
<213> ORGANISM: Homo sapiens

<400> SEQUENCE: 51

Val Lys Gly Val Val Asp His Leu Leu Leu Arg
1               5                   10

<210> SEQ ID NO 52
<211> LENGTH: 11
<212> TYPE: PRT
<213> ORGANISM: Mus sp.

<400> SEQUENCE: 52

Val Asn Lys Val Val Glu Arg Leu Leu Arg Arg
1               5                   10
```